United States Patent
Duchateau et al.

(10) Patent No.: US 8,906,607 B2
(45) Date of Patent: Dec. 9, 2014

(54) METHOD FOR MODULATING DOUBLE-STRAND BREAK-INDUCED HOMOLOGOUS RECOMBINATION

(75) Inventors: Philippe Duchateau, Livry Gargan (FR); Frédéric Paques, Bourg-la-Reine (FR); Christophe Perez-Michaut, Paris (FR); Fabien Delacote, Paris (FR)

(73) Assignee: Cellectis, Paris (FR)

( * ) Notice: Subject to any disclaimer, the term of this patent is extended or adjusted under 35 U.S.C. 154(b) by 0 days.

(21) Appl. No.: 13/695,225

(22) PCT Filed: Apr. 30, 2010

(86) PCT No.: PCT/IB2010/001286
§ 371 (c)(1),
(2), (4) Date: Mar. 25, 2013

(87) PCT Pub. No.: WO2011/135396
PCT Pub. Date: Nov. 3, 2011

(65) Prior Publication Data
US 2013/0190385 A1   Jul. 25, 2013

(51) Int. Cl.
*C12Q 1/68* (2006.01)
*C12N 15/113* (2010.01)
*C12N 15/11* (2006.01)
*C12N 15/10* (2006.01)

(52) U.S. Cl.
CPC .......... *C12N 15/1137* (2013.01); *C12N 15/111* (2013.01); *C12N 15/113* (2013.01); *C12N 15/1034* (2013.01); *C12N 15/1086* (2013.01); *C12N 2310/14* (2013.01); *C12N 2320/12* (2013.01)
USPC ........... 435/6; 536/24.5; 536/24.31; 536/24.1

(58) Field of Classification Search
CPC ......................... C12N 15/113; C12N 2310/14
See application file for complete search history.

(56) References Cited

U.S. PATENT DOCUMENTS

2011/0150897 A1*  6/2011  Meyer et al. ............... 424/158.1

OTHER PUBLICATIONS

International Search Report for International Application No. PCT/IB2010/001286, dated Feb. 21, 2011.
Wiltshire, Timothy D., et al., "Sensitivity to poly (ADP-ribose) polymerase (PARP) inhibition identifies ubiquitin-specific peptidase 11 (USP11) as a regulator of DNA double-strand break repair." The Journal of Biological Chemistry vol. 285, No. 19, pp. 14565-14571, May 7, 2010.
Sikdar, Nilabja, et al., "DNA damage responses by human ELG1 in S phase are important to maintain genomic integrity." Cell Cycle (Georgetown, Tex.) Oct. 1, 2009, vol. 8, No. 19, pp. 3199-3207.
Murakawa, Yasuhiro, et al., "Inhibitors of the proteasome suppress homologous DNA recombination in mammalian cells." Cancer Research, Sep. 15, 2007, vol. 67, No. 18, pp. 8536-8543.

\* cited by examiner

*Primary Examiner* — Kimberly Chong
(74) *Attorney, Agent, or Firm* — Law Office of Salvatore Arrigo and Scott Lee, LLP

(57) ABSTRACT

The present invention concerns a method for modulating double-strand break-induced homologous recombination through the identification of effectors that modulate said double-strand break-induced homologous recombination by uses of interfering agents; these agents are capable of modulating double-strand break-induced homologous recombination through their respective actions on said effectors. The present invention also concerns the uses of these effectors and interfering agents and derivatives, respectively, by introducing them in an eukaryotic cell in order to modulate and more particularly to increase double-strand break-induced homologous recombination and gene targeting efficiency. The present invention also relates to specific derivatives of identified effectors and interfering agents, vectors encoding them, compositions and kits comprising such derivatives in order to modulate and more particularly to increase double-strand break-induced homologous recombination and gene targeting efficiency.

19 Claims, 19 Drawing Sheets

Panel A:
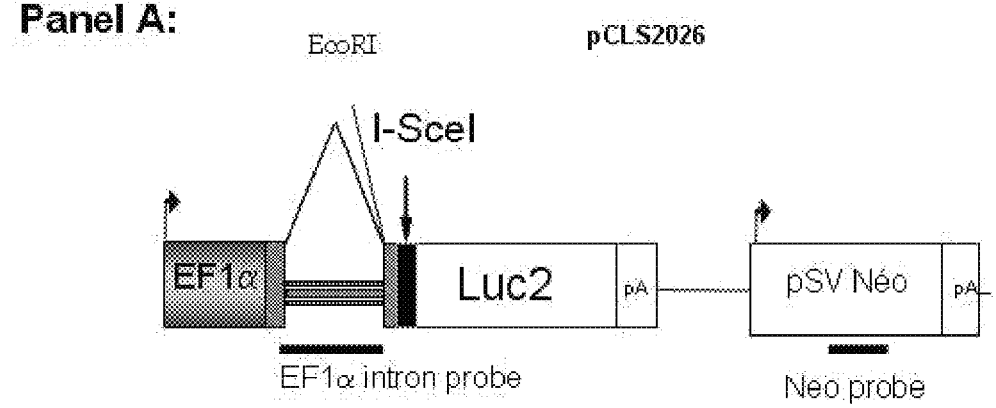
Panel B:
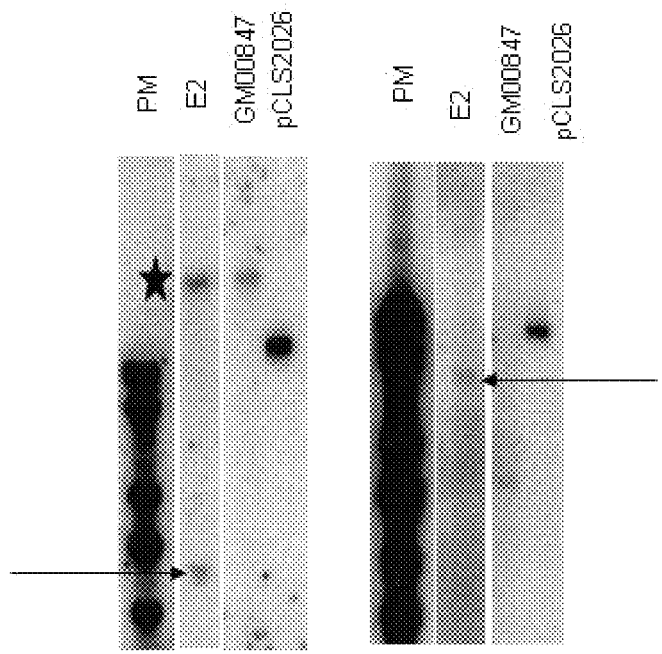
FIG. 2

Panel A:
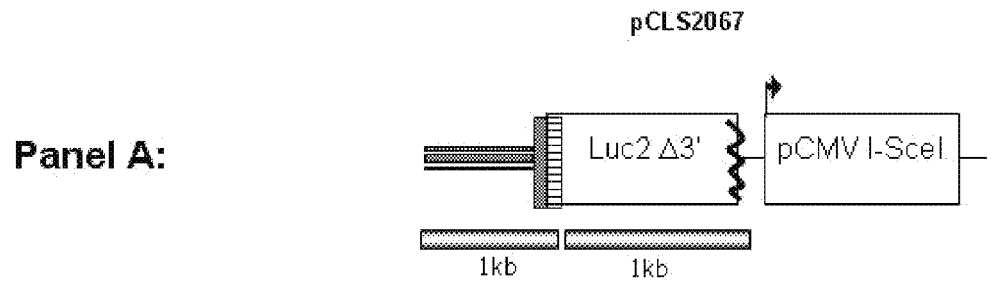
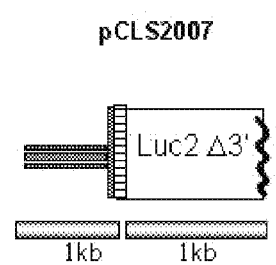
Panel B:
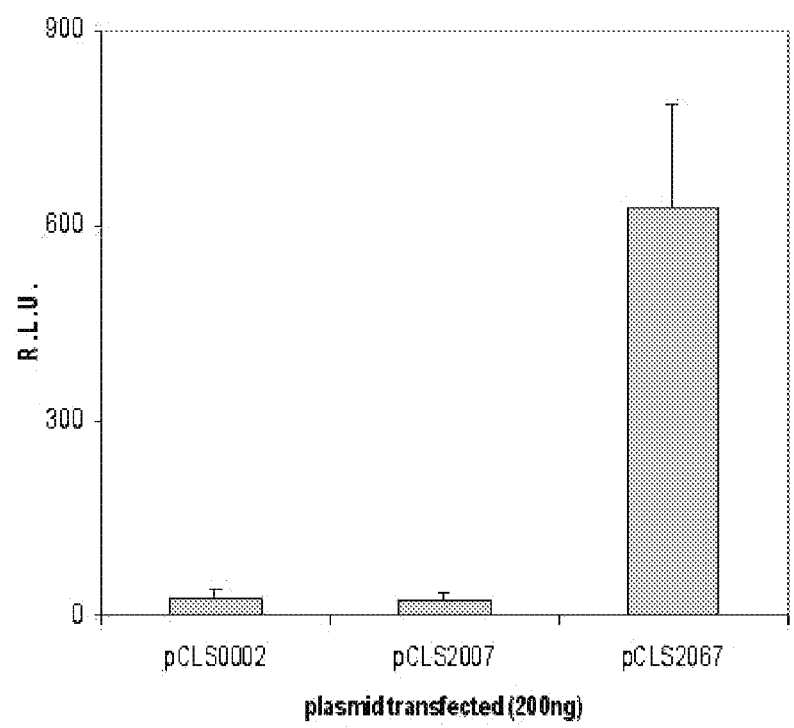
FIG.3

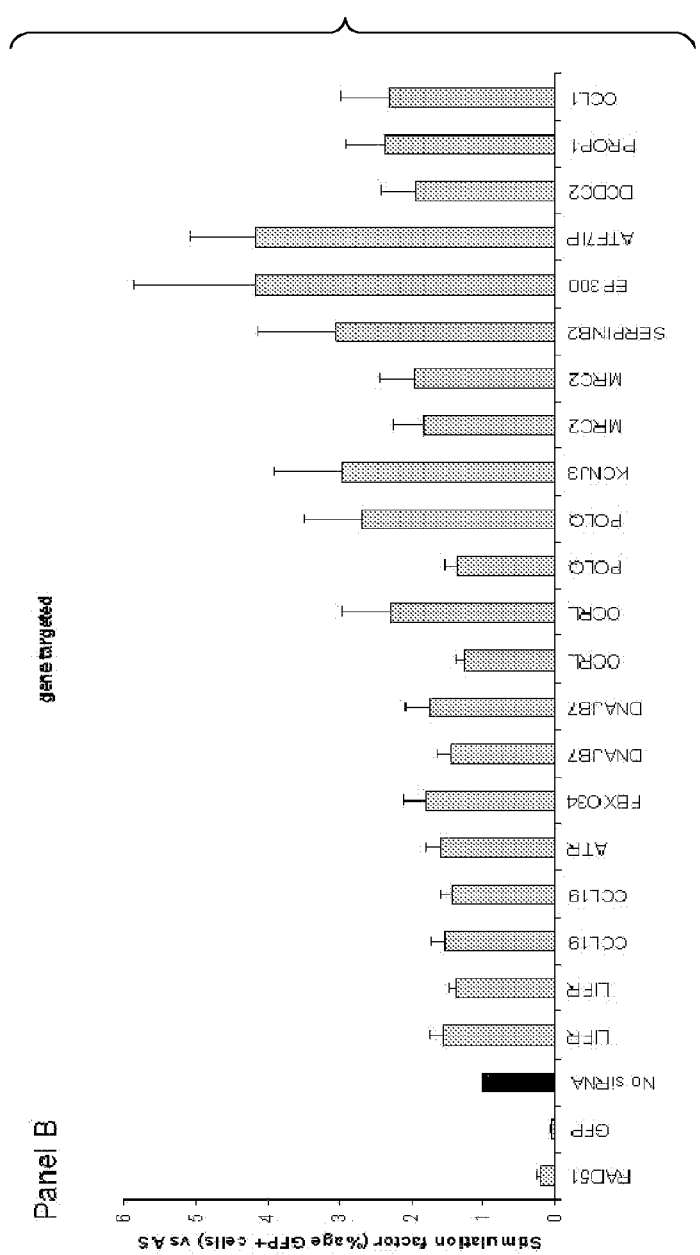

METHOD FOR MODULATING DOUBLE-STRAND BREAK-INDUCED HOMOLOGOUS RECOMBINATION

This application is a national phase application under 35 U.S.C. §371 of International Application No. PCT/IB2010/001286 filed on Apr. 30, 2010, the disclosure of which is hereby incorporated by reference herein.

FIELD OF THE INVENTION

The present invention concerns a method for modulating double-strand break-induced homologous recombination through the identification of effectors that modulate said double-strand break-induced homologous recombination by uses of interfering agents; these agents are capable of modulating double-strand break-induced homologous recombination through their respective direct or indirect actions on said effectors. The present invention also concerns the uses of these effectors, interfering agents and derivatives, respectively, by introducing them into a eukaryotic cell in order to modulate and more particularly to increase double-strand break-induced homologous recombination and gene targeting efficiency. The present invention also relates to specific derivatives of identified effectors and interfering agents, vectors encoding them, compositions and kits comprising such derivatives in order to modulate and more particularly to increase double-strand break-induced homologous recombination and gene targeting efficiency.

BACKGROUND OF THE INVENTION

Since the first gene targeting experiments in yeast more than 25 years ago (Hinnen et al, 1978; Rothstein, 1983), homologous recombination (HR) has been used to insert, replace or delete genomic sequences in a variety of cells (Thomas and Capecchi, 1987; Capecchi, 2001; Smithies, 2001). HR is a very conserved DNA maintenance pathway involved in the repair of DNA double-strand breaks (DSBs) and other DNA lesions (Paques and Haber, 1999; Sung and Klein, 2006), but it also underlies many biological phenomenon, such as the meiotic reassortiment of alleles in meiosis (Roeder, 1997). A competing pathway in DSBs repair events is the Non-Homologous End Joining (NHEJ) pathway which accounts for all DSBs repair events in the absence of an homologous repair matrix (Paques and Haber, 1999; van Gent et al, 2001). Although perfect relegation of the broken ends is probably the most frequent event, imperfect rejoining of the broken ends can result in the addition or deletion of one of several base pairs, inactivating the targeted open reading frame. Homologous gene targeting strategies have been used to knock out endogenous genes (Capecchi, M. R., Science, 1989, 244, 1288-1292, Smithies, O., Nature Medicine, 2001, 7, 1083-1086) or knock-in exogenous sequences in the chromosome. It can as well be used for gene correction, and in principle, for the correction of mutations linked with monogenic diseases. However, this application is in fact difficult, due to the low efficiency of the process ($10^{-6}$ to $10^{-9}$ of transfected cells). The frequency of HR can be significantly increased by a specific DNA double-strand break (DSB) at a locus (Rouet et al, 1994; Choulika et al, 1995). Such DSBs can be induced by meganucleases, sequence-specific endonucleases that recognize large DNA recognition target sites (12 to 30 bp).

Meganucleases show high specificity to their DNA target, these proteins being able to cleave a unique chromosomal sequence and therefore do not affect global genome integrity. Natural meganucleases are essentially represented by homing endonucleases, a widespread class of proteins found in eukaryotes, bacteria and archae (Chevalier and Stoddard, 2001). Early studies of the I-SceI and HO homing endonucleases have illustrated how the cleavage activity of these proteins can be used to initiate HR events in living cells and have demonstrated the recombinogenic properties of chromosomal DSBs (Dujon et al, 1986; Haber, 1995). Since then, meganuclease-induced HR has been successfully used for genome engineering purposes in bacteria (Posfai et al, 1999), mammalian cells (Sargent et al, 1997; Donoho et al, 1998; Cohen-Tannoudji et al, 1998), mice (Gouble et al, 2006) and plants (Puchta et al, 1996; Siebert and Puchta, 2002).

Other specialized enzymes like integrases, recombinases, transposases and endonucleases have been proposed for site-specific genome modifications. For years, the use of these enzymes remained limited, due to the challenge of retargeting their natural specificities towards desired target sites. Indeed, the target sites of these proteins, or sequences with a sufficient degree of sequence identity, should be present in the sequences neighboring the mutations to be corrected, or within the gene to be inactivated, which is usually not the case, except in the case of pre-engineered sequences.

Meganucleases have emerged as scaffolds of choice for deriving genome engineering tools cutting a desired target sequence (Paques et al. Curr Gen Ther. 2007 7:49-66). Combinatorial assembly processes allowing to engineer meganucleases with modified specificities has been described by Arnould et al. J Mol. Biol. 2006 355:443-458; Arnould et al. J Mol. Biol. 2007 371:49-65; Smith et al. NAR 2006 34:e149; Grizot et al. NAR 2009 37:5405. Briefly, these processes rely on the identifications of locally engineered variants with a substrate specificity that differs from the substrate specificity of the wild-type meganuclease by only a few nucleotides.

Although these powerful tools are available, there is still a need to further modulate double-strand break-induced homologous recombination and more particularly to increase the efficiency of gene targeting, i.e. the frequency of integration events of an exogenous gene at a targeted locus.

RNA interference is an endogenous gene silencing pathway that responds to dsRNAs by silencing homologous genes (Meister, G. & Tuschl, T., 2004). First described in *Caenorhabditis elegans* by Fire et al, the RNAi pathway functions in a broad range of eukaryotic organisms (Hannon, G. J. et al, 2002). Silencing in these initial experiments was triggered by introduction of long dsRNA. The enzyme Dicer cleaves these long dsRNAs into short-interfering RNAs (siRNAs) of approximately 21-23 nucleotides. One of the two siRNA strands is then incorporated into an RNA-induced silencing complex (RISC). RISC compares these "guide RNAs" to RNAs in the cell and efficiently cleaves target RNAs containing sequences that are perfectly, or nearly perfectly complementary to the guide RNA.

For many years it was unclear whether the RNAi pathway was functional in cultured mammalian cells and in whole mammals. However, Elbashir S. M. et al, 2001, triggered RNAi in cultured mammalian cells by transfecting them with 21 nucleotide synthetic RNA duplexes that mimicked endogenous siRNAs. McCaffrey et al, 2002, also demonstrated that siRNAs and shRNAs could efficiently silence genes in adult mice.

Introduction of chemically synthetized siRNAs can effectively mediate post-transcriptional gene silencing in mammalian cells without inducing interferon responses.

Synthetic siRNAs, targeted against a variety of genes, have been successfully used in mammalian cells to prevent expression of target mRNA (Harborth J. et al, 2001).

These discoveries of RNAi and siRNA-mediated gene silencing has led to a spectrum of opportunities for functional genomics, target validation, and the development of siRNA-based therapeutics, making it a potentially powerful tool for therapeutics and in vivo studies.

It has been demonstrated that inhibition of genes implicated in NHEJ stimulates HR and gene targeting (Allen et al, 2002; Delacote et al, 2002; Bertolini et al, 2009). NHEJ inhibition has been achieved either by using mutants, either by inhibition of gene expression through siRNAs.

In WO2007/013979, the expression of six genes supposed to be implied in NHEJ, Ku70, Ku86, DNA-PKcs, XRCC4, DNA ligase IV and Artemis, are silenced to show that these genes are clearly decreasing the random integration of a linearized GFP vector and are slightly increasing targeted integration of a HPRT matrix-like at the HPRT locus.

WO2008/113847 relates to a bipartite gene-replacement method, resulting in a combined recombination and targeted integration event in a parent eukaryotic cell with a preference for Non homologous Recombination (NHR), said eukaryotic cell having an increased HR/NHR ratio by deleting hdfA or hdfB gene of *Penicillium chrysogenum*, respectively fungal equivalents of Ku70 and Ku80 *Saccharomyces cerivisiae* genes.

None of these techniques allowed identifying genes implicated in double-strand break-induced HR.

Slabicki et al. briefly summarizes a method aiming at identifying genes involved in double strand break repair. This method is based on the measure of gene conversion events, and not of gene targeting events. This document fails to provide an accurate and detailed description of the method. In addition, the method only led to the identification of very few genes. Moreover, this document neither teaches nor suggests that modulating the identified gene in a eukaryotic cell could be useful for increasing targeted integration of a transgene.

It is thus highly desirable to construct new cell lines in which double-strand break-induced HR can be modulated, particularly in which genome targeting of a polynucleotide or gene of interest can take place with higher frequency.

Methods, agents and compositions that could be used to modulate double-strand break-induced HR would be extremely advantageous, particularly to increase the integration efficiency of a transgene into a genome at a predetermined location.

DESCRIPTION OF THE INVENTION

The present invention concerns a method for modulating double-strand break-induced homologous recombination through the identification of effectors that modulate said double-strand break-induced homologous recombination by uses of interfering agents; these agents are capable of modulating double-strand break-induced homologous recombination through their respective direct or indirect actions on said effectors. The present invention also concerns the uses of derivatives of these effectors and interfering agents, respectively, by introducing them into a eukaryotic cell in order to modulate and more particularly to increase double-strand break-induced homologous recombination and gene targeting efficiency. The present invention also relates to specific derivatives of identified effectors and interfering agents, vectors encoding them, compositions and kits comprising such derivatives in order to modulate and more particularly to increase double-strand break-induced homologous recombination and gene targeting efficiency.

More particularly, in the present invention, a method has been set up to identify, by RNA interference, genes other than those implied in NHEJ, that modulate HR induced by meganucleases. This method can be used to increase gene targeting of a transgene at a predefined locus inside a genome. Specific effector genes, i.e. genes capable of modulating HR upon endonuclease-induced DSBs, have been identified and polynucleotide derivatives sequences thereof have been used to increase gene targeting efficiency at a specific locus in a genome. Compositions and kits comprising such polynucleotide derivatives are part of the scope of the present invention.

More specifically, examples 1 to 3 disclose a powerful screening method which allowed the successful identification of more than 900 effector genes. Examples 3 and 4 confirm that silencing of some of these effector genes allows significantly increasing the efficiency of HR upon endonuclease-induced DSBs.

DEFINITIONS

The terms "effector" and "effectors" refer to any cellular target, from nucleic or protein origin that can be targeted to directly or indirectly modulate double-strand break-induced homologous recombination; it encompasses any molecule that binds to nucleic acid to modulate gene transcription or protein translation, any molecule that binds to another protein to alter at least one property of that protein, such as its activity, or any gene or gene products that could play a role directly or not in the process of double-strand break-induced homologous recombination.

The term "interfering agent" or "interfering agents" refer to any molecule and compound likely to interact with effectors. It encompasses small chemicals, small molecules, composite chemicals or molecules, from synthetic or natural origin, encompassing amino acids or nucleic acid derivatives, synthons, Active Pharmaceutical Ingredients, any chemical of industrial interest, used in the manufacturing of drugs, industrial chemicals or agricultural products. These interfering agents are part or not of molecular libraries dedicated to particular screening, commercially available or not. These interfering agents encompass polynucleotide derivatives as a non limiting example.

The term "endonuclease" refers to any wild-type or variant enzyme capable of catalyzing the hydrolysis (cleavage) of bonds between nucleic acids within of a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites" and significantly increased HR by specific meganuclease-induced DNA double-strand break (DSB) at a defined locus (Rouet et al, 1994; Choulika et al, 1995). Endonucleases can for example be a homing endonuclease (Paques et al. Curr Gen Ther. 2007 7:49-66), a chimeric Zinc-Finger nuclease (ZFN) resulting from the fusion of engineered zinc-finger domains with the catalytic domain of a restriction enzyme such as FokI (Porteus et al. Nat. Biotechnol. 2005 23:967-973) or a chemical endonuclease (Arimondo et al. Mol Cell Biol. 2006 26:324-333; Simon et al. NAR 2008 36:3531-3538; Eisenschmidt et al. NAR 2005 33:7039-7047; Cannata et al. PNAS 2008 105: 9576-9581). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer Ann NY Aced Sci 2005 1058: 151-61). Such chemical endonucleases are comprised in the term "endonuclease" according to the present invention. In the scope of the present invention is also intended any fusion between molecules able to bind DNA specific sequences and agent/reagent/chemical able to cleave DNA or interfere with cellular proteins implicated in the DSB repair (Majumdar et al. J. Biol. Chem. 2008 283, 17:11244-11252; Liu et al. NAR 2009 37:6378-6388); as a non limiting example such a fusion can be constituted by a specific DNA-sequence binding domain linked to a chemical inhibitor known to inhibate religation activity of a topoisomerase after DSB cleavage.

Endonuclease can be a homing endonuclease, also known under the name of meganuclease. Such homing endonucleases are well-known to the art (see e.g. Stoddard, Quarterly Reviews of Biophysics, 2006, 38:49-95). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease.

Examples of such endonuclease include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, I-Msol.

A homing endonuclease can be a LAGLIDADG endonuclease such as I-Scel, I-Crel, I-Ceul, I-Msol, and I-Dmol.

Said LAGLIDADG endonuclease can be I-Sce I, a member of the family that contains two LAGLIDADG motifs and functions as a monomer, its molecular mass being approximately twice the mass of other family members like I-CreI which contains only one LAGLIDADG motif and functions as homodimers.

Endonucleases mentioned in the present application encompass both wild-type (naturally-occurring) and variant endonucleases. Endonucleases according to the invention can be a "variant" endonuclease, i.e. an endonuclease that does not naturally exist in nature and that is obtained by genetic engineering or by random mutagenesis. This variant endonuclease can for example be obtained by substitution of at least one residue in the amino acid sequence of a wild-type, naturally-occurring, endonuclease with a different amino acid. Said substitution(s) can for example be introduced by site-directed mutagenesis and/or by random mutagenesis. In the frame of the present invention, such variant endonucleases remain functional, i.e. they retain the capacity of recognizing and specifically cleaving a target sequence to initiate gene targeting process.

The variant endonuclease according to the invention cleaves a target sequence that is different from the target sequence of the corresponding wild-type endonuclease. Methods for obtaining such variant endonucleases with novel specificities are well-known in the art.

Endonucleases variants may be homodimers (meganuclease comprising two identical monomers) or heterodimers (meganuclease comprising two non-identical monomers).

Endonucleases with novel specificities can be used in the method according to the present invention for gene targeting and thereby integrating a transgene of interest into a genome at a predetermined location.

Endonucleases according to the invention can be mentioned or defined as one double-strand break creating agent amongst other double-strand break creating agents well-known in the art.

Double-strand break creating agent means any agent or chemical or molecule able to create DNA (or double-stranded nucleic acids) double-strand breaks (DSBs). As previously mentioned, endonucleases can be considered as double-strand break creating agent targeting specific DNA sequences. Other agents or chemicals or molecules are double-strand break creating agents which DNA sequence targets are non-specific or non-predictable such as, in a non limiting list, alkylating agents (Methyl Methane Sulfonate or dimethane sulfonates family and analogs), zeocyn, enzyme inhibitors such as toposiomerase inhibitors (types I and II such as non limiting examples quinolones, fluoroquinolones, ciprofloxacin, irinotecan, lamellarin D, doxorubicin, etoposide) and ionizing radiations α-rays, UltraViolet, gamma-rays).

Homologous recombination (HR) refers to the very conserved DNA maintenance pathway involved in the repair of DSBs and other DNA lesions (Paques and Haber, 1999; Sung and Klein, 2006), that promotes the exchange of genetic information between endogenous sequences. In gene targeting experiments, the exchange of genetic information is promoted between an endogenous chromosomal sequence and an exogenous DNA construct. Depending of the design of the targeted construct, genes could be knocked out, knocked in, replaced, corrected or mutated, in a rational, precise and efficient manner. The process requires essentially a few hundred base pairs of homology between the targeting construct and the targeted locus (Hinnen et al, 1978) and is significantly stimulated by free DNA ends in the construct (Orr-Weaver et al, 1981; Orr-Weaver et al, 1983; Szostak et al, 1983). These free DNA ends label the construct as a substrate for the HR machinery.

In the frame of the present invention, the homologous recombination according to the invention is an "endonuclease-induced homologous recombination", i.e. an homologous recombination event taking place after a double-strand break, wherein said double-strand break is due to cleavage by an endonuclease.

The term "reporter gene", as used herein, refers to a nucleic acid sequence whose product can be easily assayed, for example, colorimetrically as an enzymatic reaction product, such as the lacZ gene which encodes for β-galactosidase. Examples of widely-used reporter molecules include enzymes such as β-galactosidase, β-glucoronidase, β-glucosidase; luminescent molecules such as green fluorescent protein and firefly luciferase; and auxotrophic markers such as His3p and Ura3p. (See, e.g., Chapter 9 in Ausubel, F. M., et al. Current Protocols in Molecular Biology, John Wiley & Sons, Inc. (1998)).

By "homologous sequence" is intended a sequence with enough identity to another one to lead to a homologous recombination between sequences, more particularly having at least 95% identity, preferably 97% identity and more preferably 99%. Preferably, homologous sequences of at least 50 bp, preferably more than 100 bp and more preferably more than 200 bp are used. Therefore, the targeting DNA construct is preferably from 200 bp to 6000 bp, more preferably from 1000 bp to 2000 bp. Indeed, shared DNA homologies are located in regions flanking upstream and downstream the site of the break and the DNA sequence to be introduced should be located between the two arms. The targeting construct may also comprise a positive selection marker between the two homology arms and eventually a negative selection marker upstream of the first homology arm or downstream of the second homology arm. The marker(s) allow(s) the selection of cells having inserted the sequence of interest by homologous recombination at the target site.

The term "flanked" refers to a polynucleotide to be linearized or excised that is flanked by a cleavage site if such a site is present at or near either or both ends of the polynucleotide. There can be one cleavage site present or near one end of the polynucleotide to be linearized or excised or there can be two cleavage sites, one at or near each end of the polynucleotide to be linearized or excised. By "near" is preferably intended in the present invention that the cleavage site is located at less than 1 kb, preferably less than 500 bp, more preferably less than 200, or 100 bp, of the end of the polynucleotide to be integrated.

By "repair matrix" (also referred to as "targeting DNA construct" or "donor construct") it is intended to mean a DNA construct comprising a first and second portions which are homologous to regions 5' and 3' of the DNA target in situ. The DNA construct also comprises a third portion positioned between the first and second portion which comprise some homology with the corresponding DNA sequence in situ or alternatively comprise no homology with the regions 5' and 3' of the DNA target in situ. The DNA construct can be part of a vector or not, linearized or not. Following cleavage of the DNA target, a homologous recombination event is stimulated between the genome of the transfected cell and the repair matrix, wherein the genomic sequence containing the DNA target is replaced by the part of the repair matrix located between the two flanking homologous sequences. Preferably, homologous sequences of at least 50 bp, preferably more than 100 bp and more preferably more than 200 bp are used. Indeed, shared DNA homologies are located in regions flanking upstream and downstream the site of the break and the DNA sequence to be introduced should be located between the two arms.

"RNA interference" refers to a sequence-specific post transcriptional gene silencing mechanism triggered by dsRNA, during which process the target RNA is degraded. RNA degradation occurs in a sequence-specific manner rather than by a sequence-independent dsRNA response, like PKR response.

The terms "interfering RNA" and "iRNA" refer to double stranded RNAs capable of triggering RNA interference of a gene. The gene thus silenced is defined as the gene targeted by the iRNA. Interfering RNAs include, e.g., siRNAs and shRNAs; an interfering RNA is also an interfering agent as described above.

"iRNA-expressing construct" and "iRNA construct" are generic terms which include small interfering RNAs (siRNAs), shRNAs and other RNA species, and which can be cleaved in vivo to form siRNAs. As mentioned before, it has been shown that the enzyme Dicer cleaves long dsRNAs into short-interfering RNAs (siRNAs) of approximately 21-23 nucleotides. One of the two siRNA strands is then incorporated into an RNA-induced silencing complex (RISC). RISC compares these "guide RNAs" to RNAs in the cell and efficiently cleaves target RNAs containing sequences that are perfectly, or nearly perfectly complementary to the guide RNA. "iRNA construct" also includes nucleic acid preparation designed to achieve an RNA interference effect, such as expression vectors able of giving rise to transcripts which form dsRNAs or hairpin RNA in cells, and or transcripts which can produce siRNAs in vivo.

A "short interfering RNA" or "siRNA" comprises a RNA duplex (double-stranded region) and can further comprises one or two single-stranded overhangs, 3' or 5' overhangs. Each molecule of the duplex can comprise between 17 and 29 nucleotides, including 17, 18, 19, 20, 21, 22, 23, 24, 25, 26, 27, 28, and 29 nucleotides. siRNAs can additionally be chemically modified.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. At least more than 200 distinct miRNAs have been identified in plants and animals. These small regulatory RNAs are believed to serve important biological functions by two predominant modes of action: (1) by repressing the translation of target mRNAs, and (2) through RNA interference, that means cleavage and degradation of mRNAs. In this latter case, miRNAs function analogously to siRNAs. miRNAs are first transcribed as part as a long, largely single-stranded primary transcript (pri-miRNA) [Lee et al., 2002, EMBO J. 21: 4663-4670]. This pri-miRNA transcript is generally and possibly invariably, synthetized by RNA polymerase II and therefore is polyadenylated and may be spliced. It contains an about 80-nucleotides long hairpin structure that encodes the mature about 22-nucleotides miRNA part of one arm of the stem. In animal cells, this primary transcript is cleaved by a nuclear RNaseIII-type enzyme called Drosha (Lee et al, 2003, Nature 425:415-419) to liberate a hairpin mRNA precursor, or pre-miRNA of about-65 nucleotides long. This pre-miRNA is then exported to the cytoplasm by exportin-5 and the GTP-bound form of the Ran cofactor (Yi et al, 2003, Genes and Development 17:3011-3016). Once in the cytoplasm, the pre-miRNA is further processed by Dicer, another RNaseIII enzyme to produce a duplex of about-22 nucleotides base pairs long that is structurally identical to a siRNA duplex (Hutvagner et al, 2001, Science 293:834-838). The binding of protein components of the RISC, or RISC cofactors, to the duplex results in incorporation of the mature, single-stranded miRNA into a RISC or RISC-like protein complex, while the other strand of the duplex is degraded (Bartel et al, 2004, Cell 116: 281-297).

Thus, one can design and express artificial miRNAs based on the features of existing miRNA genes. The miR-30 (microRNA 30) architecture can be used to express miRNAs (or siRNAs) from RNA polymerase II promoter-based expression plasmids (Zeng et al, Methods enzymol. 392:371-380). In some instances the precursor miRNA molecules may include more than one stem-loop structure. The multiple stem-loop structures may be linked to one another through a linker, such as, for example, a nucleic acid linker, a miRNA flanking sequence, other molecules, or some combination thereof.

A "short hairpin RNA (shRNA)" refers to a segment of RNA that is complementary to a portion of a target gene (complementary to one or more transcripts of a target gene), and has a stem-loop (hairpin) structure, and which can be used to silence gene expression.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" is also used herein to refer to stem-loop structures.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

By "DNA target", "DNA target sequence", "target sequence", "target-site", "target", "site", "site of interest", "recognition site", "recognition sequence", "homing recognition site", "homing site", "cleavage site" is intended a 12 to 45 bp double-stranded palindromic, partially palindromic (pseudo-palindromic) or non-palindromic polynucleotide sequence that is recognized and cleaved by a LAGLIDADG homing endonuclease. These terms refer to a distinct DNA location, preferably a genomic location, at which a double stranded break (cleavage) is to be induced by the endonuclease. The DNA target is defined by the 5' to 3' sequence of one strand of the double-stranded polynucleotide, as indicated above for C1221.

By "double-strand break-induced target sequence" is intended a sequence that is recognized by any double strand break creating agent in order to be cleaved.

By "target sequence for double-strand break-induced homologous recombination" is intended a sequence that is recognized by any double strand break creating agent, initiating the homologous recombination process.

As used herein, the term "locus" is the specific physical location of a DNA sequence (e.g. of a gene) on a chromosome. As used in this specification, the term "locus" usually refers to the specific physical location of an endonuclease's target sequence on a chromosome.

As used herein, the term "transgene" refers to a sequence encoding a polypeptide intended to be introduced into a cell, tissue or organism by recombinant technologies. Preferably, the polypeptide encoded by the transgene is either not expressed, or expressed but not biologically active, in the cell, tissue or organism in which the transgene is inserted.

By "mutation" is intended the substitution, the deletion, and/or the addition of one or more nucleotides/amino acids in a nucleic acid/amino acid sequence.

The term "Identity" refers to sequence identity between two nucleic acid molecules or polypeptides. By a polynucleotide having a sequence at least, for example, 95% "identical" to a query sequence of the present invention, it is intended that the sequence of the polynucleotide is identical to the query sequence except that the sequence may include up to five nucleotide alterations per each 100 nucleotides of the query sequence. In other words, to obtain a polynucleotide having a sequence at least 95% identical to a query sequence, up to 5% (5 of 100) of the nucleotides of the sequence may be inserted, deleted, or substituted with another nucleotide. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

The term "gene of interest" or "GOI" refers to any nucleotide sequence encoding a known or putative gene product.

By "delivery vector" or "delivery vectors" is intended any delivery vector which can be used in the present invention to put into cell contact or deliver inside cells or subcellular compartments agents/chemicals and molecules (proteins or nucleic acids) needed in the present invention. It includes, but is not limited to, transducing vectors, liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids. These delivery vectors are molecule carriers.

The terms "vector" or "vectors" refer more particularly to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example.

Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

Delivery vectors and vectors can be associated or combined with any cellular permeabilization techniques such as sonoporation or electroporation or derivatives of these techniques facilitating contact with or entry inside cells of the molecules needed in the present invention.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*.

More preferably the plant is of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata*.

More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans*.

The expression "polynucleotide derivatives" refers to polynucleotide sequences that can be deduced and constructed from the respective sequence or a part of the respective sequence of identified-effector genes according to the present invention. These derivatives can refer to mRNAs, siRNAs, dsRNAs, miRNAs, cDNAs. These derivatives can be used directly or as part of a delivery vector or vector/plasmid/construct, by introducing them into a eukaryotic cell to increase gene targeting efficiency and/or endonuclease-induced homologous recombination.

"Transfection" means "introduction" into a live cell, either in vitro or in vivo, of certain nucleic acid construct, preferably into a desired cellular location of a cell, said nucleic acid construct being functional once in the transfected cell. Such presence of the introduced nucleic acid may be stable or transient. Successful transfection will have an intended effect on the transfected cell, such as silencing or enhancing a gene target, or triggering target physiological event, like enhancing the frequency of HR.

"Modulate" or "modulation" is used to qualify the up- or down-regulation of a pathway like HR in particular conditions or not, compared to a control condition, the level of this modulation being measured by an appropriate method. More broadly, it can refer to the "modulation" of any phenomenon, like the expression level of a gene, a polynucleotide or derivative thereof (DNA, cDNA, plasmids, RNA, mRNA, interfering RNA), polypeptides, etc.

Methods According to the Invention for Identifying Effectors that Modulate Double-Strand Break-Induced Homologous Recombination In a first aspect, the present invention concerns a method for identifying effectors that modulate double-strand break-induced homologous recombination, thereby allowing the increase or decrease of double-strand break-induced homologous recombination in an eukaryotic cells. As elsewhere described, this method allows screening of interfering agents libraries covering an unlimited number of molecules. As a non limiting example, the method of the present invention allows screening for interfering RNAs, which in turn allow identifying the genes which they silence, through their capacities to stimulate or to inhibit double-strand break-induced homologous recombination, based on at least one reporter system.

This first aspect of the method of the invention is based on two successive screening steps.

The first screening step is a highly sensitive high-throughput assay measuring double-strand break-induced homologous recombination based on a compatible reporter gene, for example the luciferase gene. This method allows, in a few runs, to screen several thousands of interfering agents for their capacities to modulate the reparation of a target sequence for double-strand break-induced homologous recombination coupled to said reporter system, compared to negative, neutral or positive interfering agents taken as controls. Said target sequence for double-strand break-induced homologous recombination coupled to said reporter system is inactive due to replacement of one part of said reporter gene. It is easily understandable that the target sequence for double-strand break-induced homologous recombination can be as a non limiting example, any double-strand break-induced homologous recombination site. For this identification step a repair matrix is co-transfected with said interfering agents and a delivery vector containing a double-strand break creating agent, said repair matrix containing the missing part of said reporter gene.

Interfering agents that modulate double-strand break-induced homologous recombination can be divided in candidates that stimulate or inhibit said homologous recombination. Effectors whose interfering agents increase or decrease the expression of reporter gene detected and thus double-strand break-induced homologous recombination can also be classified as effectors stimulating or inhibiting double-strand break-induced homologous recombination.

In the second screening step of this aspect of the invention, a similar system as in the first screening step is used, except for the reporter gene employed. In this second step, the reporter gene is preferably selected to allow a qualitative and/or quantitative measurement of the modulation seen during the first screening step.

The invention therefore relates to a method for identifying effectors that modulate double-strand break-induced homologous recombination in a eukaryotic cell comprising the steps of:
- (a) providing a eukaryotic cell line expressing an inactive reporter gene, wherein the coding sequence of said reporter gene comprises a target sequence for double-strand break-induced homologous recombination;
- (b) providing an interfering agent;
- (c) contacting said eukaryotic cell with:
  - i. an interfering agent;
  - ii. a delivery vector comprising a double-strand break creating agent and a repair matrix, wherein said repair matrix consists of a sequence allowing obtaining a functional copy of the inactive reporter gene upon double-strand break-induced homologous recombination;
- (d) detecting expression of the reporter gene in the cell obtained at the end of step (c);
- (e) repeating steps (c) and (d) at least one time for each interfering agent;
- (f) identifying effectors whose interfering agent increases or decreases the expression of the reporter gene detected at step (d) as compared to a negative control; and
- (g) for the effectors identified at step (f), repeating steps (a), (c), (d) and (f) with a eukaryotic cell line expressing a different inactive reporter gene than the inactive reporter gene previously used;

whereby the effectors identified at the end of step (f) are effectors that modulate double-stranded break-induced homologous recombination in a eukaryotic cell.

In a preferred embodiment, the present invention concerns a method for identifying effector genes that modulates endonuclease-induced homologous recombination, thereby allowing the increase as a non limitative example, of gene targeting efficiency in an eukaryotic cell. As elsewhere described, this method allows screening of an interfering agents library, wherein in a non limitative example, this library is an interfering RNA library covering an unlimited number of genes. The method of the present invention allows screening for interfering RNAs, which in turn allow identifying the genes which they silence, through their capacities to stimulate or to inhibit endonuclease-induced homologous recombination, based on at least one reporter system.

In this preferred embodiment, the method of the invention is based on two successive screening steps.

The first screening step is a highly sensitive high-throughput assay measuring I-SceI induced gene targeting based on a compatible reporter gene, for example the luciferase gene. This method allows, in a few runs, to screen several thousands of interfering RNAs for their capacities to modulate the reparation of an endonuclease-induced gene targeting substrate coupled to said reporter system, compared to negative, neutral or positive interfering RNAs taken as controls. Said endonuclease-induced gene targeting substrate is inactive due to replacement of one part of said reporter gene by an endonuclease-specific site, like I-SceI. It is easily understandable that the endonuclease-specific site can be any endonuclease-specific site. For this identification step a repair matrix is co-transfected with said interfering RNAs and a vector containing an endonuclease expression cassette, said repair matrix containing the missing part of said reporter gene.

Interfering RNAs that modulate endonuclease-induced homologous recombination can be divided in candidates that stimulate or inhibit said endonuclease-induced homologous recombination. Genes from which these interfering RNAs are derived can also be classified as genes stimulating or inhibiting endonuclease-induced homologous recombination. Therefore, genes related to interfering RNAs that stimulate endonuclease-induced homologous recombination can be classified as genes whose products inhibit homologous recombination. Conversely, genes related to interfering RNAs that inhibit endonuclease-induced homologous recombination can be classified as genes whose products are necessary or stimulate homologous recombination.

In the second screening step of this aspect of the invention, a similar system as in the first screening step is used, except for the reporter gene used. In this second step, the reporter gene is preferably selected to allow a qualitative and/or quantitative measurement of the modulation seen during the first screening step.

The invention therefore relates to a method for identifying genes that modulate endonuclease-induced homologous recombination in a eukaryotic cell comprising the steps of:
- (a) providing a eukaryotic cell line expressing an inactive reporter gene, wherein the coding sequence of said reporter gene comprises a target sequence of an endonuclease;
- (b) providing an interfering RNA comprised in an interfering RNA library;
- (c) transiently co-transfecting said eukaryotic cell with:
  - i. an interfering RNA;
  - ii. a delivery vector comprising an endonuclease expression cassette and a repair matrix consisting of a sequence allowing obtaining a functional copy of said inactive reporter gene upon endonuclease-induced homologous recombination in the co-transfected cell;
- (d) detecting the signal emitted by the reporter gene in the co-transfected cell obtained at the end of step (c);
- (e) repeating step (c) and (d) at least one time for each interfering RNA of said interfering RNA library;
- (f) identifying genes whose silencing through RNA interference increases or decreases the signal detected at step (d) as compared to a negative control; and
- (g) optionally, for the genes identified at step (f), providing an interfering RNA capable of silencing said gene, and repeating steps (a), (c), (d) and (f) with a eukaryotic cell line expressing a different inactive reporter gene than the inactive reporter gene previously used;

whereby the genes identified at the end of step (f) and/or (g) are genes that modulate endonuclease-induced homologous recombination in a eukaryotic cell.

The eukaryotic cell line used at step (a) can be constructed by stably transfecting a cell line with a vector (hereafter referred to as the first vector) comprising an inactive reporter gene, i.e. a reporter gene comprising a mutation leading to a loss-of-function of the reporter gene. In other terms, an inactive reporter gene is not capable of emitting any detectable signal upon transfection into a cell. The inactive reporter gene further comprises a target sequence of an endonuclease. For example, this target sequence may be introduced into the reporting gene by replacing part of said reporter gene with said target sequence, thereby inactivating the reporter gene. In addition to the introduction of the target sequence of an endonuclease, part of the reporter gene may also be deleted. On the vector, the inactive reporter gene is paced under the control of expression signals allowing its expression. Thus, upon stable transfection of the cell line with the first vector, the cell line expresses the inactive reporter gene which is integrated in its genome.

This first vector can for example consist of, or be derived from, the pCLS2026 vector of SEQ ID NO: 1, or of the pCLS2809 vector of SEQ ID NO: 8.

The interfering RNA library used in the frame of this method is preferably representative of an entire eukaryotic transcriptome. In addition, it preferably comprises two different interfering RNAs for each gene of the eukaryotic transcriptome. Most preferably, it is comprised of iRNAs capable of targeting human genes, although it may also be comprised of iRNAs capable of targeting genes form common animal models such as mice, rats or monkeys.

At step (c), in addition to being transfected with the iRNA, the eukaryotic cell is transfected with a second vector.

The second vector comprises an endonuclease expression cassette (i.e. an endonuclease under the control of expression signals allowing its expression upon transfection into the cell). The second vector further comprises a repair matrix consisting of a sequence allowing obtaining a functional copy of the reporter gene upon endonuclease-induced homologous recombination. In other terms, this repair matrix comprises a first and a second portion which are homologous to regions 5' and 3' to the target sequence of an endonuclease on the first vector, as well as the missing part of the reporter gene (i.e. the part of the reporter gene allowing restoring its function). In order to avoid obtaining false positive, the second vector should not comprise a complete copy of the reporter gene, i.e., it should also comprise an inactive reporter gene. Therefore, a functional copy of the reporter gene (and thus a detectable signal) can only be obtained upon endonuclease-induced homologous recombination in the transfected eukaryotic cell.

The second vector can for example consist of, or be derived from, the pCLS2067 vector of SEQ ID NO: 2 or of the pCLS3496 vector of SEQ ID NO: 10.

The endonuclease present in the second vector can for example correspond to a homing endonuclease such as I-SceI, I-CreI, I-CeuI, I-MsoI, and I-DmoI. It may be a wild-type or a variant endocuclease. In a preferred embodiment, the endonuclease is a wild-type I-SceI endonuclease.

The first and second vectors may further comprise selection markers such as genes conferring resistance to an antibiotic in order to select cells co-transfected with both vectors.

In a preferred embodiment, the reporter gene used at step (c) is a high throughput screening-compatible reporter gene such as e.g. the gene encoding luciferase (including variants of this gene such as firefly or renilla luciferase genes) or other reporter genes that allow measuring a defined parameter in a large number of samples (relying on the use of multiwell plates, typically with 96, 384 or 1536 wells) as quickly as possible. Other reporter genes include in a non limitative way, the beta-galactosidase and the phosphatase alkaline genes, which are well-known in the art.

In step (d), the signal emitted by the reporter gene in the co-transfected cell is detected using assays well-known in the art.

Step (e) comprises repeating steps (c) and (d) at least one time for each interfering RNA of the interfering RNA library. For example, if the iRNA library comprises two different interfering RNAs for each gene of the eukaryotic transcriptome, each gene of the transcriptome will be tested twice.

At step (f), genes whose silencing through RNA interference increases or decreases, preferably significantly increases or decreases, the signal detected at step (d) as compared to a negative control are identified. In particular, the signal detected at step (d) is compared with the signal detected in the same conditions with at least one interfering RNA taken as a negative control. The interfering RNA taken as a negative control corresponds to a iRNA known not to hybridize and thus not to be involved in endonuclease-induced homologous recombination such as e.g. the "All Star" (AS) iRNA (Qiagen #1027280). For example, if a two-fold increase of the signal detected upon transfection with an iRNA targeting a given gene, compared to the signal detected with a negative control, said given gene is identified as a gene that modulates endonuclease-induced homologous recombination in a eukaryotic cell.

In a preferred embodiment, the method of the present invention further comprises supplementary steps of selection. In other terms, the interfering RNAs identified at step (f) are further selected through another succession of steps (a), (c), (d) and (f), wherein inactive reporter gene is different from the one previously used.

In a most preferred embodiment, steps (a) to (f) the above method are first carried out using a eukaryotic cell line expressing an inactive luciferase reporter gene. This cell line can for example correspond to a cell line obtained through stable transfection of a cell line with the pCLS2026 vector of SEQ ID NO: 1. This cell line is then co-transfected with iRNAs and the pCLS2067 vector of SEQ ID NO: 2, which carries a repair matrix for the luciferase reporter gene. Once genes whose silencing through RNA interference increases or decreases the signal detected at step (d) as compared to a negative control are identified, steps (a), (c), (d) and (f) may then be repeated with iRNAs silencing these genes. The cell line used at the second selection round may for example express an inactive GFP reporter gene, and may e.g. be obtained through stable transfection of a cell line with the pCLS2809 vector of SEQ ID NO: 8. The pCLS3496 vector of SEQ ID NO: 10, which carries a repair matrix for the GFP reporter gene, can then be used for co-transfection with iRNAs.

This second screening allows confirming that the genes identified at step (f) are genes that modulate endonuclease-induced homologous recombination in a eukaryotic cell.

In the second screening, the reporter gene is preferably a gene allowing an accurate detection of the signal and a precise qualitative and/or quantitative measurement of the HR modulation, such as e.g. the genes encoding the Green Fluorescent Protein (GFP), the Red Fluorescent Protein (RFP), the Yellow Fluorescent Protein (YFP) and the Cyano Fluorescent Protein (CFP), respectively. The reporter gene of the second screening can also be any protein antigen that can be detected using a specific antibody conjugated to a fluorescence-emitting probe or tagged by such a fluorescent probe usable in Fluorescent Activated Cell Sorting (FACS). For example cell surface expressing molecule like CD4 can be used as an expression reporter molecule detectable with a specific anti-CD4 antibody conjugated to a fluorescent protein. FACS technology and derived applications to measure expression of reporter genes are well known in the art.

As shown in Examples 1 to 3, the above method according to the invention was successfully applied to identify several hundred of genes that modulate endonuclease-induced homologous recombination in a eukaryotic cell.

Methods According to the Invention for Modulating Double-Strand Break-Induced Homologous Recombination in a Eukaryotic Cell The information obtained when carrying out the above method for identifying effectors that modulate double-strand break-induced homologous recombination in a eukaryotic cell can be used to increase or decrease double-strand break-induced homologous recombination in eukaryotic cells. Depending on the envisioned application, interfering agents that increase or interfering agents that decrease double-strand break-induced homologous recombination in a eukaryotic cell can be used.

Indeed, interfering agents that modulate double-strand break-induced homologous recombination through their respective effectors can be used directly. For a given interfering agent, it is easily understood that derivatives from said genes can be synthetized and used with the same objectives and results (equivalent interfering RNAs for example, intra or interspecies for example).

Interfering agents or derivatives can be used to modulate double-strand break-induced homologous recombination in a eukaryotic cell by introducing them with at least one delivery vector containing at least one double-strand break creating agent expression. It is easily understood that these interfering agents or derivatives can be introduced by all methods known in the art, as part or not of a vector, unique or not, under the control of an inducible promoter or not. Therefore, the effects of these interfering agents or derivatives in the cell can be permanent or transitory.

Therefore, another aspect of the invention pertains to a method for modulating double-strand break-induced homologous recombination in a eukaryotic cell, comprising the steps of:
(a) identifying an effector that is capable of modulating homologous recombination in a eukaryotic cell by the method according to claim 1 or 2; and
(b) introducing into a eukaryotic cell:
  i. at least one interfering agent capable of modulating said effector;
  ii. at least one delivery vector comprising at least one double-strand break creating agent; thereby obtaining a eukaryotic cell in which double-strand break-induced homologous recombination is modulated.

In a preferred embodiment, the information obtained when carrying out the above method can be used for identifying effector genes that modulate double-strand break-induced homologous recombination in a eukaryotic cell.

Therefore, another aspect of the invention pertains to a method for increasing double-strand break-induced homologous recombination in a eukaryotic cell, comprising the steps of:
(a) identifying a gene that is capable of modulating double-strand break-induced homologous recombination in a eukaryotic cell by the method according to claim 1 or 2 or providing a gene selected from the group of genes listed in table I or II; and
(b) introducing into a eukaryotic cell:
  i. at least one interfering agent, wherein said interfering agent is a polynucleotide silencing or encoding said gene, wherein said polynucleotide is an interfering RNA capable of silencing said gene if the signal detected at step (d) of the method according to claim 1 is increased as compared to the negative control, and is a cDNA transcribed from said gene if the signal detected at step (d) of the method according to claim 1 is decreased as compared to the negative control;
  ii. at least one delivery vector comprising at least one double-strand break creating agent;
thereby obtaining a eukaryotic cell in which double-strand break-induced homologous recombination is increased.

In a more preferred embodiment, the information obtained when carrying out the above method for identifying genes that modulate double-strand break-induced homologous recombination in a eukaryotic cell can be used to increase gene targeting efficiency in eukaryotic cells. Therefore, another aspect of the invention pertains to a method for increasing gene targeting in a eukaryotic cell, comprising the steps of:
(a) identifying a gene that is capable of modulating double-strand break-induced homologous recombination in a eukaryotic cell by the method according to claim 1 or 2 or providing a gene selected from the group of genes listed in table I or II; and
(b) introducing into a eukaryotic cell:
  i. at least one interfering agent, wherein said interfering agent is a polynucleotide silencing or encoding said gene, wherein said polynucleotide is an interfering RNA capable of silencing said gene if the signal detected at step (d) of the method according to claim 1 is increased as compared to the negative control, and is a cDNA transcribed from said gene if the signal detected at step (d) of the method according to claim 1 is decreased as compared to the negative control;
  ii. at least one delivery vector comprising at least one double-strand break creating agent;
  iii. at least a delivery vector comprising at least one donor sequence, wherein said donor sequence comprises the sequence to be introduced into the locus of interest, flanked by sequences homologous to sequences of the locus of interest.
thereby obtaining a eukaryotic cell in which gene targeting efficiency is increased.

Indeed, interfering RNAs targeting a specific gene that stimulate endonuclease-induced homologous recombination can be used directly to increase gene targeting efficiency and/or endonuclease-induced homologous recombination in eukaryotic cells through a down-regulation of said gene product. For a given interfering RNA, it is easily understood that other interfering RNAs derived from another part of the related gene (equivalent interfering RNAs) can be synthetized and used with the same objectives and results.

In case of genes whose products stimulate homologous recombination, cDNAs derived from these genes can be used to increase gene targeting efficiency and/or endonuclease-induced homologous recombination in eukaryotic cells through overexpression of said gene product.

In both cases, derivatives of these identified genes (interfering RNAs or cDNAs) can be used to increase gene targeting efficiency and/or endonuclease-induced homologous recombination in eukaryotic cells by introducing them with at least one vector containing at least an endonuclease expression cassette wherein said endonuclease is able to cleave a DNA target sequence in a locus of interest of genome of said eukaryotic cells at a position where the recombination event is desired. It is easily understood that derivatives of these identified genes can be introduced by all methods known in the art, as part or not of a vector, unique or not, under the control of an inducible promoter or not. Therefore, the effects of these derivatives in the cell can be permanent or transitory.

Therefore, another aspect of the invention pertains to a method for increasing gene targeting efficiency and/or endonuclease-induced homologous recombination in a eukaryotic cell, comprising the steps of:
(a) identifying a gene that is capable of modulating homologous recombination in a eukaryotic cell by the method according to the invention for identifying genes that modulate endonuclease-induced homologous recombination (described in the above paragraph), and/or or providing a gene selected from the group of genes listed in Table I or II herebelow; and (b) introducing into a eukaryotic cell:
  i. at least one polynucleotide silencing or encoding said gene, wherein said polynucleotide is:
    an interfering RNA capable of silencing said gene if the signal detected at step (d) of the method for identifying genes that modulate endonuclease-induced homologous recombination is increased as compared to the negative control; and
    a cDNA transcribed from said gene if the signal detected at step (d) of the method for identifying genes that modulate endonuclease-induced homologous recombination is decreased as compared to the negative control;
  ii. at least one vector comprising at least one endonuclease expression cassette, wherein said endonuclease is capable of cleaving a target sequence located in a locus of interest of the genome of said eukaryotic cell.
thereby obtaining a eukaryotic cell in which gene targeting efficiency and/or endonuclease-induced homologous recombination is increased.

In the above methods, the endonuclease present on the vector comprising at least one endonuclease expression cassette may either be the same endonuclease as the one used in the method for identifying genes that modulate endonuclease-induced homologous recombination, or a different endonuclease. This endonuclease can correspond to any of the endonucleases described in the above paragraph entitled "Definitions". It may for example be a homing endonuclease such as I-ScreI, I-CreI, I-CeuI, I-MsoI, and I-DmoI. It may be a wild-type or a variant endocuclease. In a preferred embodiment, the endonuclease is a wild-type or variant I-CreI endonuclease.

By increase in gene targeting efficiency is understood any statistically significant increase in a cell when compared to an appropriate control. Such increases can include, for example, at least 5%, 10%, 20%, 30%, 40%, 50%, 60%, 70%, 80%, 90%, 100%, 200%, 300%, 500% or greater increase in the efficiency of a gene targeting event for a polynucleotide of interest (i.e. a transgene).

In a preferred embodiment, this method further comprises the step of introducing into said eukaryotic cell a vector comprising at least one donor sequence, wherein said donor sequence comprises or consists of the sequence to be introduced into the locus of interest (i.e. a transgene), flanked by sequences homologous to sequences of the locus of interest.

As used herein, the locus of interest refers to any locus where the recombination event is desired.

In a specific embodiment, the genes that are described in WO2007/013979, in WO2008/113847 and/or in Slabicki et al. may be excluded from the scope of the present invention. In particular, the G22P1 (Ku70 or hdfA), XRCC5 (Ku80), RAD50, MRE11, XRS2, LIFL, NEIL, SIR4, Ku86, PRKDC, LIG4 (DNA ligase IV), XRCC4, RecA, Rad54, Rad51, BRCA1, SHFM1, DSBR1 and/or DCLRE1C (Artemis) gene, or a mammalian (in particular human) equivalent thereof, may be excluded from the scope of the present invention.

In a preferred embodiment according to the invention, the gene that modulates endonuclease-induced homologous recombination is a gene that decreases endonuclease-induced homologous recombination (i.e. the presence of which decreases gene targeting efficiency in a eukaryotic cell). In such a case, an interfering RNA capable of silencing said gene, introduced into the eukaryotic cell, is able to increase endonuclease-induced homologous recombination. The interfering RNA may for example be a siRNA, a miRNA or a shRNA.

The inventors have found that the genes listed in table I herebelow are capable of decreasing homologous recombination in a eukaryotic cell (see Example 2). Therefore, the gene that is capable of modulating homologous recombination in a eukaryotic cell preferably is a gene selected from the group of genes listed in Table I below.

TABLE I

List of genes decreasing gene targeting

| Gene Name | GENE ID | Target Sequence | SEQ ID |
|---|---|---|---|
| ABCB5 | 340273 | TACGTACTATAGTGTCATTAA | 13 |
| ACN9 | 57001 | CTGGGCGACCAGTACGTGAAA | 14 |
| ADAM5P | 255926 | CAAGGAGCATTTGGAAGTATT | 15 |
| ADH1A | 124 | CAGGTTCACCTGCAGGAGGAA | 16 |
| ADO | 84890 | CTGAAGCGCTTCCATCCTAAA | 17 |
| ADPRHL2 | 54936 | AGCGAGCACTTTCTCAAGCAA | 18 |
| AGA | 175 | AAGCAGGATATTCCTATCCAT | 19 |
| AGXT2 | 64902 | ATGGAGTTGTCCAGTACCCAA | 20 |
| AHSA1 | 10598 | CAGGGCATGATCTTACCTACA | 21 |
| AKAP13 | 11214 | GAGTCGGATAATAGACAGCAA | 22 |
| AKAP8 | 10270 | GAGGCCGGTAGTGATCCTCAA | 23 |
| AKR7A2 | 8574 | TGAGCGCTTCCTGTTGAATAA | 24 |
| ALAD | 210 | AAGGGTGAGCCATCAAGCTAA | 25 |
| ALDH3B1 | 221 | TTAGACTATATCAACCTACAA | 26 |
| ALG10B | 144245 | ATCAGTAACCTTCAACGAATA | 27 |
| ALS2CR8 | 79800 | CAGCAACGCTTCAATGGACTA | 28 |
| AMN1 | 196394 | TAGGTATTTGTTTCACCGAAA | 29 |
| AMN1 | 196394 | AACCGAGTTTCTGTAACTTCA | 30 |
| ANK1 | 286 | TAGTCCGTGTTCAAAGTGTAA | 31 |
| ANKRD13A | 88455 | CTCGAGTCTTACTCCGACATA | 32 |
| ANKRD17 | 26057 | CACCTCGATGTGGTTCAGTTA | 33 |
| ANKRD49 | 54851 | CTGATGAACCGTTACGTCAAA | 34 |
| ARF3 | 377 | CAGGGCTGACTGGGTATTCTA | 35 |
| ARHGAP1 | 392 | CAGATAGGTGGGTTCTAGCAA | 36 |
| ARHGAP26 | 23092 | AGGGAGTATACTAGTAGGTTA | 37 |
| ARID1B | 57492 | CAGGCCCACAGCGGTATCCAA | 38 |
| ARL14 | 80117 | ATGGGTTCGCTGGGTTCTAAA | 39 |
| ARRB2 | 409 | CTCGAACAAGATGACCAGGTA | 40 |
| ARSB | 411 | CCGCCGAGGATTTGATACCTA | 41 |
| ATF7IP | 55729 | CAGATCTTGTAGAAACGATTA | 42 |
| ATF7IP | 55729 | CCAGCAGAAGTAGAAAGTAATGAAA | 986 |
| ATP10A | 57194 | CACGAACGTTCTGGTTTAACA | 43 |
| ATP5A1 | 498 | CCCGGTATCATTCCTCGAATT | 44 |

TABLE I-continued

List of genes decreasing gene targeting

| Gene Name | GENE ID | Target Sequence | SEQ ID |
|---|---|---|---|
| ATR | 545 | CAGGCACTAATTGTTCTTCAA | 45 |
| ATR | 545 | GACCGGATACTTACAGATGTA | 46 |
| ATR | 545 | CAGCTCGTCTCTAAACCCTTCTAAA | 973 |
| ATR | 545 | AAGGACATGTGCATTACCTTA | 994 |
| ATXN8OS | 6315 | CCCTGGGTCCTTCATGTTAGA | 47 |
| AVPR2 | 554 | CTGTCTGACCATCCCTCTCAA | 48 |
| B4GALT2 | 8704 | CTACGCGTCTATGTCATCAA | 49 |
| BASP1 | 10409 | TGGGAGAATCCAAATAGTATT | 50 |
| BBC3 | 27113 | CAGCCTGTAAGATACTGTATA | 51 |
| BC37295_3 | 90485 | AACGCGATGAATTCAGCCGAA | 52 |
| BCL7C | 9274 | AAGTTGGGCGGTGTAGACCAA | 53 |
| BCR | 613 | ACGGCAGTCCATGACGGTGAA | 54 |
| BIRC6 | 57448 | TAGCGTGCGATTCAATCCAAA | 55 |
| BLOC1S3 | 388552 | CCCGCGCGCTCGCTCCTGCAA | 56 |
| BMP5 | 653 | AAGAGTCGGAGTACTCAGTAA | 57 |
| BNIP2 | 663 | CACACCGTCAGAGAATAGTAA | 58 |
| BRE | 9577 | CCGCCTCATGTTTGAATACCA | 59 |
| BTAF1 | 9044 | CCGCGTTTACTTGATATCCTT | 60 |
| BYSL | 705 | CCCGTTTGGCTGAGCACTCTA | 61 |
| C10orf13 | 2401647 | CACCTCGAGGCCTCCTACTTA | 62 |
| C10orf55 | 414236 | CTGTTCGTATCTAGTTCTCAA | 63 |
| C11orf56 | 84067 | TCCGAGGGCATGGCAGGACTA | 64 |
| C13orf31 | 144811 | CCCTGTATCGACATCCGTAAA | 65 |
| C14orf109 | 26175 | TACAACTGATTGACACGTAAA | 66 |
| C14orf28 | 122525 | AGCAGCGCACAATTAATATAA | 67 |
| C14orf45 | 80127 | CAAATCCGTGTCATATCCTAA | 68 |
| C15orf38 | 348110 | TCGCCGTAAATTCGACGCCAA | 69 |
| C15orf40 | 123207 | TCGCGCCGAGATGCCTAAGAA | 70 |
| C15orf48 | 84419 | AAGCTTATAACAATCAACCAA | 71 |
| C15orf48 | 84419 | ACCGATGTGATCCTTGATCGA | 72 |
| C15orf53 | 400359 | TCCCGTTCACAGATCCTGTAA | 73 |
| C16orf84 | 348180 | CACACCAGCCGTCGACACCAA | 74 |
| C17orf71 | 55181 | CAGGCCTACTACAGTCAGGAA | 75 |
| C19orf26 | 255057 | CAGGGTCAATGCAAGACGCAT | 76 |
| C19orf45 | 374877 | AAGATGGGACTTCCTACCAAA | 77 |
| C1orf125 | 126859 | TTGGGATATTTAATCGGCATA | 78 |
| C1orf149 | 64769 | CAACATGGCGATGCACAACAA | 79 |
| C1orf161 | 126868 | GGCAGCGGAAATTACATCAAA | 80 |
| C1QL2 | 165257 | CCCGGGTGCAAAGGCGCACAA | 81 |
| C1R | 715 | TCGGGAGAGCCCAGGATTCAA | 82 |
| C20orf151 | 140893 | CCCGCCAAGCTCCAAGCACAA | 83 |
| C20orf43 | 51507 | AAGGTTGAGAAGGTCGACAAA | 84 |
| C20orf43 | 51507 | ATCCTTGTTGGTCTAGCTAAA | 85 |
| C21orf119 | 84996 | TTCGATACTTTGCCAATTCAA | 86 |
| C21orf62 | 56245 | CAACCTGATGTGCAACTGTAA | 87 |
| C21orf66 | 94104 | CCCGTTACTATTGATTTGGTA | 88 |
| C21orf66 | 94104 | ACCCGCAGAAGTGAATATGTA | 89 |
| C21orf88 | 114041 | CCGCGGGAAGTCCCTCTTGCA | 90 |
| C22orf28 | 51493 | CTGGAATTGTTCATCGATCTA | 91 |
| C22orf39 | 128977 | CAGGTGGGTCATAATGAGGTA | 92 |
| C2orf58 | 285154 | TTCAAGCGACTAACTAGGAAA | 93 |
| C2orf63 | 130162 | AAACGGCGAGATGTAGCTGAA | 94 |
| C6orf58 | 352999 | CTGCGGTTGATTCTGGTGTAA | 95 |
| C6orf91 | 345930 | AAGCAACGTCAAGAATTCTTA | 96 |
| C9orf126 | 286205 | CAGGTTAAGTTCAGTGAACTA | 97 |
| C9orf23 | 138716 | AGCGTTGTGACTGCTCAACAT | 98 |
| C9orf72 | 203228 | CAGGGTCAGAGTATTATTCCA | 99 |
| C9orf85 | 138241 | AAGTTCTTGAGTGGCGTGTAA | 100 |
| CAND1 | 55832 | CTCATCGAATTTGAAGATCGA | 101 |
| CARTPT | 9607 | CACGAGAAGGAGCTGATCGAA | 102 |
| CASQ1 | 844 | CCCACAAATAGGAGTCGTCAA | 103 |
| CATSPER1 | 117144 | CCGGATCCTCAAGGTCTTCAA | 104 |
| CBLB | 868 | TCCGGTTAAGTTGCACTCGAT | 105 |
| CBLB | 868 | TCGGTTGGCAAACGTCCGAAA | 106 |
| CCDC147 | 159686 | CACGTTGATATTAACAGATCA | 107 |
| CCDC46 | 201134 | CACGTTTGTAGTATCATATCA | 108 |
| CCDC86 | 79080 | TCGAGTCGAACCCAGAAGAAA | 109 |
| CCDC89 | 220388 | ATGCTTCGCTCCCGCATTGAA | 110 |
| CCHCR1 | 54535 | AACGGGATGTTTCCAGTGACA | 111 |
| CCL1 | 6346 | GCCGGAAGATGTGGACAGCAA | 112 |
| CCL1 | 6346 | ACAGCAAGAGCATGCAGGTACCCTT | 989 |
| CCL19 | 6363 | CCGCCTGGTGTTTACAACTAA | 113 |
| CCL19 | 6363 | CAGATTGCAATGCTACCAATA | 114 |
| CCL19 | 6363 | GGAACTTCCACTACCTTCTCATCAA | 971 |
| CCL19 | 6363 | CCTGCTGTAGTGTTCACCACACTGA | 972 |

TABLE I-continued

List of genes decreasing gene targeting

| Gene Name | GENE ID | Target Sequence | SEQ ID |
|---|---|---|---|
| CCL25 | 6370 | CTCCCTCCTGATATCAGCTAA | 115 |
| CCL7 | 6354 | TTGGATGTATATGTCATCTCA | 116 |
| CCNL2 | 81669 | CGGAGCGTTATGGACGTGGTA | 117 |
| CD46 | 4179 | CACGATTTATTGTGGTGACAA | 118 |
| CDV3 | 55573 | AACCAATATGCTGTGCTTGAA | 119 |
| CEBPB | 1051 | CGGGCCCTGAGTAATCGCTTA | 120 |
| CENPJ | 55835 | AACGTGCGTCTCCTAATTTAT | 121 |
| CENPQ | 55166 | CTGGGAATATTCAGAGCCTAA | 122 |
| CEP68 | 23177 | CACCCTCAAATCACCTACTAA | 123 |
| CEPT1 | 10390 | TTCGGGCATATGAGTACTACA | 124 |
| CFD | 1675 | CAGGGTCACCCAAGCAACAAA | 125 |
| CFHR2 | 3080 | AATCTGGATATCATCCAACAA | 126 |
| CFI | 3426 | CCCGACCTTAAACGTATAGTA | 127 |
| CHGB | 1114 | AAAGCAGGCTTCAGCTATAAA | 128 |
| CHMP7 | 91782 | CTCGACCTTGGTAAACGGAAA | 129 |
| CHST10 | 9486 | AAGTTTGTCCTGGACCGAATA | 130 |
| CINP | 51550 | GCGGCTGATTGGCACAATTTA | 131 |
| CKB | 1152 | GCGGGCAGGTGTGCATATCAA | 132 |
| CKS1B | 1163 | AACATCTTTCTGATAACATTA | 133 |
| CLC | 1178 | CTGGTTCTACTGTGACAATCA | 134 |
| CLDN3 | 1365 | CACGGCCACCAAGGTCGTCTA | 135 |
| CLDN5 | 7122 | CACCGGCGACTACGACAAGAA | 136 |
| CLU | 1191 | ACAGACCTGCATGAAGTTCTA | 137 |
| CMPK1 | 51727 | CGCGTATATATCCCTCTAGTA | 138 |
| CNGA4 | 1262 | AAGATTGCTTACCGCATTGAA | 139 |
| CNGA4 | 1262 | TAGCATGAGCTCTGTCATCTA | 140 |
| CNNM1 | 26507 | CTGGGTTATCTGCATCTCAAA | 141 |
| CNNM1 | 26507 | CACGCTGGAGGATATCATAGA | 142 |
| COCH | 1690 | AACATTCGTTCTCTAACCATT | 143 |
| COCH | 1690 | CACCAACAGGTAAACGACTAA | 144 |
| COIL | 8161 | CCGAGTCGTCACAGATCTCAT | 145 |
| COL14A1 | 7373 | ATGGTTCATGGAGTATTGGAA | 146 |
| COL24A1 | 255631 | AACACTCTACTTGAACCTAAA | 147 |
| COL24A1 | 255631 | CAGCACGAATCTGCAAAGATT | 148 |
| COMMD4 | 54939 | CGCTGTTATGAGGAGAAGCAA | 149 |
| CORO2B | 10391 | TTCATTAGCTAGGATCTACTA | 150 |
| COX5A | 9377 | CTGGGTAACATACTTCAACAA | 151 |
| CPEB4 | 80315 | AAGGTCGTCTAAACTATTCAT | 152 |
| CPOX | 1371 | GAGGACGGTATGTAGAATTTA | 153 |
| CPSF6 | 11052 | ACCGTATTGATTCATGCTATA | 154 |
| CRK | 1398 | CAGCAGCTAACTAGAGTCCTA | 155 |
| CRKRS | 51755 | ATCGGGATATTAAGTGTTCTA | 156 |
| CSNK1G1 | 53944 | TTGGACCATGTGGGAAATATA | 157 |
| CSNK2A1 | 1457 | TCCATTGAAGCTGAAATGGTA | 158 |
| CTF8 | 54921 | AAGGGTAGTTGTGGAGCTACA | 159 |
| CTSZ | 1522 | TCGGATCAACATCAAGAGGAA | 160 |
| CTTNBP2NL | 55917 | CCGGTACTCACTAAGCGTTTA | 161 |
| CUL2 | 8453 | CGGCACAATGCCCTTATTCAA | 162 |
| CUL7 | 9820 | CACGCTACTGTGAGCACTTTA | 163 |
| CYB561D2 | 11068 | CAGGTGAGCAATGCCTACCTA | 164 |
| CYP2C8 | 1558 | ATGCCTTACACTGATGCTGTA | 165 |
| CYP4F3 | 4051 | ACGCTTGTGCGTGAATGTTCA | 166 |
| DACT2 | 168002 | CGGCAGGGAGGTGTACCCGTA | 167 |
| DARS | 1615 | TTGGATTGGAACGAGTTACTA | 168 |
| DCDC2 | 51473 | CAGGTTGAGGTTCCAGTCGAT | 169 |
| DCDC2 | 51473 | CCAGAAAGTCTAAAGGGAGTGGAAA | 987 |
| DCTN4 | 51164 | CCCAACGTCAATCAAATTCAA | 170 |
| DDEF1 | 50807 | CCCGCCCGAAATCTTTCAGAA | 171 |
| DEFB121 | 245934 | ATCCCAAGTATGTACCTGTAA | 172 |
| DEFB124 | 245937 | CTGTCTCTCCTATGCATTGAA | 173 |
| DEPDC7 | 91614 | AACGTGACTATTCCAACAATA | 174 |
| DFNB59 | 494513 | ATGGATGTCATTTCTCGTTCA | 175 |
| DIAPH3 | 81624 | CTCCGGCACAATTCAGTTCAA | 176 |
| DMN | 23336 | AAGGCGATTCCATGACAGAAA | 177 |
| DNAJA4 | 55466 | TACAGTTTGTATGGACTACTA | 178 |
| DNAJB13 | 374407 | CTCGGGATCACTCGCAATTCA | 179 |
| DNAJB7 | 150353 | CTGCGGACAATTAGTATTCAA | 180 |
| DNAJB7 | 150353 | AAGCTTATCATAAAGTGGCACTTAA | 975 |
| DNAJB7 | 150353 | CAAATGATGAGAAACGGGACATTTA | 976 |
| DNMT1 | 1786 | CCCAATGAGACTGACATCAAA | 181 |
| DNMT3B | 1789 | AAGGACTACTTTGCATGTGAA | 182 |
| DNPEP | 23549 | ATCCGAGAGGTGGCCAACAAA | 183 |
| DSE | 29940 | AAACCGTTATAGACCCAATAA | 184 |
| DSG3 | 1830 | AACCGAGATTCTACTTTCATA | 185 |
| DTL | 51514 | CCGAGTCTACTGGGTATAACA | 186 |

TABLE I-continued
List of genes decreasing gene targeting

| Gene Name | GENE ID | Target Sequence | SEQ ID |
|---|---|---|---|
| DTWD1 | 56986 | CACCTATATTTCTCAAACGAA | 187 |
| DUS2L | 54920 | AG CGGACATTGTTTACTGTGA | 188 |
| DUSP13 | 51207 | TCAGTCCATCTCTATAATAAA | 189 |
| E2F7 | 144455 | CAGAACGGTCTGAATGGACAA | 190 |
| EBI3 | 10148 | CCCAGAGATCTTCTCACTGAA | 191 |
| ECM1 | 1893 | AACCGCCTAGAGTGTGCCAAA | 192 |
| EFEMP2 | 30008 | CACGGAATGCACAGATGGCTA | 193 |
| EFEMP2 | 30008 | CCGCTCCGCTGCCGTCATCAA | 194 |
| EIF4E3 | 317649 | CTGAGTGCGCATCAAATCTGA | 195 |
| ENTPD3 | 956 | CCACTTGTTTGTGAACGGTTA | 196 |
| EP300 | 2033 | CACCGATAACTCAGACTTGAA | 197 |
| EP300 | 2033 | TTGGACTACCCTATCAAGTAA | 198 |
| EP300 | 2033 | CAGGTATGATGAACAGTCCAGTAAA | 985 |
| EPHA10 | 284656 | CTGGAGGGCGTTGTTACCCGA | 199 |
| EPS8L1 | 54869 | CAGCAGTGAGCTGTCGGTCAA | 200 |
| ERGIC3 | 51614 | AACCTGTTCAAGCAACGACTA | 201 |
| ETV6 | 2120 | CAGGTCACCTATCACGACAAA | 202 |
| FAM123C | 205147 | TCCCAAGTGTTGAGAATCCAA | 203 |
| FAM19A1 | 407738 | CACACCGATGTTGTAACAAGA | 204 |
| FAM46A | 55603 | CTGGCACCTATTCATATAGAA | 205 |
| FAM62A | 23344 | ACGCCCGACCCTAGACATCAA | 206 |
| FAM71A | 149647 | TGCCGTTGTGCTGAAAGACAA | 207 |
| FAM71C | 196472 | AAGGCGAGTATACTATATTCA | 208 |
| FAM84A | 151354 | AAGGGCGCTTATTGTTCTGAA | 209 |
| FAM90A1 | 55138 | CACGGTGGTTTCCAAGCGCAT | 210 |
| FAM98B | 283742 | CTCGTGAAGATCTATCCAAGA | 211 |
| FANCF | 2188 | AACCAGCATTAGAGCTTTATA | 212 |
| FARP2 | 9855 | CACAAGTGTGGAAGCGTTTAA | 213 |
| FATE1 | 89885 | CAGCCAAACGAGTTTGGAATA | 214 |
| FBXO34 | 55030 | TCGGTAAAGCATCATCTCGAA | 215 |
| FBXO34 | 55030 | CACCAAGAGTTTAGTGGCCCTTAAA | 974 |
| FBXO41 | 150726 | CTGGAGCTTGACCACGTGTCA | 216 |
| FBXO7 | 25793 | CAGGATGAACAACCAAGTGAT | 217 |
| FBXW10 | 10517 | CAGGATCAATGACATATCACA | 218 |
| FGF2 | 2247 | AACAATATTAGTCGTATCCAA | 219 |
| FHL2 | 2274 | CTCCCGTTGCGTCAAGTCTAA | 220 |
| FKBP6 | 8468 | CTCGGGATACCTGGAACACAT | 221 |
| FKSG30 | 440915 | CCGAGCGTGGCTATAGGTTCA | 222 |
| FLJ42953 | 400892 | GAGGCATGGAGGAGATAACAA | 223 |
| FLJ43987 | 388960 | CTGCTCGACCTGATTCTACTA | 224 |
| FLJ45537 | 401535 | AACCGGAACAAGCATTCTGAA | 225 |
| FMN2 | 56776 | CACGGGAGCCGCCGCGCATTA | 226 |
| FNDC3B | 64778 | CAGAGTATTACCACACAGCAA | 227 |
| FTH1 | 2495 | AAGCAGGTGAAAGCCATCAAA | 228 |
| FTHL2 | 2497 | CTCGGCGAATACCTCTTAGA | 229 |
| FXYD2 | 486 | CCCGTTCTACTATGACTATGA | 230 |
| GALNT7 | 51809 | CTCGGTAACTTTGAACCCAAA | 231 |
| GARNL3 | 84253 | CAGGCGGAGTTTGTTAGAATA | 232 |
| GARNL3 | 84253 | TGGCGTCTTGCTAGTGGATGA | 233 |
| GAS2 | 2620 | GACGAGTAAATTGTACAGTCA | 234 |
| GAS6 | 2621 | CAGCAGCGGCCCGGTCATCAA | 235 |
| GCM2 | 9247 | CAGCCTTGTGGAAAGGACTAA | 236 |
| GFPT2 | 9945 | ATCGATGGGAATAATCACGAA | 237 |
| GGN | 199720 | TACGCCGAGGTCCTGAAGCAA | 238 |
| GGT1 | 2678 | GAGCAGCAGAGCAGCACAATA | 239 |
| GJB1 | 2705 | CTGCACAGACATGAGACCATA | 240 |
| GJB1 | 2705 | TGGCATCTGCATCATCCTCAA | 992 |
| GJC2 | 57165 | CGCGGAGGAGGCGTGCACTAA | 241 |
| GJD2 | 57369 | AGCGAGAACGCCGCTACTCTA | 242 |
| GLT25D1 | 79709 | AGCGATTGATTCAGTCATCAA | 243 |
| GOLGA2 | 2801 | ATGGAGTCGGTTAGACAACTA | 244 |
| GPD1L | 23171 | AACCAGCATTAACATGGTAGA | 245 |
| GPM6B | 2824 | GCCCGTGTTTATGTTCTACAA | 246 |
| GPSM1 | 26086 | CTCCGAGTTCTACGAGAGGAA | 247 |
| GRID1 | 2894 | CAGCGCCATCTGGATTGTCTA | 248 |
| GRIK1 | 2897 | TTGGTTCTCCTTACCGGGATA | 249 |
| GRINA | 2907 | CCGACAGGCCTTCATCCGCAA | 250 |
| GUCY1B2 | 2974 | CAGTGTGCACGCAGTCTATAA | 251 |
| HCG3 | 414061 | CGCGATATCTATGACCGCTAT | 252 |
| HCP5 | 10866 | TAGGAGGGAGTCAGTACTGTT | 253 |
| HDDC2 | 51020 | AGGGAATATATCAACCCGATT | 254 |
| HECTD1 | 25831 | CAGCTTATAGATTGTATTCGA | 255 |
| HEXIM2 | 124790 | TCCGAACCAGACCGCCTGTAA | 256 |
| HIST1H2BF | 8343 | ATGGTAAGAAGCGCAAGCGTA | 257 |
| HIST1H2BL | 8340 | CAGCTCCAAGTAAATTCTCAA | 258 |

TABLE I-continued

List of genes decreasing gene targeting

| Gene Name | GENE ID | Target Sequence | SEQ ID |
|---|---|---|---|
| HMHA1 | 23526 | CCCGATGTGCACTACGACTTT | 259 |
| HMOX2 | 3163 | TTGGAGGTGAGTGGCCTGTAA | 260 |
| HOXA9 | 3205 | CCCATCGATCCCAATAACCCA | 261 |
| HOXB2 | 3212 | CGGCCTTTAGCCGTTCGCTTA | 262 |
| HSDL2 | 84263 | ACCCAGTTCATGAATCGCTAA | 263 |
| HUWE1 | 10075 | CCGGCTTTCACCAGTCGCTTA | 264 |
| HYAL3 | 8372 | CTGGCATAGTATGGCTTCCAA | 265 |
| HYDIN | 54768 | TGAGGCGATACTGTACAACAA | 266 |
| HYMAI | 57061 | AAGGTAATTGTCCCAATATCA | 267 |
| IARS | 3376 | CACAGTAATCTTCACACTTAA | 268 |
| ICK | 22858 | AAGGACTATTATATTATATAA | 269 |
| IFIT2 | 3433 | CCCATAGAGGTTAGTCCTGCA | 270 |
| IGF2 | 3481 | CCGGTCCTCTTTATCCACTGT | 271 |
| IGHMBP2 | 3508 | AAACGTGGTCCTTGCAACAAA | 272 |
| IKZF1 | 10320 | CACCGCTTCCACATGAGCTAA | 273 |
| IL17RE | 132014 | CACAAGGGACTTCGCTCTAAA | 274 |
| IL1F9 | 56300 | CACGATGGCATGACTAGCACA | 275 |
| ILF2 | 3608 | CTCCATAGAAGTGTCATTCCA | 276 |
| INSL3 | 3640 | CTCAGTGGCTGTACCCAACAA | 277 |
| IPO9 | 55705 | ATGGGTTGAGAGAATCGATAA | 278 |
| IQCC | 55721 | ACCGTCGTCTATACCATCAAA | 279 |
| IQCD | 115811 | CCCGAGATGGAGAGCACTAAA | 280 |
| IRF1 | 3659 | CAAGCATGGCTGGGACATCAA | 281 |
| ITGAM | 3684 | TGCCGCCATCATCTTACGGAA | 282 |
| ITM2C | 81618 | AACGCGGAGGCGGATCAACAA | 283 |
| JMJD4 | 65094 | CAGGGACTTTCCGGTGGAGGA | 284 |
| KCNA7 | 3743 | AAGCAAGGCTATCTTCTTCAA | 285 |
| KCNA7 | 3743 | AGGGCTTCCTTTGGTATCAAA | 286 |
| KCNJ3 | 3760 | ACCAGCCATAACTAACAGCAA | 287 |
| KCNJ3 | 3760 | CCCTCACAATTTGCCACGTGATCGA | 981 |
| KCNT2 | 343450 | CACATAGAGATTAACCAACAA | 288 |
| KCNV2 | 169522 | CTGGACAGAGGGCAACTATAA | 289 |
| KCNV2 | 169522 | TACGAGGAGCAGACAGACGAA | 290 |
| KIAA0090 | 23065 | AAGGTACATCGCAGTCCTGAA | 291 |
| KIAA0090 | 23065 | CAGACAGTTTCTCGAATGCGA | 292 |
| KIAA0241 | 23080 | CAGGAACCCAATGATACCAAT | 293 |
| KIAA0460 | 23248 | AGCCGGAGTGGTATAATCTTA | 294 |
| KIAA0562 | 9731 | ATGGTGGAGAGATGTCGAATA | 295 |
| KIAA1712 | 80817 | CTGGAGGACTATGGTCCTCAA | 296 |
| KIF5A | 3798 | AAGGGTTGTACTGAACGCTTT | 297 |
| KIF7 | 374654 | TACCCTCACTGGGATCAACAA | 298 |
| KIN | 22944 | CAGGAGACGCTTTGGCACTAA | 299 |
| KIN | 22944 | CCGAGTGCACTGAAGACGATA | 300 |
| KIR2DL1 | 3802 | CAAGGTCAACGGAACATTCCA | 301 |
| KIR3DX1 | 90011 | CACGTCTTTGCTGTTACTCAA | 302 |
| KLF14 | 136259 | CAACGTGTATATCATCCTAAA | 303 |
| KRT31 | 3881 | CACGACCAACGCGTGCAGCAA | 304 |
| KRT6A | 3853 | CACAAGTGACTAGTCCTATGA | 305 |
| KRT80 | 144501 | CAGCGAGATCGCGGATCTCAA | 306 |
| KRT84 | 3890 | AACGCTTTACATGGAGGAAAT | 307 |
| KRTAP13-2 | 337959 | CTACGTAGAGCTGTTATCATA | 308 |
| LAMA1 | 284217 | CCAGACGCTATTATTATTCAA | 309 |
| LARS2 | 23395 | CCCGAGAACTGCCCTCATCAA | 310 |
| LEPRE1 | 64175 | CAGCGCCATCCTTTACCTAAA | 311 |
| LEPREL2 | 10536 | GAGGGCCTATTACCAGTTGAA | 312 |
| LIFR | 3977 | TGGGTCGATCACAATCAACAA | 313 |
| LIFR | 3977 | CCAGTGGCTGTTATCAACATTTATT | 969 |
| LIFR | 3977 | CCAAATAATGTTGAGGTTCTGGAAA | 970 |
| LIFR | 3977 | TTGGAAGCCTTTACCCATTAA | 991 |
| LILRA2 | 11027 | CTGGGTTAGACGGATACAAGA | 314 |
| LIN54 | 132660 | CAGACTCCTGTGACTATATCA | 315 |
| LMAN1L | 79748 | CCCGGCGAAGGCAGCAGCCAA | 316 |
| LMNA | 4000 | CAGGCAGTCTGCTGAGAGGAA | 317 |
| LNPEP | 4012 | TCCAATGGAACTCAAAGCCTA | 318 |
| LOC100008588 | 100008588 | ACGGTCGAACTTGACTATCTA | 319 |
| LOC100008588 | 100008588 | CTGCGGCTTAATTTGACTCAA | 320 |
| LOC196913 | 196913 | CCGGCTTCCATCACTCAGATA | 321 |
| LOC255374 | 255374 | CAGGGAAGCCCTAACAGCGAA | 322 |
| LOC283951 | 283951 | TTGCCAAGTCTTTGTATAACA | 323 |
| LOC393078 | 393078 | ACGGTCTATGCCAGTTCTACA | 324 |
| LOC400759 | 400759 | TACGTGTCAGGTGTATATTAA | 325 |
| LOC401525 | 401525 | ATGGTTGTACTCACTCAGATA | 326 |
| LOC441251 | 441251 | CTGGCTATGGTCATAGTGTAT | 327 |
| LOC493754 | 493754 | TAGGTTTGAGTGTATATCTCAT | 328 |
| LPCAT1 | 79888 | TTCAAGATGTACGGAGCGCAA | 329 |

TABLE I-continued

List of genes decreasing gene targeting

| Gene Name | GENE ID | Target Sequence | SEQ ID |
|---|---|---|---|
| LPO | 4025 | CCGGGAGGTATCTAACAAGAT | 330 |
| LRDD | 55367 | CAGAATCTGCTGGACACGCTA | 331 |
| LRDD | 55367 | CCGGCTCGACCTGAGGGACAA | 332 |
| LRRC16A | 55604 | CAGGGACCTAATACCTATCAT | 333 |
| LRRC48 | 83450 | AAGATTGACAATCGAGAAGAT | 334 |
| LTBR | 4055 | TACATCTACAATGGACCAGTA | 335 |
| LYPD4 | 147719 | CCGGTCTTATCTCTGCAACAA | 336 |
| MAF1 | 84232 | CTCGAGCTTTGAAGCCATCAA | 337 |
| MAGEA10 | 4109 | AAGATCCTTCCCACTGTGGTA | 338 |
| MAN1C1 | 57134 | AAGGTCCTCAGGAAGATCGAA | 339 |
| MAP3K7IP2 | 23118 | CAGTCAATAGCCAGACCTTAA | 340 |
| MAP6 | 4135 | TACCACCAAGCCAGACGACAA | 341 |
| MAPRE2 | 10982 | CAGCAGGTGCAGCTAAATCAA | 342 |
| MBOAT5 | 10162 | TAAGGTGTATAAATCCATCTA | 343 |
| MC5R | 4161 | CGGCATTGTCTTCATCCTGTA | 344 |
| MCCC2 | 64087 | ACCCTTACTATTCCAGCGCAA | 345 |
| MCCC2 | 64087 | CCCGAGCACTTCACATATCAA | 346 |
| MDGA1 | 266727 | ACGCGGTTGTTCTATCAATAA | 347 |
| MED31 | 51003 | AGGCTAGCTGTTCCTGACATA | 348 |
| MEGF11 | 84465 | AAGAATCCGTGTGCAGTTCTA | 349 |
| MEGF11 | 84465 | AAGGTTGCGGTCATAACTCCA | 350 |
| METRNL | 284207 | CCGTGGAGTGGATGTACCCAA | 351 |
| MFN1 | 55669 | AAGGAAGTTCTTAGTGCTAGA | 352 |
| MFSD1 | 64747 | AACCCTCGGGATCACACTTAT | 353 |
| MFSD1 | 64747 | ACCGAGTATTTGGAATACGAT | 354 |
| MGA | 23269 | CTAGATGATTATGACTACGAA | 355 |
| MGC3207 | 84245 | GAGGTGAGTGCCACACCCTAA | 356 |
| MMACHC | 25974 | AACGTGCGCTATGGAGCCGAA | 357 |
| MMD | 23531 | CACGGCAGCTGCAGTGCATTA | 358 |
| MMP17 | 4326 | AAGGACAATAACGTAGAGGAA | 359 |
| MMP26 | 56547 | CTCAGTGCCGATGATATCCAA | 360 |
| MORC2 | 22880 | AACATTGGTGATCATCTTCAA | 361 |
| MRC2 | 9902 | CCGCACCAGCAACATATCCAA | 362 |
| MRC2 | 9902 | GGTGGAGCAGGAGCCTTTGATGTAT | 982 |
| MRC2 | 9902 | CCCTTCAAATATGACAACCAGTGGT | 983 |
| MRFAP1 | 93621 | CAAGTTGATGTAATACCCTGA | 363 |
| MRPL37 | 51253 | CCGGTCATCGTGGACAACCTA | 364 |
| MRPL38 | 64978 | CCCACCTATGGCATCTACTAA | 365 |
| MRPL54 | 116541 | CCGGATGCTGAGTACCCTGAA | 366 |
| MRPS12 | 6183 | CACGTTTACCCGCAAGCCGAA | 367 |
| MTF2 | 22823 | CAGGAGTTACAACTCAATCAT | 368 |
| MTX2 | 10651 | CAGTGGTGTGATGAAGCTACA | 369 |
| MXD4 | 10608 | GCGGGCCAAGGTGCACATCAA | 370 |
| N6AMT1 | 29104 | AAGCCGTGCCATTACCAACAA | 371 |
| NDNL2 | 56160 | CAGGGAGCATATTGCTGTAAA | 372 |
| NDST1 | 3340 | CTCGAACTAACTGCTAATAAA | 373 |
| NDUFS8 | 4728 | CAAGGAGAAGTTGCTCAACAA | 374 |
| NDUFV1 | 4723 | CCGCCTCATTGAGTTCTATAA | 375 |
| NDUFV1 | 4723 | CCGCTCGACGGACATCGTGAA | 993 |
| NFATC3 | 4775 | TCCCAGCGGTCTGCTCAAGAA | 376 |
| NIPBL | 25836 | AAGCGGCAATGTATGATATAA | 377 |
| NKX2-1 | 7080 | CTCCGTTACGTGTACATCCAA | 378 |
| NKX3-2 | 579 | CGCCAAGAAGGTGGCCGTAAA | 379 |
| NOL4 | 8715 | CACATTGTCCTTGATCCGTAA | 380 |
| NOLC1 | 9221 | AGCCTTCATGGACGAGTTATA | 381 |
| NPPB | 4879 | CTGAGGCGGCATTAAGAGGAA | 382 |
| NPS | 594857 | TGGAGTTGGCACAGGGATGAA | 383 |
| NSUN3 | 63899 | CTCCGTGTTCAAATGATCGAA | 384 |
| NTHL1 | 4913 | GAGCAAGGTGAAATACATCAA | 385 |
| NUBPL | 80224 | CGCCGGGAGTGAGACCCTAAA | 386 |
| NUCB1 | 4924 | CCGCGAGCACCCTAAAGTCAA | 387 |
| NUDT15 | 55270 | CAGCAGTACTCTTCTCACTAA | 388 |
| NUP50 | 10762 | CCCAAAGTAGTAGTTACCGAA | 389 |
| NUPL2 | 11097 | GACGTGGATGGAATACAACTA | 390 |
| NUPL2 | 11097 | TTGGATTGTCTGAGAACCCAT | 391 |
| NYD-SP21 | 84689 | ATCCCTAGATATGCTATCTCA | 392 |
| OAS3 | 4940 | CAGGCCGGCTCCGGCGTCAAA | 393 |
| OAZ2 | 4947 | TCCGATGAGGACTAATAGTCA | 394 |
| OCRL | 4952 | CAGCGGGAGGGTCTCATCAAA | 395 |
| OCRL | 4952 | CCCAGCTTCCGAGATGCCATAGAAA | 977 |
| OCRL | 4952 | CCAAGGAGATCTGGCTTCTAGTAGA | 978 |
| OPTC | 26254 | GAGGATTGACCTCTCCAACAA | 396 |
| OR2L2 | 26246 | AAAGCGCTAGGTTCATATCAA | 397 |
| OR2T1 | 26696 | CTGCAATTCCCGGGAGATTAA | 398 |
| OR4C16 | 219428 | CACTGTTGGGTAATTTGCTAA | 399 |

TABLE I-continued

List of genes decreasing gene targeting

| Gene Name | GENE ID | Target Sequence | SEQ ID |
|---|---|---|---|
| OR4D1 | 26689 | CTCCGAAATCTAGCTCTCATA | 400 |
| OR4Q3 | 441669 | CTGCTCCAATCTCCTATGTAT | 401 |
| OR4Q3 | 441669 | GAGCTGTGTTACTGTGCCAAA | 402 |
| OR5M9 | 390162 | CTCATTGTAGTAGCTGTGCTA | 403 |
| OR6T1 | 219874 | TCCCAAGATGCTTGTCGTCAT | 404 |
| OR8B8 | 26493 | CAAGGTGTCTTCCCTATTCTA | 405 |
| OR8S1 | 341568 | CACCCGTATAATCTCTACCAT | 406 |
| OSBPL10 | 114884 | CAGCGTAGTATAATTCTTCAT | 407 |
| OTP | 23440 | CGCCAAGTGGAAGAAGCGCAA | 408 |
| P2RX3 | 5024 | CTGGACCATCGGGATCATCAA | 409 |
| P2RY11 | 5032 | ACCCTAGGTGTTGCTGGAGAA | 410 |
| PAEP | 5047 | ATGGTACTTGCTGGACTTGAA | 411 |
| PAGE3 | 139793 | CAGGATTATACACCTGGTCAA | 412 |
| PCDHA1 | 56147 | AAGGAAGTCCTCCGATGTCAA | 413 |
| PDZD4 | 57595 | CTGCGCAAGTTTGGCCTGCAA | 414 |
| PER3 | 8863 | AGGGTTAAAGAAGTTGTACTA | 415 |
| PER4 | 168741 | TTCCATCATGGAGACATAGTA | 416 |
| PHYHIPL | 84457 | AACGTGTGACTCATTCAAGAT | 417 |
| PIK3IP1 | 113791 | GCGGGTGCGGATGAACTCCAA | 418 |
| PIP5KL1 | 138429 | TCCGAGAGGTATGACATCAAA | 419 |
| PLCB4 | 5332 | AACCCGGTAGTCTAGAACTAA | 420 |
| PLEKHA7 | 144100 | CAGCTACTTCATCGACCATAA | 421 |
| PLXDC2 | 84898 | CACAGTACATAGCACCTTTAA | 422 |
| POLE4 | 56655 | CGGGATAAGCAGAGATCTCAT | 423 |
| POLG | 5428 | CAGATGCGGGTCACACCTAAA | 424 |
| POLQ | 10721 | ATCAGTGTCTATAGCATCAAA | 425 |
| POLQ | 10721 | CCTTAAGACTGTAGGTACTATGAAA | 979 |
| POLQ | 10721 | GCTTCAGTGATGACTATCTAGTAAA | 980 |
| POMGNT1 | 55624 | CAGGCCTGGCTCAGAATCAA | 426 |
| POMGNT1 | 55624 | CCGCGTGTCTCAGCACTACA | 427 |
| POP7 | 10248 | CCGCAACAACTCAGCCATCCA | 428 |
| PORCN | 64840 | CACCGTGACATGGCACAAGAT | 429 |
| POU5F1 | 5460 | TGGGATTAAGTTCTTCATTCA | 430 |
| PPAN | 56342 | TTCCGCCACTATAGCATCAAA | 431 |
| PQLC2 | 54896 | CTCCGTGCTGTTGTTCCTCAT | 432 |
| PRB3 | 5544 | AAGAAGGTGGTCATAGCTCTA | 433 |
| PRKD2 | 25865 | TTGGGTGGTTCATTACAGCAA | 434 |
| PRO0611 | 28997 | AAGGGTTAAATTCAGAGTGAT | 435 |
| PROP1 | 5626 | AAGCAGAGAAATCTCAAGTCA | 436 |
| PROP1 | 5626 | CACCAGTCTGAGGACTGGTACCCTA | 988 |
| PROX1 | 5629 | ATGGAGAAGTACGACGTCAA | 437 |
| PRRG3 | 79057 | AAGGTCAACCCTTGGTTCTTA | 438 |
| PSMC3 | 5702 | CTGCCGAATATTGAGAGTCCA | 439 |
| PTPRO | 5800 | CACGGAAGAACCTATAGCCTA | 440 |
| PTTG2 | 10744 | AAGCTGGAGTCTAGACCTTCA | 441 |
| R3HDML | 140902 | CCGGTCCGTAGTGGATCTCAT | 442 |
| RAB6IP1 | 23258 | CAGCATGTCTATGTCCCTATT | 443 |
| RABGGTA | 5875 | CTGGACGGCGTCACCAACCTA | 444 |
| RABL2B | 11158 | CAGCGCAGTGGGCAAATCCAA | 445 |
| RALA | 5898 | CGAGCTAATGTTGACAAGGTA | 446 |
| RALGPS1 | 9649 | TAACGAAGTAATAGTAATTAA | 447 |
| RAMP2 | 10266 | CACGAGCTTCTCAACAACCAT | 448 |
| RARA | 5914 | CAGGAAATGTTGGAGAACTCA | 449 |
| RASSF7 | 8045 | TTCACTGTGTGTACACAGCAA | 450 |
| RBJ | 51277 | CAGCCCGAATTGACACGACAA | 451 |
| RBP1 | 5947 | TAGGAACTACATCATGGACTT | 452 |
| RCCD1 | 91433 | CTGCCTAAGGTCAGCATCAAT | 453 |
| RELL2 | 285613 | CAGGCCGTGGTCACTTCTCTA | 454 |
| REXO4 | 57109 | ACGCTCTGCATAATGACCTAA | 455 |
| RFFL | 117584 | TCGCAACTTTGTCAACTACAA | 456 |
| RFX4 | 5992 | CAGGCATTACCTGACAGCTTA | 457 |
| RGS3 | 5998 | CCCGCGGGCAAGGCAGACAAA | 458 |
| RGS3 | 5998 | CAGACGGATAGACATACGGAA | 459 |
| RGS3 | 5998 | CCGCTGCGACGTCCTGAGGAA | 460 |
| RHBDF1 | 64285 | CCACCTCATGTGGCCAATAAA | 461 |
| RICS | 9743 | CCCGCTCAGATTATCATGTCA | 462 |
| RIPK3 | 11035 | CAGCCTGATGTCGTGCGTCAA | 463 |
| RNASEH2B | 79621 | CAGGCTGGTCTCGGAAACGAA | 464 |
| RNF123 | 63891 | CTGCGCTACTATTGGGATGAA | 465 |
| RP6-213H19.1 | 51765 | GAGCTTTACCACCGTACGAAA | 466 |
| RPL3L | 6123 | CTGGTGCATCACAGTCGCCAA | 467 |
| RSPO1 | 284654 | TTGGAGAGTATTGTTACCCTT | 468 |
| S100A13 | 6284 | CAGCGTCAACGAGTTCAAAGA | 469 |
| SAP130 | 79595 | CTCAAACATCCCAGTCGCCAA | 470 |
| SAR1A | 56681 | CAGGCCGTAGTAAGCATTAAT | 471 |

TABLE I-continued
List of genes decreasing gene targeting

| Gene Name | GENE ID | Target Sequence | SEQ ID |
|---|---|---|---|
| SDCCAG10 | 10283 | GTGCCTGGTTTCATAGTCCAA | 472 |
| SEPT1 | 1731 | CACCACGATGATGGAGCTACA | 473 |
| SERPINA6 | 866 | CAGCAGACAGATCAACAGCTA | 474 |
| SERPINB2 | 5055 | AACCTATGACAAACTCAACAA | 475 |
| SERPINB2 | 5055 | AAATTGGCCCGTCCCTTGTTGAAGG | 984 |
| SERPINB2 | 5055 | CAGAAGGGTAGTTATCCTGAT | 990 |
| SET | 6418 | AAGAAGATAGGCTCTCAGTAA | 476 |
| SET | 6418 | CAGGAATCTTGCTCCAATAAA | 477 |
| SFTPB | 6439 | CAGGATCTCTCCGAGCAGCAA | 478 |
| SFTPC | 6440 | CCCAGTCTTGAGGCTCTCAAT | 479 |
| SGPP2 | 130367 | CAGGCGGAGACTGGAGATTGA | 480 |
| SGSH | 6448 | CCGGAAATTCCTGCAGACTCA | 481 |
| SH3BGRL | 6451 | ACGTTGTAATTTCTTATCGTA | 482 |
| SLC12A5 | 57468 | CTGCGGACAAGTTTGGCGAA | 483 |
| SLC13A2 | 9058 | ATGCCGTGGAATATCGTGTTA | 484 |
| SLC15A3 | 51296 | CCCGCAAGAGGACATCGCCAA | 485 |
| SLC22A6 | 9356 | CACCTTGATTGGCTATGTCTA | 486 |
| SLC25A2 | 83884 | TACAATTTGGTCTGTCGTGAA | 487 |
| SLC36A1 | 206358 | CCCGTCGGAAGGCCTCAACAA | 488 |
| SLC37A3 | 84255 | GAGCCGAATTATTCAATCCAA | 489 |
| SLC39A5 | 283375 | CACGCAGGACCTGGCGGACTA | 490 |
| SLC44A1 | 23446 | CCCTATGTAGCTACAACCTAA | 491 |
| SLC9A6 | 10479 | CAAGTTGATGTTGAACTCTAT | 492 |
| SMG1 | 23049 | CACCATGGTATTACAGGTTCA | 493 |
| SNORA66 | 26782 | CTGCGTGATGTGGCAGAAGCA | 494 |
| SNORA70 | 26778 | AGCAGCTTCCTTGGTAGTGTA | 495 |
| SNORD114-1 | 767577 | ATGATGATGACTGGTGGCGTA | 496 |
| SNORD114-7 | 767583 | ATGCCTGAGACTCTGAGGTTA | 497 |
| SNORD9 | 692053 | CTGTGATGAGTTGCCATGCTA | 498 |
| SNRK | 54861 | CACCACTGAATTGGAACGGAT | 499 |
| SNX4 | 8723 | TGGCGGCGATATAGTGAATTT | 500 |
| SORCS2 | 57537 | CACCGTCATCGACAATTTCTA | 501 |
| SORCS2 | 57537 | GACGCTTATAACCTACAACAA | 502 |
| SP1 | 6667 | CTAGGACGCAATAAATTTATA | 503 |
| SP100 | 6672 | AAGGAGCGATTCAAACAAGGA | 504 |
| SPATS2 | 65244 | CACAGTGTCTCTTGCACGGTA | 505 |
| SPC25 | 57405 | CGGGACTAAGAGATACCTACA | 506 |
| SPDYA | 245711 | TGGAGCTGTCAGAAACTACA | 507 |
| SPINTI | 6692 | CGGGAAGAAGAGTGCATTCTA | 508 |
| SPRED2 | 200734 | AGGCGTCTAGGTAACAAGAAA | 509 |
| SPRED3 | 399473 | AACCTTGGAGTGTACACTGAA | 510 |
| SPRED3 | 399473 | GCCAGGCTTGGTTTACAACAA | 511 |
| SPRR1B | 6699 | CAGAGTATTCCTCTCTTCACA | 512 |
| SPRYD4 | 283377 | AAAGCTAGGCATACAGCCAAA | 513 |
| SRP14P1 | 390284 | CGGGCTGAGAAGAGGGACAAA | 514 |
| SRP9 | 6726 | TCTGAAAGTAATTGTGACTAA | 515 |
| SRPK3 | 26576 | AAGATGAGGCGCAAACGGAAA | 516 |
| SRXN1 | 140809 | CAGATGTACCATGGTGATGTA | 517 |
| STK39 | 27347 | TTGGAGTATTTGTAACTTCTA | 518 |
| STS | 412 | CGGAAGTAATGGGATCTATAA | 519 |
| STXBP6 | 29091 | AAGGCGAATATTTAACTTATA | 520 |
| STYXL1 | 51657 | CAAGATTCAGAAGGACTTGAA | 521 |
| SV2A | 9900 | CAGGACGAATATTCCCGAAGA | 522 |
| SV2C | 22987 | ATGGACAGAATTGGGCGCTTA | 523 |
| SYT2 | 127833 | CACCTTCAAGGTGCCATACCA | 524 |
| TARSL2 | 123283 | CACGGTAATAGCCAAAGTCAA | 525 |
| TAS2R13 | 50838 | CAGTGTCGGTCAAATTCACTA | 526 |
| TAX1BP1 | 8887 | CAGATCAATCAGCTAATAATA | 527 |
| TBC1D13 | 54662 | ACCCTTCGTAAGAGAGTGGAA | 528 |
| TBC1D5 | 9779 | AGGAAGGTTGTTGGCCAACAA | 529 |
| TCP11L1 | 55346 | CAGCAGTCAGTTGAATACGAA | 530 |
| TCTEX1D1 | 200132 | CAGGGCTGAAATAGCTTATTA | 531 |
| TCTEX1D2 | 255758 | AAGAGGTGAAGGAGTATTCAT | 532 |
| TDRD12 | 91646 | TGGTGGGTACTTGGTATTCAA | 533 |
| TG | 7038 | AAAGGTGATCTTCGACGCCAA | 534 |
| TGFB1 | 7040 | CAGCATATATATGTTCTTCAA | 535 |
| TGIF2LX | 90316 | CTGCTAGTCGATGCAGCAGTA | 536 |
| THAP10 | 56906 | AAGTACTACATTTCTAACGTA | 537 |
| THBS2 | 7058 | AGCGTTGGGATACTTCATTAA | 538 |
| THSD1P | 374500 | CTGGATTTAGCCAGTCCTGCA | 539 |
| TMCC3 | 57458 | CTGGGTTTATCTGGTGACATA | 540 |
| TMCO3 | 55002 | GAGGAGCAGCCAGTACATCAA | 541 |
| TMED6 | 146456 | TTCCGTGGAGCTGATCGATAT | 542 |
| TMEM108 | 66000 | CAGGGAGATCCAGTCCCTTGA | 543 |
| TMEM161B | 153396 | CAGAAGATTATACCTCACTAT | 544 |

TABLE I-continued

List of genes decreasing gene targeting

| Gene Name | GENE ID | Target Sequence | SEQ ID |
|---|---|---|---|
| TMEM188 | 255919 | ACCATTAGCTGTATCACTCTA | 545 |
| TMEM33 | 55161 | CCCTTCGATATTCGTCTCGAA | 546 |
| TMEM37 | 140738 | CAGGCTTAGCCAGATGTTGAT | 547 |
| TMEM45B | 120224 | CAGCGTCTCGAGATCGTCGAA | 548 |
| TMEM48 | 55706 | CAGCATCATTTACAGAGGATA | 549 |
| TMEM49 | 81671 | TAGGGTGGAATGTGATGTTCA | 550 |
| TMEM59L | 25789 | CTGCGTGGAAGCCTATGTGAA | 551 |
| TNFAIP8L3 | 388121 | AAACCTGGATGTAGACTATTA | 552 |
| TNIP1 | 10318 | CCGGTCCATGAAGCAGCAGTA | 553 |
| TNXA | 7146 | CACAGCGACTTCATTGTCTGA | 554 |
| TOP1 | 7150 | GCCCGAGGATATAATCATCAA | 555 |
| TPRG1 | 285386 | AAGGATCAGCCTGACAATCGA | 556 |
| TRADD | 8717 | CCCGAATGTTAAGCAATGATA | 557 |
| TRH | 7200 | CTGGCAGATCCCAAGGCTCAA | 558 |
| TRIM3 | 10612 | TAGACCGGAATGGACATATCA | 559 |
| TRIM37 | 4591 | CTCGAAGGTGGTCCTACTACA | 560 |
| TRIM48 | 79097 | ATGCATAAAGACAATACAGCA | 561 |
| TRIM60 | 166655 | TTGCGTCAGGTCCTAAGACAA | 562 |
| TRSPAP1 | 54952 | CTGAGCGTGGCAATCCCTAAA | 563 |
| TSHZ2 | 128553 | CCGGCCTAATCTCACCAACAA | 564 |
| TTC17 | 55761 | CTGGATCTATATGATGGCACA | 565 |
| UBR5 | 51366 | CAGGTATGCTTGAGAAATAAT | 566 |
| UBR5 | 51366 | CTGGTATTTCTTCAATGCCGA | 567 |
| UBXD5 | 91544 | CTCCCTTAGCAAGACCCGAAA | 568 |
| UGT1A10 | 54575 | ACGATACTTGTTAAGTGGCTA | 569 |
| USP16 | 10600 | ACCCGTAATGAGAAACTTCGA | 570 |
| USP20 | 10868 | ACCGTCGTACGTGCTCAAGAA | 571 |
| USP37 | 57695 | ATCCGGGTAGAGGATCGATTA | 572 |
| VPS37D | 155382 | CGGGCTGCCCTGGCCATCAAA | 573 |
| VPS54 | 51542 | TCAGCTAAGCTTGTAGCGATA | 574 |
| VPS8 | 23355 | CAGCAGTACAAGAGACGCCAA | 575 |
| VSTM2A | 222008 | CAGGTGCGAGGATAGCTACAA | 576 |
| VWCE | 220001 | AGGCTGCTCTCTTGACGACAA | 577 |
| WDR17 | 116966 | CACCGTTATAATGAATTCAAA | 578 |
| WDR38 | 401551 | CAGCCTGCTTATCCAACTGAA | 579 |
| WFDC5 | 149708 | CAGCCCAACCATCCAGAATGA | 580 |
| WWP2 | 11060 | CTCACCTACTTTCGCTTTATA | 581 |
| XIRP1 | 165904 | ATCCAGGACGGTCTTCGGAAA | 582 |
| XIRP1 | 165904 | AAGGGCAACCCTGATGTCTCA | 583 |
| XIST | 7503 | TAAGTGCTTGAAAGACGTAAA | 584 |
| XPO7 | 23039 | CAAGCTTGTATCACGCACAAA | 585 |
| ZC3H12D | 340152 | CCGGGCTCGCATCGCGCTCTA | 586 |
| ZC3HC1 | 51530 | GAGTGTGGGATTAACAGACTA | 587 |
| ZCCHC7 | 84186 | CAGATAGCTAATAACCGAACA | 588 |
| ZDHHC22 | 283576 | CCCGCTGATAGCTGCGCAACA | 589 |
| ZDHHC4 | 55146 | TTGAGCTGTAGTTCCCGTTTA | 590 |
| ZFP106 | 64397 | CCCGCCGCATTCGCAATATTA | 591 |
| ZFP30 | 22835 | CAGCGCTGGCATAAACAATAA | 592 |
| ZFX | 7543 | GAGGACGTTGTTATAGAAGAT | 593 |
| ZMAT5 | 55954 | CTCCGCACTGGAAGACTTGAA | 594 |
| ZNF223 | 7766 | CAGAGGTTTAGAGGCACAATT | 595 |
| ZNF233 | 353355 | AATGAGATAGATACCCTTCAA | 596 |
| ZNF236 | 7776 | CACGCTGACAGCGCACATCAA | 597 |
| ZNF285A | 26974 | CAGGGACACTGCCATCGATAA | 598 |
| ZNF319 | 57567 | CTGGTCTTGAAAGAAGACTAA | 599 |
| ZNF319 | 57567 | TACAACCGTCCCAACTGCTAA | 600 |
| ZNF321 | 399669 | CAAGTGTAGTGAGCATAACAA | 601 |
| ZNF500 | 26048 | CCCGTTGAGAATGGAGTGGTA | 602 |
| ZNF559 | 84527 | TCCCGAGAGATGGCTAATGAA | 603 |
| ZNF648 | 127665 | CCAGCGCAACATGCACAGCAA | 604 |
| ZNF684 | 127396 | TAGCCGGTATTCAATCTTCAA | 605 |
| ZNF70 | 7621 | CAAGCCCTGTTCAGCATCAAA | 606 |
| ZNF701 | 55762 | AAGGATTTCGGGTGTGATTCA | 607 |
| ZNF701 | 55762 | AAGGTGTGAAATTCTCAGTTT | 608 |
| ZNF75A | 7627 | ATGGATCGTCACAAGAAAGAT | 609 |
| ZNF786 | 136051 | TAGGGCCTGGGAGAAATTCAA | 610 |
| ZSCAN1 | 284312 | CACACCAAAGGTGGTACCCAA | 611 |

More preferably, the interfering RNA targets used in the frame of the method according to the invention targets a sequence selected from the group consisting of SEQ ID Nos. 13-611 and SEQ ID Nos. 969-994.

In this table, the gene is identified by a reference to an entry in a public database. This reference refers to the database entry in force on Apr. 26, 2010.

Example 3 further confirms that some of the genes of Table I are indeed are capable of decreasing homologous recombination in a eukaryotic cell. Therefore, the gene that is capable of modulating (in particular decreasing) homologous recombination in a eukaryotic cell is a gene selected from the group of genes listed in Tables III and IV hereinbelow.

TABLE III

List of genes decreasing gene targeting

| Gene Name | GENE ID | Target Sequence | SEQ ID |
|---|---|---|---|
| SERFINB2 | 5055 | CAGAAGGGTAGTTATCCTGAT | 990 |
| EP300 | 2033 | CACCGATAACTCAGACTTGAA | 197 |
| LIFR | 3977 | TTGGAAGCCTTTACCCATTAA | 991 |
| EFEMP2 | 30008 | CACGGAATGCACAGATGGCTA | 193 |
| GJB1 | 2705 | TGGCATCTGCATCATCCTCAA | 992 |
| NDUFV1 | 4723 | CCGCTCGACGGACATCGTGAA | 993 |
| ATR | 545 | AAGGACATGTGCATTACCTTA | 994 |
| ATR | 545 | CAGGCACTAATTGTTCTTCAA | 45 |
| NPPB | 4879 | CTGAGGCGGCATTAAGAGGAA | 382 |
| CKS1B | 1163 | AACATCTTTCTGATAACATTA | 133 |
| LAMA1 | 284217 | CCAGACGCTATTATTATTCAA | 309 |
| ICK | 22858 | AAGGACTATTATATTATATAA | 269 |
| DCDC2 | 51473 | CAGGTTGAGGTTCCAGTCGAT | 169 |
| LRRC16 | 55604 | CAGGGACCTAATACCTATCAT | 333 |
| USP20 | 10868 | ACCGTCGTACGTGCTCAAGAA | 571 |
| BCR | 613 | ACGGCAGTCCATGACGGTGAA | 54 |
| FLJ35695 | 400359 | TCCCGTTCACAGATCCTGTAA | 73 |
| TOP1 | 7150 | GCCCGAGGATATAATCATCAA | 555 |
| ATF7IP | 55729 | CAGATCTTGTAGAAACGATTA | 42 |
| KIF7 | 374654 | TACCCTCACTGGGATCAACAA | 298 |
| MC5R | 4161 | CGGCATTGTCTTCATCCTGTA | 344 |
| CCDC46 | 201134 | CACGTTTGTAGTATCATATCA | 108 |
| C9orf85 | 138241 | AAGTTCTTGAGTGGCGTGTAA | 100 |
| MMP17 | 4326 | AAGGACAATAACGTAGAGGAA | 359 |
| UREB1 | 10075 | CCGGCTTTCACCAGTCGCTTA | 264 |
| LRDD | 55367 | CCGGCTCGACCTGAGGGACAA | 332 |
| CYP4F2 | 4051 | ACGCTTGTGCGTGAATGTTCA | 166 |
| CATSPER1 | 117144 | CCGGATCCTCAAGGTCTTCAA | 104 |
| LPO | 4025 | CCGGGAGGTATCTAACAAGAT | 330 |
| SMG1 | 23049 | CACCATGGTATTACAGGTTCA | 493 |
| RFFL | 117584 | TCGCAACTTTGTCAACTACAA | 456 |
| FANCF | 2188 | AACCAGCATTAGAGCTTTATA | 212 |
| WWP2 | 11060 | CTCACCTACTTTCGCTTTATA | 581 |
| ATP5A1 | 498 | CCCGGTATCATTCCTCGAATT | 44 |
| SPINT1 | 6692 | CGGGAAGAAGAGTGCATTCTA | 508 |
| ARHGAP26 | 23092 | AGGGAGTATACTAGTAGGTTA | 37 |
| CCNL2 | 81669 | CGGAGCGTTATGGACGTGGTA | 117 |
| LARS2 | 23395 | CCCGAGAACTGCCCTCATCAA | 310 |

TABLE III-continued

List of genes decreasing gene targeting

| Gene Name | GENE ID | Target Sequence | SEQ ID |
|---|---|---|---|
| UMP-CMPK | 51727 | CGCGTATATATCCCTCTAGTA | 138 |
| DNPEP | 23549 | ATCCGAGAGGTGGCCAACAAA | 183 |
| TITF1 | 7080 | CTCCGTTACGTGTACATCCAA | 378 |
| CCL7 | 6354 | TTGGATGTATATGTCATCTCA | 116 |
| KRT80 | 144501 | CAGCGAGATCGCGGATCTCAA | 306 |
| LMNA | 4000 | CAGGCAGTCTGCTGAGAGGAA | 317 |
| THAP10 | 56906 | AAGTACTACATTTCTAACGTA | 537 |
| NIPBL | 25836 | AAGCGGCAATGTATGATATAA | 377 |
| DMN | 23336 | AAGGCGATTCCATGACAGAAA | 177 |
| IGHMBP2 | 3508 | AAACGTGGTCCTTGCAACAAA | 272 |
| CHST10 | 9486 | AAGTTTGTCCTGGACCGAATA | 130 |
| CTTNBP2NL | 55917 | CCGGTACTCACTAAGCGTTTA | 161 |
| FARP2 | 9855 | CACAAGTGTGGAAGCGTTTAA | 213 |
| DNAJA4 | 55466 | TACAGTTTGTATGGACTACTA | 178 |
| SPRED3 | 399473 | AACCTTGGAGTGTACACTGAA | 510 |
| POP7 | 10248 | CCGCAACAACTCAGCCATCCA | 428 |
| PRRG3 | 79057 | AAGGTCAACCCTTGGTTCTTA | 438 |
| VPS37D | 155382 | CGGGCTGCCCTGGCCATCAAA | 573 |
| KIN | 22944 | CCGAGTGCACTGAAGACGATA | 300 |
| MRPL54 | 116541 | CCGGATGCTGAGTACCCTGAA | 366 |
| FTHL2 | 2497 | CTCGGCGGAATACCTCTTAGA | 229 |
| RBP1 | 5947 | TAGGAACTACATCATGGACTT | 452 |
| ZSCAN1 | 284312 | CACACCAAAGGTGGTACCCAA | 611 |
| TRIM3 | 10612 | TAGACCGGAATGGACATATCA | 559 |
| ZNF500 | 26048 | CCCGTTGAGAATGGAGTGGTA | 602 |
| POLE4 | 56655 | CGGGATAAGCAGAGATCTCAT | 423 |
| ZNF285 | 26974 | CAGGGACACTGCCATCGATAA | 598 |
| EP300 | 2033 | TTGGACTACCCTATCAAGTAA | 198 |

TABLE IV

List of genes decreasing gene targeting

| Gene Name | Gene ID | Target Sequence | SEQ ID |
|---|---|---|---|
| LIFR | 3977 | CCAGTGGCTGTTATCAACATTTATT | 969 |
| LIFR | 3977 | CCAAATAATGTTGAGGTTCTGGAAA | 970 |
| CCL19 | 6363 | GGAACTTCCACTACCTTCTCATCAA | 971 |
| CCL19 | 6363 | CCTGCTGTAGTGTTCACCACACTGA | 972 |

TABLE IV-continued

List of genes decreasing gene targeting

| Gene Name | Gene ID | Target Sequence | SEQ ID |
|---|---|---|---|
| ATR | 545 | CAGCTCGTCTCTAAACCCTTCTAAA | 973 |
| FBXO34 | 55030 | CACCAAGAGTTTAGTGGCCCTTAAA | 974 |
| DNAJB7 | 150353 | AAGCTTATCATAAAGTGGCACTTAA | 975 |
| DNAJB7 | 150353 | CAAATGATGAGAAACGGGACATTTA | 976 |
| OCRL | 4952 | CCCAGCTTCCGAGATGCCATAGAAA | 977 |
| OCRL | 4952 | CCAAGGAGATCTGGCTTCTAGTAGA | 978 |
| POLQ | 10721 | CCTTAAGACTGTAGGTACTATGAAA | 979 |
| POLQ | 10721 | GCTTCAGTGATGACTATCTAGTAAA | 980 |
| KCNJ3 | 3760 | CCCTCACAATTTGCCACGTGATCGA | 981 |
| MRC2 | 9902 | GGTGGAGCAGGAGCCTTTGATGTAT | 982 |
| MRC2 | 9902 | CCCTTCAAATATGACAACCAGTGGT | 983 |
| SERPINB2 | 5055 | AAATTGGCCCGTCCCTTGTTGAAGG | 984 |
| EP300 | 2033 | CAGGTATGATGAACAGTCCAGTAAA | 985 |
| ATF7IP | 55729 | CCAGCAGAAGTAGAAAGTAATGAAA | 986 |
| DCDC2 | 51473 | CCAGAAAGTCTAAAGGGAGTGGAAA | 987 |
| PROP1 | 5626 | CACCAGTCTGAGGACTGGTACCCTA | 988 |
| CCL1 | 6346 | ACAGCAAGAGCATGCAGGTACCCTT | 989 |

More preferably, the interfering RNA targets a sequence selected from the group consisting of SEQ ID Nos. 42, 197, 990, 991, 193, 992, 993, 994, 45, 382, 133, 309, 269, 169, 333, 571, 54, 73, 555, 42, 298, 344, 108, 100, 359, 264, 332, 166, 104, 330, 493, 456, 212, 581, 44, 508, 37, 117, 310, 138, 183, 378, 116, 306, 317, 537, 377, 177, 272, 130, 161, 213, 178, 510, 428, 438, 573, 300, 366, 229, 452, 611, 559, 602, 423, 598, 198 and SEQ ID Nos. 969-989.

In a specific embodiment, the interfering RNA introduced in said eukaryotic cells does not target a Non Homologous End joining gene selected from the group consisting of G22P1 (Ku70 or hdfA), XRCC5 (Ku80), Ku86, PRKDC, LIG4 (DNA ligase IV), XRCC4 and DCLRE1C (Artemis).

Interfering RNA capable of silencing a given gene can easily be obtained by the skilled in the art. Such iRNAs may for example be purchased from a provider. Alternatively, commercially available tools allow designing iRNAs targeting a given gene.

Useful interfering RNAs can be designed with a number of software program, e.g., the OligoEngine siRNA design tool available at the oligoengine.com world wide website. Database RNAi Codex (available at the codex.cshl.edu website) publishes available RNAi resources, and provides the most complete access to this growing resource.

The iRNAs used in the frame of the present invention can for example be a shRNA. shRNAs can be produced using a wide variety of well-known RNAi techniques. ShRNAs that are synthetically produced as well as miRNA that are found in nature can for example be redesigned to function as synthetic silencing shRNAs. DNA vectors that express perfect complementary shRNAs are commonly used to generate functional siRNAs.

iRNAs can be produced by chemical synthesis (e.g. in the case of siRNAs) or can be produced by recombinant technologies through an expression vector (e.g. in the case of shRNAs).

The iRNAs according to the invention may optionally be chemically modified.

In another preferred embodiment according to the invention, the gene that modulates endonuclease-induced homologous recombination is a gene that increases endonuclease-induced homologous recombination (i.e. the presence of which increases gene targeting efficiency in a eukaryotic cell). In such a case, a cDNA leading to increased expression of said gene is introduced into the eukaryotic cell.

cDNA usually refers to a double-stranded DNA that is derived from mRNA which can be obtained from prokaryotes or eukaryotes by reverse transcription. cDNA is a more convenient way to work with the coding sequence than mRNA because RNA is very easily degraded by omnipresent RNases. Methods and advantages to work with cDNA are well known in the art (1989, Molecular cloning: a laboratory manual, $2^{nd}$ edition and further ones, Cold Spring Harbor Laboratory Press, Cold Spring Harbor, N.Y.). Particularly in the context of the present invention the availability of a cDNA clone allows the corresponding protein to be expressed in a variety of contexts. The cDNA can be inserted into a variety of expression vectors for different purposes. Perhaps the most obvious use of such an approach in the present invention is to drive the expression of a defined protein involved in a protein transduction cascade to levels that allow higher frequency of endonuclease-induced HR and so, gene targeting events. As well-known in the art, one can express not only the wild type protein but also mutant proteins, said particular mutations having consequences in structure-function relationships within a protein itself (improved catalytic activity) or for association with another endogenous protein.

As used herein, the term "cDNA" encompasses both full-length cDNAs naturally transcribed from the gene and biologically active fragments thereof, such as e.g. cDNAs encoding the mature protein encoded by the gene or biologically active fragments thereof. The biologically active fragments thereof can for example code for maturation products of the protein encoded by the gene.

The inventors have found that the genes listed in table II herebelow are capable of increasing homologous recombination in a eukaryotic cell (see Example 2). Therefore, the gene that is capable of modulating homologous recombination in a eukaryotic cell preferably is a gene selected from the group of genes listed in Table II.

TABLE II

List of genes increasing gene targeting

| Gene Name | GENE ID | Target Sequence | SEQ ID |
|---|---|---|---|
| ABCA10 | 10349 | TACCATACCTTCAGAGTGTTA | 612 |
| ABCG1 | 9619 | CAAGCTGTACCTGGACTTCAT | 613 |
| ABHD2 | 11057 | ACGATCCGTTGGTGCATGAAA | 614 |
| ACOT12 | 134526 | ATGCATCGTATCTTACTTTAA | 615 |
| ACRV1 | 56 | TCCATAGATCATCAAACTTCA | 616 |
| ADAM2 | 2515 | CTGTTGGTTAGTAGACACTAA | 617 |
| ADCY10 | 55811 | CTGGCACAACTTTACCGGCAA | 618 |

TABLE II-continued

List of genes increasing gene targeting

| Gene Name | GENE ID | Target Sequence | SEQ ID |
|---|---|---|---|
| AGBL2 | 79841 | CAGCCTACCATCCAGAAGTAA | 619 |
| AGXT2L1 | 64850 | CACGACAACATTGTTGAGTAT | 620 |
| AIM1 | 202 | AACGTTTGTTGGGAGGGCAAA | 621 |
| AMTN | 401138 | TGCCTCGAATTTGGTGATACA | 622 |
| ANGEL2 | 90806 | CTGACGCAATTGGCAATGCTA | 623 |
| ANKFN1 | 162282 | CAGGACAGAATAATCCTTACA | 624 |
| ANP32A | 8125 | TTGAGCCTTCAAAGTCCTAAA | 625 |
| AP1G1 | 164 | TAGGCTGTGCATAGTGATCAT | 626 |
| APOA1 | 335 | CGGCGCCAGACTGGCCGAGTA | 627 |
| APOA2 | 336 | AGGCCAAGTCTTACTTTGAAA | 628 |
| APP | 351 | CTGGTCTTCAATTACCAAGAA | 629 |
| AQP1 | 358 | CAGCATGGCCAGCGAGTTCAA | 630 |
| ARHGEF12 | 23365 | ACCGAGAGTCACCAACAGATA | 631 |
| ARL15 | 54622 | CTGGTAATTCTCCAGAAGATA | 632 |
| ARMCX2 | 9823 | CACCATGACCTCTTAGTGAAA | 633 |
| ARPC5L | 81873 | CGGCGTTGACTTGTTAATGAA | 634 |
| ASCC3L1 | 23020 | CGCCAGCGTAAGGGCTATGAA | 635 |
| ATP2A1 | 487 | CACCAACATTGCAGCCGGCAA | 636 |
| ATXN1 | 6310 | AACCAAGAGCGGAGCAACGAA | 637 |
| AXIN1 | 8312 | CTGGATACCTGCCGACCTTAA | 638 |
| B3GALNT2 | 148789 | ATCGTTATTACCAGTCTTGGA | 639 |
| B4GALNT3 | 283358 | CACCGGTGACCCACACTTCAA | 640 |
| BFSP1 | 631 | CAAGATGATATCAGTGCGGCA | 641 |
| BPIL3 | 128859 | CCCGGACTTTCTGGCCATGAA | 642 |
| BRUNOL4 | 56853 | CCCGTCGACCATTCCCATGAA | 643 |
| BTK | 695 | CAGCTCGAAACTGTTTGGTAA | 644 |
| C11orf47 | 283294 | CAGAGGGTACAGCACAAGCAA | 645 |
| C14orf145 | 145508 | CTCGAAGGTTATTGAATCAAT | 646 |
| C14orf45 | 80127 | TTCCGTCTTCCAAGTTACCAA | 647 |
| C15orf15 | 51187 | CGGCATGATGTTCGTCCGCAA | 648 |
| C1orf216 | 127703 | CAGGCTGTGCAGCACTTACAA | 649 |
| C1orf63 | 57035 | CAGGCGCTACTCGCGGTCATA | 650 |
| C20orf19 | 55857 | AAGGCTCATACTCGAAACCAA | 651 |
| C2orf30 | 27248 | CTGCAAGTAGTTAAACTAGAA | 652 |
| C2orf49 | 79074 | CAGAACCATGACTTAACGCAT | 653 |
| C3orf54 | 389119 | CTCGGCTTGACAGCTTCCTTA | 654 |
| C3orf59 | 151963 | AAGGGCAAGTAACGTGTTCAT | 655 |
| C5 | 727 | GCCTGCGTTAATAATGATGAA | 656 |
| C5orf37 | 134359 | ATGAGCTCAGTTGTTGTGGAA | 657 |
| C6orf10 | 10665 | CTCGATCAAGTATTGGTAGTA | 658 |
| C8orf32 | 55093 | CCCTCTCAGACTTGAGCGTTA | 659 |
| C8orf76 | 84933 | TTGCTAATCATGGAGTATAAA | 660 |
| C9orf100 | 84904 | ACCGAGCGGCGCTACCAAGAA | 661 |
| CACNA1F | 778 | CTGGCCTGCACTGCTATACAA | 662 |
| CAMK4 | 814 | TTGCAAGTTAACACAACGTAA | 663 |
| CAP2 | 10486 | CAGGGTCTTAAAGGACTACAA | 664 |
| CARS2 | 79587 | CAGCACCAAGAGGGCCGTGAA | 665 |
| CASP1 | 834 | TACCTCTTCCCAGGACATTAA | 666 |
| CCDC85A | 114800 | TGGGAGTAACAGTTCACCCAA | 667 |
| CD160 | 11126 | CTCAGTTGATGTTCACCATAA | 668 |
| CD19 | 930 | CGGCCAGAGATATGTGGGTAA | 669 |
| CD47 | 961 | CACGATAAGTTTACTCCTCCA | 670 |
| CD5L | 922 | CCCTTTGACTTGAGACTAGTA | 671 |
| CD68 | 968 | CACGGTTCATCCAACAAGCAA | 672 |
| CD8B | 926 | CAGCAATACTACAACCTCACA | 673 |
| CDK2 | 1017 | CACGTTAGATTTGCCGTACCA | 674 |
| CDKN1B | 1027 | ACCGACGATTCTTCTACTCAA | 675 |
| CENPE | 1062 | CACGATACTGTTAACATGAAT | 676 |
| CENPE | 1062 | CAGGTTAATCCTACCACACAA | 677 |
| CENPO | 79172 | CTCCGGATACATCACCATTCA | 678 |
| CEP72 | 55722 | CCCGCAGTTGGTACAGTACCA | 679 |
| CHAC2 | 494143 | CCCGGCAAGCCTGGAAGAGTT | 680 |
| CIR | 9541 | CAGTAGTGAGAGTGAGAGTAA | 681 |
| CIRH1A | 84916 | CTCTATCGGCTGAATTATGAA | 682 |
| CKAP5 | 9793 | AAGGGTCGACTCAATGATTCA | 683 |
| CLIP2 | 7461 | CACGGAGACCTCTTCACGCTA | 684 |
| CMKLR1 | 1240 | CAGCCTTGGACTAGCAATTTA | 685 |
| CNOT7 | 29883 | CAGCGGCAACTGTAGATCATA | 686 |
| CNR1 | 1268 | TTCCATAGTTTAGGTACTCAA | 687 |
| CNTF | 1270 | GACCAGTATAGACAGAAGTAA | 688 |
| CNTF | 1270 | GACCAGTATAGACAGAAGTAA | 689 |
| CNTN6 | 27255 | TACAAGATTCTGTACCGGCAA | 690 |
| CPLX3 | 594855 | TCCGCGAAACCTAGTGCTGAA | 691 |
| CPN E7 | 27132 | CCCGGTGTGGGAGGCCTTCAA | 692 |
| CRYGC | 1420 | GCGGAGAGTGGTGGATTTGTA | 693 |

TABLE II-continued

List of genes increasing gene targeting

| Gene Name | GENE ID | Target Sequence | SEQ ID |
|---|---|---|---|
| CTRB1 | 1504 | CAGCATTCTGACCGTGAACAA | 694 |
| CYP2A13 | 1553 | CCAGCACTTCCTGGATAAGAA | 695 |
| DAD1 | 1603 | CAGATTTGACACTTACTGCTA | 696 |
| DAGLB | 221955 | CAGGACAGTTGTAAACGGCAT | 697 |
| DCUN1D3 | 123879 | TGCACCCATGTTGTCACTTAA | 698 |
| DDR2 | 4921 | CCGGTTCATTCCAGTCACCGA | 699 |
| DFFB | 1677 | ACGGGTCAGTAGGGATAAGAA | 700 |
| DHDDS | 79947 | AAGAACTATGTCATGGATCAA | 701 |
| DHRS4 | 10901 | ACCCTGCGGATAAGAAGGTTA | 702 |
| DHX32 | 55760 | ATGGATCAGGTAACTACTTAA | 703 |
| DHX8 | 1659 | CTCCCTAAGGTGGATGATGAA | 704 |
| DHX8 | 1659 | CGCGATCATCATGTTGGACGA | 705 |
| DIS3 | 22894 | CAGGTAGAGTTGTAGGAATAA | 706 |
| DIS3L | 115752 | TACGGTCTTGCATTAGATAAA | 707 |
| DMBT1 | 1755 | TCCGTGTACCTGCGTTGTAAA | 708 |
| DNAH3 | 55567 | CAGGGCTGAACTGCCCGACAA | 709 |
| DPH1 | 1801 | CCCTCTCAGGAGAGTGTGCAA | 710 |
| E2F1 | 1869 | CAGATGGTTATGGTGATCAAA | 711 |
| E2F6 | 1876 | AATGTTGAGATTACTTACGAA | 712 |
| EFHA1 | 221154 | TCGAGGTTTATGGGTACCACA | 713 |
| EGLN1 | 54583 | CAGATGAGAGAGCACGAGCTA | 714 |
| EID2B | 126272 | TCCGGTCAGATTACTACGGGA | 715 |
| ELOVL7 | 79993 | GACGGAGATCCATGTGATAAA | 716 |
| ELP2 | 55250 | CAGGTTCGAGTAGGTGAAGTA | 717 |
| ENTPD7 | 57089 | ATGTACCAAGTCTTACATGAA | 718 |
| EPDR1 | 54749 | CAGGACTAGAGTTCCCTCGTA | 719 |
| EPHB3 | 2049 | CCGCAGCTGACCGCCAGATTA | 720 |
| EPS8L3 | 79574 | CAGCTTAGACACCTCCAAGAA | 721 |
| ESF1 | 51575 | CTGGGATAGATTAAAGGCAAA | 722 |
| ESPL1 | 9700 | CTCCAGGAAGATCGTTTCCTA | 723 |
| ESSPL | 345062 | CAGCCTACACTTTGACCACAA | 724 |
| EVI5L | 115704 | CCCGTTGTCTCTGCTGAATCA | 725 |
| EXOC3 | 11336 | CAGGCGCATACTTGACCGGAA | 726 |
| FAM105B | 90268 | AAGCGGAAGCATACGGGAATA | 727 |
| FAM120B | 84498 | ACCTCGCAGCTTGTAAATCTA | 728 |
| FAM13A1 | 10144 | AAGGAGCAGGATGAAGTTCGA | 729 |
| FAM80B | 57494 | CTGCGGATCAATGGAGAGCTA | 730 |
| FANCB | 2187 | CCGGCTATGCCCTGAATTCAA | 731 |
| FCF1 | 51077 | ACTGCTTAGTACAGAGAGTAA | 732 |
| FEN1 | 2237 | TAAGTCCATTGTTACATGAAA | 733 |
| FEZF2 | 55079 | AACACGGAATATATACATATA | 734 |
| FFAR3 | 2865 | GTGGATCATCAGAGACATTTA | 735 |
| FLCN | 201163 | CCGGGATATATCAGCCATGAT | 736 |
| FLJ20254 | 54867 | CCCGATTCCGTGAATCAGCTA | 737 |
| FLT3LG | 2323 | CTCCTCCGACTTCGCTGTCAA | 738 |
| FOXN1 | 8456 | CAGCGTTTGCCTGGTCTGGAA | 739 |
| FTH1 | 2495 | TTGGGATGAATCAGAAATCTA | 740 |
| FTH1 | 2495 | CGCCATCAACCGCCAGATCAA | 741 |
| FZR1 | 51343 | CGGGTCGATCTTCCACATTCA | 742 |
| GAB3 | 139716 | TTCTGCGATGTTCAACTGGAA | 743 |
| GABRD | 2563 | CACCTTCATCGTGAACGCCAA | 744 |
| GALNS | 2588 | CAGGGCCATTGATGGCCTCAA | 745 |
| GALNT8 | 26290 | CTCGATTGTTGAAGGAAATCA | 746 |
| GBP1 | 2633 | ATGGGACACTTTAGACCATTA | 747 |
| GDNF | 2668 | AGGCTGGTGAGTGACAAAGTA | 748 |
| GINS1 | 9837 | CGCTGTAGGACTAGAACGAAA | 749 |
| GMFG | 9535 | CAGCTACAAGTACGTGCATGA | 750 |
| GNB2L1 | 10399 | CCCGCAGTTCCCGGACATGAT | 751 |
| GPIHBP1 | 338328 | CCAGATGACTACGACGAGGAA | 752 |
| GPR152 | 390212 | CAAATGGACACTACCATGGAA | 753 |
| GPR39 | 2863 | CGGGCAGTGACTGCTCCCAAA | 754 |
| GPR92 | 57121 | CCGGAGGTGAATGCCATGCCA | 755 |
| GRIA3 | 2892 | AGCGAATAAGAGAGAGAGTAA | 756 |
| GRIK3 | 2899 | CCGGATCGGAGGAATCTTCGA | 757 |
| GRIN2C | 2905 | CTGGACGAGATCAGCAGGGTA | 758 |
| GRK1 | 6011 | CCAGATGAAGGCGACCGGCAA | 759 |
| GRK4 | 2868 | CAGGATGTTACTCACCAAGAA | 760 |
| GZF1 | 64412 | CGGACGGACATTCACCGACAA | 761 |
| HEMGN | 55363 | TAACGAAATTATTGTGCCTAA | 762 |
| HIAT1 | 64645 | ACGGCTTAATTCAAGGAGTAA | 763 |
| HSD17B8 | 7923 | CAGGAATGCTGAATATGGGAA | 764 |
| HSPA5 | 3309 | CAAGCCCAATACAGCCATTAA | 765 |
| HTATIP | 10524 | CTGATCGAGTTCAGCTATGAA | 766 |
| ID3 | 3399 | TCCGGAACTTGTCATCTCCAA | 767 |
| IFNB1 | 3456 | CAAGGACAGGATGAACTTTGA | 768 |

TABLE II-continued

List of genes increasing gene targeting

| Gene Name | GENE ID | Target Sequence | SEQ ID |
|---|---|---|---|
| IHH | 3549 | CCGCCTGAACTCGCTGGCTAT | 769 |
| IL17B | 27190 | TTGCACCTTTGTGCCAAGAAA | 770 |
| INSL4 | 3641 | ATCCATTCTGTTGTGAAGTAA | 771 |
| INTS6 | 26512 | CGCGGTAGAGACCTTCATGAA | 772 |
| ITK | 3702 | CAGGACTTTAGTAGAGACTGA | 773 |
| KCNIP1 | 30820 | TCCAGAAACGAGGACCAATAA | 774 |
| KCNK3 | 3777 | CGCCGACGTGTCCATGGCCAA | 775 |
| KCNQ4 | 9132 | CGGGCATCTCTGAGACTCAAA | 776 |
| KCNQ4 | 9132 | CGGGCATCTCTGAGACTCAAA | 777 |
| KHDRBS3 | 10656 | CTGCGCCTGGTGAACCAAGAA | 778 |
| KIAA0391 | 9692 | CTCGTGGCACATACCATATGA | 779 |
| KIAA1683 | 80726 | CCCAGTGAGTTTGGACGCAAA | 780 |
| KIAA1797 | 54914 | GTCGTCGTATCTAGACATGAA | 781 |
| KLF5 | 688 | CAGTATCAACATGAACGTCTT | 782 |
| KLK14 | 43847 | CCCGGATGAGGTGTGCCAGAA | 783 |
| KLKB1 | 3818 | CGCTATAAAGGTGCTGAGTAA | 784 |
| KRTAP10-10 | 353333 | CTGCTCTAAGTCCGTCTGCTA | 785 |
| KRTAP5-8 | 57830 | CCCAATTTGCTGCCAGTGCAA | 786 |
| L3MBTL4 | 91133 | CTGCCCGTATTCAGACATGAA | 787 |
| LINS1 | 55180 | AACCCGGATATTGTCTGTCAA | 788 |
| LMO2 | 4005 | CAGCCCATCCATAGTAACTGA | 789 |
| LOC374443 | 374443 | CCCATCGCATTTGGAAATGGA | 790 |
| LOC400301 | 400301 | CTGCTGGGATGAAGACATGAA | 791 |
| LOC400804 | 400804 | CTCTGCGTCTATTAAGAACAA | 792 |
| LOC402641 | 402641 | ATCCAACTGACAAGACCTTAA | 793 |
| LOC729747 | 729747 | AAGGATCTTCGAATACATGAA | 794 |
| LOC790955 | 790955 | CCGGACCGAGATACCATGCCA | 795 |
| LONRF1 | 91694 | CAACTAGGATTTAGACCACTA | 796 |
| LOXL2 | 4017 | CCGGAGTTGCCTGCTCAGAAA | 797 |
| LTB4R | 1241 | AAGGCCCATGGTCAGATTGAA | 798 |
| MAD2L1BP | 9587 | CTGGGTCAGGCATTTCTATTA | 799 |
| MARCH2 | 51257 | CACGCTGGGTGCCGTGCATAA | 800 |
| MAT1A | 4143 | TTGGCTCACACTCGACATGAA | 801 |
| MED16 | 10025 | CACCCGGATCCTGGCCATGAA | 802 |
| METTL10 | 399818 | CAGCGGATACATGCACAAAGAT | 803 |
| METTL5 | 29081 | AAGAAATCAGTGGACATTGAA | 804 |
| MGLL | 11343 | AAGACAGAGGTCGACATTTAT | 805 |
| MIST | 116449 | TGGTCCGAGATTGTTCCACAA | 806 |
| MMP14 | 4323 | TGGCGGGTGAGGAATAACCAA | 807 |
| MMP3 | 4314 | AGGGATTGACTCAAAGATTGA | 808 |
| MMP7 | 4316 | ACCCATTTGATGGGCCAGGAA | 809 |
| MOBKL3 | 25843 | CACAATGGTAAGGCACATAAA | 810 |
| MPHOSPH1 | 9585 | CACAAGGTGTTACTTGCTATA | 811 |
| MRPS17 | 51373 | CAGGCTTGTTCTGGATCCCTA | 812 |
| MSH5 | 4439 | CCCGGGACTATGGCTACTCAA | 813 |
| MSH5 | 4439 | CCCGGGACTATGGCTACTCAA | 814 |
| MSLN | 10232 | CTGGACGTCCTAAAGCATAAA | 815 |
| MYBBP1A | 10514 | CCACTCGTTCTTTGTCACAAA | 816 |
| MYOZ3 | 91977 | TAGCCGGATGAACTTGAGCAA | 817 |
| MYST3 | 7994 | TGGGCGAATAGCACTTCCTAA | 818 |
| MYST3 | 7994 | TGGGCGAATAGCACTTCCTAA | 819 |
| NDRG1 | 10397 | AACGTGAACCCTTGTGCGGAA | 820 |
| NDST2 | 8509 | CTGCCTGGACCTTGACCGCTA | 821 |
| NEFH | 4744 | AAGAAGGAACCTGCTGTCGAA | 822 |
| NLGN4Y | 22829 | CACCTAGTCCCTTATGTATCA | 823 |
| NRGN | 4900 | AACAATAAAGAGGAATGTCCA | 824 |
| NUDCD1 | 84955 | AAGCGTGATATTCTCCGTGGA | 825 |
| NUDT6 | 11162 | CACGCAGAATCGGATTCATCA | 826 |
| OBFC1 | 79991 | TCAGCTTAACCTCACAACTTA | 827 |
| OGDH | 4967 | CAGGATCAATCGTGTCACCGA | 828 |
| OGDH | 4967 | GAGAAGCGCTTTGGTCTAGAA | 829 |
| ONECUT3 | 390874 | CGCCACGCCACTTTCTCCAA | 830 |
| OR2B2 | 81697 | CTGGATTAGTGGCTTTAGCAA | 831 |
| OR5AS1 | 219447 | ATGAATGGTATTTAAATCGTT | 832 |
| OR6C3 | 254786 | TCACGTATATATTAAGTGTTA | 833 |
| OR6C3 | 254786 | TCCCGTCTGCCAGTCAAAGAA | 834 |
| OR6F1 | 343169 | ACGCTTCGTAATAAGGAAGTA | 835 |
| ORC4L | 5000 | CAGTCGTAAATCAAAGAGTAA | 836 |
| OSBPL11 | 114885 | CCAGGATCTCTTAATGCTCAA | 837 |
| PAPD5 | 64282 | TAGGTAGAATAATTAGAGTAA | 838 |
| PCGF3 | 10336 | CAGCAGCGTACGGCAGACGAA | 839 |
| PDCD11 | 22984 | CTGCATTGTGAAGTTCTACAA | 840 |
| PDE11A | 50940 | TCGGATGGTTCTATACCACAA | 841 |
| PDE6B | 5158 | CACGCTGCTCATGACCGGCAA | 842 |
| PDLIM5 | 10611 | CTCTGACAATCTCTAGTCTAA | 843 |

TABLE II-continued

List of genes increasing gene targeting

| Gene Name | GENE ID | Target Sequence | SEQ ID |
|---|---|---|---|
| PER1 | 5187 | CCCGGACTCTCCACTGTTCAA | 844 |
| PFKFB2 | 5208 | CCAGAGCAAGATAGTCTACTA | 845 |
| PFKFB4 | 5210 | ACGGAGAGCGACCATCTTTAA | 846 |
| PHOX2B | 8929 | TACGCCGCAGTTCCTTACAAA | 847 |
| PLCE1 | 51196 | CCGCGGTACAATTCCCAAGAA | 848 |
| PLEKHG2 | 64857 | CAGGTTCAGCCAGACCCTCAA | 849 |
| PLEKHG7 | 440107 | CACCGCTTTGGGATAGAGATA | 850 |
| PLOD3 | 8985 | CACCGTGGACATCCACATGAA | 851 |
| PNPLA6 | 10908 | CCGGCGGTCTACAGACCTTAA | 852 |
| PRCC | 5546 | CGCCGTCAGACCCAAGCCAAA | 853 |
| PRIMA1 | 145270 | CCCTGCCGGCCTAGTATTTGA | 854 |
| PRL | 5617 | CAGCGAATTCGATAAACGGTA | 855 |
| PROKR1 | 10887 | CCGCTACAAGAAACTGCGCAA | 856 |
| PRPH2 | 5961 | GAGGAGCGATGTGATGAATAA | 857 |
| PSD3 | 23362 | AAGGACGTCGATGAGTACAAA | 858 |
| PSMD1 | 5707 | CAGTTTCGGAATAAAGTACTA | 859 |
| PSMD1 | 5707 | AAAGACCATACTGGAGTCGAA | 860 |
| PTGES | 9536 | TTGGGTGACCAGCCACTCAAA | 861 |
| PTGIS | 5740 | CTCGAGAGTATCCTTTGGCAA | 862 |
| PUS10 | 150962 | TGCGCTGTTCTTGAAATTGAA | 863 |
| RAB17 | 64284 | AAGTGAGATCCTGGAAGTGAA | 864 |
| RAB34 | 83871 | CCGCGTAATCGTAGGAACTAT | 865 |
| RABL2B | 11158 | CAGGACTTCATGGATGAGATT | 866 |
| RAET1E | 135250 | AGCGCAGGTCTTCTTGAATAA | 867 |
| REPS2 | 9185 | CCCGGTACGGATAGAGAGTAT | 868 |
| RFC1 | 5981 | TTGGAGTAATACCAAGTGGAA | 869 |
| RGL4 | 266747 | CCCGGACGACCTGGATGGCAA | 870 |
| RHEB | 6009 | CAGGGCTATTTCTAATACGTA | 871 |
| RNF111 | 54778 | CAGGCAAGGTTAGCTGCTTTA | 872 |
| RNF128 | 79589 | CAGGGCCTAGTTTCTATTAAT | 873 |
| RPL27 | 6155 | CACAAGGTACTCTGTGGATAT | 874 |
| RPL32P3 | 132241 | CCCGGCCTGAGTGAGTCTTAA | 875 |
| RPL35 | 11224 | CCGTGTTCTCACAGTTATTAA | 876 |
| RPL36 | 25873 | CGGGAGGAGCTGAGCAACGTA | 877 |
| RPS12 | 6206 | TGGAGGTGTAATGGACGTTAA | 878 |
| RPS19 | 6223 | TACCGTCAAGCTGGCCAAGCA | 879 |
| RPS6 | 6194 | AAGAAGCAGCGTACCAAGAAA | 880 |
| RPS6KB1 | 6198 | CACCTGCGTATGAATCTATGA | 881 |
| RPS7 | 6201 | TTCGAGCGCCAAGATCGTGAA | 882 |
| RTN3 | 10313 | CAGGATCTACAAGTCCGTCAT | 883 |
| SBF2 | 81846 | AACCGTGGACCTTAAAGAAGA | 884 |
| SCNN1A | 6337 | CCCGATGTATGGAAACTGCTA | 885 |
| SEC22A | 26984 | TGGCTTAATCTGTCTATGCAA | 886 |
| SELPLG | 6404 | ATGGAGATACAGACCACTCAA | 887 |
| SEMA6C | 10500 | CCGCGTAGCCCGAGTATGTAA | 888 |
| SEMA6D | 80031 | CACGGCCTTGCCGAAGCTTAT | 889 |
| SEPT12 | 124404 | CTGGGCTACATCAACGAGCAA | 890 |
| SERINC4 | 619189 | CACCAGATATCTCTCTAGCAA | 891 |
| SGEF | 26084 | TCCGAAGTATGAAGTCTGCAA | 892 |
| SH3RF2 | 153769 | CCCGATGAGCTGGACCTGCAA | 893 |
| SHBG | 6462 | CAGGCAGAATTCAATCTCCGA | 894 |
| SHFM1 | 7979 | GACAGTCGAGATGTCAGAGAA | 895 |
| SIGLEC9 | 27180 | CAGGCTTTAGAGTCAAAGTAT | 896 |
| SIPA1L2 | 57568 | CAGACCGACCTTCGGAAGGAA | 897 |
| SIVA1 | 10572 | CACGCCGTGCATGGCAGCCTT | 898 |
| SLAMF6 | 114836 | CTCCATTGTTTGAGCCAAGAA | 899 |
| SLAMF9 | 89886 | CAGGCATGGATATGACCTACA | 900 |
| SLC17A6 | 57084 | CTGCCATACTTCTTACCTCTA | 901 |
| SLC25A36 | 55186 | CCGGACCTCTTCATTGCCTAA | 902 |
| SLC30A8 | 169026 | AACACTATCTGTGGAGAGTAA | 903 |
| SLC47A2 | 146802 | CACCACGGTCTGCCCTGCAAA | 904 |
| SLCO4C1 | 353189 | ATGATTGTTAAGTAAGCTTGA | 905 |
| SLU7 | 10569 | AAGACTATGTGGAGTACTCAA | 906 |
| SMARCC1 | 6599 | CAGCGGATTTCAACCAAGAAT | 907 |
| SMCR8 | 140775 | CTCGTAGGTGTTGCTGCACAA | 908 |
| SMEK2 | 57223 | TACCATCTATATTGCGTAGTA | 909 |
| SNRPE | 6635 | TACCCTCGTGTTACTACAAGA | 910 |
| SNX29 | 92017 | TGGCGAGCTGATTGAGTTCAA | 911 |
| SOX21 | 11166 | CTGCTCGACCTGGGCTCCAAA | 912 |
| SPACA1 | 81833 | CAGCGAGACCGCGGAGAACTA | 913 |
| SPATA5L1 | 79029 | ACCCGGGAGATTTGACCGAGA | 914 |
| SPECC1L | 23384 | CCGGGTATACAATTACATGAA | 915 |
| SPEN | 23013 | CCGTGGATATGGTTCAACTT | 916 |
| SPSB2 | 84727 | CAAGGCTATGACAGTCTGCTA | 917 |
| SRP68 | 6730 | CAGAGAGATTATATCCTTGAA | 918 |

TABLE II-continued

List of genes increasing gene targeting

| Gene Name | GENE ID | Target Sequence | SEQ ID |
|---|---|---|---|
| SSR1 | 6745 | AAAGATTTGAACGGCAATGTA | 919 |
| ST8SIA4 | 7903 | CACCCAAGATGCGCTCCATTA | 920 |
| STX10 | 8677 | CAGAGAGATACTCGCAGGCAA | 921 |
| SULT1A2 | 6799 | CACGTCGTTCAAGGAGATGAA | 922 |
| SYDE1 | 85360 | CGCCGGCGAGATCTGGTACAA | 923 |
| SYN3 | 8224 | CACGCTCAAGACCCGCCCTTA | 924 |
| SYT14 | 255928 | TATGGTGTACATCGCATGAAA | 925 |
| TACR2 | 6865 | CGCGGTGATGTTTGTAGCCTA | 926 |
| TAF3 | 83860 | CAGCGGGATGTGCGAGAGTTA | 927 |
| TAF8 | 129685 | CAGAGGCTATACTCTTATAAT | 928 |
| TAF8 | 129685 | TCCCGTCGGCATTTGACGAAA | 929 |
| TBX15 | 6913 | AAGCGGTTCCATGATATTGGA | 930 |
| TCEB3B | 51224 | CTCGTTAGAGAGACAGACGAA | 931 |
| TFPI | 7035 | CAGCGACTTTAGGCTGGATAA | 932 |
| THOC4 | 10189 | CAGAGGTGGCATGACTAGAAA | 933 |
| TIAM1 | 7074 | AACGGAAATGGTAGAGTTTCA | 934 |
| TM2D2 | 83877 | ATGGCCGTGGATTGTAATACA | 935 |
| TM2D2 | 83877 | TTGGTGGTTTGTTGACCTTAT | 936 |
| TM4SF20 | 79853 | AAGCACGTTGTAAATGCATAA | 937 |
| TMBIM4 | 51643 | TAGTAGAGTCTTTACCATTAT | 938 |
| TMEM16J | 338440 | CCCTCAGTCGGTGAAGAACAA | 939 |
| TMEM24 | 9854 | AGCCGGAGCTGACCCTCAAA | 940 |
| TNNC2 | 7125 | CAGCGGCACCATCGACTTCGA | 941 |
| TNS4 | 84951 | CAGCAATGACCTCATCCGACA | 942 |
| TOB2 | 10766 | TGGGTCGCAAGTCCTTATTTA | 943 |
| TOR1B | 27348 | CGGGATCATTGACGCAATCAA | 944 |
| TRIM17 | 51127 | CAGGGACAACGTGAGCCGGAA | 945 |
| TRIM17 | 51127 | CCCGGACAGATTGAAGTGCTA | 946 |
| TRIM61 | 391712 | CAGCTGGGTAGTTTGACTGAA | 947 |
| TRPV5 | 56302 | CCCGGGAGCCAACTCCAGAAA | 948 |
| TTPA | 7274 | ACGTATTTCGAGTAAGTCTAA | 949 |
| TUG1 | 55000 | CACCGTGAGGACTACAGTCAA | 950 |
| UPK3B | 80761 | CCCGGAGACACTGGCTGACAT | 951 |
| USP43 | 124739 | CTCCGTCGAGTTGGTGGAGTA | 952 |
| VAMP4 | 8674 | TGGAACGTTGAGAATGTCCAA | 953 |
| VPRBP | 9730 | ACCGATGATTTAGATGAGCTT | 954 |
| VPS18 | 57617 | CCGGGTGCATTACGACCTCAA | 955 |
| WDFY2 | 115825 | TCCCTCACTCGTAACAATGAA | 956 |
| ZC3H18 | 124245 | CGGGCTCGAAGGCGTCGGAAA | 957 |
| ZNF10 | 7556 | ATCCGTGTAATGGAAGATTAT | 958 |
| ZNF254 | 9534 | AAGAATATAACAAATCTCCTA | 959 |
| ZNF26 | 7574 | CAGGAGACTTCGGATAATATA | 960 |
| ZNF277 | 11179 | TGGCTGCCATGTGAAGTTCAA | 961 |
| ZNF334 | 55713 | AACAACCGTTTGACTATAATA | 962 |
| ZNF438 | 220929 | CACCTTCGAGACCACATGAAT | 963 |
| ZNF503 | 84858 | CAAGTCGAGTTTCAAGCCGTA | 964 |
| ZNF697 | 90874 | CTGGTCTTTGTCGCCTAATTA | 965 |
| ZNF804B | 219578 | CACGACTCTATTGATGAGACA | 966 | iRNAs, DNA Polynucleotides and Vectors According to the Invention

In a second aspect, the present invention concerns specific interfering agents for modulating double-strand break-induced homologous recombination in a eukaryotic cell, wherein said interfering agents modulate effectors from the group listed in table I and II.

In a preferred embodiment of this second aspect, the present invention concerns specific polynucleotide derivatives identified for effector genes, which increase gene targeting efficiency and/or endonuclease-induced homologous recombination.

In a preferred embodiment of this aspect of the invention, these polynucleotide derivatives are interfering RNAs, more preferably siRNAs or shRNAs.

As indicated in the definitions hereabove, the siRNAs according to the invention are double-stranded RNAs, each RNA of the duplex comprising for example between 17 and 29 nucleotides, e.g. 17, 18, 19, 20, 21, 22, 23, 24, 25, 26, 27, 28 or 29 nucleotides.

Such siRNAs can be formed from two RNA molecules that hybridize together or can alternatively be generated from a single RNA molecule that includes a self-hybridizing portion, referred to as shRNAs. The duplex portion of a siRNA can include one or more unpaired and/or mismatched nucleotides in one or both strand of the duplex (bulges) or can contain one or more noncomplementary nucleotides pairs. Duplex of a siRNA is composed of a sense strand and of an antisense strand. Given a target transcript, only one strand of the siRNA duplex is supposed to hybridize with one strand of said target transcript. In certain embodiments, one strand (either sense, either antisense) is perfectly complementary with a region of the target transcript, either on the entire length of the considered siRNA strand (comprised between 17 and 29 nucleotides, including 17, 18, 19, 20, 21, 22, 23, 24, 25, 26, 27, 28, and 29 nucleotides), either on only a part of the considered siRNA strand, 17 to 29 or 19 to 29 nucleotides matching for example, or 18, 19, 20, 21, 22, 23, 24, 25, 26, 27, 28 from 29 nucleotides. In one embodiment it is intended that the considered strand of the siRNA duplex (either sense, either antisense) hybridizes the target transcript without a single mismatch over that length. In another embodiment, one or more mismatches between the considered strand of the siRNA duplex (either sense, either antisense) can exist.

Therefore, an aspect of the invention is drawn to an interfering RNA for increasing gene targeting efficiency and/or endonuclease-induced homologous recombination in a eukaryotic cell, wherein said interfering RNA comprises a sense RNA nucleic acid and an antisense RNA nucleic acid, and wherein said interfering RNA down-regulates the expression (most preferably silences the expression) of a gene selected from the group of genes listed in Table I. It is understood that genes equivalent to those listed in Table I in other eukaryotic species, listed in the above paragraph "definitions" are comprised in the scope of the present invention.

Preferably, said interfering RNA down-regulates the expression of a gene selected from the group of genes listed in Tables III and IV.

More preferably, the interfering RNA according to the invention targets a sequence selected from the group consisting of SEQ ID Nos. 13-611. In other terms, one strand of this iRNA (either sense, either antisense) comprises a sequence hybridizing to a sequence selected from the group consisting of SEQ ID Nos. 13-611, with or without mismatch. Preferably, there is no mismatch, meaning that one strand of this iRNA (either sense, either antisense) comprises or consists of the RNA sequence corresponding to a DNA sequence selected from the group consisting of SEQ ID Nos. 13-611.

More preferably, the interfering RNA according to the invention targets a sequence selected from the group consisting of SEQ ID Nos. 42, 197, 990, 991, 193, 992, 993, 994, 45, 382, 133, 309, 269, 169, 333, 571, 54, 73, 555, 42, 298, 344, 108, 100, 359, 264, 332, 166, 104, 330, 493, 456, 212, 581, 44, 508, 37, 117, 310, 138, 183, 378, 116, 306, 317, 537, 377, 177, 272, 130, 161, 213, 178, 510, 428, 438, 573, 300, 366, 229, 452, 611, 559, 602, 423, 598, 198 and SEQ ID Nos. 969-989.

In other terms, one strand of this iRNA (either sense, either antisense) comprises a sequence hybridizing to a sequence selected from the group consisting of SEQ ID 42, 197, 990, 991, 193, 992, 993, 994, 45, 382, 133, 309, 269, 169, 333, 571, 54, 73, 555, 42, 298, 344, 108, 100, 359, 264, 332, 166, 104, 330, 493, 456, 212, 581, 44, 508, 37, 117, 310, 138, 183, 378, 116, 306, 317, 537, 377, 177, 272, 130, 161, 213, 178, 510, 428, 438, 573, 300, 366, 229, 452, 611, 559, 602, 423, 598, 198 and SEQ ID Nos. 969-989 with or without mismatch. Preferably, there is no mismatch, meaning that one strand of this iRNA (either sense, either antisense) comprises or consists of the RNA sequence corresponding to a DNA sequence selected from the group consisting of SEQ ID Nos. 42, 197, 990, 991, 193, 992, 993, 994, 45, 382, 133, 309, 269, 169, 333, 571, 54, 73, 555, 42, 298, 344, 108, 100, 359, 264, 332, 166, 104, 330, 493, 456, 212, 581, 44, 508, 37, 117, 310, 138, 183, 378, 116, 306, 317, 537, 377, 177, 272, 130, 161, 213, 178, 510, 428, 438, 573, 300, 366, 229, 452, 611, 559, 602, 423, 598, 198 and SEQ ID Nos. 969-989.

In the iRNAs according to the invention, the sense RNA nucleic acid may for example have a length comprised between 19 and 29.

In the frame of the present invention, the interfering RNA according to the invention may further comprising a hairpin sequence, wherein the sense RNA nucleic acid and the antisense RNA nucleic acid are covalently linked by the hairpin sequence to produce a shRNA molecule.

In a specific embodiment, iRNAs targeting genes that are described in WO2007/013979, in WO2008/113847 and/or in Slabicki et al. may be excluded from the scope of the present invention. In particular, iRNAs down-regulating or silencing the G22P1 (Ku70 or hdfA), XRCC5 (Ku80), RAD50, MRE11, XRS2, LIFL, NEIL, SIR4, Ku86, PRKDC, LIG4 (DNA ligase IV), XRCC4, Rad51, BRCA1, SHFM1, DSBR1 and/or DCLRE1C (Artemis) gene, or a mammalian (in particular human) equivalent thereof, may be excluded from the scope of the present invention.

In a preferred embodiment according to the invention, the interfering RNA according to the invention as defined hereabove down-regulates the expression (most preferably silences the expression) of the EP300 gene. Indeed, as shown in Example 4, introducing such an iRNA in a eukaryotic cell leads to a two fold increase of the efficiency of targeted homologous recombination in the cell.

In a preferred embodiment, this iRNA down-regulating the expression of the EP300 gene comprises a sense RNA nucleic acid consisting of a sequence at least 70%, 75%, 80%, 85%, 90%, 95%, 99% or 100% identical to a fragment of at least 17 consecutive nucleotides of the sequence of SEQ ID No. 999. This fragment of at least 17 consecutive nucleotides of the sequence of SEQ ID No. 999 may for example include 17, 18, 19, 20, 21, 22, 23, 24, 25, 26, 27, 28, and 29 consecutive nucleotides of the sequence of SEQ ID No. 999.

The antisense RNA nucleic acid of such an iRNA may for example consist of a sequence at least 70%, 75%, 80%, 85%, 90%, 95%, 99% or 100% identical to a fragment complementary to at least 19 consecutive nucleotides of the sequence of SEQ ID No. 999. This fragment of at least 17 consecutive nucleotides of the sequence of SEQ ID No. 999 may for example include 17, 18, 19, 20, 21, 22, 23, 24, 25, 26, 27, 28, and 29 consecutive nucleotides of the sequence of SEQ ID No. 999.

The iRNA down-regulating the expression of the EP300 gene may for example target a sequence selected from the group consisting of SEQ ID No. 197, SEQ ID No. 198 and SEQ ID No. 985. In other terms, one strand of this iRNA (either sense, either antisense) comprises a sequence hybridizing to a sequence selected from the group consisting of SEQ ID No. 197, SEQ ID No. 198 and SEQ ID No. 985, with or without mismatch. Preferably, there is no mismatch, meaning that one strand of this iRNA (either sense, either antisense) comprises or consists of the RNA sequence corresponding to a DNA sequence selected from the group consisting of SEQ ID No. 197, SEQ ID No. 198 or SEQ ID No. 985.

In another preferred embodiment according to the invention, the interfering RNA according to the invention as defined hereabove down-regulates the expression (most preferably silences the expression) of the ATF7IP gene. Indeed, as shown in Example 4, introducing such an iRNA in a eukaryotic cell leads to a two fold increase of the efficiency of targeted homologous recombination in the cell.

In a preferred embodiment, this iRNA down-regulating the expression of the EP300 gene comprises a sense RNA nucleic acid consisting of a sequence at least 70%, 75%, 80%, 85%, 90%, 95%, 99% or 100% identical to a fragment of at least 17 consecutive nucleotides of the sequence of SEQ ID No. 998. This fragment of at least 17 consecutive nucleotides of the sequence of SEQ ID No. 998 may for example include 17, 18, 19, 20, 21, 22, 23, 24, 25, 26, 27, 28, and 29 consecutive nucleotides of the sequence of SEQ ID No. 998.

The antisense RNA nucleic acid of such an iRNA may for example consist of a sequence at least 70%, 75%, 80%, 85%, 90%, 95%, 99% or 100% identical to a fragment complementary to at least 19 consecutive nucleotides of the sequence of SEQ ID No. 998. This fragment of at least 17 consecutive nucleotides of the sequence of SEQ ID No. 998 may for example include 17, 18, 19, 20, 21, 22, 23, 24, 25, 26, 27, 28, and 29 consecutive nucleotides of the sequence of SEQ ID No. 998.

The iRNA down-regulating the expression of the ATF7IP gene may for example target a sequence selected from the group consisting of SEQ ID No. 42 or SEQ ID No. 986. In other terms, one strand of this iRNA (either sense, either antisense) comprises a sequence hybridizing to a sequence selected from the group consisting of SEQ ID No. 42 or SEQ ID No. 986, with or without mismatch. Preferably, there is no mismatch, meaning that one strand of this iRNA (either sense, either antisense) comprises or consists of the RNA sequence corresponding to a DNA sequence selected from the group consisting of SEQ ID No. 42 or SEQ ID No. 986.

The invention further pertains to viral vector for producing the interfering RNA according to the invention, wherein said viral vector comprises a polynucleotide sequence encoding the sense RNA nucleic acid of said interfering RNA and a polynucleotide sequence encoding the antisense RNA nucleic acid of said interfering RNA.

In such vectors, the polynucleotide sequence encoding the sense RNA nucleic acid may under the control of a first promoter, and the polynucleotide sequence encoding the antisense RNA nucleic acid may be under the control of a second promoter. These promoters may for example be selected from the group consisting of an inducible promoter, a tissue specific promoter and a RNA polymerase III promoter.

Alternatively, when the sense and the antisense nucleic acids are covalently linked by a hairpin sequence to produce a shRNA molecule, they are under the control of a single promoter.

Another aspect of the invention is drawn to an isolated DNA polynucleotide coding for the interfering RNA according to the invention, wherein said DNA polynucleotide comprises a polynucleotide sequence encoding the sense RNA nucleic acid of said interfering RNA and a polynucleotide sequence encoding the antisense RNA nucleic acid of said interfering RNA. In such a DNA polynucleotide, the sense and the antisense nucleic acids may be covalently linked by a hairpin sequence to produce a shRNA molecule upon transcription.

Still another aspect of the invention relates to a plasmidic vector comprising the DNA polynucleotide according to the invention.

Such a plasmidic vector preferably comprises a promoter, wherein the polynucleotide sequence encoding the sense RNA nucleic acid is under control of said promoter. Said promoter may for example be selected from the group consisting of an inducible promoter, a tissue specific promoter and a RNA polymerase III promoter Isolated Eukaryotic Cells According to the Invention Cells in which gene targeting efficiency is increased are useful for use in targeted insertion of transgenes into said cells.

The invention therefore relates to an isolated eukaryotic cell obtained and/or obtainable by the method according to the invention as defined in the above paragraph entitled "Methods according to the invention for increasing gene targeting efficiency and/or endonuclease-induced homologous recombination in a eukaryotic cell".

The invention further relates to an isolated eukaryotic cell, wherein said cell is stably transformed with at least one interfering RNA, viral vector, isolated DNA polynucleotide or plasmidic vector as defined in the above paragraph entitled "iRNAs, DNA polynucleotides and vectors according to the invention".

The eukaryotic cell can be any type of cell such as e.g. a CHO cell (for example a CHO-K1 or a CHO—S cell), a HEK293 cell, a Caco2 cell, an U2-OS cell, a NIH 3T3 cell, a NSO cell, a SP2 cell, and a DG44 cell taken as non limiting examples.

In a preferred embodiment, the cell is a cell suitable for production of recombinant proteins.

The eukaryotic cell is preferably an immortalized and/or a transformed cell, although primary cells are contemplated by the present invention, in particular in the frame of gene therapy.

Kits and Compositions According to the Invention

The invention further pertains to compositions and kits comprising the iRNAs, DNA polynucleotides, cDNAs, vectors and cells according to the invention described hereabove.

In this aspect of the invention, the present invention concerns a composition for modulating double-strand break-induced homologous recombination in a eukaryotic cell, wherein said composition comprises at least an interfering agent that modulate effectors from the group listed in table I and II.

In a preferred embodiment of this aspect of the invention, the invention pertains to a composition for increasing gene targeting efficiency and/or endonuclease-induced homologous recombination in a eukaryotic cell comprising at least one interfering RNA, viral vector, isolated DNA polynucleotide or plasmidic vector as defined in the above paragraph entitled "iRNAs, DNA polynucleotides and vectors according to the invention", and/or an isolated eukaryotic cell as defined in the above paragraph entitled "isolated eukaryotic cells according to the invention".

The composition preferably further comprises a carrier. The carrier can for example be a buffer, such as e.g. a buffer allowing storage of the iRNAs, DNA polynucleotides, vectors and cells according to the invention, or a pharmaceutically acceptable carrier.

In another aspect of the invention, the present invention concerns a kit for modulating double-strand break-induced homologous recombination in a eukaryotic cell, wherein said composition comprises at least an interfering agent that modulate effectors from the group listed in table I and II.

In a preferred embodiment of this aspect of the invention, the invention also pertains to a kit for increasing gene targeting efficiency and/or endonuclease-induced homologous recombination in a eukaryotic cell, wherein said kit comprises at least one interfering RNA, viral vector, isolated DNA polynucleotide or plasmidic vector as defined in the above paragraph entitled "iRNAs, DNA polynucleotides and vectors according to the invention", and/or an isolated eukaryotic cell as defined in the above paragraph entitled "isolated eukaryotic cells according to the invention".

The kit may further comprise instructions for use in increasing gene targeting efficiency and/or for use in increasing endonuclease-induced homologous recombination.

Uses According to the Invention

In a third aspect, the present invention concerns the uses of specific interfering agents for modulating double-strand break-induced homologous recombination in a eukaryotic cell, wherein said interfering agent modulates effectors from the group listed in table I and II.

In a preferred embodiment of this third aspect, the present invention concerns the uses of specific polynucleotide derivatives identified for effector genes, which increase gene targeting efficiency.

Indeed, the polynucleotides derivatives according to the invention, which include the iRNAs, DNA polynucleotides, cDNAs and vectors described hereabove, can be used to increase gene targeting efficiency and/or to increase endonuclease-induced homologous recombination in a eukaryotic cell. Indeed, upon transfection with the polynucleotides derivative, targeted endonuclease-induced insertion of a transgene will take place more efficiently in the transfected cell.

Therefore, an aspect of the invention is directed to an in vitro or ex vivo use of at least one interfering RNA, DNA polynucleotide, viral vector or plasmidic vector as defined in the above paragraph entitled "iRNAs, DNA polynucleotides and vectors according to the invention" for increasing gene targeting efficiency and/or endonuclease-induced homologous recombination in a eukaryotic cell, tissue or organ.

Modulating double-strand break-induced homologous recombination or increasing gene targeting efficiency is also useful in animal models, for which it is often desired to construct knock-in or knock-out animals, as a non limiting example.

Therefore, the invention relates to the use of specific interfering agents for modulating double-strand break-induced homologous recombination in a non-human model, wherein said interfering agent modulates effectors from the group listed in table I and II.

The invention also relates to the use of an interfering RNA according to the invention for increasing gene targeting efficiency and/or endonuclease-induced homologous recombination in a non-human animal model. The animal models thus obtained are also part of the invention.

It is further desirable to modulate double-strand break-induced homologous recombination or to increase gene targeting efficiency and/or endonuclease-induced homologous recombination in the frame of treatments by gene therapy.

Therefore, the invention further pertains to an interfering agent that modulates effectors from the group listed in table I and II or to an interfering RNA according to the invention for use as a medicament.

A preferred embodiment of the invention is drawn to an interfering agent or an interfering RNA according to the invention for use as an adjuvant in the treatment of a genetic disease by gene therapy.

As used herein, the term adjuvant refers to a compound administered in addition to the active principle aiming at treating the patient, said adjuvant increasing the efficiency of the treatment. In the present case, the interfering RNA increases the gene targeting efficiency and thus increases the efficiency of the treatment by gene therapy.

A genetic disorder is defined herein as an illness caused by abnormalities in a gene or a chromosome, and which can be cured by insertion of a functional copy of said abnormal gene (i.e. a transgene). Examples of genetic disorders include but are not limited to the Lesch-Nyhan syndrome, retinoblastoma, thalassaemia, the sickle cell disease, adenosine deaminase-deficiency, severe combined immune deficiency (SCID), Huntington's disease, adrenoleukodystrophy, the Angelman syndrome, the Canavan disease, the Celiac disease, the Charcot-Marie-Tooth disease, color blindness, Cystic fibrosis, the Down syndrome, Duchenne muscular dystrophy, Haemophilia, the Klinefelter's syndrome, Neurofibromatosis, Phenylketonuria, the Prader-Willi syndrome, the Sickle-cell disease, the Tay-Sachs disease and the Turner syndrome.

For a better understanding of the invention and to show how the same may be carried into effect, specific embodiments, methods and processes according to the present invention will now be shown by way of examples associated to referenced figures.

This workflow is divided in three steps. The first step identifies with a High Throughput Screening siRNA hits stimulating or inhibiting I-SceI induced gene targeting luciferase signal. The second step validates siRNA hits and new siRNA sequences targeting the same gene found as hit with a second screening measuring I-SceI induced gene targeting frequency. Finally step 3 validates siRNA hits by measuring their effect on Knock-In experiment at the endogenous RAG1 locus with an engineered meganuclease.

FIG. 2: I-SceI induced gene targeting model based on luciferase reporter system:

Panel A: I-SceI induced gene targeting substrate. The luciferase gene (Luc2) is inactive due to replacement of the first 22 base pair (bp) by a 24 bp I-SceI site (vertical black box).

Panel B: identification of the E2 clone harbouring a single copy of the gene targeting substrate by Southern blot after EcoRI digestion. Left panel shows hybridization with intronic sequence of EF1 alpha probe, star showing the endogenous intronic sequence of EF1 alpha which is also present in parental cell line GM00847. Right panel shows hybridization with Neo probe. Arrows represent single copy insertion of the gene targeting substrate.

FIG. 3: Characterization of E2 clone for gene targeting induction by I-SceI.

Panel A: plasmids created to perform I-SceI induced gene targeting assay: pCLS2067 has i) the first 22 bp of luciferase gene (horizontal hatched box) surrounded by 1 kb of homology, ii) an I-SceI induction cassette under the control of a CMV promoter. The pCLS2007 plasmid corresponds to pCLS2067 without I-SceI expression cassette.

Panel B: Luciferase signal induced in E2 clone

E2 clone was transfected with pCLS0002, pCLS2007 (repair matrix alone) or pCLS2067 (repair matrix and IScel induction). Luciferase activity was analyzed 72 hours post transfection.

Figure 4:
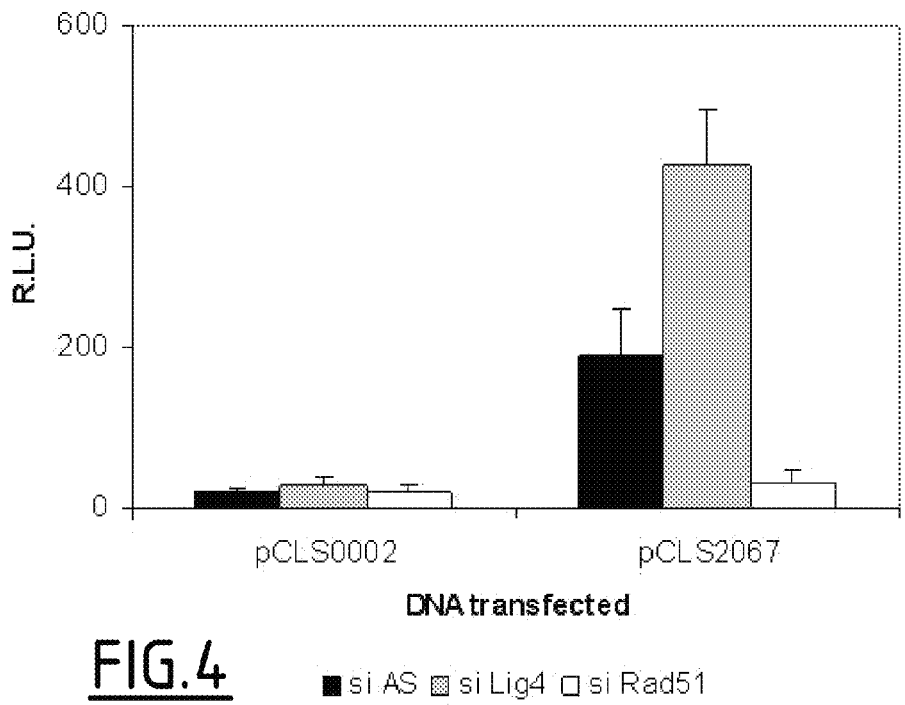

FIG. 4: Co-transfection of siRNA with DNA strategy validation.

E2 clone was co-transfected either with pCLS0002 or with pCLS2067 and with siRNAs known to modulate gene targeting: siRNA RAD51 and siRNA LIG4 and compared to co-transfection with a siRNA control All Star (AS). Luciferase activity was detected 72 hours post transfection.

Figure 5:
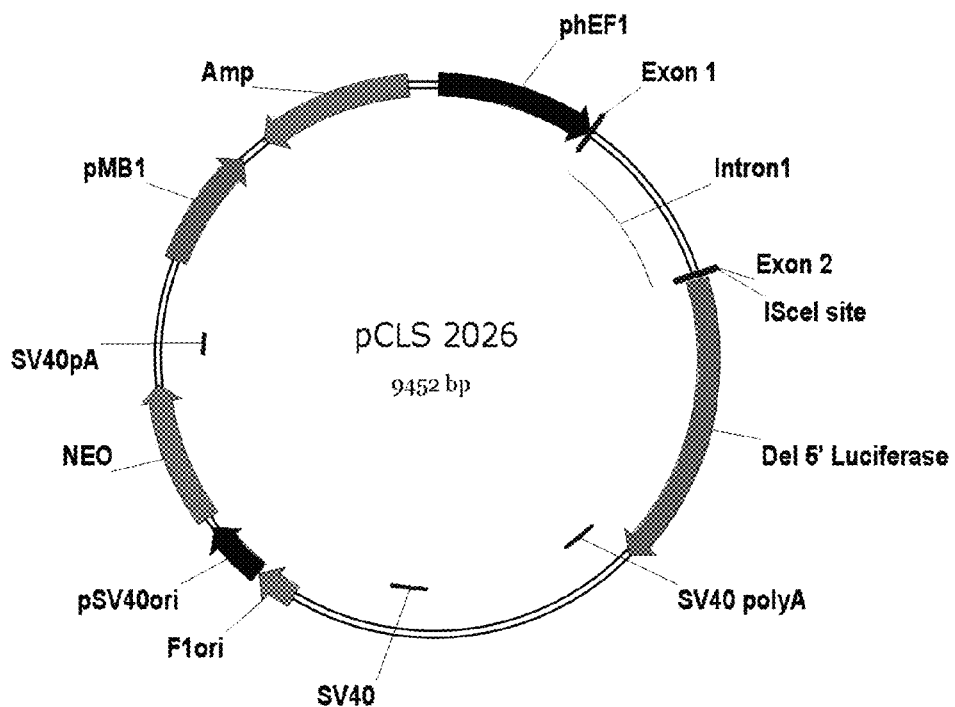
Figure 6:
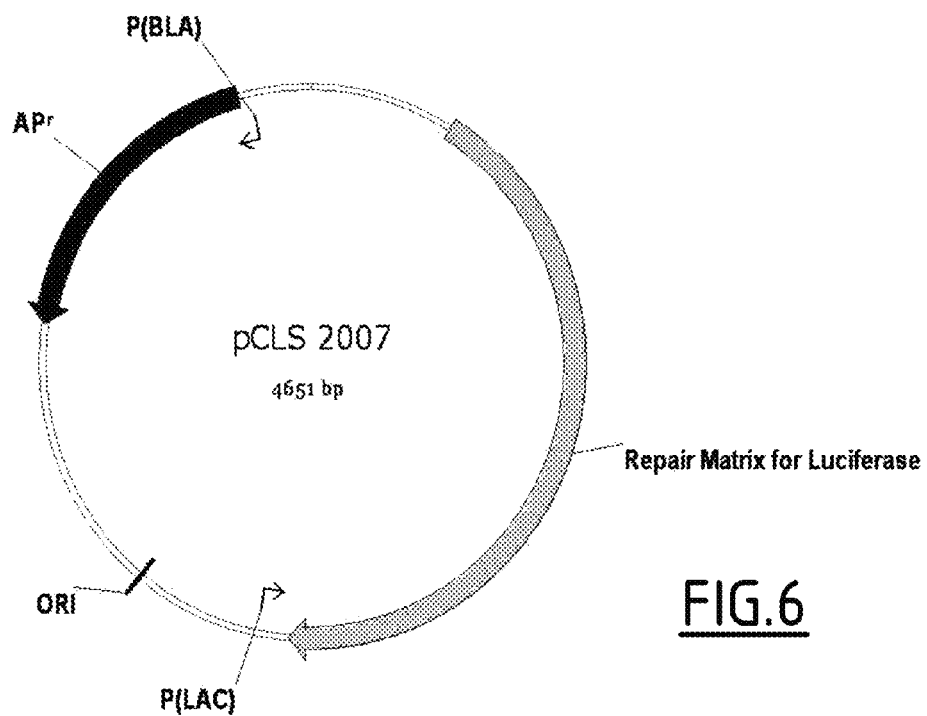
Figure 7:
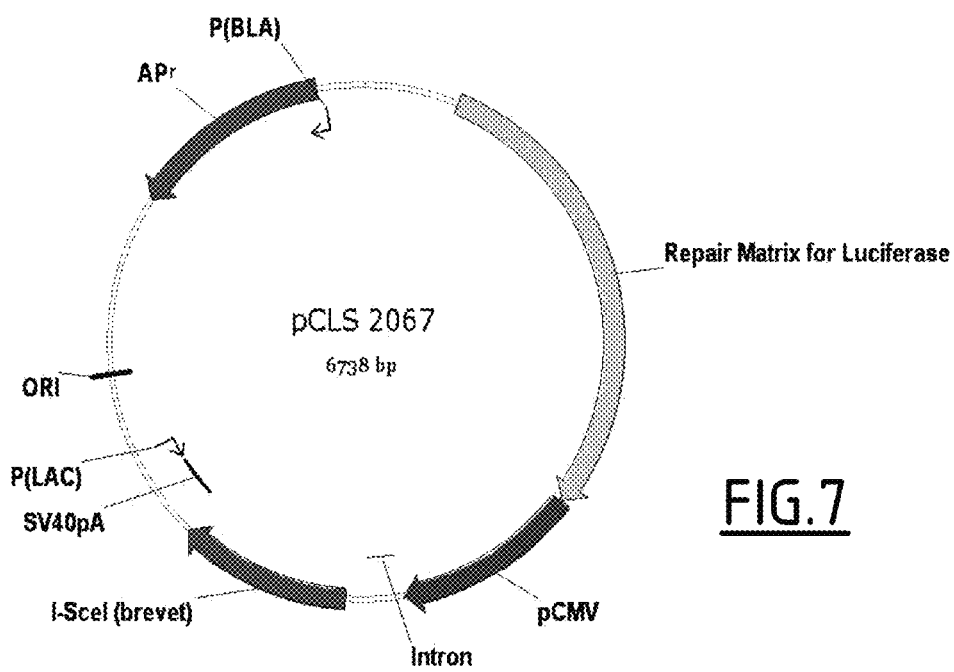
Figure 8:
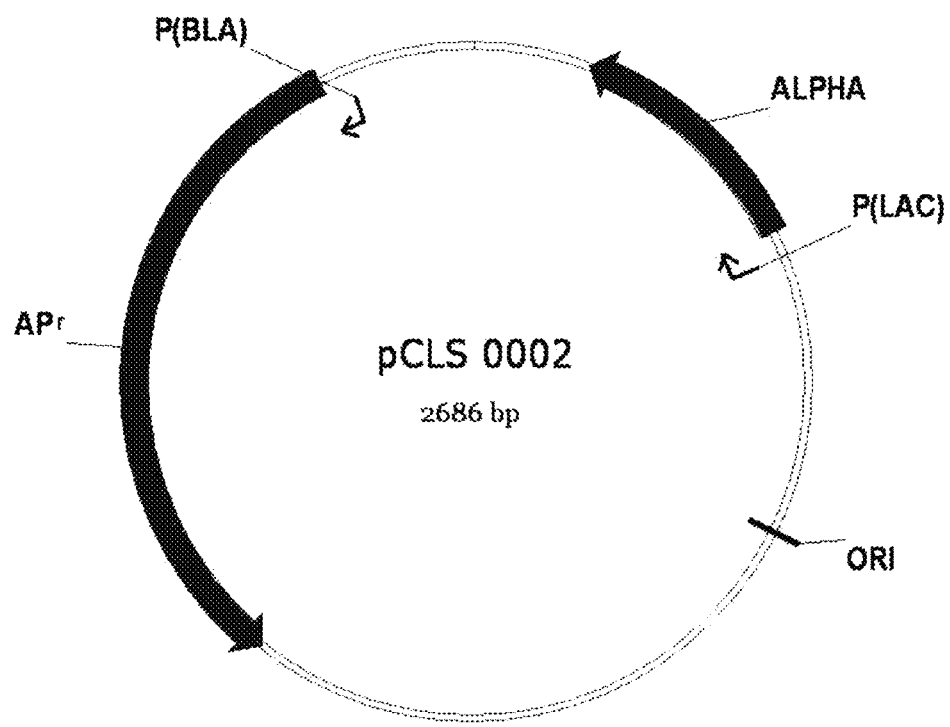

FIG. 5: Vector map of pCLS2026
FIG. 6: Vector map of pCLS2007
FIG. 7: Vector map of pCLS2067
FIG. 8: Vector map of pCLS0002
FIG. 9: Description of the process for the establishment of the HEK293 derived cellular model used for the validation of the siRNAs hits.

The structure of the cGPSHEK293 locus concerned for the targeted insertion at the I-CreI site is depicted. The vector used for gene targeting (pCLS2809) and the expression plasmid for I-CreI meganuclease (pCLS1088) are indicated. Repair plasmid used for induction of gene targeting by I-SceI (pCLS3496) is shown. The read-out of the reporter gene EGFP leading to quantification of the efficiency of gene targeting is explained.

Figure 10:
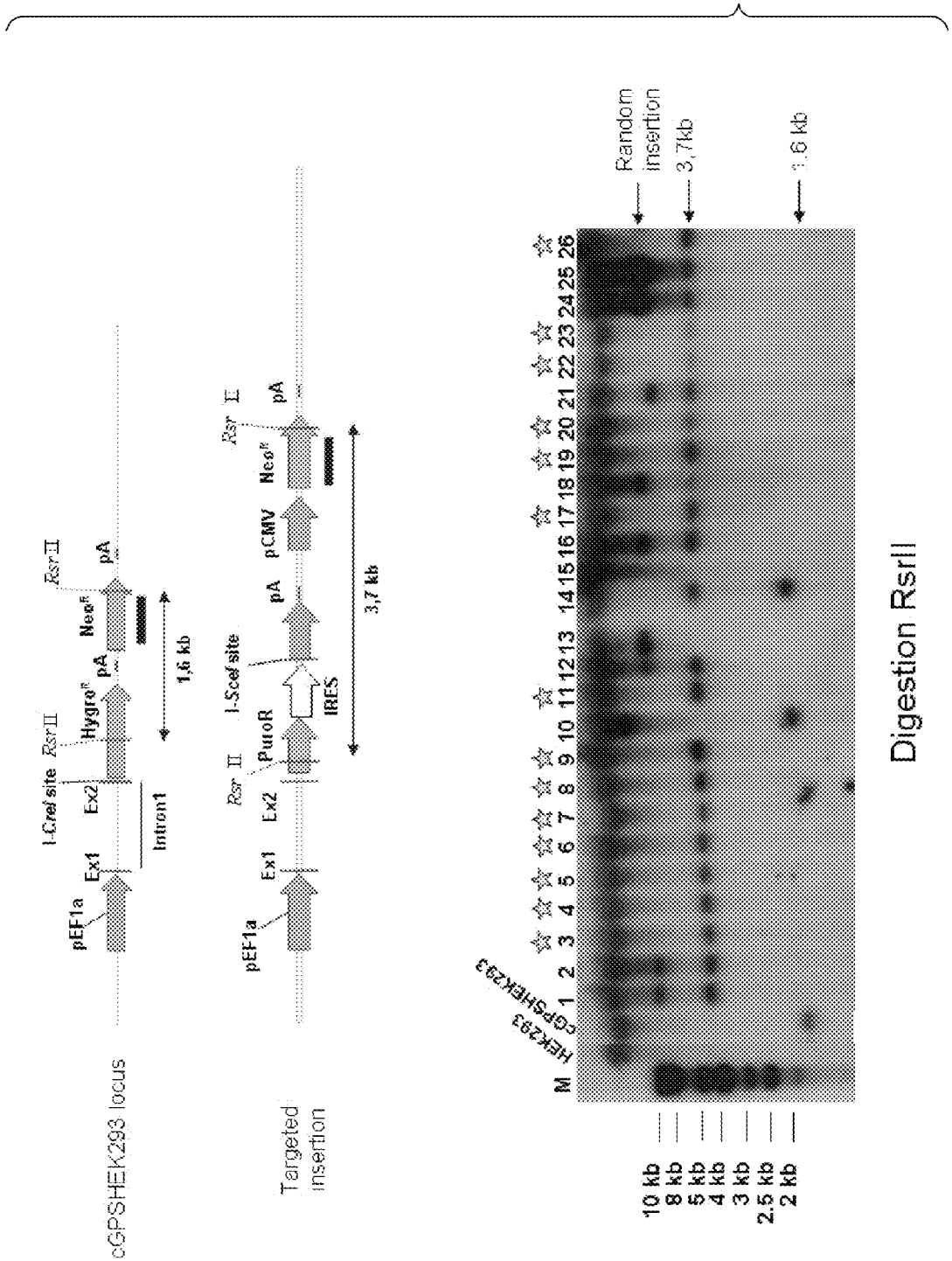

FIG. 10: Southern blot analysis of 26 clones selected after gene targeting experiment at the cGPSHEK293 locus with the pCLS2809 vector.

Figure 11:
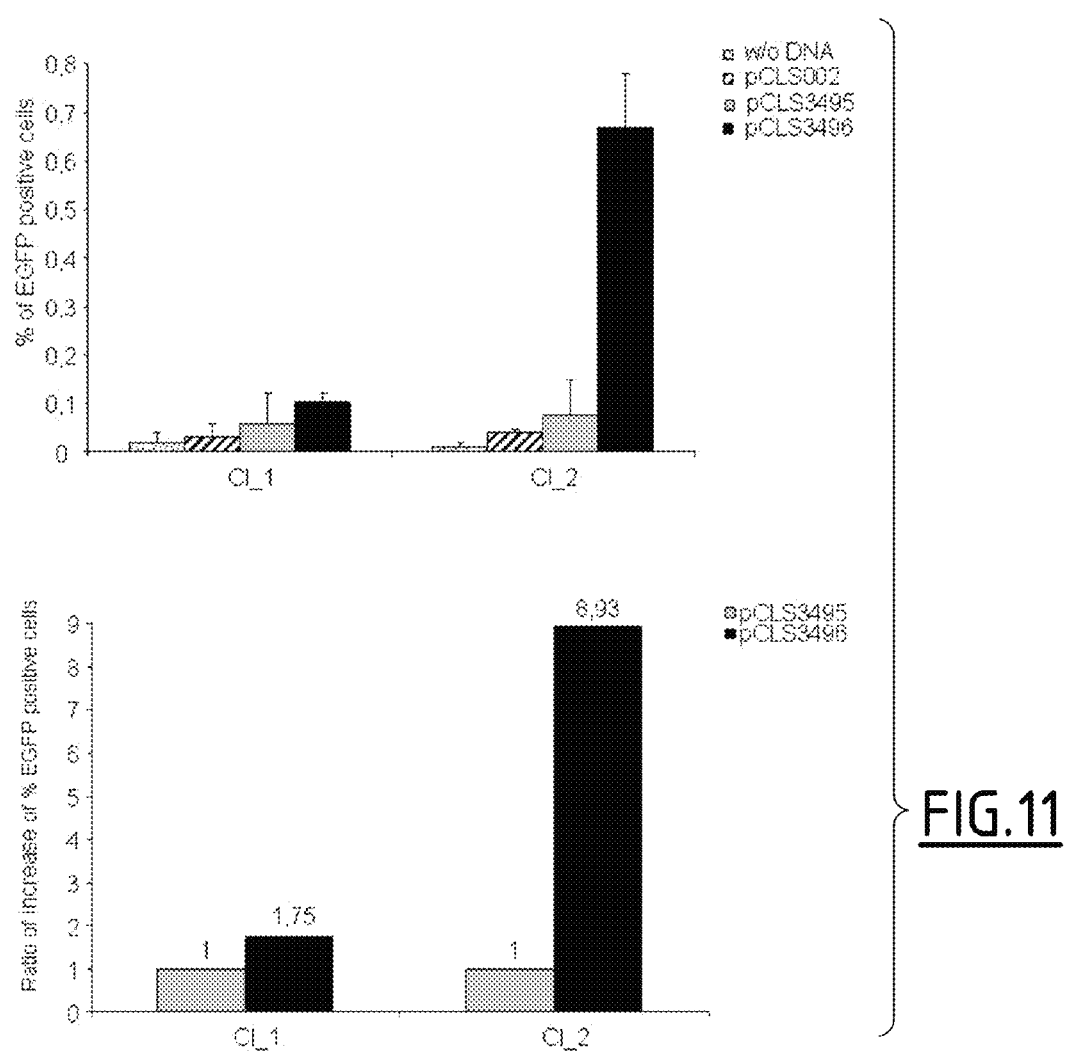

FIG. 11: Functional characterization of clones having the substrate of recombination monitoring I-SceI induced gene targeting efficiency.

Two independent clones (Cl_1 and Cl_2) were compared for their responsiveness of detection of EGFP positive cells when I-SceI is expressed. Plasmids pCLS0002, pCLS3495 and pCLS3496 used for transfections are indicated. Results are expressed as the mean of four independent experiments. For each clone, efficiency of gene targeting is monitored by comparing the percentages of EGFP positive cells obtained without I-Scel (transfection with pCLS3495 vector) and with I-Scel (transfection with pCLS3496 vector).

Figure 12:
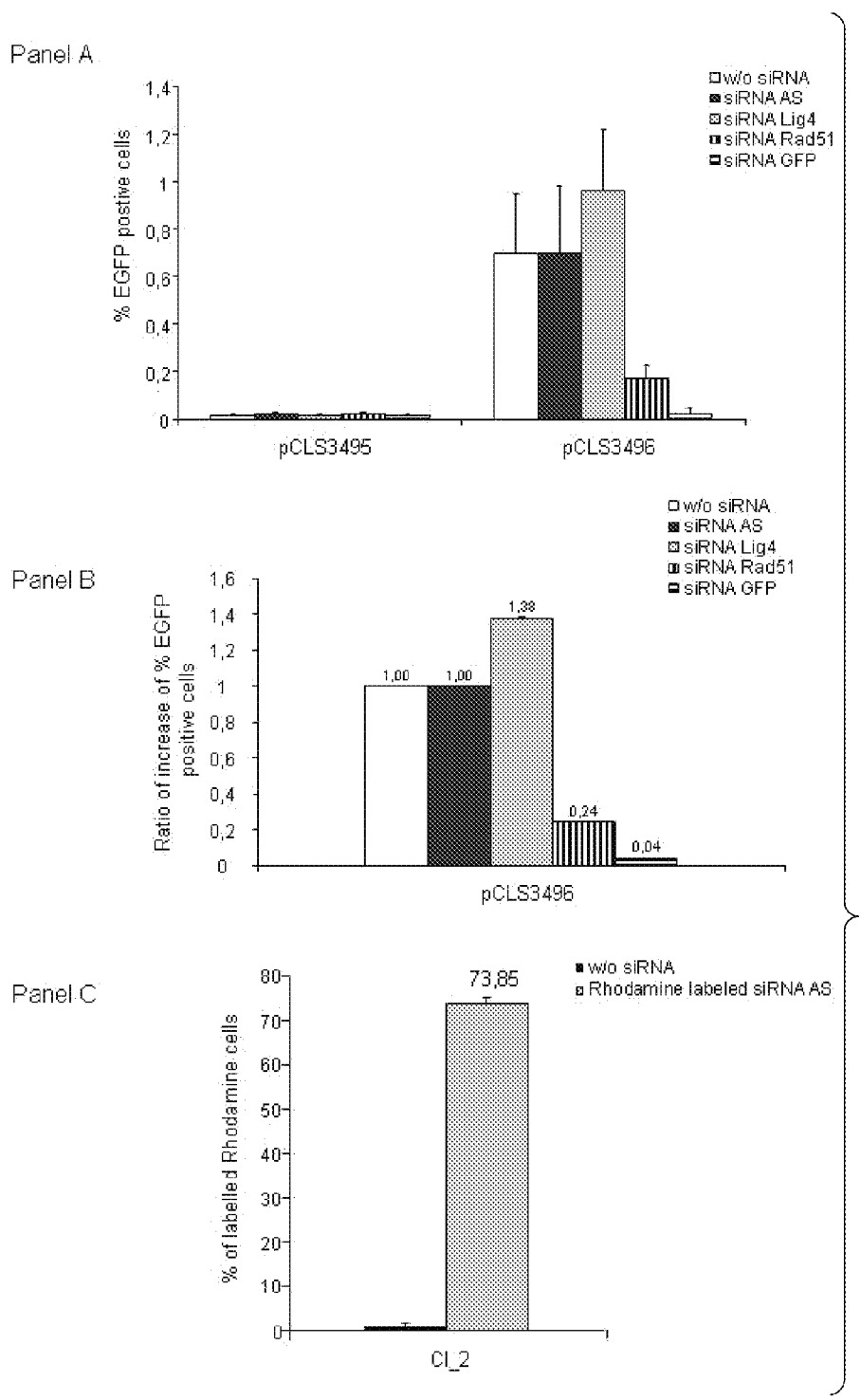

FIG. 12: Cell response of Cl__2 clone of gene targeting to effect of siRNAs known to target genes involved in double strand breaks DNA repair.

Plasmids pCLS3495 and pCLS3496 (200 ng) used for cotransfections are indicated as well as the different siRNAs tested at a final concentration of 33 nM: control siRNA AS, siRNA LIG4, siRNA RAD51 and siRNA GFP (Panel A and B). EGFP Fluorescence is detected 96 hours post transfection. Panel A represents the percentage of EGFP positive cells mean value of four independent experiments. Effect of the different siRNAs is checked by calculating the ratio of the percentage of EGFP positive cells obtained by co-transfection of pCLS3496 and a given siRNA compared to the percentage of EGFP positive cells obtained by co-transfection of pCLS3496 with the control siRNA AS (Panel B). To monitor efficiency of siRNA transfection the control siRNA AS labelled with Rhodamine was also cotransfected with 200 ng of DNA (panel C).

Figure 13:
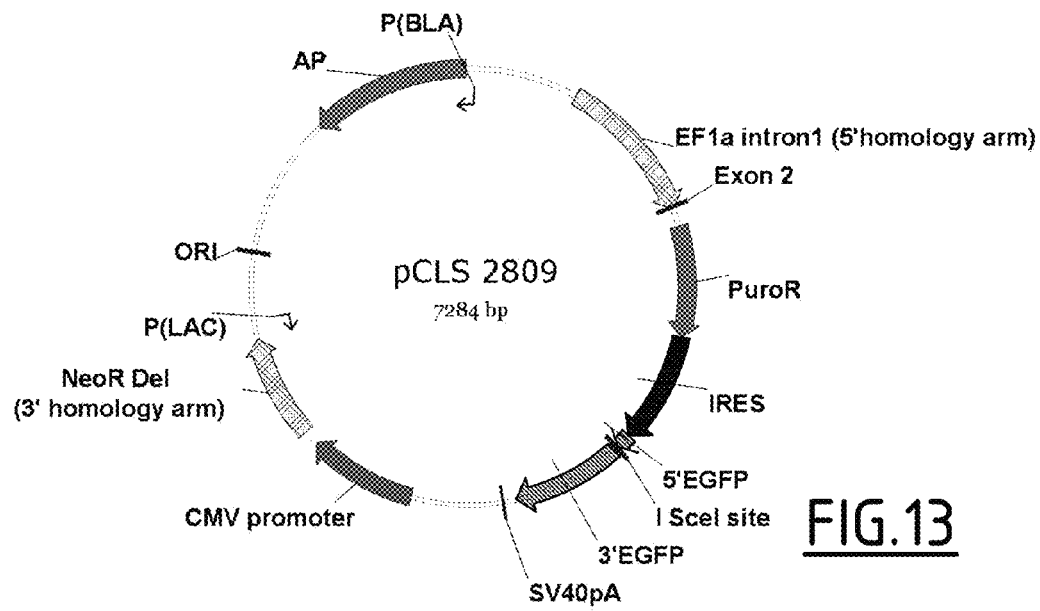

FIG. 13: Vector map of pCLS2809

Figure 14:
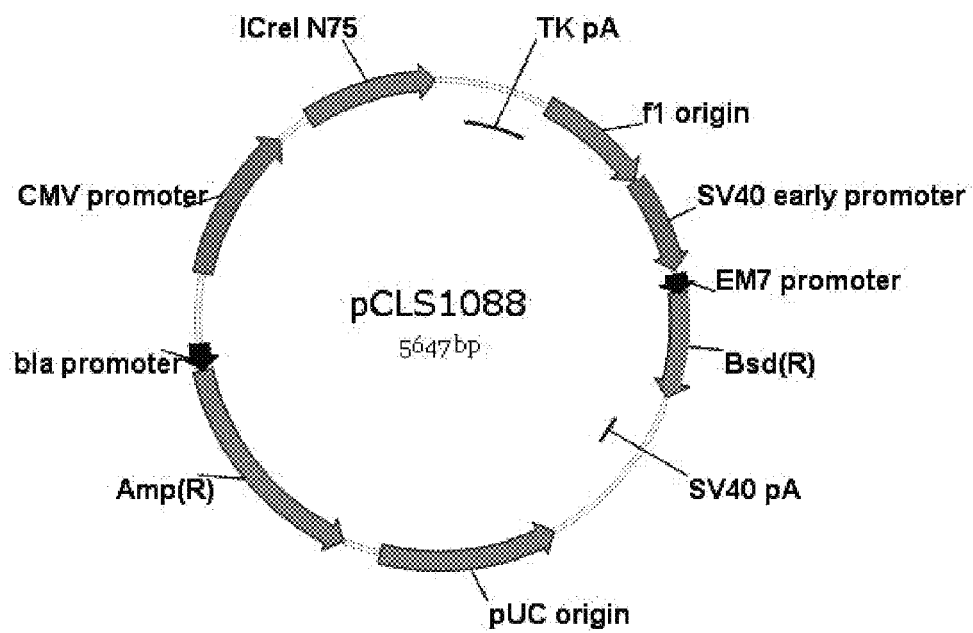

FIG. 14: Vector map of pCLS1088

Figure 15:
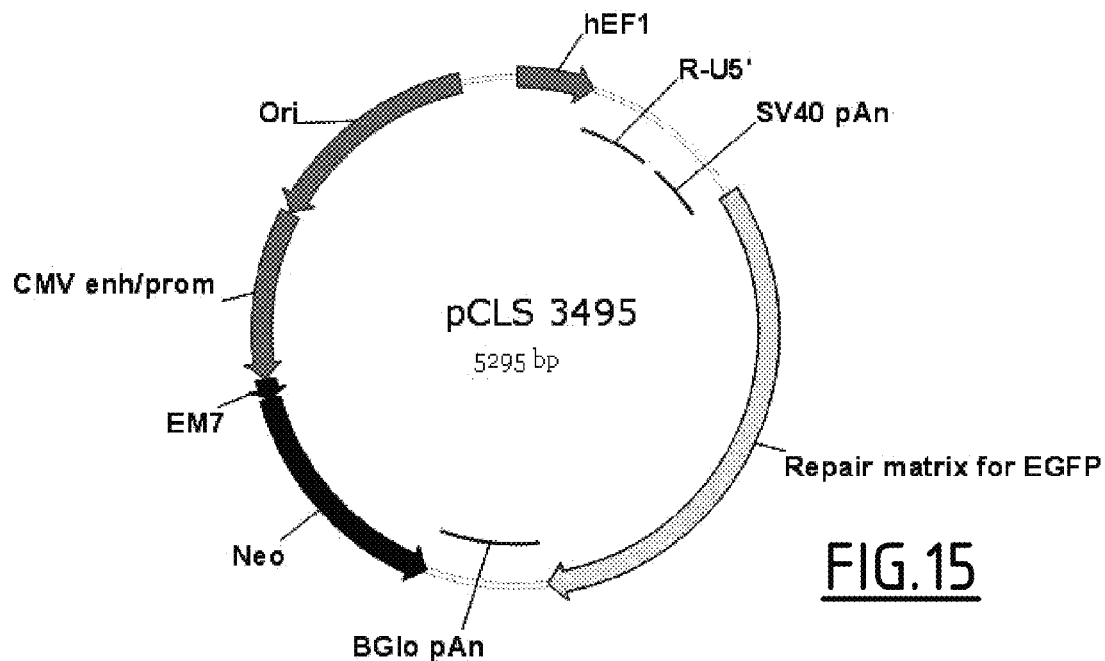

FIG. 15: Vector map of pCLS3495

Figure 16:
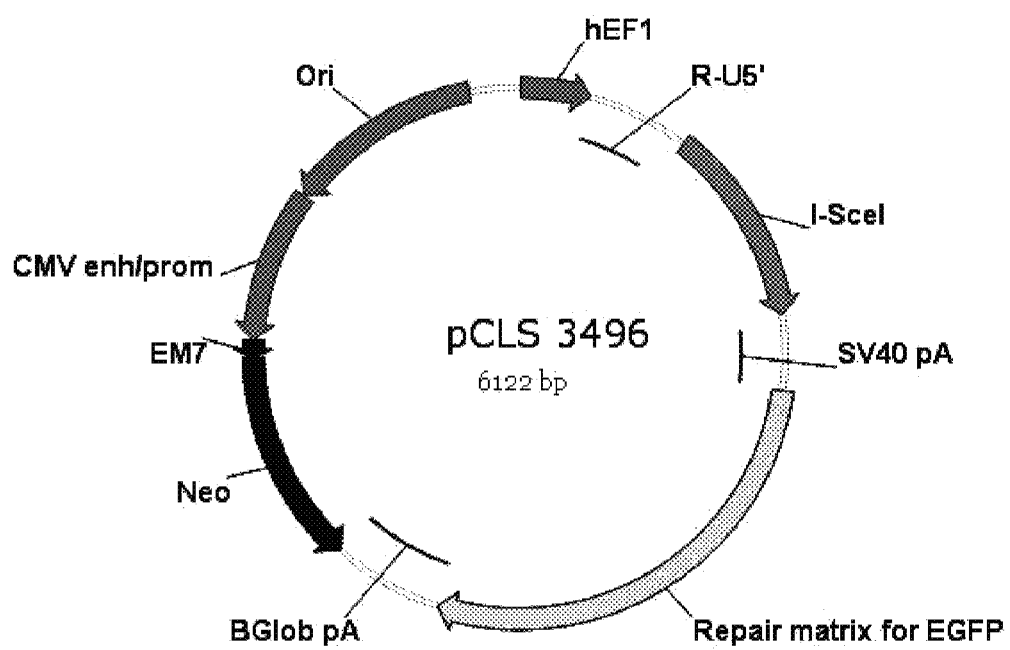

FIG. 16: Vector map of pCLS3496

Figure 17:
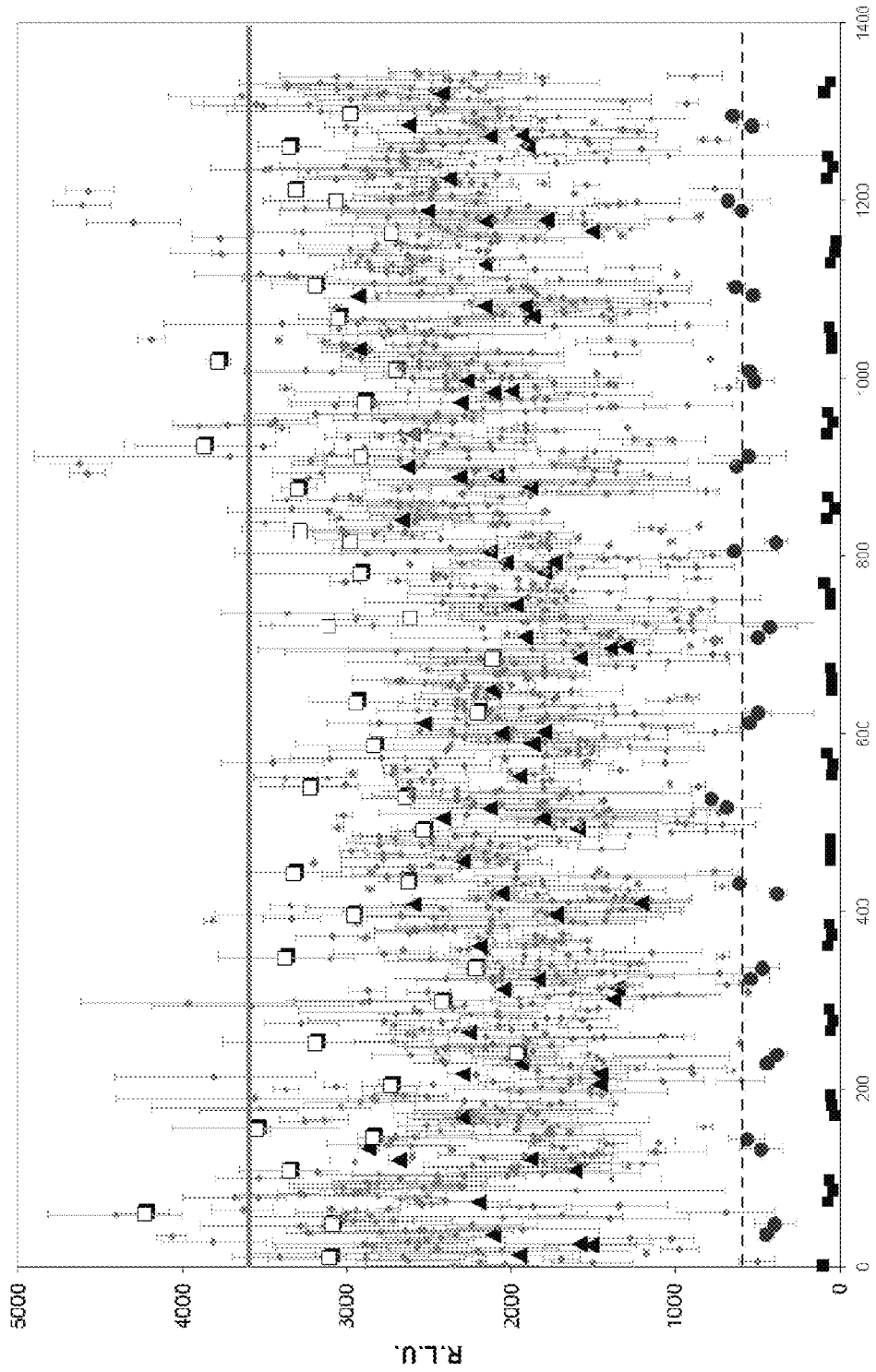

FIG. 17: Representation of the $8^{th}$ run.

During this run 14 96-well plates containing siRNA of the screen and siRNA controls were co-transfected with pCLS2067 or pCLS0002 in duplicate. Seventy-two hours post transfection luciferase activity was revealed and each dot represents the mean value per siRNA. Black boxes represent luciferase value obtained with transfection with empty vector (pCLS0002) corresponding to the background. Black triangles represent values obtained with co transfection of siRNA AS and pCLS2067, grey circles represent values obtained with co transfection of siRNA RAD51 and pCLS2067. Finally, white squares represent values obtained with co transfection of siRNA LIG4 and pCLS2067. The grey line represents the limit value for stimulating hits whereas the dotted black line represents the limit value for inhibiting hits.

Figure 18:
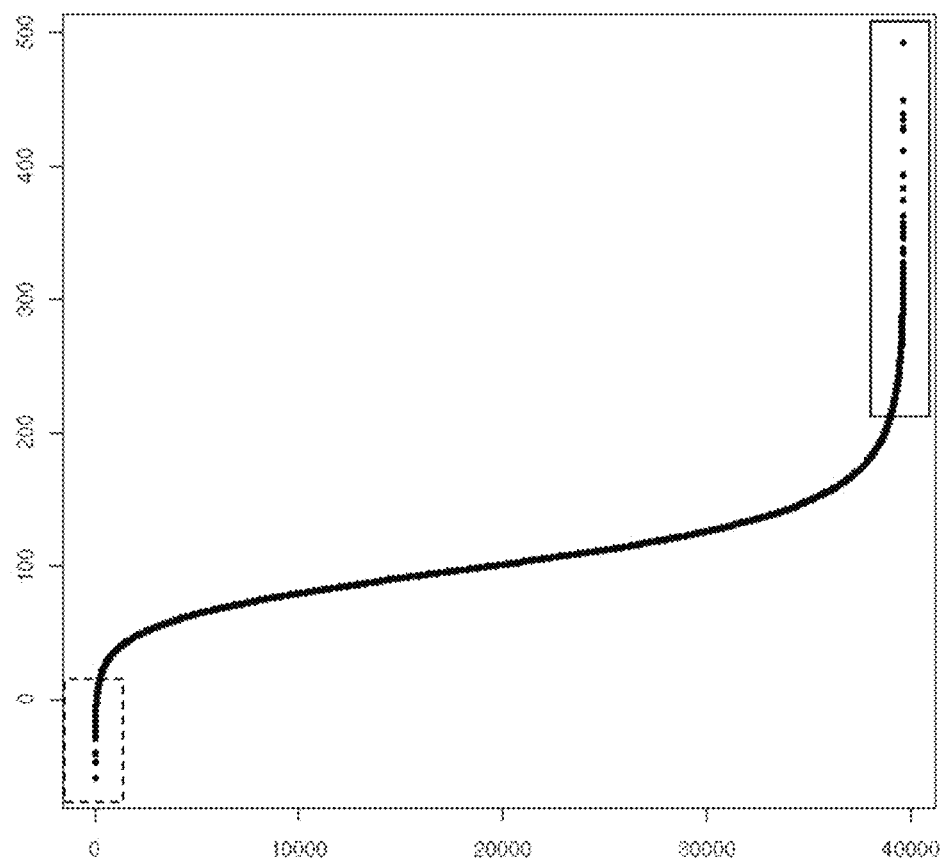

FIG. 18: Screening representation of the siRNA collection after normalization.

Each dot represents the mean value after normalization of a siRNA co-transfected with pCLS2067 in duplicate. Dots present in full line box are hits stimulating I-Scel induced gene targeting luciferase signal. Dots present in dotted line box are hits inhibiting I-Scel induced gene targeting luciferase signal.

Figure 19A:
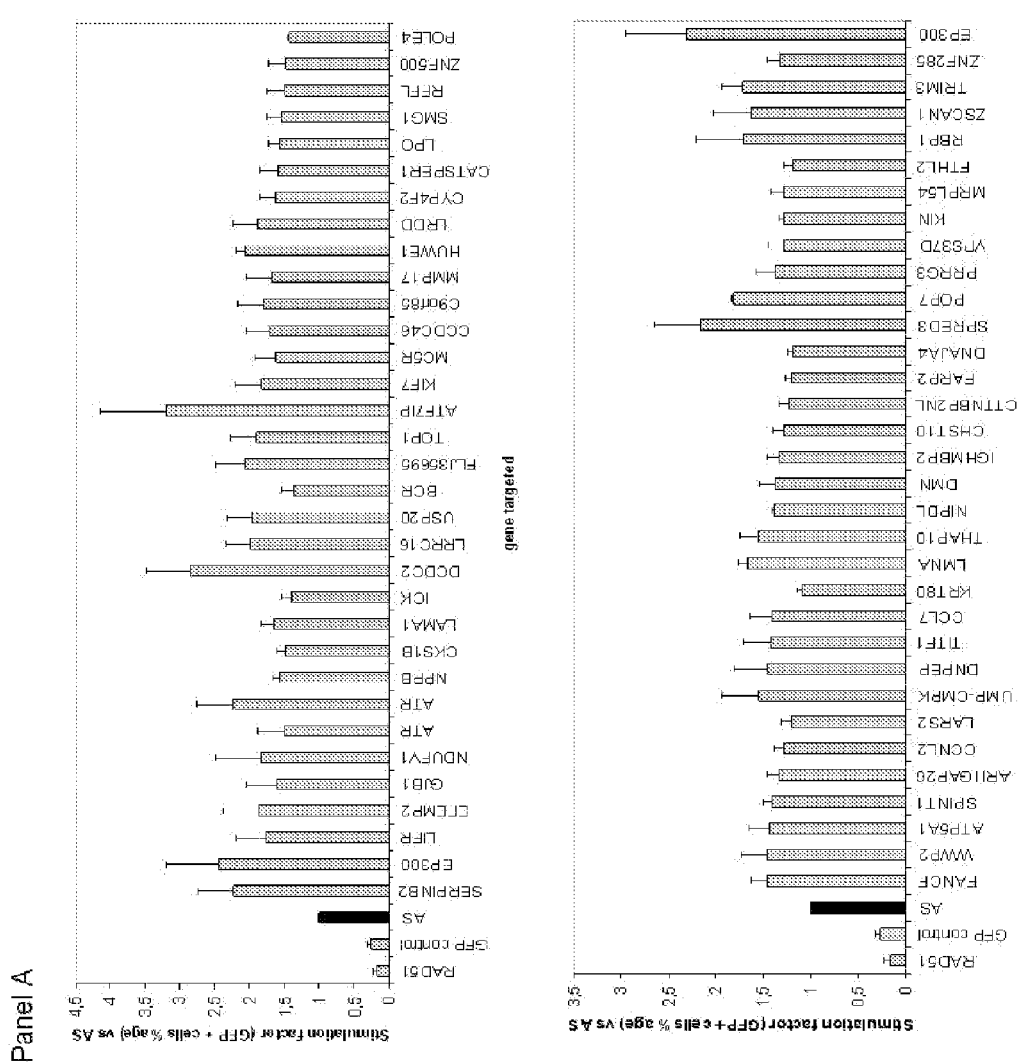

FIG. 19: Cell validation of the effect of siRNAs

Panel A: cell validation of the effect of siRNAs hits issued from the primary screen based on detection of Luciferase signal.

Cells were cotransfected with 200 ng of pCLS3496 and a panel of different siRNAs indicated at the final concentration of 33 nM. EGFP fluorescence is detected at 96 h post transfection. Results are expressed as the ratio of the percentage of EGFP positive cells in presence of the siRNA compared to siRNA AS. Three independent experiments were performed and student test statistical method revealed a significant difference (pvalue<0.05).

Panel B: cell validation of the effect of siRNAs hits with different sequences obtained from a new supplier.

Cells were co-transfected with 200 ng of pCLS3496 and a panel of different siRNAs from a new supplier at 33 nM final concentration. EGFP fluorescence is detected 96 h post transfection. Results are expressed as the stimulation factor of the percentage of EGFP positive cells in presence of the siRNA compared to no siRNA control. Three independent experiments were performed and student test statistical method revealed a significant difference (pvalue<0.05).

Figure 20:
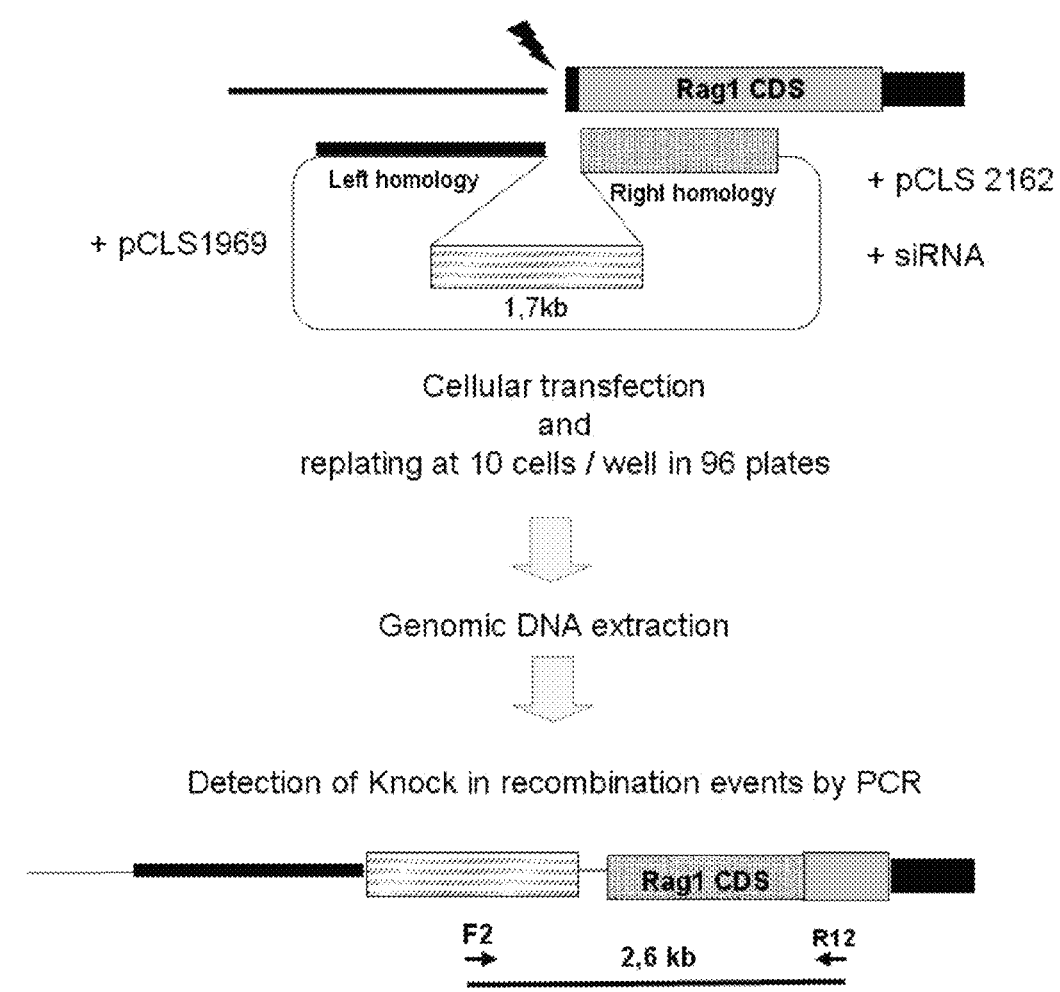

FIG. 20: Experimental outline and diagram of the Knock-In strategy used to test the effect of the siRNA.

The target sequence cleaved by the RAG meganuclease is located near the coding sequence of exon 2 for the Rag1 protein. Exon 2 is boxed, with the open reading frame shown in grey. Cleavage of the RAG endogenous locus by the engineered meganuclease yields a substrate for homologous recombination, which may use the repair plasmid containing 1.7 kb of exogenous DNA. The 1.7 kb DNA fragment is flanked by two homology arms of 2.0 kb and 1.6 kb in length. The HEK293 PuroR NeoR cell line was transfected with 3 μg of meganuclease expression plasmid (pCLS2162), 2 μg of the repair substrate (pCS1969) in presence or not of siRNA at a final concentration of 33 nM. After 72 h, cells transfected are re-plated in 96 well plates, amplified and targeted integration events were detected by amplification of a PCR fragment of 2.6 kb length.

Figure 21:
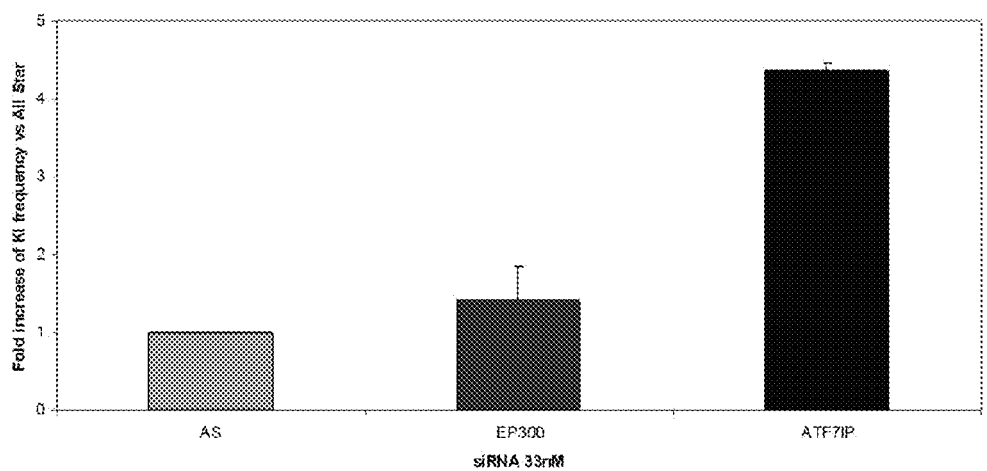

FIG. 21: Effect of siRNAs EP300 and ATF7IP on the frequency of targeted integration at the endogenous RAG1 locus, induced by a meganuclease with new specificity of cleavage.

Effect of siRNAs EP300 and ATF7IP was expressed as the increase of knock-in frequency in comparison to siRNA AS transfection.

Figure 22:
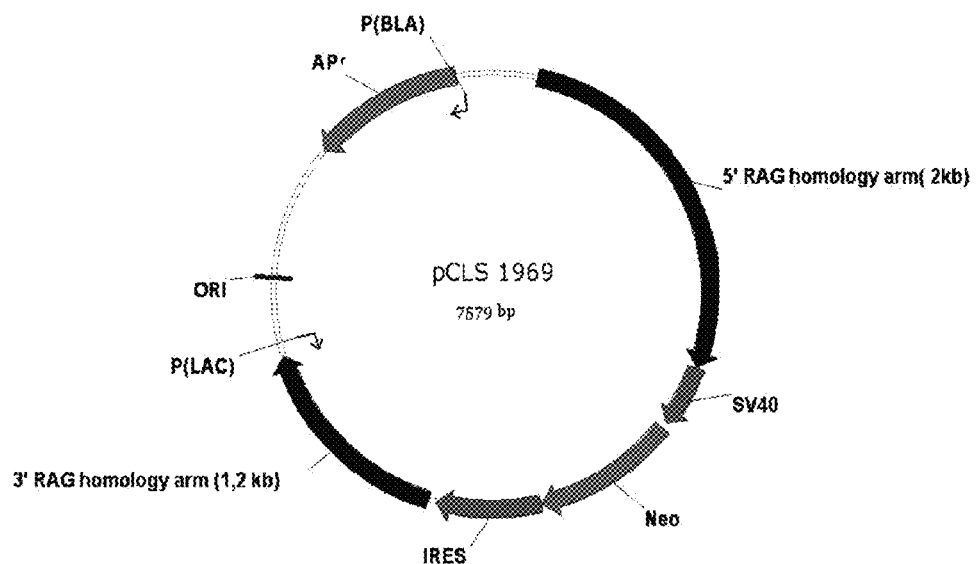

FIG. 22: Vector map of pCLS1969

Figure 23:
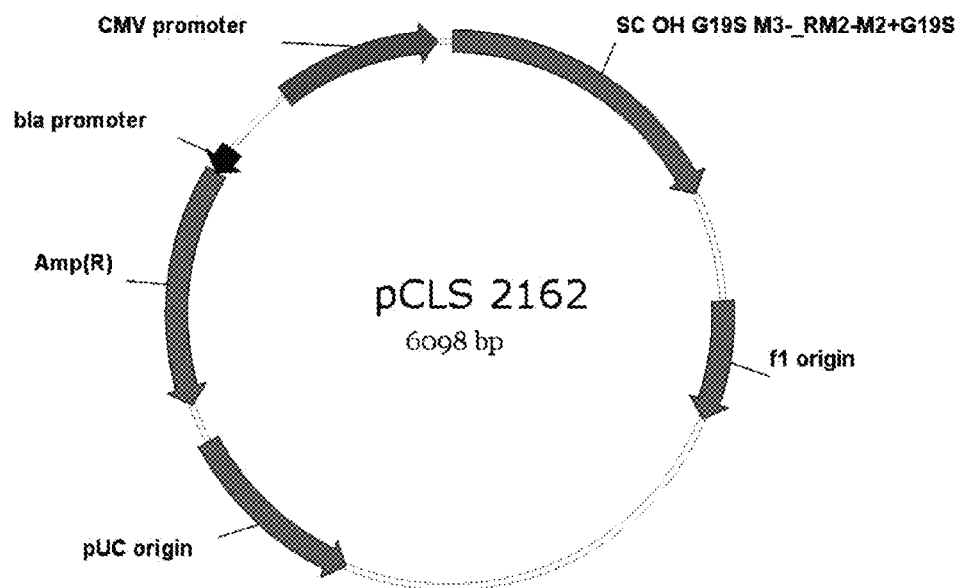

FIG. 23: Vector map of pCLS2162

DESCRIPTION OF THE SEQUENCES

SEQ ID Nos. 1 to 4 and 8 to 11 show the sequences of different plasmids used in the Examples, i.e. pCLS2026, pCLS2067, pCLS2007, pCLS0002, pCLS2809, pCLS1088 pCLS3496 and pCLS3495, respectively.

SEQ ID Nos. 5, 6 and 12 show the sequences of siRNAs used as controls, i.e. siRNA against RAD51, LIG4 and GFP, respectively.

SEQ ID NO: 7 shows the sequence of primer F2-Neo used in Example 4.

SEQ ID Nos. 13-611 and SEQ ID Nos. 969-994 show the sequences of siRNAs stimulating endonuclease-induced homologous recombination.

SEQ ID Nos. 612-966 show the sequences of siRNAs inhibiting endonuclease-induced homologous recombination.

SEQ ID Nos. 967-968 show the sequences of siRNAs respectively targeting RAD51 (gene ID #5888) and GFP (gene ID #7011696).

SEQ ID Nos. 995-997 show the sequences used in Example 4, i.e. pCLS1969, pCLS2162 and primer Rad1EX2-R12.

SEQ ID No. 998 shows the mRNA coding for the ATFIP protein.

SEQ ID No. 999 shows the mRNA coding for the EP300 protein.

EXAMPLES

Figure 1:
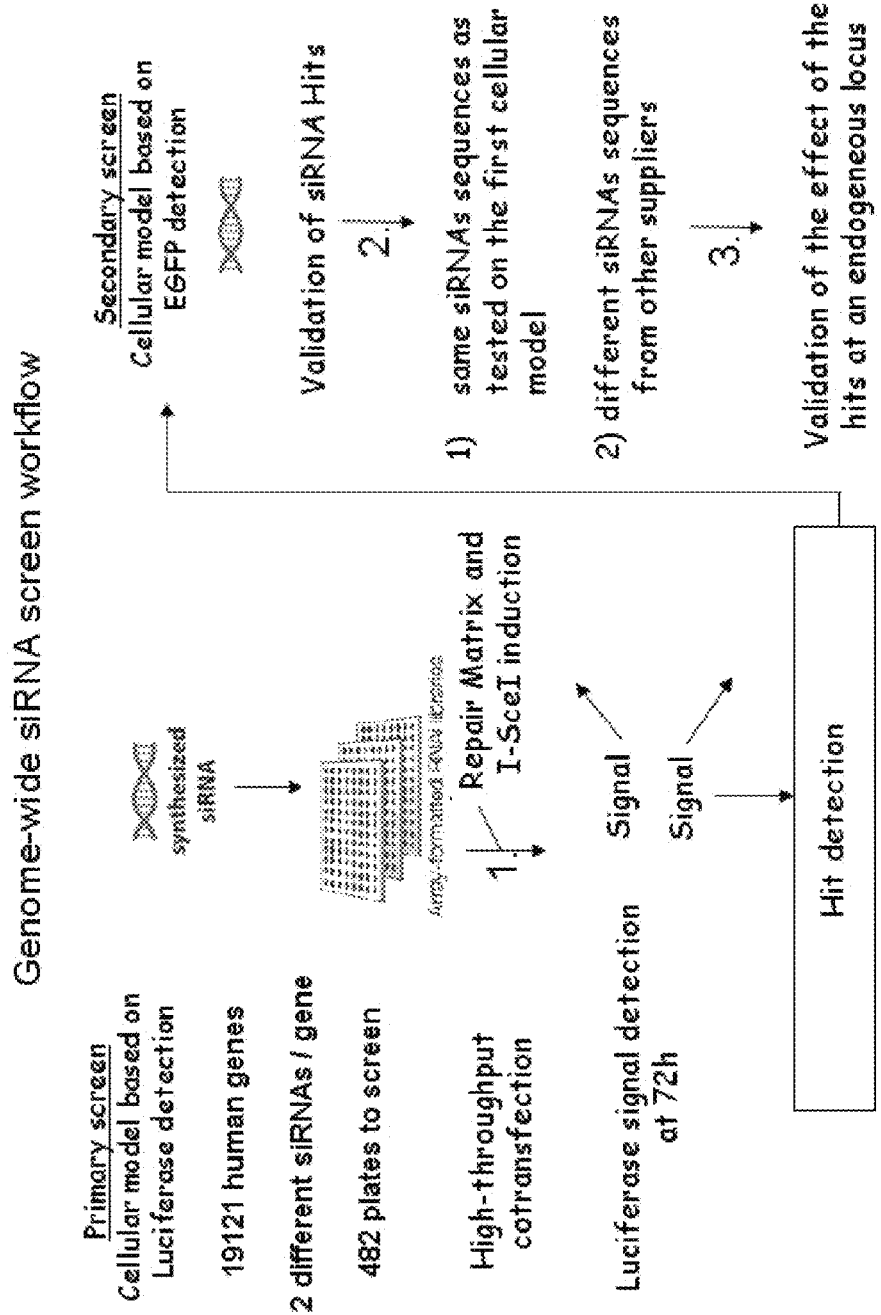
FIG. 1: Workflow description to identify siRNA effectors stimulating or inhibiting double strand break induced gene targeting.

In a first aspect, the present invention concerns a method to identify effector genes that modulates endonuclease-induced homologous recombination allowing the increasing of gene targeting efficiency. As further described in the following examples, this method allowed to screen a siRNA library covering 19121 genes with two siRNAs per gene. In the present invention, siRNAs inhibit gene expression of targeted genes. The method of the present invention allows to identify two categories of effectors stimulating or inhibiting endonuclease-induced homologous recombination. This method includes a highly sensitive high-throughput assay measuring I-SceI induced gene targeting based on Luciferase reporter system. The siRNAs hits stimulating or inhibiting the luciferase signal were then tested on a secondary screen with a new cellular model measuring I-SceI induced gene targeting efficiency. Finally, hits confirmed with the secondary screen were tested for their capacities to stimulate homologous recombination at an endogeneous locus induced by an engineered meganuclease with a new specificity of cleavage (Knock-in experiment) (FIG. 1).

Example 1

Establishment of Cell Lines Measuring I-SceI Induced Gene Targeting

Two cell lines to measure I-SceI induced gene targeting have been established. The first model based on Luciferase gene reporter was established for a high throughput screening. The second model based on GFP reporter system measures I-SceI gene targeting frequency and was used during the secondary screening.

1.1. Luciferase Reporter Based Model in GM00847

To measure gene targeting in a high-throughput screening (HTS), a cell line based on Luciferase gene reporter system has been constructed. Since gene targeting efficiency is low in human cell line the Luciferase reporter system was chosen because of its high sensitivity. Finally, co-transfection of siRNA and DNA strategy was chosen for technical and throughput reasons.

1.1.1. Materials and Methods
Cell Culture

Cell line GM0847 (skin human fibroblasts) was cultured at 37° C. with 5% $CO_2$ in Dulbecco's modified Eagle's medium (dMEM) Glutamax supplemented with 10% fetal calf serum, 2 mM L-glutamine, 100 UI/ml penicilline, 100 μg/ml streptomycine, 0.25 μg/ml amphotericine B (Fongizone). The E2 clone measuring I-SceI induced gene targeting with luciferase reporter system was maintained with 250 μg/ml of G418 (Invitrogen).

Stable Transfection to Generate Cell Line Measuring I-SceI Induced Gene Targeting with Luciferase Reporter System One million cells were electroporated with 500 ng of the gene targeting substrate plasmid (pCLS2026 of SEQ ID No. 1 and FIG. 5) linearized by PvuI, using Amaxa electroporation kit according to the manufacturer's instructions. Cells were seeded in 10 cm dishes. Two days post transfection 400 μg/ml of G418 (Invitrogen) were added on cells. Clones obtained from selection were then amplified and kept a 250 μg/ml of G418 selection. Genomic DNA was extracted to perform Southern Blot to determine if the transgene was present in a unique copy.

Southern Blot

Genomic DNA (gDNA) from clones was purified from $10^7$ cells (about a nearly confluent 10 cm dish) using the Blood and Cell culture DNA midi kit (Qiagen). 5 to 10 μg of gDNA are digested with a 10-fold excess of EcoRI restriction enzyme by overnight incubation. Digested genomic DNAs were separated on a 0.8% agarose gel and transferred on nylon membrane. Nylon membranes were then probed with a $^{32}P$ DNA probe specific for neomycin gene or EF1 alpha intronic sequence. After appropriate washes, the specific hybridization of the probe is revealed by autoradiography.

Transient Transfection in 96 Well Plate Format

Fourteen thousand cells per well were seeded in white 96 well plates one day before transfection. Per well, cells were transfected with 200 ng of DNA [pCLS2067 of SEQ ID No. 2 (FIG. 7), pCLS2007 of SEQ ID No. 3 (FIG. 6), or pCLS0002 of SEQ ID No. 4 (FIG. 8)] and with or without 33 nM final concentration of siRNA using 0.8 μl of Polyfect transfection reagent (QIAGEN). Seventy two hours post transfection 50 μl per well of ONEGlo (Promega) were added, cells were incubated in dark for 3 minutes before luciferase activity analysis (1 second/well) using PHERAStar luminometer (BMG Labtech).

1.1.2. Results

The skin human fibroblast SV40 transformed GM00847 was established with a single copy of a transgene that allows to measure gene targeting events (pCLS2026 of SEQ ID No. 1). This construction is represented in FIG. 2 panel A. It is made of EF1 alpha promoter followed by i) its intronic sequence ii) an inactive luciferase gene due to a replacement of the first 22 base pairs by a 24 base pairs I-SceI site iii) a Neomycin resistant cassette driven by a SV40 promoter. After Neomycin selection, the clone E2 was chosen for a unique copy integration verified by Southern blot (FIG. 2 panel B).

To perform gene targeting induced by I-SceI, a plasmid containing the missing sequence of Luciferase gene surrounded by 1 kb of homology (repair matrix) and I-SceI expression cassette under CMV promoter (I-SceI induction) was constructed (pCLS2067 of SEQ ID No. 2). In this construct the luciferase gene is inactive due to the 600 bp deletion of its 5' end. A control plasmid corresponding to a repair matrix alone (i.e. without I-SceI induction) was also constructed (pCLS2007 of SEQ ID No. 3). These plasmids are presented in FIG. 3 panel A.

To verify that our model is measuring I-SceI induced gene targeting, E2 clone was transfected with an empty vector (pCLS0002, SEQ ID No. 4) or with the repair matrix alone (pCLS2007 of SEQ ID No. 3) or with the repair matrix and I-SceI induction plasmid (pCLS2067 of SEQ ID No.2). Luciferase signal was analyzed 72 hours post transfection. Empty vector and repair matrix alone gave a similar and low luciferase activity showing that this assay does not detect any spontaneous gene targeting events. Only transfection with the repair matrix and I-SceI induction plasmid produced a high luciferase signal induction at 600 Relative Light Unit (R.L.U.) showing that this assay is measuring I-SceI induced gene targeting (FIG. 3 panel B).

To determine if co-transfection of siRNA and DNA strategy was applicable, siRNAs known to modulate gene targeting efficiency were tested: siRNA against RAD51 (SEQ ID No. 5) and siRNA against LIG4 (SEQ ID No. 6). The first gene codes for a protein involved in a central step of Homologous Recombination (HR), the latter is involved in Non Homologous End Joining (NHEJ). It has been shown that siRNA down regulation of NHEJ genes leads to gene targeting increase (Bertonili et al. 2009).

The E2 clone was co-transfected with pCLS2067 (SEQ ID No. 2) or an empty vector (pCLS0002 of SEQ ID No. 4) and with 33 nM final of the following siRNAs: RAD51 of SEQ ID No. 5, LIG4 of SEQ ID No. 6 and All Star (AS) (a negative control, Qiagen #1027280). Luciferase signal analyzed 72 hours post transfection showed respectively a 6 fold decrease and a 2 fold increase when cells were co-transfected with siRNAs RAD51 and LIG4 respectively compared to siRNA AS (FIG. 4). These results demonstrate that co-transfection strategy leads to modulation of gene targeting efficiency.

1.2: GFP Reporter Based Model in HEK293 Cell Line.

In order to validate the siRNAs hits issued from the primary high-throughput screening using the detection of a luciferase signal, it was useful to derive a new cellular model with a different reporter gene allowing the establishment of a correlation between the efficiency of the gene targeting induced by I-SceI and the effect of the siRNAs.

Material and Methods:

cGPSHEK293 Cell Line Culture Conditions:

cGPSHEK293 cells were sub-cultured in DMEM Glutamax medium (Invitrogen-Life Science) supplemented with penicilline (100 UI/ml), streptomycine (100 µg/ml), amphotericine B (Fongizone) (0.25 µg/ml), 10% FBS and 0.1 mg/ml of hygromycin B solution (Sigma).

cGPSHEK293 Cellular Transfection Conditions and Targeted Clones Selection

One day prior to transfection, the stable cGPSHEK293 cells were seeded in 10 cm tissue culture dishes ($10^6$ cells per dish) in complete medium.

The next day 3 µg of pCLS2809 (SEQ ID No. 8) and 2 µg of pCLS1088 (SEQ ID No. 9) plasmid DNAs were cotransfected with Lipofectamine 2000 reagent (Invitrogen) during 6 hours according to the instructions of the manufacturer.

Twenty four hours after transfection, culture medium was replaced with fresh medium supplemented with 0.4 mg/ml of G418 sulfate (Invitrogen-Life Science). After 12 days of G418 selection, the second selective agent puromycin (Sigma) was added at 0.4 µg/ml concentration. After 7-9 days of double selection, single colony clones were picked up and seeded in 96 well plates in complete medium supplemented with G418 at 0.4 mg/ml and puromycin at 0.4 µg/ml. Ten days later, double resistant clones were characterized at molecular level by Southern blotting experiments.

Southern Blotting Molecular Characterization of Insertion Clones

Genomic DNA (gDNA) from targeted clones was purified from $10^7$ cells (about a nearly confluent 10 cm dish) using the Blood and Cell culture DNA midi kit (Qiagen). 5 to 10 µg of gDNA are digested with a 10-fold excess of restriction enzyme by overnight incubation. Digested genomic DNAs were separated on a 0.8% agarose gel and transferred on nylon membrane. Nylon membranes were then probed with a $^{32}$P DNA probe specific for neomycin gene. After appropriate washes, the specific hybridization of the probe is revealed by autoradiography.

Cellular Transfection for Functional Validation of Insertion Clones

The double resistant stable cell line derived from cGPSHEK293 and harboring the substrate of recombination for the gene targeting was maintained in culture with complete DMEM Glutamax medium (Invitrogen-Life Science) supplemented with penicilline (100 UI/ml), streptomycine (100 µg/ml), amphotericine B (Fongizone) (0.25 µg/ml), 10% FBS (Sigma Aldrich Chimie), 0.2 mg/ml of G418 (Invitrogen-Life Science) or 0.4 µg/ml of puromycin.

One day prior transfection the cell line was seeded in 96 well plate at the density of 15000 cells per well in 100 µl.

The next day, cells were transfected with Polyfect transfection reagent (Qiagen). Briefly 200 ng of DNA or a mix of 200 ng of DNA with the siRNA at a final concentration of 170 nM were diluted in 30 ul of water RNAse free. On the other hand 1.35 it of Polyfect was resuspended in 20 it of DMEM without serum. Then the DNA or DNA with siRNA mixes were added to the Polyfect mix and incubated for 20 min. at room temperature. After the incubation period the total transfection mix (50 µA was added over plated cells. After, 96 h of incubation at 37° C., cells were trypsinized and the percentage of EGFP positive cells was monitored by flow cytometry analysis (Guava Instrument) and corrected by the transfection efficiency.

Figure 9:
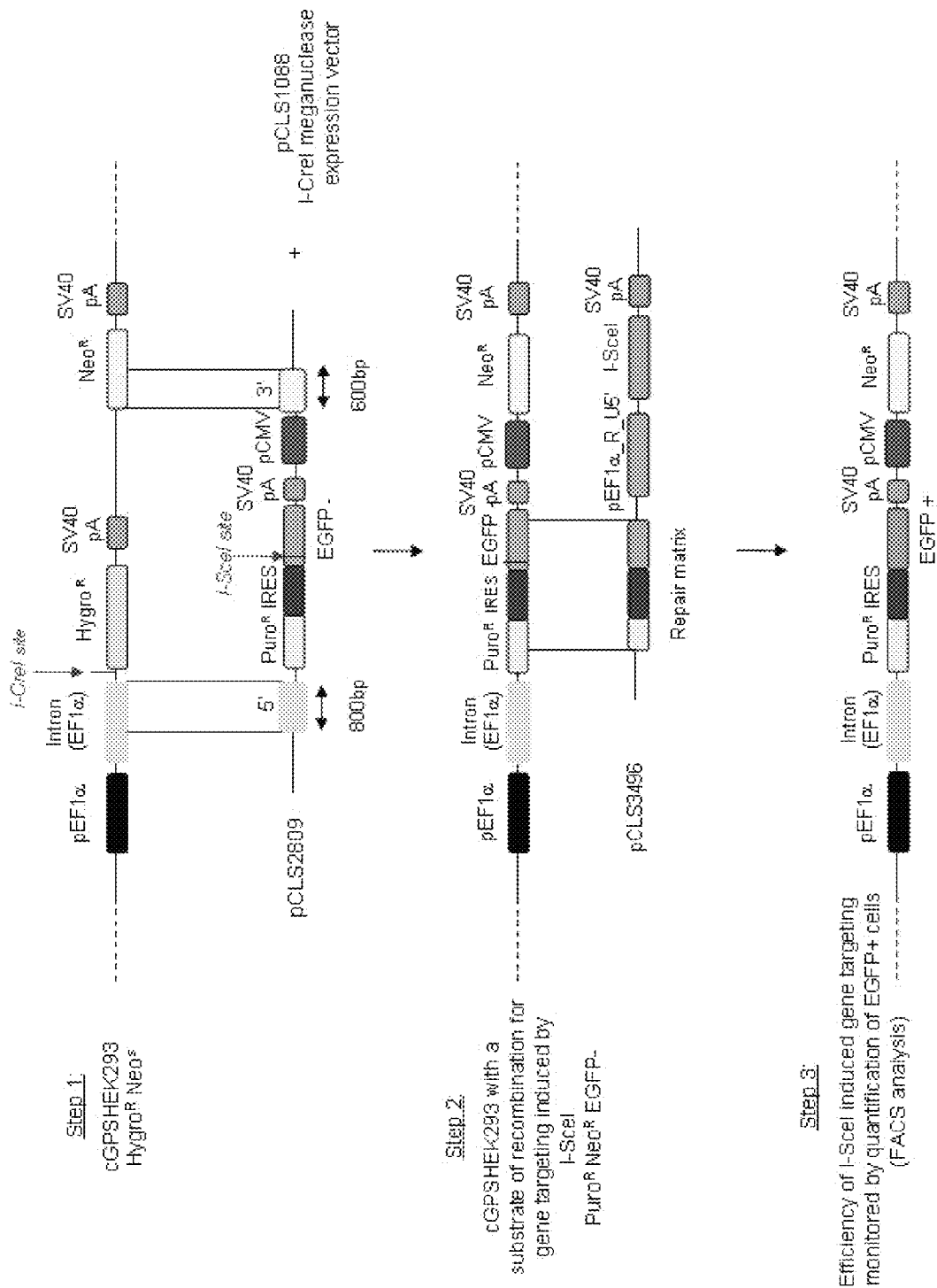

Results:

In the present example, the construct depicted in the FIG. 9 which comprises the I-CreI meganuclease target site has been first inserted as a single copy into the HEK293 cell line to create the cell line termed cGPSHEK293 that is resistant to hygromycin and sensitive to G418. In such cell line the I-CreI site located between the gene encoding the hygromycin resistant gene and the human EF1 alpha promoter is used for the subsequent insertion of a DNA sequence of interest.

In order to obtain a cell line harboring a substrate of recombination to monitor gene targeting induced by I-SceI, cGPSHEK293 cell line was then cotransfected with the plasmid pCLS2809 (SEQ ID No. 8) (FIG. 9 and FIG. 13) derived from the pTV-DS-MCS2 and the pCLS1088 (SEQ ID No. 9; FIG. 14) expression vector for I-CreI meganuclease.

The pCLS2809 (SEQ ID No. 8) plasmid contains all the characteristics to obtain by homologous recombination a highly efficient insertion event of a transgene DNA sequence of interest at the I-CreI site. It is composed of two homology arms of 0.8 and 0.6 kb length separated by (i) the puromycin resistance gene which lacks a promoter, (ii) an IRES sequence to drive translation of (iii) the downstream EGFP coding sequence interrupted by the presence of the cleavage site for the I-SceI meganuclease, (iii) an SV40 polyadenylation signal controlling the stability of the bicistronic mRNA, (iv) and a CMV promoter cloned in front (v) a C terminus inactive deleted version of the neomycin resistance gene.

Since by itself the pCLS2809 (SEQ ID No. 8) plasmid cannot induce a puromycin and neomycin resistance phenotype, selection of double resistant clones for these drugs can be obtained after a targeted insertion of the transgene at the I-CreI site. The functionality of the puromycin and neomycin genes is then restored since their expression are driven by EF1 alpha promoter and CMV promoters respectively.

As shown on FIG. 10, 26 double resistant clones picked randomly have been tested for molecular characterization by Southern Blot. A correct targeted insertion of the transgene DNA sequence is characterized by the identification of a band at 3.7 kb. Such band is effectively identified for 23 double resistant clones out of 26 clones analyzed, while a band at 1.6 kb is shown for the parental cGPSHEK293. In addition to the 3.7 kb band, a second band is present for 9 out of 23 clones that is probably due to additional insertion events or random insertion. Hence, these results demonstrate that the majority of the double resistant clones to puromycin and neomycin obtained with the method described above present at least an integration of one copy of the transgene targeted correctly at the cGPS locus.

In order to test the ability of the selected clones to achieve efficiently gene targeting induced by I-SceI, transient transfections in 96 well plate format were set up. According to the different profiles of hybridization obtained with the experiments of Southern Blot, two clones Cl_1 and Cl_2 having respectively a single targeted insertion or a targeted integration and random insertion event were tested. FIG. 11 presents the functional assays. For both clones we get a measurable increase of the percentage of EGFP positive cells with the pCLS3496 (SEQ ID No. 10) plasmid harboring a repair matrix for EGFP and an expression cassette for the meganuclease I-SceI in comparison with the transfections performed with the vector control pCLS0002 (SEQ ID No. 4) or the pCLS3495 (SEQ ID No. 11) harboring only the repair matrix for EGFP. These data indicate that the double resistant clones selected present the expected phenotype for the detection of the gene targeting activity induced by I-SceI with a best fold increase (ratio of induction of 8.93 vs 1.75) obtained for the Cl_2 that was chosen for further experiments of validation of the siRNAs hits. Depending on the efficiency of transfection of the Cl_2, the percentage of EGFP positive cells ranges from 0.3% to 1%.

To test specificity of the gene targeting mechanism of recombination induced by I-SceI leading to the detection of the EGFP positive cells, cotransfection experiments were performed with different siRNAs known to abolish the expression of key regulators involved in the repair of DNA double strand breaks: Ligase IV, a gene that promotes non homologous end joining and Rad51 gene that plays a major role in homologous recombination. As shown in FIG. 12 panel A, in agreement with the respective roles of Ligase IV and Rad51 proteins, siRNAs LIG4 (SEQ ID No. 6) and RAD51 (SEQ ID No. 5) are respectively able to increase and diminish significantly the proportion of the EGFP positive cells induced by I-SceI in comparison with a transfection experiment using the siRNA control AS (Qiagen #1027280) which have no effect. In addition, we get a transfection efficiency of 73% with a Rhodamine labelled siRNA and a nearly complete extinction of the EGFP signal induced by I-SceI with siRNA GFP (SEQ ID No. 12) targeting the expression of the reporter gene. Altogether these data imply that we have established a new cellular model and defined an experimental procedure for cotransfection of DNA with siRNA allowing testing for the potential effect of different siRNAs on the modulation of the efficiency of the gene targeting induced by I-SceI.

Example 2 siRNA Screening

A siRNA collection from QIAGEN was screened using the model measuring I-SceI induced gene targeting and based on luciferase reporter system. This siRNA collection target 19121 genes with two different siRNAs per gene. For each siRNA, co-transfection with pCLS2067 (SEQ ID No. 2) were performed in duplicates. The screen lead to identification of 599 and 355 hits stimulating and inhibiting the luciferase signal respectively.

Materials and Methods
siRNA Dilution

The siRNA collection from QIAGEN was received in 96 well plate format in solution at 10 µM concentration. On each plate columns 1 and 12 were empty allowing controls addition. During dilution process of siRNA at 333 nM concentration, H2O, siRNA AS (Qiagen #1027280), a negative control, siRNA RAD51 (SEQ ID No. 5) siRNA LIG4 (SEQ ID No. 6), two positive controls were added at 333 nM final concentration in empty wells.

HTS I-SceI Gene Targeting Assay:

Fourteen thousand cells per well were seeded in white 96 well plates one day before transfection. Per well cells were co-transfected with 200 ng of DNA (pCLS2067 of SEQ ID No. 2) and with 33 nM final concentration of siRNA using 0.8 µl of Polyfect transfection reagent (QIAGEN). Seventy two hours post transfection 50 µl per well of ONEGlo (Promega) were added, cells were incubated in dark for 3 minutes before analysis of luciferase activity (1 second/well) using PHERAStar luminometer (BMG Labtech).

Results:

Thirty-four runs were performed to screen the entire collection. For each run the mean luciferase intensity of the all run and of siRNA RAD51 of SEQ ID No. 5 and their standard deviations were calculated. A siRNA hit stimulating luciferase signal was defined for each run when its luciferase intensity was above the run mean intensity plus 2.5 times the run standard deviation. A siRNA hit inhibiting luciferase signal was defined as follows: its luciferase signal is less than the siRNA RAD51 of SEQ ID No. 5 mean luciferase activity plus 0.5 times its standard deviation. On each run I-SceI induced gene targeting was checked by comparison of induced luciferase signal between transfection of an empty vector (pCLS0002 of SEQ ID No. 4) and co-transfection of pCLS2067 (SEQ ID No. 2) and the siRNA screened. Effect of siRNA was also verified by analysing the decrease and the increase of luciferase signal with co-transfection of pCLS2067 (SEQ ID No. 2) with siRNA RAD51 of SEQ ID No. 5 or siRNA LIG4 of SEQ ID No. 6, respectively.

Typically in the $8^{th}$ run (FIG. 17), the run luciferase mean value is 2169+/−666 Relative Light Unit (R.L.U.). No induction (transfection with pCLS0002 of SEQ ID No. 4) has a 64+/−17 R.L.U. showing that I-SceI induced gene targeting was efficient. The siRNA LIG4 of SEQ ID No. 6 and siRNA RAD51 of SEQ ID No. 5 shows a run mean value of 3004+/−463 and 535+/−100 R.L.U. respectively, demonstrating that siRNAs were active. Moreover in this run all siRNAs having a luciferase signal greater than 3834 R.L.U. (above the grey line) or lower than 585 (under the dotted line) were considered as a positive or negative hits respectively.

To compare the screen form run to run, normalization was applied on each run to get the run mean luciferase signal equal to 100 R.L.U. FIG. 18 represents data of all runs after normalization and shows the hits stimulating or inhibiting I-SceI induced gene targeting luciferase signal.

The 599 siRNAs hits that stimulate I-SceI induced gene targeting luciferase signal are presented in table I at pages 26-38 of the present description. Interestingly, 34 genes were considered as hit with both siRNAs.

The 355 siRNAs hits that inhibits I-SceI induced gene targeting luciferase signal are presented in table II at pages 42-49 of the present description. Thirteen genes were considered as inhibiting hits with both siRNAs.

Example 3

Validation of the siRNAs Hits on New Cellular Model

The high-throughput screening of the siRNA human genome wide library has allowed identifying several hundreds of potential hits leading to an increase of the I-SceI luciferase signal.

To correlate such effect to an improvement of the gene targeting efficiency induced by I-SceI, siRNAs were tested in the new cellular model described in example 2.2 with the read out of a different reporter gene.

Material and Methods:
Double Resistant cGPSHEK293 PuroR NeoR Cell Line Culture Conditions Same protocol as described in example 2.2 except that the complete culture medium DMEM Glutamax medium with penicilline (100 UI/ml), streptomycine (100 µg/ml), amphotericine B (Fongizone) (0.25 µg/ml), 10% FBS is supplemented with 0.2 mg/ml of G418 sulfate (Invitrogen-Life Science) or 0.4 µg/ml of puromycin.

Cellular Transfection in 96 Well Format for Functional Validation of siRNAs Hits Same protocol of cotransfection as described in example 2.2 with 200 ng of DNA plasmid and siRNA at a final concentration of 33 nM.

Results:

In this example, the effect of 66 different siRNAs was first monitored in the new cellular model using the same siRNAs as those used during the primary screening, and targeting the expression of 64 different genes (cf. table III at pages 39-40 of the present description). Co-transfections experiments were performed with the siRNAs hits and pCLS3496 (SEQ ID No. 10) carrying the repair matrix for the EGFP gene and the expression cassette for I-SceI meganuclease. Genes were chosen based on the high luciferase signal stimulation obtained during the primary screening. Co-transfections were performed at least in triplicates and the potential effect of siRNAs hits was assessed using the statistical Student test analysis. The ratio of EGFP positive cells percentage calculated between a siRNA hit and siRNA control AS leads to determine the stimulation factor of each siRNA. Two siRNA controls were used to validate siRNA transfection, siRNAs RAD51 (SEQ ID No. 967) and GFP (SEQ ID No. 968). Typically, as shown in FIG. 19 panel A, siRNAs controls inhibited the percentage of EGFP positive cells compared to the siRNA control AS demonstrating that siRNAs were active. Moreover, the stimulation factor of the different tested siRNAs was ranging from 1.2 to 3 with the largest increase (superior to a 2 fold stimulation) obtained with 9 siRNAs targeting the expression of the seven following genes: ATF7IP (SEQ ID No. 42), DCD2 (SEQ ID No. 169), EP300 (with two different siRNAs SEQ ID No. 197 and SEQ ID No. 198), ATR (SEQ ID No. 45), SERPINB2 (SEQ ID No. 990), SPRED3 (SEQ ID No. 510), HUWE1 (SEQ ID No. 264) and a gene with unknown function FLJ35695 (SEQ ID No. 73). Such data are in agreement with the functional results issued from the primary screening. Moreover, as an example with EP300 and ATR, the fact that siRNAs targeting two different sequences within the same gene have an effect confirm the pertinence of the potential hits identified with the cellular model based on detection of luciferase signal.

In a second step, sequences of 20 siRNAs from another supplier (Invitrogen), targeting fourteen genes, were also tested (cf. table IV at page 40 of the present description). For the genes LIFR, CCL19, DNAJB7, OCRL, POLQ and MRC2, two sets of siRNAs were selected. As for the precedent experiment siRNAs against RAD51 and GFP from this supplier were used as controls. In this example, as shown in FIG. 19 panel B, using the same functional assay and the statistical analysis method as described previously, effect of the siRNAs was also demonstrated, with a stimulation factor of GFP positive cells ranging from 1.3 to 4. The strongest stimulation factor (superior to a 2-fold factor) was obtained with siRNAs targeting the following genes: ATF7IP, EP300, SERPINB2, KCNJ3, POLQ, PROP1 and OCRL. Moreover, the robustness of ATF7IP, EP300, ATR, SERPINB2, LIFR, CCL19, DCDC2, DNAJB7, OCRL and POLQ hits was confirmed since different sequences of siRNAs provided by a same supplier or designed by two different manufacturers have an effect on the efficiency of the gene targeting induced by I-SceI.

Altogether the results of this analysis and the fact that siRNAs scored positive with two cellular models and with sequences of different origin confirm that the hits identified increase homologous recombination induced by a meganuclease.

Example 4

Validation of the siRNA Effect on the Efficiency of Homologous Gene Targeting Induced by an Engineered Meganuclease at an Endogenous RAG1 Locus siRNAs hits that can modulate the efficiency of gene targeting induced by I-SceI with two independent cellular models based in the detection of two different read outs have been identified. It was useful to test the effect of such siRNAs on modulation of the efficiency of homologous recombination at a natural chromosomal endogenous locus.

Material and Methods:

Cellular Transfection of HEK293 Cell Line and PCR Analysis of Homologous Recombination Events The donor plasmid pCLS1969 (SEQ ID No. 995) for Knock In experiment contained left and right homology arms, 2000 bp and 1200 bp in length respectively, generated by PCR amplification of the human RAG1 locus. An exogenous DNA fragment was inserted between these two arms. This sequence consisted of a 1.7 kb DNA fragment derived from a neomycin expression plasmid. HEK293 cell line was plated at a density of $1 \times 10^6$ cells per 10 cm dish in complete medium (DMEM supplemented with 2 mM L-glutamine, penicillin (100 IU/ml), streptomycin (100 mg/ml), amphotericin B (Fongizone: 0.25 mg/ml, Invitrogen-Life Science) and 10% FBS). The next day, cells were transfected in the presence of Polyfect reagent (QIAGEN) according to the manufacturer's protocol. Typically cells were co-transfected with 2 μg of the donor plasmid pCLS1969, 3 μg of meganuclease expression vector pCLS2162 (SEQ ID No. 996) in presence or not of siRNA at a final concentration of 33 nM with 90 μl of Polyfect. After 72 h of incubation at 37° C., cells were treated with trypsin, dispensed at a density of 10 cells in 96-well plates and subsequently amplified. DNA was extracted with the ZR-96 genomic DNA kit (Zymo research) according to the manufacturer's protocol. PCR amplification reactions were performed with the primers F2-Neo: 5'-AGGATCTCCTGT-CATCTCAC-3' SEQ ID No 7 and Rad1EX2-R12: 5'-CTTTCACAGTCCTGTACATCTTGT-3' SEQ ID No 998 in order to detect the targeted integrations of the 1700 bp exogenous fragment.

Results:

This example refers to the analysis of the ability of siRNAs hits targeting EP300 and ATF7IP genes to increase the frequency of homologous recombination at an endogenous locus in human cells induced by expression of an engineered meganuclease cleaving at RAG1 locus. As described in FIG. 20 and in Material and Methods, the HEK293 cell line was co-transfected with the donor repair plasmid (pCLS1969, SEQ ID No. 995), the meganuclease encoding vector (pCLS2162, SEQ ID No. 996) and either the control siRNA AS (Qiagen #1027280) or siRNA EP300 (SEQ ID No. 197) or siRNA ATF7IP (SEQ ID No. 42). Frequency of homologous recombination was quantified after PCR screening for specific detection of knock-in targeted events.

As shown in FIG. 21, frequency of targeted homologous recombination at RAG1 locus was increased 1.4 and 4-fold with siRNAs EP300 and ATF7IP respectively compared to transfection with de siRNA control AS. These results indicate that siRNAs hits that have been identified for their capacity to stimulate I-SceI induced gene targeting efficiency are also able to increase the efficiency of homologous gene insertion induced by I-CreI meganuclease with a modified specificity and at a natural locus. Since the effect observed with siRNAs EP300 and ATF7IP seems not to be restricted to I-SceI meganuclease, these effectors may be useful to improve genome engineering at different chromosomal locus cleaved by distinct custom meganucleases.

LIST OF REFERENCES CITED IN THE DESCRIPTION

1. Hinnen et al. Proc Natl Acad Sci USA. 1978. 75: 1929-33.
2. Rothstein et al. Methods Enzymol 1983 101: 202-211
3. Thomas and Capecchi Cell 1987 51(3): 503-12
4. Capecchi et al. Nat Med 2001 7(10): 1086-90
5. Smithies et al. Nat Med 2001 7(10): 1083-6
6. Paques and Haber Microbiol Mol Biol Rev 1999 63(2): 349-404
7. Sung and Klein Nat. Rev. Mol. Cell. Biol 2006 7: 739-750
8. Roeder et al Genes Dev 1997 11: 2600-2621
9. Van Gent et al. Nat Rev Genet. 2001 2(3): 196-206
10. Capecchi et al. Trends Genet. 1989 5(3): 70-6.
11. Rouet et al. Mol Cell Biol 1994 14(12): 8096-106.
12. Rouet et al. Proc Natl Acad Sci USA 1994 91(13): 6064-8.
13. Choulika et al. Mol Cell Biol 1995 15(4): 1968-73.
14. Chevalier and Stoddard Nucleic Acids Res 2001 29(18): 3757-74.
15. Dujon et al. Basic Life Sci. 1986 40: 5-27
16. Haber Bioessays 1995 17: 609-620
17. Posfai et al. Nucleic Acids Res 1999 27(22): 4409-15.
18. Sargent et al. Mol Cell Biol 1997 17(1): 267-77.
19. Donoho et al. Mol Cell Biol 1998 18(7): 4070-8.
20. Cohen-Tannoudji et al. Mol Cell Biol 1998 18(3): 1444-8.
21. Gouble et al. J Gene Med 2006 8(5): 616-22.
22. Puchta et al. Proc Natl Acad Sci USA 1996 93(10): 5055-60.
23. Siebert and Puchta Plant Cell 2002 14(5): 1121-31.
24. Páques and Duchateau Curr Gene Ther 2007 7(1): 49-66.
25. Arnould et al. J Mol Biol 2006 355(3): 443-58.
26. Arnould et al. J Mol Biol 2007 371(1): 49-65.
27. Smith et al. Nucleic Acids Res 2006 34(22): e149.
28. Grizot et al. Nucleic Acids Res 2009 37(16): 5405-19
29. Meister and Tuschl Nature 2004 431: 343-9
30. Hannon Nature 2002 418: 244-51
31. Elbashir et al. Nature 2001 411: 494-8
32. McCaffrey et al. Nature 2002 418: 38-9
33. Harborth et al J Cell Sci 2001 114(Pt 24): 4557-65.
34. Allen et al. Proc Natl Acad Sci USA 2002 99(6): 3758-63.
35. Delacote et al. Nucleic Acids Res 2002 30(15): 3454-63.
36. Bertolini et al, Mol Biotechnol 2009 41(2):106-14.
37. Slabicki et al. American Society of Gene and Cell Therapy, 2009.
38. Porteus and Carroll Nat Biotechnol 2005 23(8): 967-73.
39. Arimondo et al. Mol Cell Biol. 2006 26:324-333.
40. Simon et al. Nucleic Acids Res 2008 36:3531-3538.
41. Eisenschmidt et al. Nucleic Acids Res 2005 33: 7039-7047.
42. Kalish and Glazer Ann NY Acad Sci 2005 1058: 151-61.
43. Majumdar et al. J. Biol. Chem. 2008 283, 17:11244-11252
44. Liu et al. NAR 2009 37:6378-6388
45. Cannata et al. Proc Natl Acad Sci USA 2008 105: 9576-9581.
46. Stoddard et al. Quarterly Reviews of Biophysics 2006 38:49-95.
47. Orr-Weaver et al. Proc Natl Acad Sci USA 1981 78: 6354-6358
48. Orr-Weaver et al. Methods Enzymol 1983 101: 228-245
49. Szostak et al Cell 1983 33: 25-35.
50. Lee et al. EMBO J. 2002 21: 4663-4670
51. Lee et al. Nature 2003 425: 415-419
52. Yi et al. Genes and Development 2003 17: 3011-3016
53. Hutvagner et al. 2001 Science 293: 834-838
54. Bartel et al. 2004 Cell 116: 281-297
55. Zeng et al. 2005 Methods Enzymol 2005 392:371-380

The invention claimed is:

1. A method of generating a recombinant cell through double-stranded break-induced homologous recombination comprising introducing into a eukaryotic cell:
   i. an endonuclease capable of generating a double-stranded break in the eukaryotic cell,
   ii. a donor sequence flanked by sequences homologous to the sequences of the locus where the recombination event is desired, and
   iii. an interfering RNA that comprises a sense RNA nucleic acid and an antisense RNA nucleic acid that down-regulates the expression of EP300 or ATF71 P;
   wherein the interfering RNA increases the generation of a recombinant cell by double-stranded break-induced homologous recombination.

2. The method of claim 1, wherein the interfering RNA is an siRNA that targets a sequence comprising SEQ ID NO:197.

3. The method of claim 1, wherein said interfering RNA is an siRNA that targets a sequence comprising SEQ ID NO:198.

4. The method of claim 1, wherein said interfering RNA is an siRNA that targets a sequence comprising SEQ ID NO:42.

5. The method of claim 1, wherein said antisense RNA further comprises a hairpin sequence, wherein the sense RNA nucleic acid and the antisense RNA nucleic acid are covalently linked by the hairpin sequence to produce a single shRNA molecule.

6. The method of claim 1, wherein said eukaryotic cell is a plant cell.

7. The method of claim 1, wherein said eukaryotic cell is a mammalian cell.

8. The method of claim 1, wherein the endonuclease is I-Scel.

9. The method of claim 1, wherein the endonuclease is I-Crel.

10. The method of claim 1, wherein the endonuclease is I-Ceul.

11. The method of claim 1, wherein the endonuclease is I-Msol.

12. The method of claim 1, wherein the endonuclease is I-Dmol.

13. A kit for generating a recombinant cell through double-stranded break-induced homologous recombination comprising:
   i. an endonuclease or an expression vector encoding the endonuclease capable of generating a double-stranded break in a eukaryotic cell, and
   ii. an interfering RNA or an expression vector encoding the interfering RNA that comprises a sense RNA nucleic acid and an antisense RNA nucleic acid;
   wherein the interfering RNA down-regulates the expression of EP300 or ATF71 P.

14. The kit of claim 13, wherein the endonuclease is I-Scel.

15. The kit of claim 13, wherein the endonuclease is I-Crel.

16. The kit of claim 13, wherein the endonuclease is I-Ceul.

17. The kit of claim 13, wherein the endonuclease is I-Msol.

18. The kit of claim 13, wherein the endonuclease is I-Dmol.

19. The kit of claim 13, wherein said interfering RNA is an siRNA that targets a sequence selected from the group consisting of SEQ ID Nos. 197, 198, and 42.

* * * * *

```
SEQUENCE LISTING

<160> NUMBER OF SEQ ID NOS: 999

<210> SEQ ID NO 1
<211> LENGTH: 9452
<212> TYPE: DNA
<213> ORGANISM: Artificial
<220> FEATURE:
<223> OTHER INFORMATION: pCLS2026

<400> SEQUENCE: 1
gacggatcgg gagatctaaa gctaactgta ggactgagtc tattctaaac tgaaagcctg      60
gacatctgga gtaccagggg gagatgacgt gttacgggct tccataaaag cagctggctt     120
tgaatggaag gagccaagag gccagcacag gagcggattc gtcgctttca cggccatcga     180
gccgaacctc tcgcaagtcc gtgagccgtt aaggaggccc ccagtcccga cccttcgccc     240
caagcccctc ggggtccccg ggcctggtac tccttgccac acgggagggg cgcggaagcc     300
ggggcggagg aggagccaac cccgggctgg gctgagaccc gcagaggaag acgctctagg     360
gatttgtccc ggactagcga gatggcaagg ctgaggacgg gaggctgatt gagaggcgaa     420
ggtacaccct aatctcaata caacctttgg agctaagcca gcaatggtag agggaagatt     480
ctgcacgtcc cttccaggcg gcctcccgt caccacccc cccaaccgc ccgaccgga        540 gctgagagta attcatacaa aaggactcgc ccctgccttg gggaatccca gggaccgtcg     600
ttaaactccc actaacgtag aacccagaga tcgctgcgtt cccgccccct cacccgcccg     660
```

```
ctctcgtcat cactgaggtg gagaagagca tgcgtgaggc tccggtgccc gtcagtgggc    720
agagcgcaca tcgcccacag tccccgagaa gttgggggga ggggtcggca attgaaccgg    780
tgcctagaga aggtggcgcg gggtaaactg ggaaagtgat gtcgtgtact ggctccgcct    840
ttttcccgag ggtgggggag aaccgtatat aagtgcagta gtcgccgtga acgttctttt    900
tcgcaacggg tttgccgcca gaacacaggt aagtgccgtg tgtggttccc gcgggcctgg    960
cctctttacg ggttatggcc cttgcgtgcc ttgaattact tccacgcccc tggctgcagt   1020
acgtgattct tgatcccgag cttcgggttg gaagtgggtg ggagagttcg aggccttgcg   1080
cttaaggagc cccttcgcct cgtgcttgag ttgaggcctg gcttgggcgc tggggccgcc   1140
gcgtgcgaat ctggtggcac cttcgcgcct gtctcgctgc tttcgataag tctctagcca   1200
tttaaaattt ttgatgacct gctgcgacgc ttttttttctg gcaagatagt cttgtaaatg   1260
cgggccaaga tctgcacact ggtatttcgg ttttgggc cgcgggcggc gacggggccc    1320
gtgcgtccca gcgcacatgt tcggcgaggc ggggcctgcg agcgcggcca ccgagaatcg   1380
gacgggggta gtctcaagct ggccggcctg ctctggtgcc tggcctcgcg ccgccgtgta   1440
tcgcccgcc ctgggcggca aggctggccc ggtcggcacc agttgcgtga gcggaaagat   1500
ggccgcttcc cggccctgct gcagggagct caaaatggag gacgcggcgc tcgggagagc   1560
gggcgggtga gtcacccaca caaaggaaaa gggccttttcc gtcctcagcc gtcgcttcat   1620
gtgactccac ggagtaccgg gcgccgtcca ggcacctcga ttagttctcg agcttttgga   1680
gtacgtcgtc tttaggttgg ggggaggggt tttatgcgat ggagtttccc cacactgagt   1740
gggtggagac tgaagttagg ccagcttggc acttgatgta attctccttg gaatttgccc   1800
tttttgagtt tggatcttgg ttcattctca agcctcagac agtggttcaa agttttttttc   1860
ttccatttca ggtgtcgtgg aattcaacgc tagggataac agggtaatag aagggcccag   1920
cgccattcta cccactcgaa gacgggaccg ccggcgagca gctgcacaaa gccatgaagc   1980
gctacgccct ggtgccggc accatcgcct ttaccgacgc acatatcgag gtggacatta   2040
cctacgccga gtacttcgag atgagcgttc ggctggcaga agctatgaag cgctatgggc   2100
tgaatacaaa ccatcggatc gtggtgtgca gcgagaatag cttgcagttc ttcatgcccg   2160
tgttgggtgc cctgttcatc ggtgtggctg tggccccagc taacgacatc tacaacgagc   2220
gcgagctgct gaacagcatg ggcatcagcc agcccaccgt cgtattcgtg agcaagaaag   2280
ggctgcaaaa gatcctcaac gtgcaaaaga agctaccgat catacaaaag atcatcatca   2340
tggatagcaa gaccgactac cagggcttcc aaagcatgta caccttcgtg acttcccatt   2400
tgccacccgg cttcaacgag tacgacttcg tgcccgagag cttcgaccgg gacaaaacca   2460
tcgcctgat catgaacagt agtggcagta ccggattgcc caagggcgta gcctaccgc   2520
accgcaccgc ttgtgtccga ttcagtcatg cccgcgaccc catcttcggc aaccagatca   2580
tccccgacac cgctatcctc agcgtggtgc catttcacca cggcttcggc atgttccaca   2640
cgctgggcta cttgatctgc ggctttcggg tcgtgctcat gtaccgcttc gaggaggagc   2700
tattcttgcg cagcttgcaa gactataaga ttcaatctgc cctgctggtg cccacactat   2760
ttagcttctt cgctaagagc actctcatcg acaagtacga cctaagcaac ttgcacgaga   2820
tcgccagcgg cggggcgccg ctcagcaagg aggtaggtga ggccgtggcc aaacgcttcc   2880
acctaccagg catccgccag ggctacgccc tgacagaaac aaccagcgcc attctgatca   2940
cccccgaagg ggacgacaag cctggcgcag taggcaaggt ggtgcccttc ttcgaggcta   3000
```

```
aggtggtgga cttggacacc ggtaagacac tgggtgtgaa ccagcgcggc gagctgtgcg    3060
tccgtggccc catgatcatg agcggctacg ttaacaaccc cgaggctaca aacgctctca    3120
tcgacaagga cggctggctg cacagcggcg acatcgccta ctgggacgag gacgagcact    3180
tcttcatcgt ggaccggctg aagagcctga tcaaatacaa gggctaccag gtagccccag    3240
ccgaactgga gagcatcctg ctgcaacacc ccaacatctt cgacgccggg gtcgccggcc    3300
tgcccgacga cgatgccggc gagctgcccg ccgcagtcgt cgtgctggaa cacggtaaaa    3360
ccatgaccga gaaggagatc gtggactatg tggccagcca ggttacaacc gccaagaagc    3420
tgcgcggtgg tgttgtgttc gtggacgagg tgcctaaagg actgaccggc aagttggacg    3480
cccgcaagat ccgcgagatt ctcattaagg ccaagaaggg cggcaagatc gccgtgtaat    3540
aattctagag tcggggcggc cggccgcttc gagcagacat gataagatac attgatgagt    3600
ttggacaaac cacaactaga atgcagtgaa aaaaatgctt tatttgtgaa atttgtgatg    3660
ctattgcttt atttgtaacc attataagct gcaataaaca agttaacaac aacaattgca    3720
ttcattttat gtttcaggtt caggggagg tgtgggaggt tttttaaagc aagtaaaacc    3780
tctacaaatg tggtaagcta gccaccatgg cttccaaggt gtacgacccc gagcaacgca    3840
aacgcatgat cactgggcct cagtggtggg ctcgctgcaa gcaaatgaac gtgctggact    3900
ccttcatcaa ctactatgat tccgagaagc acgccgagaa cgccgtgatt tttctgcatg    3960
gtaacgctgc ctccagctac ctgtggaggc acgtcgtgcc tcacatcgag cccgtggcta    4020
gatgcatcat ccctgatctg atcggaatgg gtaagtccgg caagagcggg aatggctcat    4080
atcgcctcct ggatcactac aagtacctca ccgcttggtt cgagctgctg aaccttccaa    4140
agaaaatcat ctttgtgggc cacgactggg gggcttgtct ggcctttcac tactcctacg    4200
agcaccaaga caagatcaag gccatcgtcc atgctgagag tgtcgtggac gtgatcgagt    4260
cctgggacga gtggcctgac atcgaggagg atatcgccct gatcaagagc gaagagggcg    4320
agaaaatggt gcttgagaat aacttcttcg tcgagaccat gctcccaagc aagatcatgc    4380
ggaaactgga gcctgaggag ttcgctgcct acctggagcc attcaaggag aagggcgagg    4440
ttagacggcc taccctctcc tggcctcgcg agatccctct cgttaaggga ggcaagcccg    4500
acgtcgtcca gattgtccgc aactacaacg cctaccttcg ggccagcgac gatctgccta    4560
agatgttcat cgagtccgac cctgggttct tttccaacgc tattgtcgag ggagctaaga    4620
agttccctaa caccgagttc gtgaaggtga agggcctcca cttcagccag gaggacgctc    4680
cagatgaaat gggtaagtac atcaagagct tcgtggagcg cgtgctgaag aacgagcagt    4740
aattctagag cggccgcttc gagcagacat gataagatac attgatgagt ttggacaaac    4800
cacaactaga atgcagtgaa aaaaatgctt tatttgtgaa atttgtgatg ctattgcttt    4860
atttgtaacc attataagct gcaataaaca agttaacaac aacaattgca ttcattttat    4920
gtttcaggtt caggggagg tgtgggaggt tttttaaagc aagtaaaacc tctacaaatg    4980
tggtaaaatc gataaggatc cgcggccgct cgagtctaga gggcccgttt aaacccgctg    5040
atcagcctcg actgtgcctt ctagttgcca gccatctgtt gtttgcccct cccccgtgcc    5100
ttccttgacc ctggaaggtg ccactcccac tgtcctttcc taataaaatg aggaaattgc    5160
atcgcattgt ctgagtaggt gtcattctat tctggggggt ggggtggggc aggacagcaa    5220 ggggaggat tggaagaca atagcaggca tgctggggat gcggtgggct ctatggcttc    5280
tgaggcggaa agaaccagct ggggctctag ggggtatccc cacgcgccct gtagcggcgc    5340
attaagcgcg gcgggtgtgg tggttacgcg cagcgtgacc gctacacttg ccagcgccct    5400
```

```
agcgcccgct cctttcgctt tcttcccttc ctttctcgcc acgttcgccg gctttccccg    5460
tcaagctcta aatcggggc tccctttagg gttccgattt agtgctttac ggcacctcga     5520
ccccaaaaaa cttgattagg gtgatggttc acgtagtggg ccatcgccct gatagacggt    5580
ttttcgccct tgacgttgg agtccacgtt ctttaatagt ggactcttgt tccaaactgg     5640
aacaacactc aaccctatct cggtctattc ttttgattta taagggattt tgccgatttc    5700
ggcctattgg ttaaaaaatg agctgattta acaaaaattt aacgcgaatt aattctgtgg    5760
aatgtgtgtc agttagggtg tggaaagtcc ccaggctccc cagcaggcag aagtatgcaa    5820
agcatgcatc tcaattagtc agcaaccagg tgtggaaagt ccccaggctc ccagcaggc     5880 agaagtatgc aaagcatgca tctcaattag tcagcaacca tagtcccgcc cctaactccg    5940
cccatcccgc ccctaactcc gcccagttcc gcccattctc cgccccatgg ctgactaatt    6000 tttttattt atgcagaggc cgaggccgcc tctgcctctg agctattcca gaagtagtga    6060
ggaggctttt ttggaggcct aggcttttgc aaaaagctcc cgggagcttg tatatccatt    6120
ttcggatctg atcaagagac aggatgagga tcgtttcgca tgattgaaca agatggattg    6180
cacgcaggtt ctccggccgc ttgggtggag aggctattcg gctatgactg ggcacaacag    6240
acaatcggct gctctgatgc cgccgtgttc cggctgtcag cgcaggggcg cccggttctt    6300
tttgtcaaga ccgacctgtc cggtgccctg aatgaactgc aggacgaggc agcgcggcta    6360
tcgtggctgg ccacgacggg cgttccttgc gcagctgtgc tcgacgttgt cactgaagcg    6420
ggaagggact ggctgctatt gggcgaagtg ccggggcagg atctcctgtc atctcacctt    6480
gctcctgccg agaaagtatc catcatggct gatgcaatgc ggcggctgca tacgcttgat    6540
ccggctacct gcccattcga ccaccaagcg aaacatcgca tcgagcgagc acgtactcgg    6600
atggaagccg gtcttgtcga tcaggatgat ctggacgaag agcatcaggg gctcgcgcca    6660
gccgaactgt tcgccaggct caaggcgcgc atgcccgacg gcgaggatct cgtcgtgacc    6720
catggcgatg cctgcttgcc gaatatcatg gtggaaaatg gccgcttttc tggattcatc    6780
gactgtggcc ggctgggtgt ggcggaccgc tatcaggaca tagcgttggc tacccgtgat    6840
attgctgaag agcttggcgg cgaatgggct gaccgcttcc tcgtgcttta cggtatcgcc    6900
gctcccgatt cgcagcgcat cgccttctat cgccttcttg acgagttctt ctgagcggga    6960
ctctggggtt cgaaatgacc gaccaagcga cgcccaacct gccatcacga gatttcgatt    7020
ccaccgccgc cttctatgaa aggttgggct tcggaatcgt tttccgggac gccggctgga    7080
tgatcctcca gcgcggggat ctcatgctgg agttcttcgc ccaccccaac ttgtttattg    7140
cagcttataa tggttacaaa taaagcaata gcatcacaaa tttcacaaat aaagcatttt    7200
tttcactgca ttctagttgt ggtttgtcca aactcatcaa tgtatcttat catgtctgta    7260
taccgtcgac ctctagctag agcttggcgt aatcatggtc atagctgttt cctgtgtgaa    7320
attgttatcc gctcacaatt ccacacaaca tacgagccgg aagcataaag tgtaaagcct    7380
ggggtgccta atgagtgagc taactcacat taattgcgtt gcgctcactg cccgctttcc    7440
agtcgggaaa cctgtcgtgc cagctgcatt aatgaatcgg ccaacgcgcg gggagaggcg    7500
gtttgcgtat tgggcgctct tccgcttcct cgctcactga ctcgctgcgc tcggtcgttc    7560
ggctgcggcg agcggtatca gctcactcaa aggcggtaat acggttatcc acagaatcag    7620
gggataacgc aggaaagaac atgtgagcaa aaggccagca aaaggccagg aaccgtaaaa    7680
aggccgcgtt gctggcgttt ttccataggc tccgcccccc tgacgagcat cacaaaaatc    7740
```

| | |
|---|---|
| gacgctcaag tcagaggtgg cgaaacccga caggactata aagataccag gcgtttcccc | 7800 |
| ctggaagctc cctcgtgcgc tctcctgttc cgaccctgcc gcttaccgga tacctgtccg | 7860 |
| cctttctccc ttcgggaagc gtggcgcttt ctcatagctc acgctgtagg tatctcagtt | 7920 |
| cggtgtaggt cgttcgctcc aagctgggct gtgtgcacga accccccgtt cagcccgacc | 7980 |
| gctgcgcctt atccggtaac tatcgtcttg agtccaaccc ggtaagacac gacttatcgc | 8040 |
| cactggcagc agccactggt aacaggatta gcagagcgag gtatgtaggc ggtgctacag | 8100 |
| agttcttgaa gtggtggcct aactacggct acactagaag aacagtattt ggtatctgcg | 8160 |
| ctctgctgaa gccagttacc ttcggaaaaa gagttggtag ctcttgatcc ggcaaacaaa | 8220 |
| ccaccgctgg tagcggtttt tttgtttgca agcagcagat tacgcgcaga aaaaaggat | 8280 |
| ctcaagaaga ccctttgatc ttttctacgg ggtctgacgc tcagtggaac gaaaactcac | 8340 |
| gttaagggat tttggtcatg agattatcaa aaaggatctt cacctagatc cttttaaatt | 8400 |
| aaaaatgaag ttttaaatca atctaaagta tatatgagta aacttggtct gacagttacc | 8460 |
| aatgcttaat cagtgaggca cctatctcag cgatctgtct atttcgttca tccatagttg | 8520 |
| cctgactccc cgtcgtgtag ataactacga tacgggaggg cttaccatct ggccccagtg | 8580 |
| ctgcaatgat accgcgagac ccacgctcac cggctccaga tttatcagca ataaaccagc | 8640 |
| cagccggaag ggccgagcgc agaagtggtc ctgcaacttt atccgcctcc atccagtcta | 8700 |
| ttaattgttg ccgggaagct agagtaagta gttcgccagt taatagtttg cgcaacgttg | 8760 |
| ttgccattgc tacaggcatc gtggtgtcac gctcgtcgtt tggtatggct tcattcagct | 8820 |
| ccggttccca acgatcaagg cgagttacat gatcccccat gttgtgcaaa aaagcggtta | 8880 |
| gctccttcgg tcctccgatc gttgtcagaa gtaagttggc cgcagtgtta tcactcatgg | 8940 |
| ttatggcagc actgcataat tctcttactg tcatgccatc cgtaagatgc ttttctgtga | 9000 |
| ctggtgagta ctcaaccaag tcattctgag aatagtgtat gcggcgaccg agttgctctt | 9060 |
| gcccggcgtc aatacgggat aataccgcgc cacatagcag aactttaaaa gtgctcatca | 9120 |
| ttggaaaacg ttcttcgggg cgaaaactct caaggatctt accgctgttg agatccagtt | 9180 |
| cgatgtaacc cactcgtgca cccaactgat cttcagcatc ttttactttc accagcgttt | 9240 |
| ctgggtgagc aaaaacagga aggcaaaatg ccgcaaaaaa gggaataagg gcgacacgga | 9300 |
| aatgttgaat actcatactc ttcctttttc aatattattg aagcatttat cagggttatt | 9360 |
| gtctcatgag cggatacata tttgaatgta tttagaaaaa taaacaaata ggggttccgc | 9420 |
| gcacatttcc ccgaaaagtg ccacctgacg tt | 9452 |

<210> SEQ ID NO 2
<211> LENGTH: 6738
<212> TYPE: DNA
<213> ORGANISM: Artificial
<220> FEATURE:
<223> OTHER INFORMATION: pCLS2067

<400> SEQUENCE: 2

| | |
|---|---|
| ctcgcgcgtt tcggtgatga cggtgaaaac ctctgacaca tgcagctccc ggagacggtc | 60 |
| acagcttgtc tgtaagcgga tgccgggagc agacaagccc gtcagggcgc gtcagcgggt | 120 |
| gttggcgggt gtcggggctg gcttaactat gcggcatcag agcagattgt actgagagtg | 180 |
| caccatatgc ggtgtgaaat accgcacaga tgcgtaagga gaaaataccg catcaggcgc | 240 |
| cattcgccat tcaggctgcg caactgttgg gaagggcgat cggtgcgggc ctcttcgcta | 300 |
| ttacgccagc tggcgaaagg gggatgtgct gcaaggcgat taagttgggt aacgccaggg | 360 |

```
ttttcccagt cacgacgttg taaaacgacg gccagtgaat tcgattttgc cgccagaaca    420
caggtaagtg ccgtgtgtgg ttcccgcggg cctggcctct ttacgggtta tggcccttgc    480
gtgccttgaa ttacttccac gcccctggct gcagtacgtg attcttgatc ccgagcttcg    540
ggttggaagt gggtgggaga gttcgaggcc ttgcgcttaa ggagcccctt cgcctcgtgc    600
ttgagttgag gcctggcttg ggcgctgggg ccgccgcgtg cgaatctggt ggcaccttcg    660
cgcctgtctc gctgctttcg ataagtctct agccatttaa aatttttgat gacctgctgc    720
gacgcttttt ttctggcaag atagtcttgt aaatgcgggc caagatctgc acactggtat    780
ttcggttttt ggggccgcgg gcggcgacgg ggcccgtgcg tcccagcgca catgttcggc    840
gaggcggggc ctgcgagcgc ggccaccgag aatcggacgg gggtagtctc aagctggccg    900
gcctgctctg gtgcctggcc tcgcgccgcc gtgtatcgcc ccgccctggg cggcaaggct    960
ggcccggtcg gcaccagttg cgtgagcgga agatggccg cttcccggcc ctgctgcagg    1020
gagctcaaaa tggaggacgc ggcgctcggg agagcgggcg ggtgagtcac ccacacaaag    1080
gaaaagggcc tttccgtcct cagccgtcgc ttcatgtgac tccacggagt accgggcgcc    1140
gtccaggcac ctcgattagt tctcgagctt tggagtacg tcgtctttag gttgggggga    1200
ggggttttat gcgatggagt ttccccacac tgagtgggtg gagactgaag ttaggccagc    1260
ttggcacttg atgtaattct ccttggaatt tgccttttt gagtttggat cttggttcat    1320
tctcaagcct cagacagtgg ttcaaagttt ttttcttcca tttcaggtgt cgtggaattc    1380
atggaagatg ccaaaaacat taagaagggc ccagcgccat tctacccact cgaagacggg    1440
accgccggcg agcagctgca caaagccatg aagcgctacg ccctggtgcc cggcaccatc    1500
gcctttaccg acgcacatat cgaggtggac attacctacg ccgagtactt cgagatgagc    1560
gttcggctgg cagaagctat gaagcgctat gggctgaata caaaccatcg gatcgtggtg    1620
tgcagcgaga atagcttgca gttcttcatg cccgtgttgg gtgccctgtt catcggtgtg    1680
gctgtggccc cagctaacga catctacaac gagcgcgagc tgctgaacag catgggcatc    1740
agccagccca ccgtcgtatt cgtgagcaag aaagggctgc aaaagatcct caacgtgcaa    1800
aagaagctac cgatcataca aaagatcatc atcatggata gcaagaccga ctaccagggc    1860
ttccaaagca tgtacacctt cgtgacttcc catttgccac ccggcttcaa cgagtacgac    1920
ttcgtgcccg agagcttcga ccgggacaaa accatcgccc tgatcatgaa cagtagtggc    1980
agtaccggat tgcccaaggg cgtagcccta ccgcaccgca ccgcttgtgt ccgattcagt    2040
catgcccgcg accccatctt cggcaaccag atcatccccg acaccgctat cctcagcgtg    2100
gtgccatttc accacggctt cggcatgttc accacgctgg gctacttgat ctgcggcttt    2160
cgggtcgtgc tcatgtaccg cttcgaggag gagctattct tgcgcagctt gcaagactat    2220
aagattcaat ctgccctgct ggtgcccaca ctatttagct tcttcgctaa gagcactctc    2280
atcgacaagt acgacctaag caacttgcac gagatcgcca gcggcggggc gccgctcagc    2340
aaggaggtag gtgaggccgt ggccaaacgc ttccacctac caggatctgt caatattggc    2400
cattagccat attattcatt ggttatatag cataaatcaa tattggctat tggccattgc    2460
atacgttgta tctatatcat aatatgtaca tttatattgg ctcatgtcca atatgaccgc    2520
catgttggca ttgattattg actagttatt aatagtaatc aattacgggg tcattagttc    2580
atagcccata tatggagttc cgcgttacat aacttacggt aaatggcccg cctggctgac    2640
cgcccaacga ccccgcccca ttgacgtcaa taatgacgta tgttcccata gtaacgccaa    2700
```

-continued

```
tagggacttt ccattgacgt caatgggtgg agtatttacg gtaaactgcc cacttggcag    2760
tacatcaagt gtatcatatg ccaagtccgc ccctattga cgtcaatgac ggtaaatggc     2820
ccgcctggca ttatgcccag tacatgacct tacgggactt tcctacttgg cagtacatct    2880
acgtattagt catcgctatt accatggtga tgcggttttg gcagtacacc aatgggcgtg    2940
gatagcggtt tgactcacgg ggatttccaa gtctccaccc cattgacgtc aatgggagtt    3000
tgttttggca ccaaaatcaa cgggactttc caaaatgtcg taataacccc gccccgttga    3060
cgcaaatggg cggtaggcgt gtacggtggg aggtctatat aagcagaggt cgtttagtga    3120
accgtcagat cactagtagc tttattgcgg tagtttatca cagttaaatt gctaacgcag    3180
tcagtgctcg actgatcaca ggtaagtatc aaggttacaa gacaggttta aggaggccaa    3240
tagaaactgg gcttgtcgag acagagaaga ttcttgcgtt tctgataggc acctattggt    3300
cttactgaca tccactttgc ctttctctcc acaggggtac cgccatcatg aagtttaaac    3360
aagcttgaat tcaagcttcg acggcctctg agctattcca gaagtagtga ggaggctttt    3420
ttggaggcct agagccatgg ccaaaaacat caaaaaaaac caggtaatga acctcggtcc    3480
gaactctaaa ctgctgaaag aatacaaatc ccagctgatc gaactgaaca tcgaacagtt    3540
cgaagcaggt atcggtctga tcctgggtga tgcttacatc cgttctcgtg atgaaggtaa    3600
aacctactgt atgcagttcg agtggaaaaa caaagcatac atggaccacg tatgtctgct    3660
gtacgatcag tgggtactgt ccccgccgca caaaaagaa cgtgttaacc acctgggtaa     3720
cctggtaatc acctggggcg cccagacttt caaacaccaa gctttcaaca aactggctaa    3780
cctgttcatc gttaacaaca aaaaaaccat cccgaacaac ctggttgaaa actacctgac    3840
cccgatgtct ctggcatact ggttcatgga tgatggtggt aaatgggatt acaacaaaaa    3900
ctctaccaac aaatcgatcg tactgaacac ccagtctttc actttcgaag aagtagaata    3960
cctggttaag ggtctgcgta acaaattcca actgaactgt tacgtaaaaa tcaacaaaaa    4020
caaaccgatc atctacatcg attctatgtc ttacctgatc ttctacaacc tgatcaaacc    4080
gtacctgatc ccgcagatga tgtacaaact gccgaacact atctcctccg aaactttcct    4140
gaaagcggcc gcactcgagc accaccacca ccaccactga gatcgggatc cctcgaggct    4200
agcgcggccg cgtttaaaca gagctcgatg agtttggaca aaccacaact agaatgcagt    4260
gaaaaaaatg ctttatttgt gaaatttgtg atgctattgc tttatttgta accattataa    4320
gctgcaataa acaagttaac aacaacaatt gcattcattt tatgtttcag gttcaggggg    4380
aggtgtggga ggttttttaa agcaagtaaa acctctacaa atgtggtact aagaggggg    4440
agaccaaagg gcgagacgtt aaggcctcac gatcctctag agtcgacctg caggcatgca    4500
agcttggcgt aatcatggtc atagctgttt cctgtgtgaa attgttatcc gctcacaatt    4560
ccacacaaca tacgagccgg aagcataaag tgtaaagcct ggggtgccta atgagtgagc    4620
taactcacat taattgcgtt gcgctcactg cccgctttcc agtcgggaaa cctgtcgtgc    4680
cagctgcatt aatgaatcgg ccaacgcgcg gggagaggcg gtttgcgtat tgggcgctct    4740
tccgcttcct cgctcactga ctcgctgcgc tcggtcgttc ggctgcggcg agcggtatca    4800
gctcactcaa aggcggtaat acggttatcc acagaatcag gggataacgc aggaaagaac    4860
atgtgagcaa aaggccagca aaaggccagg aaccgtaaaa aggccgcgtt gctggcgttt    4920
ttccataggc tccgcccccc tgacgagcat cacaaaaatc gacgctcaag tcagaggtgg    4980
cgaaacccga caggactata aagataccag gcgtttcccc ctggaagctc cctcgtgcgc    5040
tctcctgttc cgaccctgcc gcttaccgga tacctgtccg cctttctccc ttcgggaagc    5100
```

```
gtggcgcttt ctcatagctc acgctgtagg tatctcagtt cggtgtaggt cgttcgctcc    5160
aagctgggct gtgtgcacga accccccgtt cagcccgacc gctgcgcctt atccggtaac    5220
tatcgtcttg agtccaaccc ggtaagacac gacttatcgc cactggcagc agccactggt    5280
aacaggatta gcagagcgag gtatgtaggc ggtgctacag agttcttgaa gtggtggcct    5340
aactacggct acactagaag gacagtattt ggtatctgcg ctctgctgaa gccagttacc    5400
ttcggaaaaa gagttggtag ctcttgatcc ggcaaacaaa ccaccgctgg tagcggtggt    5460
ttttttgttt gcaagcagca gattacgcgc agaaaaaaag gatctcaaga agatcctttg    5520
atcttttcta cggggtctga cgctcagtgg aacgaaaact cacgttaagg gattttggtc    5580
atgagattat caaaaaggat cttcacctag atccttttaa attaaaaatg aagttttaaa    5640
tcaatctaaa gtatatatga gtaaacttgg tctgacagtt accaatgctt aatcagtgag    5700
gcacctatct cagcgatctg tctatttcgt tcatccatag ttgcctgact ccccgtcgtg    5760
tagataacta cgatacggga gggcttacca tctggcccca gtgctgcaat gataccgcga    5820
gacccacgct caccggctcc agatttatca gcaataaacc agccagccgg aagggccgag    5880
cgcagaagtg gtcctgcaac tttatccgcc tccatccagt ctattaattg ttgccgggaa    5940
gctagagtaa gtagttcgcc agttaatagt ttgcgcaacg ttgttgccat tgctacaggc    6000
atcgtggtgt cacgctcgtc gtttggtatg gcttcattca gctccggttc caacgatca    6060 aggcgagtta catgatcccc catgttgtgc aaaaaagcgg ttagctcctt cggtcctccg    6120
atcgttgtca gaagtaagtt ggccgcagtg ttatcactca tggttatggc agcactgcat    6180
aattctctta ctgtcatgcc atccgtaaga tgcttttctg tgactggtga gtactcaacc    6240
aagtcattct gagaatagtg tatgcggcga ccgagttgct cttgcccggc gtcaatacgg    6300
gataataccg cgccacatag cagaacttta aaagtgctca tcattggaaa acgttcttcg    6360
gggcgaaaac tctcaaggat cttaccgctg ttgagatcca gttcgatgta acccactcgt    6420
gcacccaact gatcttcagc atcttttact ttcaccagcg tttctgggtg agcaaaaaca    6480
ggaaggcaaa atgccgcaaa aaagggaata agggcgacac ggaaatgttg aatactcata    6540
ctcttccttt ttcaatatta ttgaagcatt tatcagggtt attgtctcat gagcggatac    6600
atatttgaat gtatttagaa aaataaacaa ataggggttc cgcgcacatt tccccgaaaa    6660
gtgccacctg acgtctaaga aaccattatt atcatgacat taacctataa aaataggcgt    6720
atcacgaggc cctttcgt                                                 6738
```

<210> SEQ ID NO 3
<211> LENGTH: 4651
<212> TYPE: DNA
<213> ORGANISM: Artificial
<220> FEATURE:
<223> OTHER INFORMATION: pCLS2007

<400> SEQUENCE: 3

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
```

```
tttcccagtc acgacgttgt aaaacgacgg ccagtgaatt cgattttgcc gccagaacac    420
aggtaagtgc cgtgtgtggt tcccgcgggc ctggcctctt tacgggttat ggcccttgcg    480
tgccttgaat tacttccacg cccctggctg cagtacgtga ttcttgatcc cgagcttcgg    540
gttggaagtg ggtgggagag ttcgaggcct gcgcttaag gagccccttc gcctcgtgct     600
tgagttgagg cctggcttgg gcgctgggc cgccgcgtgc gaatctggtg gccaccttcgc    660
gcctgtctcg ctgctttcga taagtctcta gccatttaaa attttgatg acctgctgcg     720
acgctttttt tctggcaaga tagtcttgta aatgcgggcc aagatctgca cactggtatt    780
tcggttttg gggccgcggg cggcgacggg gcccgtgcgt cccagcgcac atgttcggcg     840
aggcggggcc tgcgagcgcg gccaccgaga atcggacggg ggtagtctca agctggccgg    900
cctgctctgg tgcctggcct cgcgccgccg tgtatcgccc cgccctgggc ggcaaggctg    960
gcccggtcgg caccagttgc gtgagcggaa agatggccgc ttcccggccc tgctgcaggg   1020
agctcaaaat ggaggacgcg cgctcgggga gagcgggcgg gtgagtcacc cacacaaagg   1080
aaaagggcct ttccgtcctc agccgtcgct tcatgtgact ccacggagta ccgggcgccg   1140
tccaggcacc tcgattagtt ctcgagcttt tggagtacgt cgtctttagg ttgggggggag  1200
gggttttatg cgatggagtt tccccacact gagtgggtgg agactgaagt taggccagct   1260
tggcacttga tgtaattctc cttggaattt gccctttttg agtttggatc ttggttcatt   1320
ctcaagcctc agacagtggt tcaaagtttt tttcttccat ttcaggtgtc gtggaattca   1380
tggaagatgc caaaaacatt aagaagggcc cagcgccatt ctacccactc gaagacggga   1440
ccgccggcga gcagctgcac aaagccatga agcgctacgc cctggtgccc ggcaccatcg   1500
cctttaccga cgcacatatc gaggtggaca ttacctacgc cgagtacttc gagatgagcg   1560
ttcggctggc agaagctatg aagcgctatg ggctgaatac aaaccatcgg atcgtggtgt   1620
gcagcgagaa tagcttgcag ttcttcatgc ccgtgttggg tgccctgttc atcggtgtgg   1680
ctgtggcccc agctaacgac atctacaacg agcgcgagct gctgaacagc atgggcatca   1740
gccagcccac cgtcgtattc gtgagcaaga aagggctgca aaagatcctc aacgtgcaaa   1800
agaagctacc gatcatacaa aagatcatca tcatggatag caagaccgac taccagggct   1860
tccaaagcat gtacaccttc gtgacttccc atttgccacc cggcttcaac gagtacgact   1920
tcgtgcccga gagcttcgac cgggacaaaa ccatcgccct gatcatgaac agtagtggca   1980
gtaccggatt gcccaagggc gtagccctac cgcaccgcac cgcttgtgtc cgattcagtc   2040
atgcccgcga cccatcttc ggcaaccaga tcatccccga caccgctatc ctcagcgtgg    2100
tgccattcca ccacggcttc ggcatgttca ccacgctggg ctacttgatc tgcggctttc   2160
gggtcgtgct catgtaccgc ttcgaggagg agctattctt gcgcagcttg caagactata   2220
agattcaatc tgccctgctg gtgcccacac tatttagctt cttcgctaag agcactctca   2280
tcgacaagta cgacctaagc aacttgcacg agatcgccag cggcggggcg ccgctcagca   2340
aggaggtagg tgaggccgtg gccaaacgct tccacctacc aggatcctct agagtcgacc   2400
tgcaggcatg caagcttggc gtaatcatgg tcatagctgt ttcctgtgtg aaattgttat   2460
ccgctcacaa ttccacacaa catacgagcc ggaagcataa agtgtaaagc ctggggtgcc   2520
taatgagtga gctaactcac attaattgcg ttgcgctcac tgcccgcttt ccagtcggga   2580
aacctgtcgt gccagctgca ttaatgaatc ggccaacgcg cggggagagg cggtttgcgt   2640
attgggcgct cttccgcttc ctcgctcact gactcgctgc gctcggtcgt tcggctgcgg   2700
cgagcggtat cagctcactc aaaggcggta atacggttat ccacagaatc agggggataac   2760
```

```
gcaggaaaga acatgtgagc aaaaggccag caaaaggcca ggaaccgtaa aaaggccgcg    2820
ttgctggcgt ttttccatag gctccgcccc cctgacgagc atcacaaaaa tcgacgctca    2880
agtcagaggt ggcgaaaccc gacaggacta taaagatacc aggcgtttcc ccctggaagc    2940
tccctcgtgc gctctcctgt tccgaccctg ccgcttaccg gatacctgtc cgcctttctc    3000
ccttcgggaa gcgtggcgct ttctcatagc tcacgctgta ggtatctcag ttcggtgtag    3060
gtcgttcgct ccaagctggg ctgtgtgcac gaaccccccg ttcagcccga ccgctgcgcc    3120
ttatccggta actatcgtct tgagtccaac ccggtaagac acgacttatc gccactggca    3180
gcagccactg gtaacaggat tagcagagcg aggtatgtag gcggtgctac agagttcttg    3240
aagtggtggc ctaactacgg ctacactaga aggacagtat ttggtatctg cgctctgctg    3300
aagccagtta ccttcggaaa aagagttggt agctcttgat ccggcaaaca aaccaccgct    3360
ggtagcggtg gtttttttgt ttgcaagcag cagattacgc gcagaaaaaa aggatctcaa    3420
gaagatcctt tgatcttttc tacggggtct gacgctcagt ggaacgaaaa ctcacgttaa    3480
gggattttgg tcatgagatt atcaaaaagg atcttcacct agatcctttt aaattaaaaa    3540
tgaagtttta aatcaatcta agtatatat gagtaaactt ggtctgacag ttaccaatgc    3600
ttaatcagtg aggcacctat ctcagcgatc tgtctatttc gttcatccat agttgcctga    3660
ctccccgtcg tgtagataac tacgatacgg gagggcttac catctggccc cagtgctgca    3720
atgataccgc gagacccacg ctcaccggct ccagatttat cagcaataaa ccagccagcc    3780
ggaagggccg agcgcagaag tggtcctgca actttatccg cctccatcca gtctattaat    3840
tgttgccggg aagctagagt aagtagttcg ccagttaata gtttgcgcaa cgttgttgcc    3900
attgctacag gcatcgtggt gtcacgctcg tcgtttggta tggcttcatt cagctccggt    3960
tcccaacgat caaggcgagt tacatgatcc cccatgttgt gcaaaaaagc ggttagctcc    4020
ttcggtcctc cgatcgttgt cagaagtaag ttggccgcag tgttatcact catggttatg    4080
gcagcactgc ataattctct tactgtcatg ccatccgtaa gatgcttttc tgtgactggt    4140
gagtactcaa ccaagtcatt ctgagaatag tgtatgcggc gaccgagttg ctcttgcccg    4200
gcgtcaatac gggataatac cgcgccacat agcagaactt taaaagtgct catcattgga    4260
aaacgttctt cggggcgaaa actctcaagg atcttaccgc tgttgagatc cagttcgatg    4320
taacccactc gtgcacccaa ctgatcttca gcatctttta ctttcaccag cgtttctggg    4380
tgagcaaaaa caggaaggca aaatgccgca aaaagggaa taaggcgac acggaaatgt    4440 tgaatactca tactcttcct ttttcaatat tattgaagca tttatcaggg ttattgtctc    4500
atgagcggat acatatttga atgtatttag aaaaataaac aaatagggt tccgcgcaca    4560 tttccccgaa aagtgccacc tgacgtctaa gaaaccatta ttatcatgac attaacctat    4620 aaaaatagc gtatcacgag gccctttcgt c                                   4651
```

<210> SEQ ID NO 4
<211> LENGTH: 2686
<212> TYPE: DNA
<213> ORGANISM: Artificial
<220> FEATURE:
<223> OTHER INFORMATION: pCLS2002

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg ttatccaca    780
gaatcagggg ataacgcagg aaagaacatg tgagcaaaag gccagcaaaa ggccaggaac    840
cgtaaaaagg ccgcgttgct ggcgtttttc cataggctcc gccccctga cgagcatcac    900
aaaaatcgac gctcaagtca gaggtggcga acccgacag gactataaag ataccaggcg    960
tttccccctg gaagctccct cgtgcgctct cctgttccga ccctgccgct taccggatac    1020
ctgtccgcct ttctcccttc gggaagcgtg gcgctttctc atagctcacg ctgtaggtat    1080
ctcagttcgg tgtaggtcgt tcgctccaag ctgggctgtg tgcacgaacc cccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaaggac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccat gttgtgcaaa    2040
aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttccttttc aatattattg aagcatttat    2520
```

```
cagggttatt gtctcatgag cggatacata tttgaatgta tttagaaaaa taaacaaata      2580
ggggttccgc gcacatttcc ccgaaaagtg ccacctgacg tctaagaaac cattattatc      2640
atgacattaa cctataaaaa taggcgtatc acgaggccct ttcgtc                     2686

<210> SEQ ID NO 5
<211> LENGTH: 21
<212> TYPE: DNA
<213> ORGANISM: Artificial
<220> FEATURE:
<223> OTHER INFORMATION: Target sequence in RAD51

<400> SEQUENCE: 5
caggataaag cttccgggaa a                                                   21

<210> SEQ ID NO 6
<211> LENGTH: 21
<212> TYPE: DNA
<213> ORGANISM: Artificial
<220> FEATURE:
<223> OTHER INFORMATION: Target sequence in LIG4

<400> SEQUENCE: 6
aaggacaata acgtagagga a                                                   21

<210> SEQ ID NO 7
<211> LENGTH: 20
<212> TYPE: DNA
<213> ORGANISM: Artificial
<220> FEATURE:
<223> OTHER INFORMATION: primer F2-neo

<400> SEQUENCE: 7
aggatctcct gtcatctcac                                                     20

<210> SEQ ID NO 8
<211> LENGTH: 7284
<212> TYPE: DNA
<213> ORGANISM: Artificial
<220> FEATURE:
<223> OTHER INFORMATION: pCLS2809

<400> SEQUENCE: 8
attattgaag catttatcag ggttattgtc tcatgagcgg atacatattt gaatgtattt       60
agaaaaataa acaaataggg gttccgcgca catttccccg aaaagtgcca cctgacgtct      120
aagaaaccat tattatcatg acattaacct ataaaaatag gcgtatcacg aggccctttc      180
gtctcgcgcg tttcggtgat gacggtgaaa acctctgaca catgcagctc ccggagacgg      240
tcacagcttg tctgtaagcg gatgccggga gcagacaagc ccgtcagggc gcgtcagcgg      300
gtgttggcgg gtgtcggggc tggcttaact atgcggcatc agagcagatt gtactgagag      360
tgcaccatat gcggtgtgaa ataccgcaca gatgcgtaag gagaaaatac cgcatcaggc      420
gccattcgcc attcaggctg cgcaactgtt gggaagggcg atcggtgcgg gcctcttcgc      480
tattacgcca gctggcgaaa gggggatgtg ctgcaaggcg attaagttgg gtaacgccag      540
ggttttccca gtcacgacgt tgtaaaacga cggccagtga attttaagga gcccttcgc       600 ctcgtgcttg agttgaggcc tggcttgggc gctggggccg ccgcgtgcga atctggtggc      660
accttcgcgc ctgtctcgct gctttcgata agtctctagc catttaaaat ttttgatgac      720
ctgctgcgac gcttttttc tggcaagata gtcttgtaaa tgcgggccaa gatcgatctg      780
```

```
cacactggta tttcggtttt tggggccgcg ggcggcgacg gggcccgtgc gtcccagcgc    840
acatgttcgg cgaggcgggg cctgcgagcg cggccaccga gaatcggacg ggggtagtct    900
caagctggcc ggcctgctct ggtgcctggc ctcgcgccgc cgtgtatcgc cccgccctgg    960
gcggcaaggc tgggcccggtc ggcaccagtt gcgtgagcgg aaagatggcc gcttcccggc   1020
cctgctgcag ggagctcaaa atggaggacg cggcgctcgg gagagcgggc gggtgagtca   1080
cccacacaaa ggaaaagggc cttccgtcc tcagccgtcg cttcatgtga ctccacggag    1140
taccgggcgc cgtccaggca cctcgattag ttctcgagct tttggagtac gtcgtcttta   1200
ggttgggggg aggggtttta tgcgatggag tttccccaca ctgagtgggt ggagactgaa   1260
gttaggccag cttggcactt gatgtaattc tccttggaat ttgccctttt tgagtttgga   1320
tcttggttca ttctcaagcc tcagacagtg gttcaaagtt tttttcttcc atttcaggtg   1380
tcgtggaatt ggctagagct tgcatgcctg caggtcggcc gccacgaccg gtgccgccac   1440
catcccctga cccacgcccc tgaccccctca aaggagacg accttccatg accgagtaca   1500
agcccacggt gcgcctcgcc acccgcgacg acgtccccccg ggccgtacgc accctcgccg   1560
ccgcgttcgc cgactacccc gccacgcgcc acaccgtcga cccggaccgc cacatcgagc   1620
gggtcaccga gctgcaagaa ctcttcctca cgcgcgtcgg gctcgacatc ggcaaggtgt   1680
gggtcgcgga cgacgcgcc gcggtggcgg tctggaccac gccggagagc gtcgaagcgg   1740
gggcggtgtt cgccgagatc ggcccgcgca tggccgagtt gagcggttcc cggctggccg   1800
cgcagcaaca gatggaaggc ctcctggcgc cgcaccggcc caaggagccc gcgtggttcc   1860
tggccaccgt cggcgtctcg cccgaccacc agggcaaggg tctgggcagc gccgtcgtgc   1920
tccccggagt ggaggcggcc gagcgcgccg gggtgcccgc cttcctggag acctccgcgc   1980
cccgcaacct cccttctac gagcggctcg gcttcaccgt caccgccgac gtcgaggtgc   2040
ccgaaggacc gcgcacctgg tgcatgaccc gcaagcccgg tgcctgacgc ccgcggatcc   2100
gccctctcc ctcccccccc cctaacgtta ctggccgaag ccgcttggaa taaggccggt   2160
gtgcgtttgt ctatatgtta ttttccacca tattgccgtc ttttggcaat gtgagggccc   2220
ggaaacctgg ccctgtcttc ttgacgagca ttcctagggg tctttcccct ctcgccaaag   2280
gaatgcaagg tctgttgaat gtcgtgaagg aagcagttcc tctggaagct tcttgaagac   2340
aaacaacgtc tgtagcgacc ctttgcaggc agcggaaccc cccacctggc gacaggtgcc   2400
tctgcggcca aaagccacgt gtataagata cacctgcaaa ggcggcacaa ccccagtgcc   2460
acgttgtgag ttggatagtt gtggaaagag tcaaatggct ctcctcaagc gtattcaaca   2520
aggggctgaa ggatgcccag aaggtacccc attgtatggg atctgatctg gggcctcggt   2580
gcacatgctt tacatgtgtt tagtcgaggt taaaaaaacg tctaggcccc ccgaaccacg   2640
gggacgtggt tttcctttga aaaacacgat gataatatgg ccacaaccat ggtgagcaag   2700
ggcgaggagc tgttcaccgg ggtggtgccc atcctggtcg agctggacgg cgacgtaaac   2760
ggccactagt gctagggata acagggtaat atactagttc agcgtgtccg gcgagggcga   2820
gggcgatgcc acctacggca agctgaccct gaagttcatc tgcaccaccg gcaagctgcc   2880
cgtgccctgg cccaccctcg tgaccaccct gacctacggc gtgcagtgct tcagccgcta   2940
ccccgaccac atgaagcagc acgacttctt caagtccgcc atgcccgaag gctacgtcca   3000
ggagcgcacc atcttcttca aggacgacgg caactacaag acccgcgccg aggtgaagtt   3060
cgagggcgac accctggtga accgcatcga gctgaagggc atcgacttca aggaggacgg   3120
caacatcctg gggcacaagc tggagtacaa ctacaacagc cacaacgtct atatcatggc   3180
```

| | |
|---|---|
| cgacaagcag aagaacggca tcaaggtgaa cttcaagatc cgccacaaca tcgaggacgg | 3240 |
| cagcgtgcag ctcgccgacc actaccagca gaacaccccc atcggcgacg cccccgtgct | 3300 |
| gctgcccgac aaccactacc tgagcaccca gtccgccctg agcaaagacc ccaacgagaa | 3360 |
| gcgcgatcac atggtcctgc tggagttcgt gaccgccgcc gggatcactc tcggcatgga | 3420 |
| cgagctgtac aagtaaagcg gcctaatggt tacaaataaa gcaatagcat cacaaatttc | 3480 |
| acaaataaag cattttttc actgcattct agttgtggtt tgtccaaact catcaatgta | 3540 |
| tcttatcatg tctggatccg agaaccatca gatgtttcca gggtgcccca aggacctgaa | 3600 |
| atgaccctgt gccttatttg aactaaccaa tcagttcgct tctcgcttct gttcgcgcgc | 3660 |
| ttctgctccc cgagctcaat aaaagagccc acaaccctc actcggggcg ccagtcctcc | 3720 |
| gattgactga gtcgcccggg tacccgtgta tccaataaac cctcttgcag ttgcagttgc | 3780 |
| atccgacttg tggtctcgct gttccttggg agggtctcct ctgagtgatt gactaccgcg | 3840 |
| gccgctcgag tctagagggc ccgtttaaac ccgctgatca attgcatgaa gaatctgctt | 3900 |
| agggttaggc gttttgcgct gcttcgcgat gtacgggcca gatatacgcg ttgacattga | 3960 |
| ttattgacta gttattaata gtaatcaatt acggggtcat tagttcatag cccatatatg | 4020 |
| gagttccgcg ttacataact tacggtaaat ggcccgcctg gctgaccgcc caacgacccc | 4080 |
| cgcccattga cgtcaataat gacgtatgtt cccatagtaa cgccaatagg gactttccat | 4140 |
| tgacgtcaat gggtggagta tttacggtaa actgcccact tggcagtaca tcaagtgtat | 4200 |
| catatgccaa gtacgccccc tattgacgtc aatgacggta atggcccgc ctggcattat | 4260 |
| gcccagtaca tgaccttatg ggactttcct acttggcagt acatctacgt attagtcatc | 4320 |
| gctattacca tggtgatgcg gttttggcag tacatcaatg ggcgtggata gcggtttgac | 4380 |
| tcacgggat ttccaagtct ccaccccatt gacgtcaatg ggagtttgtt ttggcaccaa | 4440 |
| aatcaacggg actttccaaa atgtcgtaac aactccgccc cattgacgca aatgggcggt | 4500 |
| aggcgtgtac ggtgggaggt ctatataagc agagctctct ggctaactag agaacccact | 4560 |
| gcttactggc ttatcgaaat taatacgact cactataggg agacccaagc tggctaggat | 4620 |
| caagagacag gatgaggatc gtttcgcatg attgaacaag atggattgca cgcaggttct | 4680 |
| ccggccgctt gggtggagag gctattcggc tatgactggg cacaacagac aatcggctgc | 4740 |
| tctgatgccg ccgtgttccg gctgtcagcg caggggcgcc cggttctttt tgtcaagacc | 4800 |
| gacctgtccg gtgccctgaa tgaactgcag gacgaggcag cgcggctatc gtggctggcc | 4860 |
| acgacgggcg ttccttgcgc agctgtgctc gacgttgtca ctgaagcggg aagggactgg | 4920 |
| ctgctattgg gcgaagtgcc ggggcaggat ctcctgtcat ctcaccttgc tcctgccgag | 4980 |
| aaagtatcca tcatggctga tgcaatgcgg cggctgcata cgcttgatcc ggctacctgc | 5040 |
| ccattcgacc accaagcgaa acatcgcatc gagcgagcac gtactcggat ggaagccggt | 5100 |
| cttgtcgatc aggatgatct ggacgaagag catcaggggc tcgcgccagc cgaactgttc | 5160 |
| gccaggctca aggcgcgaat cgagctcgg tacccgggga tcctctagag tcgacctgca | 5220 |
| ggcatgcaag cttggcgtaa tcatggtcat agctgtttcc tgtgtgaaat tgttatccgc | 5280 |
| tcacaattcc acacaacata cgagccgaa gcataaagtg taaagcctgg ggtgcctaat | 5340 |
| gagtgagcta actcacatta attgcgttgc gctcactgcc cgctttccag tcgggaaacc | 5400 |
| tgtcgtgcca gctgcattaa tgaatcggcc aacgcgcggg gagaggcggt ttgcgtattg | 5460 |
| ggcgctcttc cgcttcctcg ctcactgact cgctgcgctc ggtcgttcgg ctgcggcgag | 5520 |

| | |
|---|---|
| cggtatcagc tcactcaaag gcggtaatac ggttatccac agaatcaggg gataacgcag | 5580 |
| gaaagaacat gtgagcaaaa ggccagcaaa aggccaggaa ccgtaaaaag gccgcgttgc | 5640 |
| tggcgttttt ccataggctc cgcccccctg acgagcatca caaaaatcga cgctcaagtc | 5700 |
| agaggtggcg aaacccgaca ggactataaa gataccaggc gtttccccct ggaagctccc | 5760 |
| tcgtgcgctc tcctgttccg accctgccgc ttaccggata cctgtccgcc tttctccctt | 5820 |
| cgggaagcgt ggcgctttct catagctcac gctgtaggta tctcagttcg gtgtaggtcg | 5880 |
| ttcgctccaa gctgggctgt gtgcacgaac cccccgttca gcccgaccgc tgcgccttat | 5940 |
| ccggtaacta tcgtcttgag tccaacccgg taagacacga cttatcgcca ctggcagcag | 6000 |
| ccactggtaa caggattagc agagcgaggt atgtaggcgg tgctacagag ttcttgaagt | 6060 |
| ggtggcctaa ctacggctac actagaagga cagtatttgg tatctgcgct ctgctgaagc | 6120 |
| cagttacctt cggaaaaaga gttggtagct cttgatccgg caaacaaacc accgctggta | 6180 |
| gcggtggttt ttttgtttgc aagcagcaga ttacgcgcag aaaaaaagga tctcaagaag | 6240 |
| atcctttgat cttttctacg gggtctgacg ctcagtggaa cgaaaactca cgttaaggga | 6300 |
| ttttggtcat gagattatca aaaaggatct tcacctagat ccttttaaat taaaaatgaa | 6360 |
| gttttaaatc aatctaaagt atatatgagt aaacttggtc tgacagttac caatgcttaa | 6420 |
| tcagtgaggc acctatctca gcgatctgtc tatttcgttc atccatagtt gcctgactcc | 6480 |
| ccgtcgtgta gataactacg atacgggagg gcttaccatc tggccccagt gctgcaatga | 6540 |
| taccgcgaga cccacgctca ccggctccag atttatcagc aataaaccag ccagccggaa | 6600 |
| gggccgagcg cagaagtggt cctgcaactt tatccgcctc catccagtct attaattgtt | 6660 |
| gccgggaagc tagagtaagt agttcgccag ttaatagttt gcgcaacgtt gttgccattg | 6720 |
| ctacaggcat cgtggtgtca cgctcgtcgt ttggtatggc ttcattcagc tccggttccc | 6780 |
| aacgatcaag gcgagttaca tgatccccca tgttgtgcaa aaaagcggtt agctccttcg | 6840 |
| gtcctccgat cgttgtcaga agtaagttgg ccgcagtgtt atcactcatg gttatggcag | 6900 |
| cactgcataa ttctcttact gtcatgccat ccgtaagatg cttttctgtg actggtgagt | 6960 |
| actcaaccaa gtcattctga gaatagtgta tgcggcgacc gagttgctct tgcccggcgt | 7020 |
| caatacggga taataccgcg ccacatagca gaactttaaa agtgctcatc attggaaaac | 7080 |
| gttcttcggg gcgaaaactc tcaaggatct taccgctgtt gagatccagt tcgatgtaac | 7140 |
| ccactcgtgc acccaactga tcttcagcat cttttacttt caccagcgtt tctgggtgag | 7200 |
| caaaaacagg aaggcaaaat gccgcaaaaa agggaataag ggcgacacgg aaatgttgaa | 7260 |
| tactcatact cttccttttt caat | 7284 |

<210> SEQ ID NO 9
<211> LENGTH: 5647
<212> TYPE: DNA
<213> ORGANISM: Artificial
<220> FEATURE:
<223> OTHER INFORMATION: pCLS1088

<400> SEQUENCE: 9

| | |
|---|---|
| gttgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |

```
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagtt aagctatcaa caagtttgta caaaaaagca ggcttcgaag gagatagaac    720 catgccaat accaaatata acaaagagtt cctgctgtac ctggccggct tgtggacgg     780 tgacggtagc atcatcgctc agattaaacc aaaccagtct tataagttta acatcagct    840 aagcttgacc tttcaggtga ctcaaaagac ccagcgccgt tggtttctgg acaaactagt    900
ggatgaaatt ggcgttggtt acgtacgtga tcgcggatcc gtttccaact acatcttaag    960
cgaaatcaag ccgctgcaca acttcctgac tcaactgcag ccgtttctga actgaaaca    1020 gaaacaggca aacctggttc tgaaaattat cgaacagctg ccgtctgcaa agaatcccc    1080 ggacaaattc ctggaagttt gtacctgggt ggatcagatt gcagctctga cgattctaa    1140 gacgcgtaaa accacttctg aaaccgttcg tgctgtgctg gacagcctga gcgagaagaa    1200
gaaatcctcc ccggcggccg actaaaccca gctttcttgt acaaagtggt tgatctagag    1260
ggcccgcggt tcgaaggtaa gcctatccct aaccctctcc tcggtctcga ttctacgcgt    1320
accggttagt aatgagttta acgggggag ctaactgaa acacggaagg agacaatacc    1380
ggaaggaacc cgcgctatga cggcaataaa aagacagaat aaaacgcacg ggtgttgggt    1440
cgtttgttca taaacgcggg gttcggtccc agggctggca ctctgtcgat accccaccga    1500
gaccccattg gggccaatac gcccgcgttt cttccttttc cccaccccac ccccaagtt    1560 cgggtgaagg cccagggctc gcagccaacg tcggggcggc aggccctgcc atagcagatc    1620
tgcgcagctg gggctctagg gggtatcccc acgcgccctg tagcggcgca ttaagcgcgg    1680
cgggtgtggt ggttacgcgc agcgtgaccg ctacacttgc cagcgcccta gcgcccgctc    1740
ctttcgcttt cttcccttcc tttctcgcca cgttcgccgg cttcccccgt caagctctaa    1800
atcggggcat cccctttaggg ttccgattta gtgctttacg gcacctcgac cccaaaaaac    1860
ttgattaggg tgatggttca cgtagtgggc catcgccctg atagacggtt tttcgccctt    1920
tgacgttgga gtccacgttc tttaatagtg gactcttgtt ccaaactgga caacactca    1980 accctatctc ggtctattct tttgatttat aagggatttt ggggatttcg gcctattggt    2040
taaaaaatga gctgatttaa caaaaattta acgcgaatta attctgtgga atgtgtgtca    2100
gttagggtgt ggaaagtccc caggctcccc agcaggcaga agtatgcaaa gcatgcatct    2160
caattagtca gcaaccaggt gtggaaagtc cccaggctcc ccagcaggca gaagtatgca    2220
aagcatgcat ctcaattagt cagcaaccat agtcccgccc ctaactccgc ccatcccgcc    2280
cctaactccg cccagttccg cccattctcc gccccatggc tgactaattt ttttattta    2340 tgcagaggcc gaggccgcct ctgcctctga gctattccag aagtagtgag gaggcttttt    2400
tggaggccta ggcttttgca aaaagctccc gggagcttgt atatccattt tcggatctga    2460
tcagcacgtg ttgacaatta atcatcggca tagtatatcg gcatagtata atacgacaag    2520
gtgaggaact aaaccatggc caagcctttg tctcaagaag aatccaccct cattgaaaga    2580
gcaacggcta caatcaacag catccccatc tctgaagact acagcgtcgc cagcgcagct    2640
```

```
ctctctagcg acggccgcat cttcactggt gtcaatgtat atcattttac tgggggacct    2700
tgtgcagaac tcgtggtgct gggcactgct gctgctgcgg cagctggcaa cctgacttgt    2760
atcgtcgcga tcggaaatga gaacaggggc atcttgagcc cctgcggacg gtgccgacag    2820
gtgcttctcg atctgcatcc tgggatcaaa gccatagtga aggacagtga tggacagccg    2880
acggcagttg ggattcgtga attgctgccc tctggttatg tgtgggaggg ctaagcactt    2940
cgtggccgag gagcaggact gacacgtgct acgagatttc gattccaccg ccgccttcta    3000
tgaaaggttg ggcttcggaa tcgttttccg ggacgccggc tggatgatcc tccagcgcgg    3060
ggatctcatg ctggagttct tcgcccaccc caacttgttt attgcagctt ataatggtta    3120
caaataaagc aatagcatca caaatttcac aaataaagca ttttttttcac tgcattctag   3180
ttgtggtttg tccaaactca tcaatgtatc ttatcatgtc tgtataccgt cgacctctag    3240
ctagagcttg gcgtaatcat ggtcatagct gtttcctgtg tgaaattgtt atccgctcac    3300
aattccacac aacatacgag ccggaagcat aaagtgtaaa gcctggggtg cctaatgagt    3360
gagctaactc acattaattg cgttgcgctc actgcccgct ttccagtcgg gaaacctgtc    3420
gtgccagctg cattaatgaa tcggccaacg cgcggggaga ggcggtttgc gtattgggcg    3480
ctcttccgct tcctcgctca ctgactcgct gcgctcggtc gttcggctgc ggcgagcggt    3540
atcagctcac tcaaaggcgg taatacggtt atccacagaa tcaggggata acgcaggaaa    3600
gaacatgtga gcaaaaggcc agcaaaaggc caggaaccgt aaaaaggccg cgttgctggc    3660
gttttttccat aggctccgcc cccctgacga gcatcacaaa aatcgacgct caagtcagag   3720
gtggcgaaac ccgacaggac tataaagata ccaggcgttt ccccctggaa gctccctcgt    3780
gcgctctcct gttccgaccc tgccgcttac cggatacctg tccgcctttc tcccttcggg    3840
aagcgtggcg ctttctcata gctcacgctg taggtatctc agttcggtgt aggtcgttcg    3900
ctccaagctg ggctgtgtgc acgaaccccc cgttcagccc gaccgctgcg ccttatccgg    3960
taactatcgt cttgagtcca acccggtaag acacgactta tcgccactgg cagcagccac    4020
tggtaacagg attagcagag cgaggtatgt aggcggtgct acagagttct tgaagtggtg    4080
gcctaactac ggctacacta agaacagtt atttggtatc tgcgctctgc tgaagccagt     4140
taccttcgga aaagagttg gtagctcttg atccggcaaa caaaccaccg ctggtagcgg     4200
tttttttgtt tgcaagcagc agattacgcg cagaaaaaaa ggatctcaag aagatccttt    4260
gatcttttct acggggtctg acgctcagtg gaacgaaaac tcacgttaag ggattttggt    4320
catgagatta tcaaaaagga tcttcaccta gatcctttta aattaaaaat gaagttttaa    4380
atcaatctaa agtatatatg agtaaacttg gtctgacagt taccaatgct taatcagtga    4440
ggcacctatc tcagcgatct gtctatttcg ttcatccata gttgcctgac tccccgtcgt    4500
gtagataact acgatacggg agggcttacc atctggcccc agtgctgcaa tgataccgcg    4560
agacccacgc tcaccggctc cagatttatc agcaataaac cagccagccg aagggccga    4620
gcgcagaagt ggtcctgcaa ctttatccgc ctccatccag tctattaatt gttgccggga    4680
agctagagta agtagttcgc cagttaatag tttgcgcaac gttgttgcca ttgctacagg    4740
catcgtggtg tcacgctcgt cgtttggtat ggcttcattc agctccggtt cccaacgatc    4800
aaggcgagtt acatgatccc ccatgttgtg caaaaaagcg gttagctcct tcggtcctcc    4860
gatcgttgtc agaagtaagt tggccgcagt gttatcactc atggttatgg cagcactgca    4920
taattctctt actgtcatgc catccgtaag atgcttttct gtgactggtg agtactcaac    4980
caagtcattc tgagaatagt gtatgcggcg accgagttgc tcttgcccgg cgtcaatacg    5040
```

-continued

```
ggataatacc gcgccacata gcagaacttt aaaagtgctc atcattggaa aacgttcttc    5100
ggggcgaaaa ctctcaagga tcttaccgct gttgagatcc agttcgatgt aacccactcg    5160
tgcacccaac tgatcttcag catcttttac tttcaccagc gtttctgggt gagcaaaaac    5220
aggaaggcaa aatgccgcaa aaagggaat aagggcgaca cggaaatgtt gaatactcat    5280
actcttcctt tttcaatatt attgaagcat ttatcagggt tattgtctca tgagcggata    5340
catatttgaa tgtatttaga aaataaaca aatagggtt ccgcgcacat ttccccgaaa    5400
agtgccacct gacgtcgacg gatcgggaga tctcccgatc ccctatggtg cactctcagt    5460
acaatctgct ctgatgccgc atagttaagc cagtatctgc tccctgcttg tgtgttggag    5520
gtcgctgagt agtgcgcgag caaaatttaa gctacaacaa ggcaaggctt gaccgacaat    5580
tgcatgaaga atctgcttag ggttaggcgt tttgcgctgc ttcgcgatgt acgggccaga    5640
tatacgc                                                              5647
```

<210> SEQ ID NO 10
<211> LENGTH: 6122
<212> TYPE: DNA
<213> ORGANISM: Artificial
<220> FEATURE:
<223> OTHER INFORMATION: pCLS3496

<400> SEQUENCE: 10

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggtctct ccacgctttg cctgaccctg cttgctcaac     480
tctacgtctt tgtttcgttt tctgttctgc gccgttacag atccaagctg tgaccggcgc     540
ctacctgaga tcaccggcgt gtcgacggat caattcaagc ttcgacggcc tctgagctat     600
tccagaagta gtgaggaggc ttttttggag gcctagagcc atggcaaaa acatcaaaaa     660 aaaccaggta atgaacctcg gtccgaactc taaactgctg aaagaataca atcccagct     720 gatcgaactg aacatcgaac agttcgaagc aggtatcggt ctgatcctgg gtgatgctta     780
catccgttct cgtgatgaag gtaaaaccta ctgtatgcag ttcgagtgga aaacaaagc     840 atacatggac cacgtatgtc tgctgtacga tcagtgggta ctgtccccgc cgcacaaaaa     900
agaacgtgtt aaccacctgg gtaacctggt aatcacctgg ggcgcccaga ctttcaaaca     960
ccaagctttc aacaaactgg ctaacctgtt catcgttaac aacaaaaaaa ccatcccgaa    1020
caacctggtt gaaaactacc tgaccccgat gtctctggca tactggttca tggatgatgg    1080
tggtaaatgg gattacaaca aaaactctac caacaaatcg atcgtactga acacccagtc    1140
tttcactttc gaagaagtag aatacctggt taagggtctg cgtaacaaat ccaactgaa    1200 ctgttacgta aaaatcaaca aaaacaaacc gatcatctac atcgattcta tgtcttacct    1260
gatcttctac aacctgatca aaccgtacct gatcccgcag atgatgtaca aactgccgaa    1320
cactatctcc tccgaaactt tcctgaaagc ggccgcactc gagcaccacc accaccacca    1380
```

```
ctgagatcgg gatcgatcca gcgctctgca gccatgggct agctggccag acatgataag    1440
atacattgat gagtttggac aaaccacaac tagaatgcag tgaaaaaaat gctttatttg    1500
tgaaatttgt gatgctattg ctttatttgt aaccattata agctgcaata aacaagttaa    1560
caacaacaat tgcattcatt ttatgtttca ggttcagggg gaggtgtggg aggttttta    1620 aagcaagtaa aacctctaca aatgtggtat ggaattctta accggaccgc cacatcgagc    1680
gggtcaccga gctgcaagaa ctcttcctca cgcgcgtcgg gctcgacatc ggcaaggtgt    1740
gggtcgcgga cgacggcgcc gcggtggcgg tctggaccac gccggagagc gtcgaagcgg    1800
gggcggtgtt cgccgagatc ggcccgcgca tggccgagtt gagcggttcc cggctggccg    1860
cgcagcaaca gatggaaggc ctcctggcgc cgcaccggcc caaggagccc gcgtggttcc    1920
tggccaccgt cggcgtctcg cccgaccacc agggcaaggg tctgggcagc gccgtcgtgc    1980
tccccggagt ggaggcggcc gagcgcgccg gggtgcccgc cttcctggag acctccgcgc    2040
cccgcaacct ccccttctac gagcggctcg gcttcaccgt caccgccgac gtcgaggtgc    2100
ccgaaggacc gcgcacctgg tgcatgaccc gcaagcccgg tgcctgacgc ccgcggatcc    2160
gcccctctcc ctcccccccc cctaacgtta ctggccgaag ccgcttggaa taaggccggt    2220
gtgcgtttgt ctatatgtta ttttccacca tattgccgtc ttttggcaat gtgagggccc    2280
ggaaacctgg ccctgtcttc ttgacgagca ttcctagggg tctttcccct ctcgccaaag    2340
gaatgcaagg tctgttgaat gtcgtgaagg aagcagttcc tctggaagct tcttgaagac    2400
aaacaacgtc tgtagcgacc ctttgcaggc agcggaaccc cccacctggc gacaggtgcc    2460
tctgcggcca aaagccacgt gtataagata cacctgcaaa ggcggcacaa ccccagtgcc    2520
acgttgtgag ttggatagtt gtggaaagag tcaaatggct ctcctcaagc gtattcaaca    2580
aggggctgaa ggatgcccag aaggtacccc attgtatggg atctgatctg gggcctcggt    2640
gcacatgctt tacatgtgtt tagtcgaggt taaaaaaacg tctaggcccc ccgaaccacg    2700
gggacgtggt tttcctttga aaaacacgat gataatatgg ccacaaccat ggtgagcaag    2760
ggcgaggagc tgttcaccgg ggtggtgccc atcctggtcg agctggacgg cgacgtaaac    2820
ggccacaagt tcagcgtgtc cggcgagggc gagggcgatg ccacctacgg caagctgacc    2880
ctgaagttca tctgcaccac cggcaagctg cccgtgccct ggcccaccct cgtgaccacc    2940
ctgacctacg gcgtgcagtg cttcagccgc taccccgacc acatgaagca gcacgacttc    3000
ttcaagtccg ccatgcccga aggctacgtc caggagcgca ccatcttctt caaggacgac    3060
ggcaactaca agacccgcgc cgaggtgaag ttcgagggcg acaccctggt gaaccgcatc    3120
gagctgaagg gcatcgactt caaggaggac ggcaacatcc tggggcacaa gctggagtac    3180
aactacaaca gccacaacgt ctatatcatg gccgacaagc agaagaacgg catcaaggtg    3240
aacttcaaga tccgccacaa catcgaggac ggcagcgtgc agctcgccga ccactaccag    3300
cagaacaccc ccatcggcga cggccccgtg ctgctgcccg acaaccacta cctgagcacc    3360
cattaagaat tctaaaatac agcatagcaa aactttaacc tccaaatcaa gcctctactt    3420
gaatcctttt ctgagggatg aataaggcat aggcatcagg gctgttgcc aatgtgcatt    3480 agctgtttgc agcctcacct tctttcatgg agtttaagat atagtgtatt ttcccaaggt    3540
ttgaactagc tcttcatttc tttatgtttt aaatgcactg acctcccaca ttcccttttt    3600
agtaaaatat tcagaaataa tttaaataca tcattgcaat gaaaataaat gttttttatt    3660
aggcagaatc cagatgctca aggcccttca taatatcccc cagtttagta gttgaactta    3720
gggaacaaag gaacctttaa tagaaattgg acagcaagaa agcgagcttc tagctttaga    3780
```

```
agaactcatc aagaagtctg tagaaggcaa ttctctggga gtcagggget gcaatgccat    3840 agagcactag gaacctgtct geccactctc cccctagctc ttctgctatg tccctggttg    3900
ctagggcaat gtcctggtac ctgtcagcca ctcccagcct gccacagtct atgaagccag    3960
agaaccttcc attttcaacc atgatgttgg gaaggcaggc atccccatga gtcaccacta    4020
ggtcctcacc atctggcatg gatgccttga gcctggcaaa tagttcagca ggggccaggc    4080
cctggtgttc ttcatccaag tcatcttggt ccaccaggcc agcctccatc ctggttctgg    4140
ccctctctat cctgtgcttg gctggtggt caaaggggca ggtggctggg tcaagggtgt    4200
ggagtcttct catggcatca gccatgattg cactttctc agctggagct aggtgagagg    4260
aaaggaggtc ctgcccaggc acctcaccta gtaggagcca gtcccttcca gcttctgtga    4320
ccacatcaag gacagctgca caggggaccc cagttgttgc caaccaggag agtctggcag    4380
cctcatcctg gagctcattg agagccccac tgaggtctgt ctttacaaaa aggactggcc    4440
tgccttgggc tgaaagtctg aaaactgctg catcagagca accaatggtc tgctgtgccc    4500
agtcatagcc aaacagtctc tcaacccagg cagctggaga acctgcatgt aggccatctt    4560
gttcaatcat gatggccctc ctatagtgag tcgtattata ctatgccgat atactatgcc    4620
gatgattaat tgtcaaaaca gcgtggatgg cgtctccagc ttatctgacg gttcactaaa    4680
cgagctctgc ttatatagac ctcccaccgt acacgcctac cgcccatttg cgtcaatggg    4740
gcggagttgt tacgacattt tggaaagtcc cgttgattta ctagtcaaaa caaactccca    4800
ttgacgtcaa tggggtggag acttggaaat ccccgtgagt caaaccgcta tccacgccca    4860
ttgatgtact gccaaaaccg catcatcatg gtaatagcga tgactaatac gtagatgtac    4920
tgccaagtag gaaagtccca taaggtcatg tactgggcat aatgccaggc gggccattta    4980
ccgtcattga cgtcaatagg gggcgtactt ggcatatgat acacttgatg tactgccaag    5040
tgggcagttt accgtaaata ctccacccat tgacgtcaat ggaaagtccc tattggcgtt    5100
actatgggaa catacgtcat tattgacgtc aatgggcggg ggtcgttggg cggtcagcca    5160
ggcgggccat ttaccgtaag ttatgtaacg cctgcaggtt aattaagaac atgtgagcaa    5220
aaggccagca aaaggccagg aaccgtaaaa aggccgcgtt gctggcgttt ttccataggc    5280
tccgcccccc tgacgagcat cacaaaaatc gacgctcaag tcagaggtgg cgaaacccga    5340
caggactata aagataccag gcgtttcccc ctggaagctc cctcgtgcgc tctcctgttc    5400
cgaccctgcc gcttaccgga tacctgtccg cctttctccc ttcgggaagc gtggcgcttt    5460
ctcatagctc acgctgtagg tatctcagtt cggtgtaggt cgttcgctcc aagctgggct    5520
gtgtgcacga accccccgtt cagcccgacc gctgcgcctt atccggtaac tatcgtcttg    5580
agtccaaccc ggtaagacac gacttatcgc cactggcagc agccactggt aacaggatta    5640
gcagagcgag gtatgtaggc ggtgctacag agttcttgaa gtggtggcct aactacggct    5700
acactagaag aacagtattt ggtatctgcg ctctgctgaa gccagttacc ttcggaaaaa    5760
gagttggtag ctcttgatcc ggcaaacaaa ccaccgctgg tagcggtggt ttttttgttt    5820
gcaagcagca gattacgcgc agaaaaaaag gatctcaaga gatcctttg atcttttcta    5880 cggggtctga cgctcagtgg aacgaaaact cacgttaagg gattttggtc atgctagtt    5940 aattaacatt taaatcagcg gccgcaataa aatatcttta ttttcattac atctgtgtgt    6000 tggtttttg tgtgaatcgt aactaacata cgctctccat caaaacaaaa cgaaacaaaa    6060
caaactagca aaataggctg tccccagtgc aagtgcaggt gccagaacat ttctctatcg    6120
``` aa                                                            6122

<210> SEQ ID NO 11
<211> LENGTH: 5295
<212> TYPE: DNA
<213> ORGANISM: Artificial
<220> FEATURE:
<223> OTHER INFORMATION: pCLS3495

<400> SEQUENCE: 11

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg gaccggcgc      540
ctacctgaga tcaccggcgt gtcgacggat ccagcgctct gcagccatgg gctagctggc     600
cagacatgat aagatacatt gatgagtttg gacaaaccac aactagaatg cagtgaaaaa     660
aatgctttat ttgtgaaatt tgtgatgcta ttgctttatt tgtaaccatt ataagctgca     720
ataaacaagt taacaacaac aattgcattc attttatgtt tcaggttcag ggggaggtgt     780
gggaggtttt ttaaagcaag taaaacctct acaaatgtgg tatggaattc ttaaccggac     840
cgccacatcg agcgggtcac cgagctgcaa gaactcttcc tcacgcgcgt cgggctcgac     900
atcggcaagg tgtgggtcgc ggacgacggc gccgcggtgg cggtctggac cacgccggag     960
agcgtcgaag cggggggcggt gttcgccgag atcggcccgc gcatggccga gttgagcggt    1020
tcccggctgg ccgcgcagca acagatggaa ggcctcctgg cgccgcaccg gcccaaggag    1080
cccgcgtggt tcctggccac cgtcggcgtc tcgcccgacc accagggcaa gggtctgggc    1140
agcgccgtcg tgctccccgg agtggaggcg gccgagcgcg ccggggtgcc cgccttcctg    1200
gagacctccg cgccccgcaa cctccccttc tacgagcggc tcggcttcac cgtcaccgcc    1260
gacgtcgagg tgcccgaagg accgcgcacc tggtgcatga cccgcaagcc cggtgcctga    1320
cgcccgcgga tccgcccctc tccctccccc cccctaacg ttactggccg aagccgcttg    1380
gaataaggcc ggtgtgcgtt tgtctatatg ttattttcca ccatattgcc gtcttttggc    1440
aatgtgaggg cccggaaacc tggccctgtc ttcttgacga gcattcctag ggtctttcc    1500
cctctcgcca aaggaatgca aggtctgttg aatgtcgtga aggaagcagt tcctctggaa    1560
gcttcttgaa gacaaacaac gtctgtagcg acccttgca ggcagcggaa cccccacct    1620
ggcgacaggt gcctctgcgg ccaaaagcca cgtgtataag atacacctgc aaaggcggca    1680
caaccccagt gccacgttgt gagttggata gttgtggaaa gagtcaaatg gctctcctca    1740
agcgtattca acaaggggct gaaggatgcc cagaaggtac cccattgtat gggatctgat    1800
ctggggcctc ggtgcacatg ctttacatgt gtttagtcga ggttaaaaaa acgtctaggc    1860
ccccgaacc acggggacgt ggttttcctt tgaaaacac gatgataata tggccacaac    1920
catggtgagc aagggcgagg agctgttcac cggggtggtg cccatcctgg tcgagctgga    1980
cggcgacgta aacggccaca agttcagcgt gtccggcgag ggcgagggcg atgccaccta    2040
```

```
cggcaagctg accctgaagt tcatctgcac caccggcaag ctgcccgtgc cctggcccac    2100
cctcgtgacc accctgacct acggcgtgca gtgcttcagc cgctaccccg accacatgaa    2160
gcagcacgac ttcttcaagt ccgccatgcc cgaaggctac gtccaggagc gcaccatctt    2220
cttcaaggac gacggcaact acaagacccg cgccgaggtg aagttcgagg gcgacaccct    2280
ggtgaaccgc atcgagctga agggcatcga cttcaaggag gacggcaaca tcctggggca    2340
caagctggag tacaactaca acagccacaa cgtctatatc atggccgaca gcagaagaa    2400 cggcatcaag gtgaacttca gatccgcca acatcgag gacggcagcg tgcagctcgc    2460
cgaccactac cagcagaaca cccccatcgg cgacggcccc gtgctgctgc ccgacaacca    2520
ctacctgagc acccattaag aattctaaaa tacagcatag caaaacttta acctccaaat    2580
caagcctcta cttgaatcct ttctgagggg atgaataagg cataggcatc aggggctgtt    2640
gccaatgtgc attagctgtt tgcagcctca ccttctttca tggagtttaa gatatagtgt    2700
attttcccaa ggtttgaact agctcttcat ttctttatgt tttaaatgca ctgacctccc    2760
acattccctt tttagtaaaa tattcagaaa taatttaat acatcattgc aatgaaaata    2820 aatgttttt attaggcaga atccagatgc tcaaggccct tcataatatc ccccagttta    2880
gtagttggac ttagggaaca aaggaaccttt aatagaaat tggacagcaa gaaagcgagc    2940
ttctagcttt agaagaactc atcaagaagt ctgtagaagg caattctctg ggagtcaggg    3000
gctgcaatgc catagagcac taggaacctg tctgcccact ctcccctag ctcttctgct    3060 atgtccctgg ttgctagggc aatgtcctgg tacctgtcag ccactcccag cctgccacag    3120
tctatgaagc cagagaacct tccattttca accatgatgt tgggaaggca ggcatcccca    3180
tgagtcacca ctaggtcctc accatctggc atggatgcct tgagcctggc aaatagttca    3240
gcaggggcca ggccctggtg ttcttcatcc aagtcatctt ggtccaccag gccagcctcc    3300
atcctggttc tggccctctc tatcctgtgc ttggcctggt ggtcaaaggg gcaggtggct    3360
gggtcaaggg tgtggagtct tctcatggca tcagccatga ttgacacttt ctcagctgga    3420
gctaggtgag aggaaaggag gtcctgccca ggcacctcac ctagtaggag ccagtccctt    3480
ccagcttctg tgaccacatc aaggacagct gcacagggga ccccagttgt tgccaaccag    3540
gagagtctgg cagcctcatc ctggagctca ttgagagccc cactgaggtc tgtctttaca    3600
aaaaggactg gcctgccttg ggctgaaagt ctgaaaactg ctgcatcaga gcaaccaatg    3660
gtctgctgtg cccagtcata gccaaacagt ctctcaaccc aggcagctgg agaacctgca    3720
tgtaggccat cttgttcaat catgatggcc tcctatagt gagtcgtatt atactatgcc    3780
gatatactat gccgatgatt aattgtcaaa acagcgtgga tggcgtctcc agcttatctg    3840
acggttcact aaacgagctc tgcttatata gacctcccac cgtacacgcc taccgcccat    3900
ttgcgtcaat ggggcggagt tgttacgaca ttttggaaag tcccgttgat ttactagtca    3960
aaacaaactc ccattgacgt caatggggtg gagacttgga atccccgtg agtcaaaccg    4020 ctatccacgc ccattgatgt actgccaaaa ccgcatcatc atggtaatag cgatgactaa    4080
tacgtagatg tactgccaag taggaaagtc ccataaggtc atgtactggg cataatgcca    4140
ggcgggccat ttaccgtcat tgacgtcaat aggggcgta cttggcatat gatacacttg    4200
atgtactgcc aagtgggcag tttaccgtaa atactccacc cattgacgtc aatggaaagt    4260
ccctattggc gttactatgg gaacatacgt cattattgac gtcaatgggc ggggtcgtt    4320 gggcggtcag ccaggcgggc catttaccgt aagttatgta acgcctgcag gttaattaag    4380
```

-continued

```
aacatgtgag caaaaggcca gcaaaaggcc aggaaccgta aaaaggccgc gttgctggcg    4440 ttttttccata ggctccgccc ccctgacgag catcacaaaa atcgacgctc aagtcagagg   4500
tggcgaaacc cgacaggact ataaagatac caggcgtttc ccccrggaag ctccctcgtg    4560
cgctctcctg ttccgaccct gccgcttacc ggatacctgt ccgcctttct cccttcggga   4620
agcgtggcgc tttctcatag ctcacgctgt aggtatctca gttcggtgta ggtcgttcgc   4680
tccaagctgg gctgtgtgca cgaaccccccc gttcagcccg accgctgcgc cttatccggt  4740
aactatcgtc ttgagtccaa cccggtaaga cacgacttat cgccactggc agcagccact   4800
ggtaacagga ttagcagagc gaggtatgta ggcggtgcta cagagttctt gaagtggtgg    4860
cctaactacg gctacactag aagaacagta tttggtatct gcgctctgct gaagccagtt    4920
accttcggaa aaagagttgg tagctcttga tccggcaaac aaaccaccgc tggtagcggt    4980
ggtttttttg tttgcaagca gcagattacg cgcagaaaaa aaggatctca agaagatcct    5040
ttgatctttt ctacggggtc tgacgctcag tggaacgaaa actcacgtta agggattttg    5100
gtcatggcta gttaattaac atttaaatca gcggccgcaa taaaatatct ttattttcat    5160
tacatctgtg tgttggtttt tgtgtgaat cgtaactaac atacgctctc catcaaaaca    5220
aaacgaaaca aaacaaacta gcaaatagg ctgtccccag tgcaagtgca ggtgccagaa     5280
catttctcta tcgaa                                                    5295
```

```
<210> SEQ ID NO 12
<211> LENGTH: 21
<212> TYPE: DNA
<213> ORGANISM: Artificial
<220> FEATURE:
<223> OTHER INFORMATION: Target sequence in GFP

<400> SEQUENCE: 12
aagcagcacg acttcttcaa g                                             21

<210> SEQ ID NO 13
<211> LENGTH: 21
<212> TYPE: DNA
<213> ORGANISM: Artificial
<220> FEATURE:
<223> OTHER INFORMATION: Target sequence in the gene ABCB5

<400> SEQUENCE: 13
tacgtactat agtgtcatta a                                             21

<210> SEQ ID NO 14
<211> LENGTH: 21
<212> TYPE: DNA
<213> ORGANISM: Artificial
<220> FEATURE:
<223> OTHER INFORMATION: Target sequence in the gene ACN9

<400> SEQUENCE: 14
ctgggcgacc agtacgtgaa a                                             21

<210> SEQ ID NO 15
<211> LENGTH: 21
<212> TYPE: DNA
<213> ORGANISM: Artificial
<220> FEATURE:
<223> OTHER INFORMATION: Target sequence in the gene ADAM5P

<400> SEQUENCE: 15
caaggagcat ttggaagtat t                                             21
```

<210> SEQ ID NO 16
<211> LENGTH: 21
<212> TYPE: DNA
<213> ORGANISM: Artificial
<220> FEATURE:
<223> OTHER INFORMATION: Target sequence in the gene ADH1A

<400> SEQUENCE: 16
caggttcacc tgcaggagga a                                              21

<210> SEQ ID NO 17
<211> LENGTH: 21
<212> TYPE: DNA
<213> ORGANISM: Artificial
<220> FEATURE:
<223> OTHER INFORMATION: Target sequence in the gene ADO

<400> SEQUENCE: 17
ctgaagcgct tccatcctaa a                                              21

<210> SEQ ID NO 18
<211> LENGTH: 21
<212> TYPE: DNA
<213> ORGANISM: Artificial
<220> FEATURE:
<223> OTHER INFORMATION: Target sequence in the gene ADPRHL2

<400> SEQUENCE: 18
agcgagcact ttctcaagca a                                              21

<210> SEQ ID NO 19
<211> LENGTH: 21
<212> TYPE: DNA
<213> ORGANISM: Artificial
<220> FEATURE:
<223> OTHER INFORMATION: Target sequence in the gene AGA

<400> SEQUENCE: 19
aagcaggata ttcctatcca t                                              21

<210> SEQ ID NO 20
<211> LENGTH: 21
<212> TYPE: DNA
<213> ORGANISM: Artificial
<220> FEATURE:
<223> OTHER INFORMATION: Target sequence in the gene AGXT2

<400> SEQUENCE: 20
atggagttgt ccagtaccca a                                              21

<210> SEQ ID NO 21
<211> LENGTH: 21
<212> TYPE: DNA
<213> ORGANISM: Artificial
<220> FEATURE:
<223> OTHER INFORMATION: Target sequence in the gene AHSA1

<400> SEQUENCE: 21
cagggcatga tcttacctac a                                              21

<210> SEQ ID NO 22
<211> LENGTH: 21
<212> TYPE: DNA
<213> ORGANISM: Artificial
<220> FEATURE:

<223> OTHER INFORMATION: Target sequence in the gene AKAP13

<400> SEQUENCE: 22
gagtcggata atagacagca a                                              21

<210> SEQ ID NO 23
<211> LENGTH: 21
<212> TYPE: DNA
<213> ORGANISM: Artificial
<220> FEATURE:
<223> OTHER INFORMATION: Target sequence in the gene AKAP8

<400> SEQUENCE: 23
gaggccggta gtgatcctca a                                              21

<210> SEQ ID NO 24
<211> LENGTH: 21
<212> TYPE: DNA
<213> ORGANISM: Artificial
<220> FEATURE:
<223> OTHER INFORMATION: Target sequence in the gene AKR7A2

<400> SEQUENCE: 24
tgagcgcttc ctgttgaata a                                              21

<210> SEQ ID NO 25
<211> LENGTH: 21
<212> TYPE: DNA
<213> ORGANISM: Artificial
<220> FEATURE:
<223> OTHER INFORMATION: Target sequence in the gene ALAD

<400> SEQUENCE: 25
aagggtgagc catcaagcta a                                              21

<210> SEQ ID NO 26
<211> LENGTH: 21
<212> TYPE: DNA
<213> ORGANISM: Artificial
<220> FEATURE:
<223> OTHER INFORMATION: Target sequence in the gene ALDH3B1

<400> SEQUENCE: 26
ttagactata tcaacctaca a                                              21

<210> SEQ ID NO 27
<211> LENGTH: 21
<212> TYPE: DNA
<213> ORGANISM: Artificial
<220> FEATURE:
<223> OTHER INFORMATION: Target sequence in the gene ALG10B

<400> SEQUENCE: 27
atcagtaacc ttcaacgaat a                                              21

<210> SEQ ID NO 28
<211> LENGTH: 21
<212> TYPE: DNA
<213> ORGANISM: Artificial
<220> FEATURE:
<223> OTHER INFORMATION: Target sequence in the gene ALS2CR8

<400> SEQUENCE: 28
cagcaacgct tcaatggact a                                              21

```
<210> SEQ ID NO 29
<211> LENGTH: 21
<212> TYPE: DNA
<213> ORGANISM: Artificial
<220> FEATURE:
<223> OTHER INFORMATION: Target sequence in the gene AMN1

<400> SEQUENCE: 29
taggtatttg tttcaccgaa a                                       21

<210> SEQ ID NO 30
<211> LENGTH: 21
<212> TYPE: DNA
<213> ORGANISM: Artificial
<220> FEATURE:
<223> OTHER INFORMATION: Target sequence in the gene AMN1

<400> SEQUENCE: 30
aaccgagttt ctgtaacttc a                                       21

<210> SEQ ID NO 31
<211> LENGTH: 21
<212> TYPE: DNA
<213> ORGANISM: Artificial
<220> FEATURE:
<223> OTHER INFORMATION: Target sequence in the gene ANK1

<400> SEQUENCE: 31
tagtccgtgt tcaaagtgta a                                       21

<210> SEQ ID NO 32
<211> LENGTH: 21
<212> TYPE: DNA
<213> ORGANISM: Artificial
<220> FEATURE:
<223> OTHER INFORMATION: Target sequence in the gene ANKRD13A

<400> SEQUENCE: 32
ctcgagtctt actccgacat a                                       21

<210> SEQ ID NO 33
<211> LENGTH: 21
<212> TYPE: DNA
<213> ORGANISM: Artificial
<220> FEATURE:
<223> OTHER INFORMATION: Target sequence in the gene ANKRD17

<400> SEQUENCE: 33
cacctcgatg tggttcagtt a                                       21

<210> SEQ ID NO 34
<211> LENGTH: 21
<212> TYPE: DNA
<213> ORGANISM: Artificial
<220> FEATURE:
<223> OTHER INFORMATION: Target sequence in the gene ANKRD49

<400> SEQUENCE: 34
ctgatgaacc gttacgtcaa a                                       21

<210> SEQ ID NO 35
<211> LENGTH: 21
<212> TYPE: DNA
<213> ORGANISM: Artificial
<220> FEATURE:
<223> OTHER INFORMATION: Target sequence in the gene ARF3
```

```
<400> SEQUENCE: 35
cagggctgac tgggtattct a                                              21

<210> SEQ ID NO 36
<211> LENGTH: 21
<212> TYPE: DNA
<213> ORGANISM: Artificial
<220> FEATURE:
<223> OTHER INFORMATION: Target sequence in the gene ARHGAP1

<400> SEQUENCE: 36
cagataggtg ggttctagca a                                              21

<210> SEQ ID NO 37
<211> LENGTH: 21
<212> TYPE: DNA
<213> ORGANISM: Artificial
<220> FEATURE:
<223> OTHER INFORMATION: Target sequence in the gene ARHGAP26

<400> SEQUENCE: 37
agggagtata ctagtaggtt a                                              21

<210> SEQ ID NO 38
<211> LENGTH: 21
<212> TYPE: DNA
<213> ORGANISM: Artificial
<220> FEATURE:
<223> OTHER INFORMATION: Target sequence in the gene ARID1B

<400> SEQUENCE: 38
caggcccaca gcggtatcca a                                              21

<210> SEQ ID NO 39
<211> LENGTH: 21
<212> TYPE: DNA
<213> ORGANISM: Artificial
<220> FEATURE:
<223> OTHER INFORMATION: Target sequence in the gene ARL14

<400> SEQUENCE: 39
atgggttcgc tgggttctaa a                                              21

<210> SEQ ID NO 40
<211> LENGTH: 21
<212> TYPE: DNA
<213> ORGANISM: Artificial
<220> FEATURE:
<223> OTHER INFORMATION: Target sequence in the gene ARRB2

<400> SEQUENCE: 40
ctcgaacaag atgaccaggt a                                              21

<210> SEQ ID NO 41
<211> LENGTH: 21
<212> TYPE: DNA
<213> ORGANISM: Artificial
<220> FEATURE:
<223> OTHER INFORMATION: Target sequence in the gene ARSB

<400> SEQUENCE: 41
ccgccgagga tttgatacct a                                              21

<210> SEQ ID NO 42
<211> LENGTH: 21
```

```
<212> TYPE: DNA
<213> ORGANISM: Artificial
<220> FEATURE:
<223> OTHER INFORMATION: Target sequence in the gene ATF7IP

<400> SEQUENCE: 42
cagatcttgt agaaacgatt a                                              21

<210> SEQ ID NO 43
<211> LENGTH: 21
<212> TYPE: DNA
<213> ORGANISM: Artificial
<220> FEATURE:
<223> OTHER INFORMATION: Target sequence in the gene ATP10A

<400> SEQUENCE: 43
cacgaacgtt ctggtttaac a                                              21

<210> SEQ ID NO 44
<211> LENGTH: 21
<212> TYPE: DNA
<213> ORGANISM: Artificial
<220> FEATURE:
<223> OTHER INFORMATION: Target sequence in the gene ATP5A1

<400> SEQUENCE: 44
cccggtatca ttcctcgaat t                                              21

<210> SEQ ID NO 45
<211> LENGTH: 21
<212> TYPE: DNA
<213> ORGANISM: Artificial
<220> FEATURE:
<223> OTHER INFORMATION: Target sequence in the gene ATR

<400> SEQUENCE: 45
caggcactaa ttgttcttca a                                              21

<210> SEQ ID NO 46
<211> LENGTH: 21
<212> TYPE: DNA
<213> ORGANISM: Artificial
<220> FEATURE:
<223> OTHER INFORMATION: Target sequence in the gene ATR

<400> SEQUENCE: 46
gaccggatac ttacagatgt a                                              21

<210> SEQ ID NO 47
<211> LENGTH: 21
<212> TYPE: DNA
<213> ORGANISM: Artificial
<220> FEATURE:
<223> OTHER INFORMATION: Target sequence in the gene ATXN8OS

<400> SEQUENCE: 47
ccctgggtcc ttcatgttag a                                              21

<210> SEQ ID NO 48
<211> LENGTH: 21
<212> TYPE: DNA
<213> ORGANISM: Artificial
<220> FEATURE:
<223> OTHER INFORMATION: Target sequence in the gene AVPR2

<400> SEQUENCE: 48
```
ctgtctgacc atccctctca a                                           21

<210> SEQ ID NO 49
<211> LENGTH: 21
<212> TYPE: DNA
<213> ORGANISM: Artificial
<220> FEATURE:
<223> OTHER INFORMATION: Target sequence in the gene B4GALT2

<400> SEQUENCE: 49
ctacggcgtc tatgtcatca a                                           21

<210> SEQ ID NO 50
<211> LENGTH: 21
<212> TYPE: DNA
<213> ORGANISM: Artificial
<220> FEATURE:
<223> OTHER INFORMATION: Target sequence in the gene BASP1

<400> SEQUENCE: 50
tgggagaatc caaatagtat t                                           21

<210> SEQ ID NO 51
<211> LENGTH: 21
<212> TYPE: DNA
<213> ORGANISM: Artificial
<220> FEATURE:
<223> OTHER INFORMATION: Target sequence in the gene BBC3

<400> SEQUENCE: 51
cagcctgtaa gatactgtat a                                           21

<210> SEQ ID NO 52
<211> LENGTH: 21
<212> TYPE: DNA
<213> ORGANISM: Artificial
<220> FEATURE:
<223> OTHER INFORMATION: Target sequence in the gene BC37295_3

<400> SEQUENCE: 52
aacgcgatga attcagccga a                                           21

<210> SEQ ID NO 53
<211> LENGTH: 21
<212> TYPE: DNA
<213> ORGANISM: Artificial
<220> FEATURE:
<223> OTHER INFORMATION: Target sequence in the gene BCL7C

<400> SEQUENCE: 53
aagttgggcg gtgtagacca a                                           21

<210> SEQ ID NO 54
<211> LENGTH: 21
<212> TYPE: DNA
<213> ORGANISM: Artificial
<220> FEATURE:
<223> OTHER INFORMATION: Target sequence in the gene BCR

<400> SEQUENCE: 54
acggcagtcc atgacggtga a                                           21

<210> SEQ ID NO 55
<211> LENGTH: 21
<212> TYPE: DNA
<213> ORGANISM: Artificial

```
<220> FEATURE:
<223> OTHER INFORMATION: Target sequence in the gene BIRC6

<400> SEQUENCE: 55
tagcgtgcga ttcaatccaa a                                              21

<210> SEQ ID NO 56
<211> LENGTH: 21
<212> TYPE: DNA
<213> ORGANISM: Artificial
<220> FEATURE:
<223> OTHER INFORMATION: Target sequence in the gene BLOC1S3

<400> SEQUENCE: 56
cccgcgcgct cgctcctgca a                                              21

<210> SEQ ID NO 57
<211> LENGTH: 21
<212> TYPE: DNA
<213> ORGANISM: Artificial
<220> FEATURE:
<223> OTHER INFORMATION: Target sequence in the gene BMP5

<400> SEQUENCE: 57
aagagtcgga gtactcagta a                                              21

<210> SEQ ID NO 58
<211> LENGTH: 21
<212> TYPE: DNA
<213> ORGANISM: Artificial
<220> FEATURE:
<223> OTHER INFORMATION: Target sequence in the gene BNIP2

<400> SEQUENCE: 58
cacaccgtca gagaatagta a                                              21

<210> SEQ ID NO 59
<211> LENGTH: 21
<212> TYPE: DNA
<213> ORGANISM: Artificial
<220> FEATURE:
<223> OTHER INFORMATION: Target sequence in the gene BRE

<400> SEQUENCE: 59
ccgcctcatg tttgaatacc a                                              21

<210> SEQ ID NO 60
<211> LENGTH: 21
<212> TYPE: DNA
<213> ORGANISM: Artificial
<220> FEATURE:
<223> OTHER INFORMATION: Target sequence in the gene BTAF1

<400> SEQUENCE: 60
ccgcgtttac ttgatatcct t                                              21

<210> SEQ ID NO 61
<211> LENGTH: 21
<212> TYPE: DNA
<213> ORGANISM: Artificial
<220> FEATURE:
<223> OTHER INFORMATION: Target sequence in the gene BYSL

<400> SEQUENCE: 61
cccgtttggc tgagcactct a                                              21
```

```
<210> SEQ ID NO 62
<211> LENGTH: 21
<212> TYPE: DNA
<213> ORGANISM: Artificial
<220> FEATURE:
<223> OTHER INFORMATION: Target sequence in the gene C10orf132

<400> SEQUENCE: 62
cacctcgagg cctcctactt a                                              21

<210> SEQ ID NO 63
<211> LENGTH: 21
<212> TYPE: DNA
<213> ORGANISM: Artificial
<220> FEATURE:
<223> OTHER INFORMATION: Target sequence in the gene C10orf55

<400> SEQUENCE: 63
ctgttcgtat ctagttctca a                                              21

<210> SEQ ID NO 64
<211> LENGTH: 21
<212> TYPE: DNA
<213> ORGANISM: Artificial
<220> FEATURE:
<223> OTHER INFORMATION: Target sequence in the gene C11orf56

<400> SEQUENCE: 64
tccgagggca tggcaggact a                                              21

<210> SEQ ID NO 65
<211> LENGTH: 21
<212> TYPE: DNA
<213> ORGANISM: Artificial
<220> FEATURE:
<223> OTHER INFORMATION: Target sequence in the gene C13orf31

<400> SEQUENCE: 65
ccctgtatcg acatccgtaa a                                              21

<210> SEQ ID NO 66
<211> LENGTH: 21
<212> TYPE: DNA
<213> ORGANISM: Artificial
<220> FEATURE:
<223> OTHER INFORMATION: Target sequence in the gene C14orf109

<400> SEQUENCE: 66
tacaactgat tgacacgtaa a                                              21

<210> SEQ ID NO 67
<211> LENGTH: 21
<212> TYPE: DNA
<213> ORGANISM: Artificial
<220> FEATURE:
<223> OTHER INFORMATION: Target sequence in the gene C14orf28

<400> SEQUENCE: 67
agcagcgcac aattaatata a                                              21

<210> SEQ ID NO 68
<211> LENGTH: 21
<212> TYPE: DNA
<213> ORGANISM: Artificial
<220> FEATURE:
<223> OTHER INFORMATION: Target sequence in the gene C14orf45
```

<400> SEQUENCE: 68
caaatccgtg tcatatccta a    21

<210> SEQ ID NO 69
<211> LENGTH: 21
<212> TYPE: DNA
<213> ORGANISM: Artificial
<220> FEATURE:
<223> OTHER INFORMATION: Target sequence in the gene C15orf38

<400> SEQUENCE: 69
tcgccgtaaa ttcgacgcca a    21

<210> SEQ ID NO 70
<211> LENGTH: 21
<212> TYPE: DNA
<213> ORGANISM: Artificial
<220> FEATURE:
<223> OTHER INFORMATION: Target sequence in the gene C15orf40

<400> SEQUENCE: 70
tcgcgccgag atgcctaaga a    21

<210> SEQ ID NO 71
<211> LENGTH: 21
<212> TYPE: DNA
<213> ORGANISM: Artificial
<220> FEATURE:
<223> OTHER INFORMATION: Target sequence in the gene C15orf48

<400> SEQUENCE: 71
aagcttataa caatcaacca a    21

<210> SEQ ID NO 72
<211> LENGTH: 21
<212> TYPE: DNA
<213> ORGANISM: Artificial
<220> FEATURE:
<223> OTHER INFORMATION: Target sequence in the gene C15orf48

<400> SEQUENCE: 72
accgatgtga tccttgatcg a    21

<210> SEQ ID NO 73
<211> LENGTH: 21
<212> TYPE: DNA
<213> ORGANISM: Artificial
<220> FEATURE:
<223> OTHER INFORMATION: Target sequence in the gene C15orf53

<400> SEQUENCE: 73
tcccgttcac agatcctgta a    21

<210> SEQ ID NO 74
<211> LENGTH: 21
<212> TYPE: DNA
<213> ORGANISM: Artificial
<220> FEATURE:
<223> OTHER INFORMATION: Target sequence in the gene C16orf84

<400> SEQUENCE: 74
cacaccagcc gtcgacacca a    21

<210> SEQ ID NO 75

```
<211> LENGTH: 21
<212> TYPE: DNA
<213> ORGANISM: Artificial
<220> FEATURE:
<223> OTHER INFORMATION: Target sequence in the gene C17orf71

<400> SEQUENCE: 75
caggcctact acagtcagga a                                              21

<210> SEQ ID NO 76
<211> LENGTH: 21
<212> TYPE: DNA
<213> ORGANISM: Artificial
<220> FEATURE:
<223> OTHER INFORMATION: Target sequence in the gene C19orf26

<400> SEQUENCE: 76
cagggtcaat gcaagacgca t                                              21

<210> SEQ ID NO 77
<211> LENGTH: 21
<212> TYPE: DNA
<213> ORGANISM: Artificial
<220> FEATURE:
<223> OTHER INFORMATION: Target sequence in the gene C19orf45

<400> SEQUENCE: 77
aagatgggac ttcctaccaa a                                              21

<210> SEQ ID NO 78
<211> LENGTH: 21
<212> TYPE: DNA
<213> ORGANISM: Artificial
<220> FEATURE:
<223> OTHER INFORMATION: Target sequence in the gene C1orf125

<400> SEQUENCE: 78
ttgggatatt taatcggcat a                                              21

<210> SEQ ID NO 79
<211> LENGTH: 21
<212> TYPE: DNA
<213> ORGANISM: Artificial
<220> FEATURE:
<223> OTHER INFORMATION: Target sequence in the gene C1orf149

<400> SEQUENCE: 79
caacatggcg atgcacaaca a                                              21

<210> SEQ ID NO 80
<211> LENGTH: 21
<212> TYPE: DNA
<213> ORGANISM: Artificial
<220> FEATURE:
<223> OTHER INFORMATION: Target sequence in the gene C1orf161

<400> SEQUENCE: 80
ggcagcggaa attacatcaa a                                              21

<210> SEQ ID NO 81
<211> LENGTH: 21
<212> TYPE: DNA
<213> ORGANISM: Artificial
<220> FEATURE:
<223> OTHER INFORMATION: Target sequence in the gene C1QL2

<400> SEQUENCE: 81
```

```
cccgggtgca aaggcgcaca a                                              21

<210> SEQ ID NO 82
<211> LENGTH: 21
<212> TYPE: DNA
<213> ORGANISM: Artificial
<220> FEATURE:
<223> OTHER INFORMATION: Target sequence in the gene C1R

<400> SEQUENCE: 82
tcgggagagc ccaggattca a                                              21

<210> SEQ ID NO 83
<211> LENGTH: 21
<212> TYPE: DNA
<213> ORGANISM: Artificial
<220> FEATURE:
<223> OTHER INFORMATION: Target sequence in the gene C20orf151

<400> SEQUENCE: 83
cccgccaagc tccaagcaca a                                              21

<210> SEQ ID NO 84
<211> LENGTH: 21
<212> TYPE: DNA
<213> ORGANISM: Artificial
<220> FEATURE:
<223> OTHER INFORMATION: Target sequence in the gene C20orf43

<400> SEQUENCE: 84
aaggttgaga aggtcgacaa a                                              21

<210> SEQ ID NO 85
<211> LENGTH: 21
<212> TYPE: DNA
<213> ORGANISM: Artificial
<220> FEATURE:
<223> OTHER INFORMATION: Target sequence in the gene C20orf43

<400> SEQUENCE: 85
atccttgttg gtctagctaa a                                              21

<210> SEQ ID NO 86
<211> LENGTH: 21
<212> TYPE: DNA
<213> ORGANISM: Artificial
<220> FEATURE:
<223> OTHER INFORMATION: Target sequence in the gene C21orf119

<400> SEQUENCE: 86
ttcgatactt tgccaattca a                                              21

<210> SEQ ID NO 87
<211> LENGTH: 21
<212> TYPE: DNA
<213> ORGANISM: Artificial
<220> FEATURE:
<223> OTHER INFORMATION: Target sequence in the gene C21orf62

<400> SEQUENCE: 87
caacctgatg tgcaactgta a                                              21

<210> SEQ ID NO 88
<211> LENGTH: 21
<212> TYPE: DNA
```

<213> ORGANISM: Artificial
<220> FEATURE:
<223> OTHER INFORMATION: Target sequence in the gene C21orf66

<400> SEQUENCE: 88
cccgttacta ttgatttggt a     21

<210> SEQ ID NO 89
<211> LENGTH: 21
<212> TYPE: DNA
<213> ORGANISM: Artificial
<220> FEATURE:
<223> OTHER INFORMATION: Target sequence in the gene C21orf66

<400> SEQUENCE: 89
acccgcagaa gtgaatatgt a     21

<210> SEQ ID NO 90
<211> LENGTH: 21
<212> TYPE: DNA
<213> ORGANISM: Artificial
<220> FEATURE:
<223> OTHER INFORMATION: Target sequence in the gene C21orf88

<400> SEQUENCE: 90
ccgcgggaag tccctcttgc a     21

<210> SEQ ID NO 91
<211> LENGTH: 21
<212> TYPE: DNA
<213> ORGANISM: Artificial
<220> FEATURE:
<223> OTHER INFORMATION: Target sequence in the gene C22orf28

<400> SEQUENCE: 91
ctggaattgt tcatcgatct a     21

<210> SEQ ID NO 92
<211> LENGTH: 21
<212> TYPE: DNA
<213> ORGANISM: Artificial
<220> FEATURE:
<223> OTHER INFORMATION: Target sequence in the gene C22orf39

<400> SEQUENCE: 92
caggtgggtc ataatgaggt a     21

<210> SEQ ID NO 93
<211> LENGTH: 21
<212> TYPE: DNA
<213> ORGANISM: Artificial
<220> FEATURE:
<223> OTHER INFORMATION: Target sequence in the gene C2orf58

<400> SEQUENCE: 93
ttcaagcgac taactaggaa a     21

<210> SEQ ID NO 94
<211> LENGTH: 21
<212> TYPE: DNA
<213> ORGANISM: Artificial
<220> FEATURE:
<223> OTHER INFORMATION: Target sequence in the gene C2orf63

<400> SEQUENCE: 94
aaacggcgag atgtagctga a     21

<210> SEQ ID NO 95
<211> LENGTH: 21
<212> TYPE: DNA
<213> ORGANISM: Artificial
<220> FEATURE:
<223> OTHER INFORMATION: Target sequence in the gene C6orf58

<400> SEQUENCE: 95
ctgcggttga ttctggtgta a                                              21

<210> SEQ ID NO 96
<211> LENGTH: 21
<212> TYPE: DNA
<213> ORGANISM: Artificial
<220> FEATURE:
<223> OTHER INFORMATION: Target sequence in the gene C6orf91

<400> SEQUENCE: 96
aagcaacgtc aagaattctt a                                              21

<210> SEQ ID NO 97
<211> LENGTH: 21
<212> TYPE: DNA
<213> ORGANISM: Artificial
<220> FEATURE:
<223> OTHER INFORMATION: Target sequence in the gene C9orf126

<400> SEQUENCE: 97
caggttaagt tcagtgaact a                                              21

<210> SEQ ID NO 98
<211> LENGTH: 21
<212> TYPE: DNA
<213> ORGANISM: Artificial
<220> FEATURE:
<223> OTHER INFORMATION: Target sequence in the gene C9orf23

<400> SEQUENCE: 98
agcgttgtga ctgctcaaca t                                              21

<210> SEQ ID NO 99
<211> LENGTH: 21
<212> TYPE: DNA
<213> ORGANISM: Artificial
<220> FEATURE:
<223> OTHER INFORMATION: Target sequence in the gene C9orf72

<400> SEQUENCE: 99
cagggtcaga gtattattcc a                                              21

<210> SEQ ID NO 100
<211> LENGTH: 21
<212> TYPE: DNA
<213> ORGANISM: Artificial
<220> FEATURE:
<223> OTHER INFORMATION: Target sequence in the gene C9orf85

<400> SEQUENCE: 100
aagttcttga gtggcgtgta a                                              21

<210> SEQ ID NO 101
<211> LENGTH: 21
<212> TYPE: DNA
<213> ORGANISM: Artificial
<220> FEATURE:

<223> OTHER INFORMATION: Target sequence in the gene CAND1

<400> SEQUENCE: 101
ctcatcgaat tgaagatcg a                                              21

<210> SEQ ID NO 102
<211> LENGTH: 21
<212> TYPE: DNA
<213> ORGANISM: Artificial
<220> FEATURE:
<223> OTHER INFORMATION: Target sequence in the gene CARTPT

<400> SEQUENCE: 102
cacgagaagg agctgatcga a                                             21

<210> SEQ ID NO 103
<211> LENGTH: 21
<212> TYPE: DNA
<213> ORGANISM: Artificial
<220> FEATURE:
<223> OTHER INFORMATION: Target sequence in the gene CASQ1

<400> SEQUENCE: 103
cccacaaata ggagtcgtca a                                             21

<210> SEQ ID NO 104
<211> LENGTH: 21
<212> TYPE: DNA
<213> ORGANISM: Artificial
<220> FEATURE:
<223> OTHER INFORMATION: Target sequence in the gene CATSPER1

<400> SEQUENCE: 104
ccggatcctc aaggtcttca a                                             21

<210> SEQ ID NO 105
<211> LENGTH: 21
<212> TYPE: DNA
<213> ORGANISM: Artificial
<220> FEATURE:
<223> OTHER INFORMATION: Target sequence in the gene CBLB

<400> SEQUENCE: 105
tccggttaag ttgcactcga t                                             21

<210> SEQ ID NO 106
<211> LENGTH: 21
<212> TYPE: DNA
<213> ORGANISM: Artificial
<220> FEATURE:
<223> OTHER INFORMATION: Target sequence in the gene CBLB

<400> SEQUENCE: 106
tcggttggca aacgtccgaa a                                             21

<210> SEQ ID NO 107
<211> LENGTH: 21
<212> TYPE: DNA
<213> ORGANISM: Artificial
<220> FEATURE:
<223> OTHER INFORMATION: Target sequence in the gene CCDC147

<400> SEQUENCE: 107
cacgttgata ttaacagatc a                                             21

```
<210> SEQ ID NO 108
<211> LENGTH: 21
<212> TYPE: DNA
<213> ORGANISM: Artificial
<220> FEATURE:
<223> OTHER INFORMATION: Target sequence in the gene CCDC46

<400> SEQUENCE: 108
cacgtttgta gtatcatatc a                                              21

<210> SEQ ID NO 109
<211> LENGTH: 21
<212> TYPE: DNA
<213> ORGANISM: Artificial
<220> FEATURE:
<223> OTHER INFORMATION: Target sequence in the gene CCDC86

<400> SEQUENCE: 109
tcgagtcgaa cccagaagaa a                                              21

<210> SEQ ID NO 110
<211> LENGTH: 21
<212> TYPE: DNA
<213> ORGANISM: Artificial
<220> FEATURE:
<223> OTHER INFORMATION: Target sequence in the gene CCDC89

<400> SEQUENCE: 110
atgcttcgct cccgcattga a                                              21

<210> SEQ ID NO 111
<211> LENGTH: 21
<212> TYPE: DNA
<213> ORGANISM: Artificial
<220> FEATURE:
<223> OTHER INFORMATION: Target sequence in the gene CCHCR1

<400> SEQUENCE: 111
aacgggatgt ttccagtgac a                                              21

<210> SEQ ID NO 112
<211> LENGTH: 21
<212> TYPE: DNA
<213> ORGANISM: Artificial
<220> FEATURE:
<223> OTHER INFORMATION: Target sequence in the gene CCL1

<400> SEQUENCE: 112
gccggaagat gtggacagca a                                              21

<210> SEQ ID NO 113
<211> LENGTH: 21
<212> TYPE: DNA
<213> ORGANISM: Artificial
<220> FEATURE:
<223> OTHER INFORMATION: Target sequence in the gene CCL19

<400> SEQUENCE: 113
ccgcctggtg tttacaacta a                                              21

<210> SEQ ID NO 114
<211> LENGTH: 21
<212> TYPE: DNA
<213> ORGANISM: Artificial
<220> FEATURE:
<223> OTHER INFORMATION: Target sequence in the gene CCL19
```

```
<400> SEQUENCE: 114
cagattgcaa tgctaccaat a                                              21

<210> SEQ ID NO 115
<211> LENGTH: 21
<212> TYPE: DNA
<213> ORGANISM: Artificial
<220> FEATURE:
<223> OTHER INFORMATION: Target sequence in the gene CCL25

<400> SEQUENCE: 115
ctccctcctg atatcagcta a                                              21

<210> SEQ ID NO 116
<211> LENGTH: 21
<212> TYPE: DNA
<213> ORGANISM: Artificial
<220> FEATURE:
<223> OTHER INFORMATION: Target sequence in the gene CCL7

<400> SEQUENCE: 116
ttggatgtat atgtcatctc a                                              21

<210> SEQ ID NO 117
<211> LENGTH: 21
<212> TYPE: DNA
<213> ORGANISM: Artificial
<220> FEATURE:
<223> OTHER INFORMATION: Target sequence in the gene CCNL2

<400> SEQUENCE: 117
cggagcgtta tggacgtggt a                                              21

<210> SEQ ID NO 118
<211> LENGTH: 21
<212> TYPE: DNA
<213> ORGANISM: Artificial
<220> FEATURE:
<223> OTHER INFORMATION: Target sequence in the gene CD46

<400> SEQUENCE: 118
cacgatttat tgtggtgaca a                                              21

<210> SEQ ID NO 119
<211> LENGTH: 21
<212> TYPE: DNA
<213> ORGANISM: Artificial
<220> FEATURE:
<223> OTHER INFORMATION: Target sequence in the gene CDV3

<400> SEQUENCE: 119
aaccaatatg ctgtgcttga a                                              21

<210> SEQ ID NO 120
<211> LENGTH: 21
<212> TYPE: DNA
<213> ORGANISM: Artificial
<220> FEATURE:
<223> OTHER INFORMATION: Target sequence in the gene CEBPB

<400> SEQUENCE: 120
cgggccctga gtaatcgctt a                                              21

<210> SEQ ID NO 121
<211> LENGTH: 21
```

<212> TYPE: DNA
<213> ORGANISM: Artificial
<220> FEATURE:
<223> OTHER INFORMATION: Target sequence in the gene CENPJ

<400> SEQUENCE: 121
aacgtgcgtc tcctaattta t                                              21

<210> SEQ ID NO 122
<211> LENGTH: 21
<212> TYPE: DNA
<213> ORGANISM: Artificial
<220> FEATURE:
<223> OTHER INFORMATION: Target sequence in the gene CENPQ

<400> SEQUENCE: 122
ctgggaatat tcagagccta a                                              21

<210> SEQ ID NO 123
<211> LENGTH: 21
<212> TYPE: DNA
<213> ORGANISM: Artificial
<220> FEATURE:
<223> OTHER INFORMATION: Target sequence in the gene CEP68

<400> SEQUENCE: 123
caccctcaaa tcacctacta a                                              21

<210> SEQ ID NO 124
<211> LENGTH: 21
<212> TYPE: DNA
<213> ORGANISM: Artificial
<220> FEATURE:
<223> OTHER INFORMATION: Target sequence in the gene CEPT1

<400> SEQUENCE: 124
ttcgggcata tgagtactac a                                              21

<210> SEQ ID NO 125
<211> LENGTH: 21
<212> TYPE: DNA
<213> ORGANISM: Artificial
<220> FEATURE:
<223> OTHER INFORMATION: Target sequence in the gene CFD

<400> SEQUENCE: 125
cagggtcacc caagcaacaa a                                              21

<210> SEQ ID NO 126
<211> LENGTH: 21
<212> TYPE: DNA
<213> ORGANISM: Artificial
<220> FEATURE:
<223> OTHER INFORMATION: Target sequence in the gene CFHR2

<400> SEQUENCE: 126
aatctggata tcatccaaca a                                              21

<210> SEQ ID NO 127
<211> LENGTH: 21
<212> TYPE: DNA
<213> ORGANISM: Artificial
<220> FEATURE:
<223> OTHER INFORMATION: Target sequence in the gene CFI

<400> SEQUENCE: 127

```
cccgaccetta aacgtatagt a                                          21
```

<210> SEQ ID NO 128
<211> LENGTH: 21
<212> TYPE: DNA
<213> ORGANISM: Artificial
<220> FEATURE:
<223> OTHER INFORMATION: Target sequence in the gene CHGB

<400> SEQUENCE: 128

```
aaagcaggct tcagctataa a                                           21
```

<210> SEQ ID NO 129
<211> LENGTH: 21
<212> TYPE: DNA
<213> ORGANISM: Artificial
<220> FEATURE:
<223> OTHER INFORMATION: Target sequence in the gene CHMP7

<400> SEQUENCE: 129

```
ctcgaccttg gtaaacggaa a                                           21
```

<210> SEQ ID NO 130
<211> LENGTH: 21
<212> TYPE: DNA
<213> ORGANISM: Artificial
<220> FEATURE:
<223> OTHER INFORMATION: Target sequence in the gene CHST10

<400> SEQUENCE: 130

```
aagtttgtcc tggaccgaat a                                           21
```

<210> SEQ ID NO 131
<211> LENGTH: 21
<212> TYPE: DNA
<213> ORGANISM: Artificial
<220> FEATURE:
<223> OTHER INFORMATION: Target sequence in the gene CINP

<400> SEQUENCE: 131

```
gcggctgatt ggcacaattt a                                           21
```

<210> SEQ ID NO 132
<211> LENGTH: 21
<212> TYPE: DNA
<213> ORGANISM: Artificial
<220> FEATURE:
<223> OTHER INFORMATION: Target sequence in the gene CKB

<400> SEQUENCE: 132

```
gcgggcaggt gtgcatatca a                                           21
```

<210> SEQ ID NO 133
<211> LENGTH: 21
<212> TYPE: DNA
<213> ORGANISM: Artificial
<220> FEATURE:
<223> OTHER INFORMATION: Target sequence in the gene CKS1B

<400> SEQUENCE: 133

```
aacatctttc tgataacatt a                                           21
```

<210> SEQ ID NO 134
<211> LENGTH: 21
<212> TYPE: DNA
<213> ORGANISM: Artificial

```
<220> FEATURE:
<223> OTHER INFORMATION: Target sequence in the gene CLC

<400> SEQUENCE: 134
ctggttctac tgtgacaatc a                                              21

<210> SEQ ID NO 135
<211> LENGTH: 21
<212> TYPE: DNA
<213> ORGANISM: Artificial
<220> FEATURE:
<223> OTHER INFORMATION: Target sequence in the gene CLDN3

<400> SEQUENCE: 135
cacggccacc aaggtcgtct a                                              21

<210> SEQ ID NO 136
<211> LENGTH: 21
<212> TYPE: DNA
<213> ORGANISM: Artificial
<220> FEATURE:
<223> OTHER INFORMATION: Target sequence in the gene CLDN5

<400> SEQUENCE: 136
caccggcgac tacgacaaga a                                              21

<210> SEQ ID NO 137
<211> LENGTH: 21
<212> TYPE: DNA
<213> ORGANISM: Artificial
<220> FEATURE:
<223> OTHER INFORMATION: Target sequence in the gene CLU

<400> SEQUENCE: 137
acagacctgc atgaagttct a                                              21

<210> SEQ ID NO 138
<211> LENGTH: 21
<212> TYPE: DNA
<213> ORGANISM: Artificial
<220> FEATURE:
<223> OTHER INFORMATION: Target sequence in the gene CMPK1

<400> SEQUENCE: 138
cgcgtatata tccctctagt a                                              21

<210> SEQ ID NO 139
<211> LENGTH: 21
<212> TYPE: DNA
<213> ORGANISM: Artificial
<220> FEATURE:
<223> OTHER INFORMATION: Target sequence in the gene CNGA4

<400> SEQUENCE: 139
aagattgctt accgcattga a                                              21

<210> SEQ ID NO 140
<211> LENGTH: 21
<212> TYPE: DNA
<213> ORGANISM: Artificial
<220> FEATURE:
<223> OTHER INFORMATION: Target sequence in the gene CNGA4

<400> SEQUENCE: 140
tagcatgagc tctgtcatct a                                              21
```

<210> SEQ ID NO 141
<211> LENGTH: 21
<212> TYPE: DNA
<213> ORGANISM: Artificial
<220> FEATURE:
<223> OTHER INFORMATION: Target sequence in the gene CNNM1

<400> SEQUENCE: 141
ctgggttatc tgcatctcaa a            21

<210> SEQ ID NO 142
<211> LENGTH: 21
<212> TYPE: DNA
<213> ORGANISM: Artificial
<220> FEATURE:
<223> OTHER INFORMATION: Target sequence in the gene CNNM1

<400> SEQUENCE: 142
cacgctggag gatatcatag a            21

<210> SEQ ID NO 143
<211> LENGTH: 21
<212> TYPE: DNA
<213> ORGANISM: Artificial
<220> FEATURE:
<223> OTHER INFORMATION: Target sequence in the gene COCH

<400> SEQUENCE: 143
aacattcgtt ctctaaccat t            21

<210> SEQ ID NO 144
<211> LENGTH: 21
<212> TYPE: DNA
<213> ORGANISM: Artificial
<220> FEATURE:
<223> OTHER INFORMATION: Target sequence in the gene COCH

<400> SEQUENCE: 144
caccaacagg taaacgacta a            21

<210> SEQ ID NO 145
<211> LENGTH: 21
<212> TYPE: DNA
<213> ORGANISM: Artificial
<220> FEATURE:
<223> OTHER INFORMATION: Target sequence in the gene COIL

<400> SEQUENCE: 145
ccgagtcgtc acagatctca t            21

<210> SEQ ID NO 146
<211> LENGTH: 21
<212> TYPE: DNA
<213> ORGANISM: Artificial
<220> FEATURE:
<223> OTHER INFORMATION: Target sequence in the gene COL14A1

<400> SEQUENCE: 146
atggttcatg gagtattgga a            21

<210> SEQ ID NO 147
<211> LENGTH: 21
<212> TYPE: DNA
<213> ORGANISM: Artificial
<220> FEATURE:
<223> OTHER INFORMATION: Target sequence in the gene COL24A1

<400> SEQUENCE: 147
aacactctac ttgaacctaa a                                         21

<210> SEQ ID NO 148
<211> LENGTH: 21
<212> TYPE: DNA
<213> ORGANISM: Artificial
<220> FEATURE:
<223> OTHER INFORMATION: Target sequence in the gene COL24A1

<400> SEQUENCE: 148
cagcacgaat ctgcaaagat t                                         21

<210> SEQ ID NO 149
<211> LENGTH: 21
<212> TYPE: DNA
<213> ORGANISM: Artificial
<220> FEATURE:
<223> OTHER INFORMATION: Target sequence in the gene COMMD4

<400> SEQUENCE: 149
cgctgttatg aggagaagca a                                         21

<210> SEQ ID NO 150
<211> LENGTH: 21
<212> TYPE: DNA
<213> ORGANISM: Artificial
<220> FEATURE:
<223> OTHER INFORMATION: Target sequence in the gene CORO2B

<400> SEQUENCE: 150
ttcattagct aggatctact a                                         21

<210> SEQ ID NO 151
<211> LENGTH: 21
<212> TYPE: DNA
<213> ORGANISM: Artificial
<220> FEATURE:
<223> OTHER INFORMATION: Target sequence in the gene COX5A

<400> SEQUENCE: 151
ctgggtaaca tacttcaaca a                                         21

<210> SEQ ID NO 152
<211> LENGTH: 21
<212> TYPE: DNA
<213> ORGANISM: Artificial
<220> FEATURE:
<223> OTHER INFORMATION: Target sequence in the gene CPEB4

<400> SEQUENCE: 152
aaggtcgtct aaactattca t                                         21

<210> SEQ ID NO 153
<211> LENGTH: 21
<212> TYPE: DNA
<213> ORGANISM: Artificial
<220> FEATURE:
<223> OTHER INFORMATION: Target sequence in the gene CPOX

<400> SEQUENCE: 153
gaggacggta tgtagaattt a                                         21

<210> SEQ ID NO 154

```
<211> LENGTH: 21
<212> TYPE: DNA
<213> ORGANISM: Artificial
<220> FEATURE:
<223> OTHER INFORMATION: Target sequence in the gene CPSF6

<400> SEQUENCE: 154
accgtattga ttcatgctat a                                               21

<210> SEQ ID NO 155
<211> LENGTH: 21
<212> TYPE: DNA
<213> ORGANISM: Artificial
<220> FEATURE:
<223> OTHER INFORMATION: Target sequence in the gene CRK

<400> SEQUENCE: 155
cagcagctaa ctagagtcct a                                               21

<210> SEQ ID NO 156
<211> LENGTH: 21
<212> TYPE: DNA
<213> ORGANISM: Artificial
<220> FEATURE:
<223> OTHER INFORMATION: Target sequence in the gene CRKRS

<400> SEQUENCE: 156
atcgggatat taagtgttct a                                               21

<210> SEQ ID NO 157
<211> LENGTH: 21
<212> TYPE: DNA
<213> ORGANISM: Artificial
<220> FEATURE:
<223> OTHER INFORMATION: Target sequence in the gene CSNK1G1

<400> SEQUENCE: 157
ttggaccatg tgggaaatat a                                               21

<210> SEQ ID NO 158
<211> LENGTH: 21
<212> TYPE: DNA
<213> ORGANISM: Artificial
<220> FEATURE:
<223> OTHER INFORMATION: Target sequence in the gene CSNK2A1

<400> SEQUENCE: 158
tccattgaag ctgaaatggt a                                               21

<210> SEQ ID NO 159
<211> LENGTH: 21
<212> TYPE: DNA
<213> ORGANISM: Artificial
<220> FEATURE:
<223> OTHER INFORMATION: Target sequence in the gene CTF8

<400> SEQUENCE: 159
aagggtagtt gtggagctac a                                               21

<210> SEQ ID NO 160
<211> LENGTH: 21
<212> TYPE: DNA
<213> ORGANISM: Artificial
<220> FEATURE:
<223> OTHER INFORMATION: Target sequence in the gene CTSZ

<400> SEQUENCE: 160
```
tcggatcaac atcaagagga a                                         21

<210> SEQ ID NO 161
<211> LENGTH: 21
<212> TYPE: DNA
<213> ORGANISM: Artificial
<220> FEATURE:
<223> OTHER INFORMATION: Target sequence in the gene CTTNBP2NL

<400> SEQUENCE: 161
ccggtactca ctaagcgttt a                                         21

<210> SEQ ID NO 162
<211> LENGTH: 21
<212> TYPE: DNA
<213> ORGANISM: Artificial
<220> FEATURE:
<223> OTHER INFORMATION: Target sequence in the gene CUL2

<400> SEQUENCE: 162
cggcacaatg cccttattca a                                         21

<210> SEQ ID NO 163
<211> LENGTH: 21
<212> TYPE: DNA
<213> ORGANISM: Artificial
<220> FEATURE:
<223> OTHER INFORMATION: Target sequence in the gene CUL7

<400> SEQUENCE: 163
cacgctactg tgagcacttt a                                         21

<210> SEQ ID NO 164
<211> LENGTH: 21
<212> TYPE: DNA
<213> ORGANISM: Artificial
<220> FEATURE:
<223> OTHER INFORMATION: Target sequence in the gene CYB561D2

<400> SEQUENCE: 164
caggtgagca atgcctacct a                                         21

<210> SEQ ID NO 165
<211> LENGTH: 21
<212> TYPE: DNA
<213> ORGANISM: Artificial
<220> FEATURE:
<223> OTHER INFORMATION: Target sequence in the gene CYP2C8

<400> SEQUENCE: 165
atgccttaca ctgatgctgt a                                         21

<210> SEQ ID NO 166
<211> LENGTH: 21
<212> TYPE: DNA
<213> ORGANISM: Artificial
<220> FEATURE:
<223> OTHER INFORMATION: Target sequence in the gene CYP4F3

<400> SEQUENCE: 166
acgcttgtgc gtgaatgttc a                                         21

<210> SEQ ID NO 167
<211> LENGTH: 21
<212> TYPE: DNA

```
<213> ORGANISM: Artificial
<220> FEATURE:
<223> OTHER INFORMATION: Target sequence in the gene DACT2

<400> SEQUENCE: 167
cggcagggag gtgtacccgt a                                              21

<210> SEQ ID NO 168
<211> LENGTH: 21
<212> TYPE: DNA
<213> ORGANISM: Artificial
<220> FEATURE:
<223> OTHER INFORMATION: Target sequence in the gene DARS

<400> SEQUENCE: 168
ttggattgga acgagttact a                                              21

<210> SEQ ID NO 169
<211> LENGTH: 21
<212> TYPE: DNA
<213> ORGANISM: Artificial
<220> FEATURE:
<223> OTHER INFORMATION: Target sequence in the gene DCDC2

<400> SEQUENCE: 169
caggttgagg ttccagtcga t                                              21

<210> SEQ ID NO 170
<211> LENGTH: 21
<212> TYPE: DNA
<213> ORGANISM: Artificial
<220> FEATURE:
<223> OTHER INFORMATION: Target sequence in the gene DCTN4

<400> SEQUENCE: 170
cccaacgtca atcaaattca a                                              21

<210> SEQ ID NO 171
<211> LENGTH: 21
<212> TYPE: DNA
<213> ORGANISM: Artificial
<220> FEATURE:
<223> OTHER INFORMATION: Target sequence in the gene DDEF1

<400> SEQUENCE: 171
cccgcccgaa atctttcaga a                                              21

<210> SEQ ID NO 172
<211> LENGTH: 21
<212> TYPE: DNA
<213> ORGANISM: Artificial
<220> FEATURE:
<223> OTHER INFORMATION: Target sequence in the gene DEFB121

<400> SEQUENCE: 172
atcccaagta tgtacctgta a                                              21

<210> SEQ ID NO 173
<211> LENGTH: 21
<212> TYPE: DNA
<213> ORGANISM: Artificial
<220> FEATURE:
<223> OTHER INFORMATION: Target sequence in the gene DEFB124

<400> SEQUENCE: 173
ctgtctctcc tatgcattga a                                              21
```

```
<210> SEQ ID NO 174
<211> LENGTH: 21
<212> TYPE: DNA
<213> ORGANISM: Artificial
<220> FEATURE:
<223> OTHER INFORMATION: Target sequence in the gene DEPDC7

<400> SEQUENCE: 174
aacgtgacta ttccaacaat a                                              21

<210> SEQ ID NO 175
<211> LENGTH: 21
<212> TYPE: DNA
<213> ORGANISM: Artificial
<220> FEATURE:
<223> OTHER INFORMATION: Target sequence in the gene DFNB59

<400> SEQUENCE: 175
atggatgtca tttctcgttc a                                              21

<210> SEQ ID NO 176
<211> LENGTH: 21
<212> TYPE: DNA
<213> ORGANISM: Artificial
<220> FEATURE:
<223> OTHER INFORMATION: Target sequence in the gene DIAPH3

<400> SEQUENCE: 176
ctccggcaca attcagttca a                                              21

<210> SEQ ID NO 177
<211> LENGTH: 21
<212> TYPE: DNA
<213> ORGANISM: Artificial
<220> FEATURE:
<223> OTHER INFORMATION: Target sequence in the gene DMN

<400> SEQUENCE: 177
aaggcgattc catgacagaa a                                              21

<210> SEQ ID NO 178
<211> LENGTH: 21
<212> TYPE: DNA
<213> ORGANISM: Artificial
<220> FEATURE:
<223> OTHER INFORMATION: Target sequence in the gene DNAJA4

<400> SEQUENCE: 178
tacagtttgt atggactact a                                              21

<210> SEQ ID NO 179
<211> LENGTH: 21
<212> TYPE: DNA
<213> ORGANISM: Artificial
<220> FEATURE:
<223> OTHER INFORMATION: Target sequence in the gene DNAJB13

<400> SEQUENCE: 179
ctcgggatca ctcgcaattc a                                              21

<210> SEQ ID NO 180
<211> LENGTH: 21
<212> TYPE: DNA
<213> ORGANISM: Artificial
<220> FEATURE:
```

```
<223> OTHER INFORMATION: Target sequence in the gene DNAJB7

<400> SEQUENCE: 180
ctgcggacaa ttagtattca a                                           21

<210> SEQ ID NO 181
<211> LENGTH: 21
<212> TYPE: DNA
<213> ORGANISM: Artificial
<220> FEATURE:
<223> OTHER INFORMATION: Target sequence in the gene DNMT1

<400> SEQUENCE: 181
cccaatgaga ctgacatcaa a                                           21

<210> SEQ ID NO 182
<211> LENGTH: 21
<212> TYPE: DNA
<213> ORGANISM: Artificial
<220> FEATURE:
<223> OTHER INFORMATION: Target sequence in the gene DNMT3B

<400> SEQUENCE: 182
aaggactact ttgcatgtga a                                           21

<210> SEQ ID NO 183
<211> LENGTH: 21
<212> TYPE: DNA
<213> ORGANISM: Artificial
<220> FEATURE:
<223> OTHER INFORMATION: Target sequence in the gene DNPEP

<400> SEQUENCE: 183
atccgagagg tggccaacaa a                                           21

<210> SEQ ID NO 184
<211> LENGTH: 21
<212> TYPE: DNA
<213> ORGANISM: Artificial
<220> FEATURE:
<223> OTHER INFORMATION: Target sequence in the gene DSE

<400> SEQUENCE: 184
aaaccgttat agacccaata a                                           21

<210> SEQ ID NO 185
<211> LENGTH: 21
<212> TYPE: DNA
<213> ORGANISM: Artificial
<220> FEATURE:
<223> OTHER INFORMATION: Target sequence in the gene DSG3

<400> SEQUENCE: 185
aaccgagatt ctactttcat a                                           21

<210> SEQ ID NO 186
<211> LENGTH: 21
<212> TYPE: DNA
<213> ORGANISM: Artificial
<220> FEATURE:
<223> OTHER INFORMATION: Target sequence in the gene DTL

<400> SEQUENCE: 186
ccgagtctac tgggtataac a                                           21
```

```
<210> SEQ ID NO 187
<211> LENGTH: 21
<212> TYPE: DNA
<213> ORGANISM: Artificial
<220> FEATURE:
<223> OTHER INFORMATION: Target sequence in the gene DTWD1

<400> SEQUENCE: 187
cacctatatt tctcaaacga a                                              21

<210> SEQ ID NO 188
<211> LENGTH: 21
<212> TYPE: DNA
<213> ORGANISM: Artificial
<220> FEATURE:
<223> OTHER INFORMATION: Target sequence in the gene DUS2L

<400> SEQUENCE: 188
agcggacatt gtttactgtg a                                              21

<210> SEQ ID NO 189
<211> LENGTH: 21
<212> TYPE: DNA
<213> ORGANISM: Artificial
<220> FEATURE:
<223> OTHER INFORMATION: Target sequence in the gene DUSP13

<400> SEQUENCE: 189
tcagtccatc tctataataa a                                              21

<210> SEQ ID NO 190
<211> LENGTH: 21
<212> TYPE: DNA
<213> ORGANISM: Artificial
<220> FEATURE:
<223> OTHER INFORMATION: Target sequence in the gene E2F7

<400> SEQUENCE: 190
cagaacggtc tgaatggaca a                                              21

<210> SEQ ID NO 191
<211> LENGTH: 21
<212> TYPE: DNA
<213> ORGANISM: Artificial
<220> FEATURE:
<223> OTHER INFORMATION: Target sequence in the gene EBI3

<400> SEQUENCE: 191
cccagagatc ttctcactga a                                              21

<210> SEQ ID NO 192
<211> LENGTH: 21
<212> TYPE: DNA
<213> ORGANISM: Artificial
<220> FEATURE:
<223> OTHER INFORMATION: Target sequence in the gene ECM1

<400> SEQUENCE: 192
aaccgcctag agtgtgccaa a                                              21

<210> SEQ ID NO 193
<211> LENGTH: 21
<212> TYPE: DNA
<213> ORGANISM: Artificial
<220> FEATURE:
<223> OTHER INFORMATION: Target sequence in the gene EFEMP2
```

<400> SEQUENCE: 193
cacggaatgc acagatggct a                                              21

<210> SEQ ID NO 194
<211> LENGTH: 21
<212> TYPE: DNA
<213> ORGANISM: Artificial
<220> FEATURE:
<223> OTHER INFORMATION: Target sequence in the gene EFEMP2

<400> SEQUENCE: 194
ccgctccgct gccgtcatca a                                              21

<210> SEQ ID NO 195
<211> LENGTH: 21
<212> TYPE: DNA
<213> ORGANISM: Artificial
<220> FEATURE:
<223> OTHER INFORMATION: Target sequence in the gene EIF4E3

<400> SEQUENCE: 195
ctgagtgcgc atcaaatctg a                                              21

<210> SEQ ID NO 196
<211> LENGTH: 21
<212> TYPE: DNA
<213> ORGANISM: Artificial
<220> FEATURE:
<223> OTHER INFORMATION: Target sequence in the gene ENTPD3

<400> SEQUENCE: 196
ccacttgttt gtgaacggtt a                                              21

<210> SEQ ID NO 197
<211> LENGTH: 21
<212> TYPE: DNA
<213> ORGANISM: Artificial
<220> FEATURE:
<223> OTHER INFORMATION: Target sequence in the gene EP300

<400> SEQUENCE: 197
caccgataac tcagacttga a                                              21

<210> SEQ ID NO 198
<211> LENGTH: 21
<212> TYPE: DNA
<213> ORGANISM: Artificial
<220> FEATURE:
<223> OTHER INFORMATION: Target sequence in the gene EP300

<400> SEQUENCE: 198
ttggactacc ctatcaagta a                                              21

<210> SEQ ID NO 199
<211> LENGTH: 21
<212> TYPE: DNA
<213> ORGANISM: Artificial
<220> FEATURE:
<223> OTHER INFORMATION: Target sequence in the gene EPHA10

<400> SEQUENCE: 199
ctggagggcg ttgttacccg a                                              21

<210> SEQ ID NO 200
<211> LENGTH: 21

```
<212> TYPE: DNA
<213> ORGANISM: Artificial
<220> FEATURE:
<223> OTHER INFORMATION: Target sequence in the gene EPS8L1

<400> SEQUENCE: 200
cagcagtgag ctgtcggtca a                                              21

<210> SEQ ID NO 201
<211> LENGTH: 21
<212> TYPE: DNA
<213> ORGANISM: Artificial
<220> FEATURE:
<223> OTHER INFORMATION: Target sequence in the gene ERGIC3

<400> SEQUENCE: 201
aacctgttca agcaacgact a                                              21

<210> SEQ ID NO 202
<211> LENGTH: 21
<212> TYPE: DNA
<213> ORGANISM: Artificial
<220> FEATURE:
<223> OTHER INFORMATION: Target sequence in the gene ETV6

<400> SEQUENCE: 202
caggtcacct atcacgacaa a                                              21

<210> SEQ ID NO 203
<211> LENGTH: 21
<212> TYPE: DNA
<213> ORGANISM: Artificial
<220> FEATURE:
<223> OTHER INFORMATION: Target sequence in the gene FAM123C

<400> SEQUENCE: 203
tcccaagtgt tgagaatcca a                                              21

<210> SEQ ID NO 204
<211> LENGTH: 21
<212> TYPE: DNA
<213> ORGANISM: Artificial
<220> FEATURE:
<223> OTHER INFORMATION: Target sequence in the gene FAM19A1

<400> SEQUENCE: 204
cacaccgatg ttgtaacaag a                                              21

<210> SEQ ID NO 205
<211> LENGTH: 21
<212> TYPE: DNA
<213> ORGANISM: Artificial
<220> FEATURE:
<223> OTHER INFORMATION: Target sequence in the gene FAM46A

<400> SEQUENCE: 205
ctggcaccta ttcatataga a                                              21

<210> SEQ ID NO 206
<211> LENGTH: 21
<212> TYPE: DNA
<213> ORGANISM: Artificial
<220> FEATURE:
<223> OTHER INFORMATION: Target sequence in the gene FAM62A

<400> SEQUENCE: 206
```
acgcccgacc ctagacatca a                                               21

<210> SEQ ID NO 207
<211> LENGTH: 21
<212> TYPE: DNA
<213> ORGANISM: Artificial
<220> FEATURE:
<223> OTHER INFORMATION: Target sequence in the gene FAM71A

<400> SEQUENCE: 207
tgccgttgtg ctgaaagaca a                                               21

<210> SEQ ID NO 208
<211> LENGTH: 21
<212> TYPE: DNA
<213> ORGANISM: Artificial
<220> FEATURE:
<223> OTHER INFORMATION: Target sequence in the gene FAM71C

<400> SEQUENCE: 208
aaggcgagta tactatattc a                                               21

<210> SEQ ID NO 209
<211> LENGTH: 21
<212> TYPE: DNA
<213> ORGANISM: Artificial
<220> FEATURE:
<223> OTHER INFORMATION: Target sequence in the gene FAM84A

<400> SEQUENCE: 209
aagggcgctt attgttctga a                                               21

<210> SEQ ID NO 210
<211> LENGTH: 21
<212> TYPE: DNA
<213> ORGANISM: Artificial
<220> FEATURE:
<223> OTHER INFORMATION: Target sequence in the gene FAM90A1

<400> SEQUENCE: 210
cacggtggtt tccaagcgca t                                               21

<210> SEQ ID NO 211
<211> LENGTH: 21
<212> TYPE: DNA
<213> ORGANISM: Artificial
<220> FEATURE:
<223> OTHER INFORMATION: Target sequence in the gene FAM98B

<400> SEQUENCE: 211
ctcgtgaaga tctatccaag a                                               21

<210> SEQ ID NO 212
<211> LENGTH: 21
<212> TYPE: DNA
<213> ORGANISM: Artificial
<220> FEATURE:
<223> OTHER INFORMATION: Target sequence in the gene FANCF

<400> SEQUENCE: 212
aaccagcatt agagctttat a                                               21

<210> SEQ ID NO 213
<211> LENGTH: 21
<212> TYPE: DNA
<213> ORGANISM: Artificial

```
<220> FEATURE:
<223> OTHER INFORMATION: Target sequence in the gene FARP2

<400> SEQUENCE: 213
cacaagtgtg gaagcgttta a                                              21

<210> SEQ ID NO 214
<211> LENGTH: 21
<212> TYPE: DNA
<213> ORGANISM: Artificial
<220> FEATURE:
<223> OTHER INFORMATION: Target sequence in the gene FATE1

<400> SEQUENCE: 214
cagccaaacg agtttggaat a                                              21

<210> SEQ ID NO 215
<211> LENGTH: 21
<212> TYPE: DNA
<213> ORGANISM: Artificial
<220> FEATURE:
<223> OTHER INFORMATION: Target sequence in the gene FBXO34

<400> SEQUENCE: 215
tcggtaaagc atcatctcga a                                              21

<210> SEQ ID NO 216
<211> LENGTH: 21
<212> TYPE: DNA
<213> ORGANISM: Artificial
<220> FEATURE:
<223> OTHER INFORMATION: Target sequence in the gene FBXO41

<400> SEQUENCE: 216
ctggagcttg accacgtgtc a                                              21

<210> SEQ ID NO 217
<211> LENGTH: 21
<212> TYPE: DNA
<213> ORGANISM: Artificial
<220> FEATURE:
<223> OTHER INFORMATION: Target sequence in the gene FBXO7

<400> SEQUENCE: 217
caggatgaac aaccaagtga t                                              21

<210> SEQ ID NO 218
<211> LENGTH: 21
<212> TYPE: DNA
<213> ORGANISM: Artificial
<220> FEATURE:
<223> OTHER INFORMATION: Target sequence in the gene FBXW10

<400> SEQUENCE: 218
caggatcaat gacatatcac a                                              21

<210> SEQ ID NO 219
<211> LENGTH: 21
<212> TYPE: DNA
<213> ORGANISM: Artificial
<220> FEATURE:
<223> OTHER INFORMATION: Target sequence in the gene FGF2

<400> SEQUENCE: 219
aacaatatta gtcgtatcca a                                              21
```

```
<210> SEQ ID NO 220
<211> LENGTH: 21
<212> TYPE: DNA
<213> ORGANISM: Artificial
<220> FEATURE:
<223> OTHER INFORMATION: Target sequence in the gene FHL2

<400> SEQUENCE: 220
ctcccgttgc gtcaagtcta a                                          21

<210> SEQ ID NO 221
<211> LENGTH: 21
<212> TYPE: DNA
<213> ORGANISM: Artificial
<220> FEATURE:
<223> OTHER INFORMATION: Target sequence in the gene FKBP6

<400> SEQUENCE: 221
ctcgggatac ctggaacaca t                                          21

<210> SEQ ID NO 222
<211> LENGTH: 21
<212> TYPE: DNA
<213> ORGANISM: Artificial
<220> FEATURE:
<223> OTHER INFORMATION: Target sequence in the gene FKSG30

<400> SEQUENCE: 222
ccgagcgtgg ctataggttc a                                          21

<210> SEQ ID NO 223
<211> LENGTH: 21
<212> TYPE: DNA
<213> ORGANISM: Artificial
<220> FEATURE:
<223> OTHER INFORMATION: Target sequence in the gene FLJ42953

<400> SEQUENCE: 223
gaggcatgga ggagataaca a                                          21

<210> SEQ ID NO 224
<211> LENGTH: 21
<212> TYPE: DNA
<213> ORGANISM: Artificial
<220> FEATURE:
<223> OTHER INFORMATION: Target sequence in the gene FLJ43987

<400> SEQUENCE: 224
ctgctcgacc tgattctact a                                          21

<210> SEQ ID NO 225
<211> LENGTH: 21
<212> TYPE: DNA
<213> ORGANISM: Artificial
<220> FEATURE:
<223> OTHER INFORMATION: Target sequence in the gene FLJ45537

<400> SEQUENCE: 225
aaccggaaca agcattctga a                                          21

<210> SEQ ID NO 226
<211> LENGTH: 21
<212> TYPE: DNA
<213> ORGANISM: Artificial
<220> FEATURE:
<223> OTHER INFORMATION: Target sequence in the gene FMN2
```

```
<400> SEQUENCE: 226
cacgggagcc gccgcgcatt a                                              21

<210> SEQ ID NO 227
<211> LENGTH: 21
<212> TYPE: DNA
<213> ORGANISM: Artificial
<220> FEATURE:
<223> OTHER INFORMATION: Target sequence in the gene FNDC3B

<400> SEQUENCE: 227
cagagtatta ccacacagca a                                              21

<210> SEQ ID NO 228
<211> LENGTH: 21
<212> TYPE: DNA
<213> ORGANISM: Artificial
<220> FEATURE:
<223> OTHER INFORMATION: Target sequence in the gene FTH1

<400> SEQUENCE: 228
aagcaggtga aagccatcaa a                                              21

<210> SEQ ID NO 229
<211> LENGTH: 21
<212> TYPE: DNA
<213> ORGANISM: Artificial
<220> FEATURE:
<223> OTHER INFORMATION: Target sequence in the gene FTHL2

<400> SEQUENCE: 229
ctcggcggaa tacctcttag a                                              21

<210> SEQ ID NO 230
<211> LENGTH: 21
<212> TYPE: DNA
<213> ORGANISM: Artificial
<220> FEATURE:
<223> OTHER INFORMATION: Target sequence in the gene FXYD2

<400> SEQUENCE: 230
cccgttctac tatgactatg a                                              21

<210> SEQ ID NO 231
<211> LENGTH: 21
<212> TYPE: DNA
<213> ORGANISM: Artificial
<220> FEATURE:
<223> OTHER INFORMATION: Target sequence in the gene GALNT7

<400> SEQUENCE: 231
ctcggtaact ttgaacccaa a                                              21

<210> SEQ ID NO 232
<211> LENGTH: 21
<212> TYPE: DNA
<213> ORGANISM: Artificial
<220> FEATURE:
<223> OTHER INFORMATION: Target sequence in the gene GARNL3

<400> SEQUENCE: 232
caggcggagt ttgttagaat a                                              21

<210> SEQ ID NO 233
```

-continued

```
<210> SEQ ID NO 233
<211> LENGTH: 21
<212> TYPE: DNA
<213> ORGANISM: Artificial
<220> FEATURE:
<223> OTHER INFORMATION: Target sequence in the gene GARNL3

<400> SEQUENCE: 233
tggcgtcttg ctagtggatg a                                              21

<210> SEQ ID NO 234
<211> LENGTH: 21
<212> TYPE: DNA
<213> ORGANISM: Artificial
<220> FEATURE:
<223> OTHER INFORMATION: Target sequence in the gene GAS2

<400> SEQUENCE: 234
gacgagtaaa ttgtacagtc a                                              21

<210> SEQ ID NO 235
<211> LENGTH: 21
<212> TYPE: DNA
<213> ORGANISM: Artificial
<220> FEATURE:
<223> OTHER INFORMATION: Target sequence in the gene GAS6

<400> SEQUENCE: 235
cagcagcggc ccggtcatca a                                              21

<210> SEQ ID NO 236
<211> LENGTH: 21
<212> TYPE: DNA
<213> ORGANISM: Artificial
<220> FEATURE:
<223> OTHER INFORMATION: Target sequence in the gene GCM2

<400> SEQUENCE: 236
cagccttgtg gaaaggacta a                                              21

<210> SEQ ID NO 237
<211> LENGTH: 21
<212> TYPE: DNA
<213> ORGANISM: Artificial
<220> FEATURE:
<223> OTHER INFORMATION: Target sequence in the gene GFPT2

<400> SEQUENCE: 237
atcgatggga ataatcacga a                                              21

<210> SEQ ID NO 238
<211> LENGTH: 21
<212> TYPE: DNA
<213> ORGANISM: Artificial
<220> FEATURE:
<223> OTHER INFORMATION: Target sequence in the gene GGN

<400> SEQUENCE: 238
tacgccgagg tcctgaagca a                                              21

<210> SEQ ID NO 239
<211> LENGTH: 21
<212> TYPE: DNA
<213> ORGANISM: Artificial
<220> FEATURE:
<223> OTHER INFORMATION: Target sequence in the gene GGT1

<400> SEQUENCE: 239
```

```
gagcagcaga gcagcacaat a                                              21

<210> SEQ ID NO 240
<211> LENGTH: 21
<212> TYPE: DNA
<213> ORGANISM: Artificial
<220> FEATURE:
<223> OTHER INFORMATION: Target sequence in the gene GJB1

<400> SEQUENCE: 240
ctgcacagac atgagaccat a                                              21

<210> SEQ ID NO 241
<211> LENGTH: 21
<212> TYPE: DNA
<213> ORGANISM: Artificial
<220> FEATURE:
<223> OTHER INFORMATION: Target sequence in the gene GJC2

<400> SEQUENCE: 241
cgcggaggag gcgtgcacta a                                              21

<210> SEQ ID NO 242
<211> LENGTH: 21
<212> TYPE: DNA
<213> ORGANISM: Artificial
<220> FEATURE:
<223> OTHER INFORMATION: Target sequence in the gene GJD2

<400> SEQUENCE: 242
agcgagaacg ccgctactct a                                              21

<210> SEQ ID NO 243
<211> LENGTH: 21
<212> TYPE: DNA
<213> ORGANISM: Artificial
<220> FEATURE:
<223> OTHER INFORMATION: Target sequence in the gene GLT25D1

<400> SEQUENCE: 243
agcgattgat tcagtcatca a                                              21

<210> SEQ ID NO 244
<211> LENGTH: 21
<212> TYPE: DNA
<213> ORGANISM: Artificial
<220> FEATURE:
<223> OTHER INFORMATION: Target sequence in the gene GOLGA2

<400> SEQUENCE: 244
atggagtcgg ttagacaact a                                              21

<210> SEQ ID NO 245
<211> LENGTH: 21
<212> TYPE: DNA
<213> ORGANISM: Artificial
<220> FEATURE:
<223> OTHER INFORMATION: Target sequence in the gene GPD1L

<400> SEQUENCE: 245
aaccagcatt aacatggtag a                                              21

<210> SEQ ID NO 246
<211> LENGTH: 21
<212> TYPE: DNA
```

```
<213> ORGANISM: Artificial
<220> FEATURE:
<223> OTHER INFORMATION: Target sequence in the gene GPM6B

<400> SEQUENCE: 246
gcccgtgttt atgttctaca a                                              21

<210> SEQ ID NO 247
<211> LENGTH: 21
<212> TYPE: DNA
<213> ORGANISM: Artificial
<220> FEATURE:
<223> OTHER INFORMATION: Target sequence in the gene GPSM1

<400> SEQUENCE: 247
ctccgagttc tacgagagga a                                              21

<210> SEQ ID NO 248
<211> LENGTH: 21
<212> TYPE: DNA
<213> ORGANISM: Artificial
<220> FEATURE:
<223> OTHER INFORMATION: Target sequence in the gene GRID1

<400> SEQUENCE: 248
cagcgccatc tggattgtct a                                              21

<210> SEQ ID NO 249
<211> LENGTH: 21
<212> TYPE: DNA
<213> ORGANISM: Artificial
<220> FEATURE:
<223> OTHER INFORMATION: Target sequence in the gene GRIK1

<400> SEQUENCE: 249
ttggttctcc ttaccgggat a                                              21

<210> SEQ ID NO 250
<211> LENGTH: 21
<212> TYPE: DNA
<213> ORGANISM: Artificial
<220> FEATURE:
<223> OTHER INFORMATION: Target sequence in the gene GRINA

<400> SEQUENCE: 250
ccgacaggcc ttcatccgca a                                              21

<210> SEQ ID NO 251
<211> LENGTH: 21
<212> TYPE: DNA
<213> ORGANISM: Artificial
<220> FEATURE:
<223> OTHER INFORMATION: Target sequence in the gene GUCY1B2

<400> SEQUENCE: 251
cagtgtgcac gcagtctata a                                              21

<210> SEQ ID NO 252
<211> LENGTH: 21
<212> TYPE: DNA
<213> ORGANISM: Artificial
<220> FEATURE:
<223> OTHER INFORMATION: Target sequence in the gene HCG3

<400> SEQUENCE: 252
cgcgatatct atgaccgcta t                                              21
```

```
<210> SEQ ID NO 253
<211> LENGTH: 21
<212> TYPE: DNA
<213> ORGANISM: Artificial
<220> FEATURE:
<223> OTHER INFORMATION: Target sequence in the gene HCP5

<400> SEQUENCE: 253
taggagggag tcagtactgt t                                              21

<210> SEQ ID NO 254
<211> LENGTH: 21
<212> TYPE: DNA
<213> ORGANISM: Artificial
<220> FEATURE:
<223> OTHER INFORMATION: Target sequence in the gene HDDC2

<400> SEQUENCE: 254
agggaatata tcaacccgat t                                              21

<210> SEQ ID NO 255
<211> LENGTH: 21
<212> TYPE: DNA
<213> ORGANISM: Artificial
<220> FEATURE:
<223> OTHER INFORMATION: Target sequence in the gene HECTD1

<400> SEQUENCE: 255
cagcttatag attgtattcg a                                              21

<210> SEQ ID NO 256
<211> LENGTH: 21
<212> TYPE: DNA
<213> ORGANISM: Artificial
<220> FEATURE:
<223> OTHER INFORMATION: Target sequence in the gene HEXIM2

<400> SEQUENCE: 256
tccgaaccag accgcctgta a                                              21

<210> SEQ ID NO 257
<211> LENGTH: 21
<212> TYPE: DNA
<213> ORGANISM: Artificial
<220> FEATURE:
<223> OTHER INFORMATION: Target sequence in the gene HIST1H2BF

<400> SEQUENCE: 257
atggtaagaa gcgcaagcgt a                                              21

<210> SEQ ID NO 258
<211> LENGTH: 21
<212> TYPE: DNA
<213> ORGANISM: Artificial
<220> FEATURE:
<223> OTHER INFORMATION: Target sequence in the gene HIST1H2BL

<400> SEQUENCE: 258
cagctccaag taaattctca a                                              21

<210> SEQ ID NO 259
<211> LENGTH: 21
<212> TYPE: DNA
<213> ORGANISM: Artificial
<220> FEATURE:
```

<223> OTHER INFORMATION: Target sequence in the gene HMHA1

<400> SEQUENCE: 259
cccgatgtgc actacgactt t                                               21

<210> SEQ ID NO 260
<211> LENGTH: 21
<212> TYPE: DNA
<213> ORGANISM: Artificial
<220> FEATURE:
<223> OTHER INFORMATION: Target sequence in the gene HMOX2

<400> SEQUENCE: 260
ttggaggtga gtggcctgta a                                               21

<210> SEQ ID NO 261
<211> LENGTH: 21
<212> TYPE: DNA
<213> ORGANISM: Artificial
<220> FEATURE:
<223> OTHER INFORMATION: Target sequence in the gene HOXA9

<400> SEQUENCE: 261
cccatcgatc ccaataaccc a                                               21

<210> SEQ ID NO 262
<211> LENGTH: 21
<212> TYPE: DNA
<213> ORGANISM: Artificial
<220> FEATURE:
<223> OTHER INFORMATION: Target sequence in the gene HOXB2

<400> SEQUENCE: 262
cggcctttag ccgttcgctt a                                               21

<210> SEQ ID NO 263
<211> LENGTH: 21
<212> TYPE: DNA
<213> ORGANISM: Artificial
<220> FEATURE:
<223> OTHER INFORMATION: Target sequence in the gene HSDL2

<400> SEQUENCE: 263
acccagttca tgaatcgcta a                                               21

<210> SEQ ID NO 264
<211> LENGTH: 21
<212> TYPE: DNA
<213> ORGANISM: Artificial
<220> FEATURE:
<223> OTHER INFORMATION: Target sequence in the gene HUWE1

<400> SEQUENCE: 264
ccggctttca ccagtcgctt a                                               21

<210> SEQ ID NO 265
<211> LENGTH: 21
<212> TYPE: DNA
<213> ORGANISM: Artificial
<220> FEATURE:
<223> OTHER INFORMATION: Target sequence in the gene HYAL3

<400> SEQUENCE: 265
ctggcatagt atggcttcca a                                               21

```
<210> SEQ ID NO 266
<211> LENGTH: 21
<212> TYPE: DNA
<213> ORGANISM: Artificial
<220> FEATURE:
<223> OTHER INFORMATION: Target sequence in the gene HYDIN

<400> SEQUENCE: 266
tgaggcgata ctgtacaaca a                                              21

<210> SEQ ID NO 267
<211> LENGTH: 21
<212> TYPE: DNA
<213> ORGANISM: Artificial
<220> FEATURE:
<223> OTHER INFORMATION: Target sequence in the gene HYMAI

<400> SEQUENCE: 267
aaggtaattg tcccaatatc a                                              21

<210> SEQ ID NO 268
<211> LENGTH: 21
<212> TYPE: DNA
<213> ORGANISM: Artificial
<220> FEATURE:
<223> OTHER INFORMATION: Target sequence in the gene IARS

<400> SEQUENCE: 268
cacagtaatc ttcacactta a                                              21

<210> SEQ ID NO 269
<211> LENGTH: 21
<212> TYPE: DNA
<213> ORGANISM: Artificial
<220> FEATURE:
<223> OTHER INFORMATION: Target sequence in the gene ICK

<400> SEQUENCE: 269
aaggactatt atattatata a                                              21

<210> SEQ ID NO 270
<211> LENGTH: 21
<212> TYPE: DNA
<213> ORGANISM: Artificial
<220> FEATURE:
<223> OTHER INFORMATION: Target sequence in the gene IFIT2

<400> SEQUENCE: 270
cccatagagg ttagtcctgc a                                              21

<210> SEQ ID NO 271
<211> LENGTH: 21
<212> TYPE: DNA
<213> ORGANISM: Artificial
<220> FEATURE:
<223> OTHER INFORMATION: Target sequence in the gene IGF2

<400> SEQUENCE: 271
ccggtcctct ttatccactg t                                              21

<210> SEQ ID NO 272
<211> LENGTH: 21
<212> TYPE: DNA
<213> ORGANISM: Artificial
<220> FEATURE:
<223> OTHER INFORMATION: Target sequence in the gene IGHMBP2
```

```
<400> SEQUENCE: 272
aaacgtggtc cttgcaacaa a                                              21

<210> SEQ ID NO 273
<211> LENGTH: 21
<212> TYPE: DNA
<213> ORGANISM: Artificial
<220> FEATURE:
<223> OTHER INFORMATION: Target sequence in the gene IKZF1

<400> SEQUENCE: 273
caccgcttcc acatgagcta a                                              21

<210> SEQ ID NO 274
<211> LENGTH: 21
<212> TYPE: DNA
<213> ORGANISM: Artificial
<220> FEATURE:
<223> OTHER INFORMATION: Target sequence in the gene IL17RE

<400> SEQUENCE: 274
cacaagggac ttcgctctaa a                                              21

<210> SEQ ID NO 275
<211> LENGTH: 21
<212> TYPE: DNA
<213> ORGANISM: Artificial
<220> FEATURE:
<223> OTHER INFORMATION: Target sequence in the gene IL1F9

<400> SEQUENCE: 275
cacgatggca tgactagcac a                                              21

<210> SEQ ID NO 276
<211> LENGTH: 21
<212> TYPE: DNA
<213> ORGANISM: Artificial
<220> FEATURE:
<223> OTHER INFORMATION: Target sequence in the gene ILF2

<400> SEQUENCE: 276
ctccatagaa gtgtcattcc a                                              21

<210> SEQ ID NO 277
<211> LENGTH: 21
<212> TYPE: DNA
<213> ORGANISM: Artificial
<220> FEATURE:
<223> OTHER INFORMATION: Target sequence in the gene INSL3

<400> SEQUENCE: 277
ctcagtggct gtacccaaca a                                              21

<210> SEQ ID NO 278
<211> LENGTH: 21
<212> TYPE: DNA
<213> ORGANISM: Artificial
<220> FEATURE:
<223> OTHER INFORMATION: Target sequence in the gene IPO9

<400> SEQUENCE: 278
atgggttgag agaatcgata a                                              21

<210> SEQ ID NO 279
<211> LENGTH: 21
```

```
<212> TYPE: DNA
<213> ORGANISM: Artificial
<220> FEATURE:
<223> OTHER INFORMATION: Target sequence in the gene IQCC

<400> SEQUENCE: 279
accgtcgtct ataccatcaa a                                            21

<210> SEQ ID NO 280
<211> LENGTH: 21
<212> TYPE: DNA
<213> ORGANISM: Artificial
<220> FEATURE:
<223> OTHER INFORMATION: Target sequence in the gene IQCD

<400> SEQUENCE: 280
cccgagatgg agagcactaa a                                            21

<210> SEQ ID NO 281
<211> LENGTH: 21
<212> TYPE: DNA
<213> ORGANISM: Artificial
<220> FEATURE:
<223> OTHER INFORMATION: Target sequence in the gene IRF1

<400> SEQUENCE: 281
caagcatggc tgggacatca a                                            21

<210> SEQ ID NO 282
<211> LENGTH: 21
<212> TYPE: DNA
<213> ORGANISM: Artificial
<220> FEATURE:
<223> OTHER INFORMATION: Target sequence in the gene ITGAM

<400> SEQUENCE: 282
tgccgccatc atcttacgga a                                            21

<210> SEQ ID NO 283
<211> LENGTH: 21
<212> TYPE: DNA
<213> ORGANISM: Artificial
<220> FEATURE:
<223> OTHER INFORMATION: Target sequence in the gene ITM2C

<400> SEQUENCE: 283
aacgcggagg cggatcaaca a                                            21

<210> SEQ ID NO 284
<211> LENGTH: 21
<212> TYPE: DNA
<213> ORGANISM: Artificial
<220> FEATURE:
<223> OTHER INFORMATION: Target sequence in the gene JMJD4

<400> SEQUENCE: 284
cagggacttt ccggtggagg a                                            21

<210> SEQ ID NO 285
<211> LENGTH: 21
<212> TYPE: DNA
<213> ORGANISM: Artificial
<220> FEATURE:
<223> OTHER INFORMATION: Target sequence in the gene KCNA7

<400> SEQUENCE: 285
```

```
aagcaaggct atcttcttca a                                              21

<210> SEQ ID NO 286
<211> LENGTH: 21
<212> TYPE: DNA
<213> ORGANISM: Artificial
<220> FEATURE:
<223> OTHER INFORMATION: Target sequence in the gene KCNA7

<400> SEQUENCE: 286
agggcttcct ttggtatcaa a                                              21

<210> SEQ ID NO 287
<211> LENGTH: 21
<212> TYPE: DNA
<213> ORGANISM: Artificial
<220> FEATURE:
<223> OTHER INFORMATION: Target sequence in the gene KCNJ3

<400> SEQUENCE: 287
accagccata actaacagca a                                              21

<210> SEQ ID NO 288
<211> LENGTH: 21
<212> TYPE: DNA
<213> ORGANISM: Artificial
<220> FEATURE:
<223> OTHER INFORMATION: Target sequence in the gene KCNT2

<400> SEQUENCE: 288
cacatagaga ttaaccaaca a                                              21

<210> SEQ ID NO 289
<211> LENGTH: 21
<212> TYPE: DNA
<213> ORGANISM: Artificial
<220> FEATURE:
<223> OTHER INFORMATION: Target sequence in the gene KCNV2

<400> SEQUENCE: 289
ctggacagag ggcaactata a                                              21

<210> SEQ ID NO 290
<211> LENGTH: 21
<212> TYPE: DNA
<213> ORGANISM: Artificial
<220> FEATURE:
<223> OTHER INFORMATION: Target sequence in the gene KCNV2

<400> SEQUENCE: 290
tacgaggagc agacagacga a                                              21

<210> SEQ ID NO 291
<211> LENGTH: 21
<212> TYPE: DNA
<213> ORGANISM: Artificial
<220> FEATURE:
<223> OTHER INFORMATION: Target sequence in the gene KIAA0090

<400> SEQUENCE: 291
aaggtacatc gcagtcctga a                                              21

<210> SEQ ID NO 292
<211> LENGTH: 21
<212> TYPE: DNA
<213> ORGANISM: Artificial
```

```
<220> FEATURE:
<223> OTHER INFORMATION: Target sequence in the gene KIAA0090

<400> SEQUENCE: 292
cagacagttt ctcgaatgcg a                                              21

<210> SEQ ID NO 293
<211> LENGTH: 21
<212> TYPE: DNA
<213> ORGANISM: Artificial
<220> FEATURE:
<223> OTHER INFORMATION: Target sequence in the gene KIAA0241

<400> SEQUENCE: 293
caggaaccca atgataccaa t                                              21

<210> SEQ ID NO 294
<211> LENGTH: 21
<212> TYPE: DNA
<213> ORGANISM: Artificial
<220> FEATURE:
<223> OTHER INFORMATION: Target sequence in the gene KIAA0460

<400> SEQUENCE: 294
agccggagtg gtataatctt a                                              21

<210> SEQ ID NO 295
<211> LENGTH: 21
<212> TYPE: DNA
<213> ORGANISM: Artificial
<220> FEATURE:
<223> OTHER INFORMATION: Target sequence in the gene KIAA0562

<400> SEQUENCE: 295
atggtggaga gatgtcgaat a                                              21

<210> SEQ ID NO 296
<211> LENGTH: 21
<212> TYPE: DNA
<213> ORGANISM: Artificial
<220> FEATURE:
<223> OTHER INFORMATION: Target sequence in the gene KIAA1712

<400> SEQUENCE: 296
ctggaggact atggtcctca a                                              21

<210> SEQ ID NO 297
<211> LENGTH: 21
<212> TYPE: DNA
<213> ORGANISM: Artificial
<220> FEATURE:
<223> OTHER INFORMATION: Target sequence in the gene KIF5A

<400> SEQUENCE: 297
aagggttgta ctgaacgctt t                                              21

<210> SEQ ID NO 298
<211> LENGTH: 21
<212> TYPE: DNA
<213> ORGANISM: Artificial
<220> FEATURE:
<223> OTHER INFORMATION: Target sequence in the gene KIF7

<400> SEQUENCE: 298
taccctcact gggatcaaca a                                              21
```

```
<210> SEQ ID NO 299
<211> LENGTH: 21
<212> TYPE: DNA
<213> ORGANISM: Artificial
<220> FEATURE:
<223> OTHER INFORMATION: Target sequence in the gene KIN

<400> SEQUENCE: 299
caggagacgc tttggcacta a                                              21

<210> SEQ ID NO 300
<211> LENGTH: 21
<212> TYPE: DNA
<213> ORGANISM: Artificial
<220> FEATURE:
<223> OTHER INFORMATION: Target sequence in the gene KIN

<400> SEQUENCE: 300
ccgagtgcac tgaagacgat a                                              21

<210> SEQ ID NO 301
<211> LENGTH: 21
<212> TYPE: DNA
<213> ORGANISM: Artificial
<220> FEATURE:
<223> OTHER INFORMATION: Target sequence in the gene KIR2DL1

<400> SEQUENCE: 301
caaggtcaac ggaacattcc a                                              21

<210> SEQ ID NO 302
<211> LENGTH: 21
<212> TYPE: DNA
<213> ORGANISM: Artificial
<220> FEATURE:
<223> OTHER INFORMATION: Target sequence in the gene KIR3DX1

<400> SEQUENCE: 302
cacgtctttg ctgttactca a                                              21

<210> SEQ ID NO 303
<211> LENGTH: 21
<212> TYPE: DNA
<213> ORGANISM: Artificial
<220> FEATURE:
<223> OTHER INFORMATION: Target sequence in the gene KLF14

<400> SEQUENCE: 303
caacgtgtat atcatcctaa a                                              21

<210> SEQ ID NO 304
<211> LENGTH: 21
<212> TYPE: DNA
<213> ORGANISM: Artificial
<220> FEATURE:
<223> OTHER INFORMATION: Target sequence in the gene KRT31

<400> SEQUENCE: 304
cacgaccaac gcgtgcagca a                                              21

<210> SEQ ID NO 305
<211> LENGTH: 21
<212> TYPE: DNA
<213> ORGANISM: Artificial
<220> FEATURE:
<223> OTHER INFORMATION: Target sequence in the gene KRT6A
```

<400> SEQUENCE: 305
cacaagtgac tagtcctatg a                                              21

<210> SEQ ID NO 306
<211> LENGTH: 21
<212> TYPE: DNA
<213> ORGANISM: Artificial
<220> FEATURE:
<223> OTHER INFORMATION: Target sequence in the gene KRT80

<400> SEQUENCE: 306
cagcgagatc gcggatctca a                                              21

<210> SEQ ID NO 307
<211> LENGTH: 21
<212> TYPE: DNA
<213> ORGANISM: Artificial
<220> FEATURE:
<223> OTHER INFORMATION: Target sequence in the gene KRT84

<400> SEQUENCE: 307
aacgctttac atggaggaaa t                                              21

<210> SEQ ID NO 308
<211> LENGTH: 21
<212> TYPE: DNA
<213> ORGANISM: Artificial
<220> FEATURE:
<223> OTHER INFORMATION: Target sequence in the gene KRTAP13-2

<400> SEQUENCE: 308
ctacgtagag ctgttatcat a                                              21

<210> SEQ ID NO 309
<211> LENGTH: 21
<212> TYPE: DNA
<213> ORGANISM: Artificial
<220> FEATURE:
<223> OTHER INFORMATION: Target sequence in the gene LAMA1

<400> SEQUENCE: 309
ccagacgcta ttattattca a                                              21

<210> SEQ ID NO 310
<211> LENGTH: 21
<212> TYPE: DNA
<213> ORGANISM: Artificial
<220> FEATURE:
<223> OTHER INFORMATION: Target sequence in the gene LARS2

<400> SEQUENCE: 310
cccgagaact gccctcatca a                                              21

<210> SEQ ID NO 311
<211> LENGTH: 21
<212> TYPE: DNA
<213> ORGANISM: Artificial
<220> FEATURE:
<223> OTHER INFORMATION: Target sequence in the gene LEPRE1

<400> SEQUENCE: 311
cagcgccatc ctttacctaa a                                              21

<210> SEQ ID NO 312

```
<211> LENGTH: 21
<212> TYPE: DNA
<213> ORGANISM: Artificial
<220> FEATURE:
<223> OTHER INFORMATION: Target sequence in the gene LEPREL2

<400> SEQUENCE: 312
gagggcctat taccagttga a                                          21

<210> SEQ ID NO 313
<211> LENGTH: 21
<212> TYPE: DNA
<213> ORGANISM: Artificial
<220> FEATURE:
<223> OTHER INFORMATION: Target sequence in the gene LIFR

<400> SEQUENCE: 313
tgggtcgatc acaatcaaca a                                          21

<210> SEQ ID NO 314
<211> LENGTH: 21
<212> TYPE: DNA
<213> ORGANISM: Artificial
<220> FEATURE:
<223> OTHER INFORMATION: Target sequence in the gene LILRA2

<400> SEQUENCE: 314
ctgggttaga cggatacaag a                                          21

<210> SEQ ID NO 315
<211> LENGTH: 21
<212> TYPE: DNA
<213> ORGANISM: Artificial
<220> FEATURE:
<223> OTHER INFORMATION: Target sequence in the gene LIN54

<400> SEQUENCE: 315
cagactcctg tgactatatc a                                          21

<210> SEQ ID NO 316
<211> LENGTH: 21
<212> TYPE: DNA
<213> ORGANISM: Artificial
<220> FEATURE:
<223> OTHER INFORMATION: Target sequence in the gene LMAN1L

<400> SEQUENCE: 316
cccggcgaag gcagcagcca a                                          21

<210> SEQ ID NO 317
<211> LENGTH: 21
<212> TYPE: DNA
<213> ORGANISM: Artificial
<220> FEATURE:
<223> OTHER INFORMATION: Target sequence in the gene LMNA

<400> SEQUENCE: 317
caggcagtct gctgagagga a                                          21

<210> SEQ ID NO 318
<211> LENGTH: 21
<212> TYPE: DNA
<213> ORGANISM: Artificial
<220> FEATURE:
<223> OTHER INFORMATION: Target sequence in the gene LNPEP

<400> SEQUENCE: 318
```

```
tccaatggaa ctcaaagcct a                                              21

<210> SEQ ID NO 319
<211> LENGTH: 21
<212> TYPE: DNA
<213> ORGANISM: Artificial
<220> FEATURE:
<223> OTHER INFORMATION: Target sequence in the gene LOC100008588

<400> SEQUENCE: 319
acggtcgaac ttgactatct a                                              21

<210> SEQ ID NO 320
<211> LENGTH: 21
<212> TYPE: DNA
<213> ORGANISM: Artificial
<220> FEATURE:
<223> OTHER INFORMATION: Target sequence in the gene LOC100008588

<400> SEQUENCE: 320
ctgcggctta atttgactca a                                              21

<210> SEQ ID NO 321
<211> LENGTH: 21
<212> TYPE: DNA
<213> ORGANISM: Artificial
<220> FEATURE:
<223> OTHER INFORMATION: Target sequence in the gene LOC196913

<400> SEQUENCE: 321
ccggcttcca tcactcagat a                                              21

<210> SEQ ID NO 322
<211> LENGTH: 21
<212> TYPE: DNA
<213> ORGANISM: Artificial
<220> FEATURE:
<223> OTHER INFORMATION: Target sequence in the gene LOC255374

<400> SEQUENCE: 322
cagggaagcc ctaacagcga a                                              21

<210> SEQ ID NO 323
<211> LENGTH: 21
<212> TYPE: DNA
<213> ORGANISM: Artificial
<220> FEATURE:
<223> OTHER INFORMATION: Target sequence in the gene LOC283951

<400> SEQUENCE: 323
ttgccaagtc tttgtataac a                                              21

<210> SEQ ID NO 324
<211> LENGTH: 21
<212> TYPE: DNA
<213> ORGANISM: Artificial
<220> FEATURE:
<223> OTHER INFORMATION: Target sequence in the gene LOC393078

<400> SEQUENCE: 324
acggtctatg ccagttctac a                                              21

<210> SEQ ID NO 325
<211> LENGTH: 21
<212> TYPE: DNA
```

```
<213> ORGANISM: Artificial
<220> FEATURE:
<223> OTHER INFORMATION: Target sequence in the gene LOC400759

<400> SEQUENCE: 325
tacgtgtcag gtgtatatta a                                              21

<210> SEQ ID NO 326
<211> LENGTH: 21
<212> TYPE: DNA
<213> ORGANISM: Artificial
<220> FEATURE:
<223> OTHER INFORMATION: Target sequence in the gene LOC401525

<400> SEQUENCE: 326
atggttgtac tcactcagat a                                              21

<210> SEQ ID NO 327
<211> LENGTH: 21
<212> TYPE: DNA
<213> ORGANISM: Artificial
<220> FEATURE:
<223> OTHER INFORMATION: Target sequence in the gene LOC441251

<400> SEQUENCE: 327
ctggctatgg tcatagtgta t                                              21

<210> SEQ ID NO 328
<211> LENGTH: 21
<212> TYPE: DNA
<213> ORGANISM: Artificial
<220> FEATURE:
<223> OTHER INFORMATION: Target sequence in the gene LOC493754

<400> SEQUENCE: 328
taggtttgag tgatatctca t                                              21

<210> SEQ ID NO 329
<211> LENGTH: 21
<212> TYPE: DNA
<213> ORGANISM: Artificial
<220> FEATURE:
<223> OTHER INFORMATION: Target sequence in the gene LPCAT1

<400> SEQUENCE: 329
ttcaagatgt acggagcgca a                                              21

<210> SEQ ID NO 330
<211> LENGTH: 21
<212> TYPE: DNA
<213> ORGANISM: Artificial
<220> FEATURE:
<223> OTHER INFORMATION: Target sequence in the gene LPO

<400> SEQUENCE: 330
ccgggaggta tctaacaaga t                                              21

<210> SEQ ID NO 331
<211> LENGTH: 21
<212> TYPE: DNA
<213> ORGANISM: Artificial
<220> FEATURE:
<223> OTHER INFORMATION: Target sequence in the gene LRDD

<400> SEQUENCE: 331
cagaatctgc tggacacgct a                                              21
```

```
<210> SEQ ID NO 332
<211> LENGTH: 21
<212> TYPE: DNA
<213> ORGANISM: Artificial
<220> FEATURE:
<223> OTHER INFORMATION: Target sequence in the gene LRDD

<400> SEQUENCE: 332
ccggctcgac ctgagggaca a                                          21

<210> SEQ ID NO 333
<211> LENGTH: 21
<212> TYPE: DNA
<213> ORGANISM: Artificial
<220> FEATURE:
<223> OTHER INFORMATION: Target sequence in the gene LRRC16A

<400> SEQUENCE: 333
cagggaccta atacctatca t                                          21

<210> SEQ ID NO 334
<211> LENGTH: 21
<212> TYPE: DNA
<213> ORGANISM: Artificial
<220> FEATURE:
<223> OTHER INFORMATION: Target sequence in the gene LRRC48

<400> SEQUENCE: 334
aagattgaca atcgagaaga t                                          21

<210> SEQ ID NO 335
<211> LENGTH: 21
<212> TYPE: DNA
<213> ORGANISM: Artificial
<220> FEATURE:
<223> OTHER INFORMATION: Target sequence in the gene LTBR

<400> SEQUENCE: 335
tacatctaca atggaccagt a                                          21

<210> SEQ ID NO 336
<211> LENGTH: 21
<212> TYPE: DNA
<213> ORGANISM: Artificial
<220> FEATURE:
<223> OTHER INFORMATION: Target sequence in the gene LYPD4

<400> SEQUENCE: 336
ccggtcttat ctctgcaaca a                                          21

<210> SEQ ID NO 337
<211> LENGTH: 21
<212> TYPE: DNA
<213> ORGANISM: Artificial
<220> FEATURE:
<223> OTHER INFORMATION: Target sequence in the gene MAF1

<400> SEQUENCE: 337
ctcgagcttt gaagccatca a                                          21

<210> SEQ ID NO 338
<211> LENGTH: 21
<212> TYPE: DNA
<213> ORGANISM: Artificial
<220> FEATURE:
```

<223> OTHER INFORMATION: Target sequence in the gene MAGEA10

<400> SEQUENCE: 338
aagatccttc ccactgtggt a                                              21

<210> SEQ ID NO 339
<211> LENGTH: 21
<212> TYPE: DNA
<213> ORGANISM: Artificial
<220> FEATURE:
<223> OTHER INFORMATION: Target sequence in the gene MAN1C1

<400> SEQUENCE: 339
aaggtcctca ggaagatcga a                                              21

<210> SEQ ID NO 340
<211> LENGTH: 21
<212> TYPE: DNA
<213> ORGANISM: Artificial
<220> FEATURE:
<223> OTHER INFORMATION: Target sequence in the gene MAP3K7IP2

<400> SEQUENCE: 340
cagtcaatag ccagacctta a                                              21

<210> SEQ ID NO 341
<211> LENGTH: 21
<212> TYPE: DNA
<213> ORGANISM: Artificial
<220> FEATURE:
<223> OTHER INFORMATION: Target sequence in the gene MAP6

<400> SEQUENCE: 341
taccaccaag ccagacgaca a                                              21

<210> SEQ ID NO 342
<211> LENGTH: 21
<212> TYPE: DNA
<213> ORGANISM: Artificial
<220> FEATURE:
<223> OTHER INFORMATION: Target sequence in the gene MAPRE2

<400> SEQUENCE: 342
cagcaggtgc agctaaatca a                                              21

<210> SEQ ID NO 343
<211> LENGTH: 21
<212> TYPE: DNA
<213> ORGANISM: Artificial
<220> FEATURE:
<223> OTHER INFORMATION: Target sequence in the gene MBOAT5

<400> SEQUENCE: 343
taaggtgtat aaatccatct a                                              21

<210> SEQ ID NO 344
<211> LENGTH: 21
<212> TYPE: DNA
<213> ORGANISM: Artificial
<220> FEATURE:
<223> OTHER INFORMATION: Target sequence in the gene MC5R

<400> SEQUENCE: 344
cggcattgtc ttcatcctgt a                                              21

```
<210> SEQ ID NO 345
<211> LENGTH: 21
<212> TYPE: DNA
<213> ORGANISM: Artificial
<220> FEATURE:
<223> OTHER INFORMATION: Target sequence in the gene MCCC2

<400> SEQUENCE: 345
acccttacta ttccagcgca a                                              21

<210> SEQ ID NO 346
<211> LENGTH: 21
<212> TYPE: DNA
<213> ORGANISM: Artificial
<220> FEATURE:
<223> OTHER INFORMATION: Target sequence in the gene MCCC2

<400> SEQUENCE: 346
cccgagcact tcacatatca a                                              21

<210> SEQ ID NO 347
<211> LENGTH: 21
<212> TYPE: DNA
<213> ORGANISM: Artificial
<220> FEATURE:
<223> OTHER INFORMATION: Target sequence in the gene MDGA1

<400> SEQUENCE: 347
acgcggttgt tctatcaata a                                              21

<210> SEQ ID NO 348
<211> LENGTH: 21
<212> TYPE: DNA
<213> ORGANISM: Artificial
<220> FEATURE:
<223> OTHER INFORMATION: Target sequence in the gene MED31

<400> SEQUENCE: 348
aggctagctg ttcctgacat a                                              21

<210> SEQ ID NO 349
<211> LENGTH: 21
<212> TYPE: DNA
<213> ORGANISM: Artificial
<220> FEATURE:
<223> OTHER INFORMATION: Target sequence in the gene MEGF11

<400> SEQUENCE: 349
aagaatccgt gtgcagttct a                                              21

<210> SEQ ID NO 350
<211> LENGTH: 21
<212> TYPE: DNA
<213> ORGANISM: Artificial
<220> FEATURE:
<223> OTHER INFORMATION: Target sequence in the gene MEGF11

<400> SEQUENCE: 350
aaggttgcgg tcataactcc a                                              21

<210> SEQ ID NO 351
<211> LENGTH: 21
<212> TYPE: DNA
<213> ORGANISM: Artificial
<220> FEATURE:
<223> OTHER INFORMATION: Target sequence in the gene METRNL
```

```
<400> SEQUENCE: 351
ccgtggagtg gatgtaccca a                                              21

<210> SEQ ID NO 352
<211> LENGTH: 21
<212> TYPE: DNA
<213> ORGANISM: Artificial
<220> FEATURE:
<223> OTHER INFORMATION: Target sequence in the gene MFN1

<400> SEQUENCE: 352
aaggaagttc ttagtgctag a                                              21

<210> SEQ ID NO 353
<211> LENGTH: 21
<212> TYPE: DNA
<213> ORGANISM: Artificial
<220> FEATURE:
<223> OTHER INFORMATION: Target sequence in the gene MFSD1

<400> SEQUENCE: 353
aaccctcggg atcacactta t                                              21

<210> SEQ ID NO 354
<211> LENGTH: 21
<212> TYPE: DNA
<213> ORGANISM: Artificial
<220> FEATURE:
<223> OTHER INFORMATION: Target sequence in the gene MFSD1

<400> SEQUENCE: 354
accgagtatt tggaatacga t                                              21

<210> SEQ ID NO 355
<211> LENGTH: 21
<212> TYPE: DNA
<213> ORGANISM: Artificial
<220> FEATURE:
<223> OTHER INFORMATION: Target sequence in the gene MGA

<400> SEQUENCE: 355
ctagatgatt atgactacga a                                              21

<210> SEQ ID NO 356
<211> LENGTH: 21
<212> TYPE: DNA
<213> ORGANISM: Artificial
<220> FEATURE:
<223> OTHER INFORMATION: Target sequence in the gene MGC3207

<400> SEQUENCE: 356
gaggtgagtg ccacaccta a                                               21

<210> SEQ ID NO 357
<211> LENGTH: 21
<212> TYPE: DNA
<213> ORGANISM: Artificial
<220> FEATURE:
<223> OTHER INFORMATION: Target sequence in the gene MMACHC

<400> SEQUENCE: 357
aacgtgcgct atggagccga a                                              21

<210> SEQ ID NO 358
<211> LENGTH: 21
```

```
<212> TYPE: DNA
<213> ORGANISM: Artificial
<220> FEATURE:
<223> OTHER INFORMATION: Target sequence in the gene MMD

<400> SEQUENCE: 358
cacggcagct gcagtgcatt a                                              21

<210> SEQ ID NO 359
<211> LENGTH: 21
<212> TYPE: DNA
<213> ORGANISM: Artificial
<220> FEATURE:
<223> OTHER INFORMATION: Target sequence in the gene MMP17

<400> SEQUENCE: 359
aaggacaata acgtagagga a                                              21

<210> SEQ ID NO 360
<211> LENGTH: 21
<212> TYPE: DNA
<213> ORGANISM: Artificial
<220> FEATURE:
<223> OTHER INFORMATION: Target sequence in the gene MMP26

<400> SEQUENCE: 360
ctcagtgccg atgatatcca a                                              21

<210> SEQ ID NO 361
<211> LENGTH: 21
<212> TYPE: DNA
<213> ORGANISM: Artificial
<220> FEATURE:
<223> OTHER INFORMATION: Target sequence in the gene MORC2

<400> SEQUENCE: 361
aacattggtg atcatcttca a                                              21

<210> SEQ ID NO 362
<211> LENGTH: 21
<212> TYPE: DNA
<213> ORGANISM: Artificial
<220> FEATURE:
<223> OTHER INFORMATION: Target sequence in the gene MRC2

<400> SEQUENCE: 362
ccgcaccagc aacatatcca a                                              21

<210> SEQ ID NO 363
<211> LENGTH: 21
<212> TYPE: DNA
<213> ORGANISM: Artificial
<220> FEATURE:
<223> OTHER INFORMATION: Target sequence in the gene MRFAP1

<400> SEQUENCE: 363
caagttgatg taatacccctg a                                             21

<210> SEQ ID NO 364
<211> LENGTH: 21
<212> TYPE: DNA
<213> ORGANISM: Artificial
<220> FEATURE:
<223> OTHER INFORMATION: Target sequence in the gene MRPL37

<400> SEQUENCE: 364
```
ccggtcatcg tggacaacct a                                             21

<210> SEQ ID NO 365
<211> LENGTH: 21
<212> TYPE: DNA
<213> ORGANISM: Artificial
<220> FEATURE:
<223> OTHER INFORMATION: Target sequence in the gene MRPL38

<400> SEQUENCE: 365
cccacctatg gcatctacta a                                             21

<210> SEQ ID NO 366
<211> LENGTH: 21
<212> TYPE: DNA
<213> ORGANISM: Artificial
<220> FEATURE:
<223> OTHER INFORMATION: Target sequence in the gene MRPL54

<400> SEQUENCE: 366
ccggatgctg agtaccctga a                                             21

<210> SEQ ID NO 367
<211> LENGTH: 21
<212> TYPE: DNA
<213> ORGANISM: Artificial
<220> FEATURE:
<223> OTHER INFORMATION: Target sequence in the gene MRPS12

<400> SEQUENCE: 367
cacgtttacc cgcaagccga a                                             21

<210> SEQ ID NO 368
<211> LENGTH: 21
<212> TYPE: DNA
<213> ORGANISM: Artificial
<220> FEATURE:
<223> OTHER INFORMATION: Target sequence in the gene MTF2

<400> SEQUENCE: 368
caggagttac aactcaatca t                                             21

<210> SEQ ID NO 369
<211> LENGTH: 21
<212> TYPE: DNA
<213> ORGANISM: Artificial
<220> FEATURE:
<223> OTHER INFORMATION: Target sequence in the gene MTX2

<400> SEQUENCE: 369
cagtggtgtg atgaagctac a                                             21

<210> SEQ ID NO 370
<211> LENGTH: 21
<212> TYPE: DNA
<213> ORGANISM: Artificial
<220> FEATURE:
<223> OTHER INFORMATION: Target sequence in the gene MXD4

<400> SEQUENCE: 370
gcgggccaag gtgcacatca a                                             21

<210> SEQ ID NO 371
<211> LENGTH: 21
<212> TYPE: DNA
<213> ORGANISM: Artificial

```
<220> FEATURE:
<223> OTHER INFORMATION: Target sequence in the gene N6AMT1

<400> SEQUENCE: 371
aagccgtgcc attaccaaca a                                              21

<210> SEQ ID NO 372
<211> LENGTH: 21
<212> TYPE: DNA
<213> ORGANISM: Artificial
<220> FEATURE:
<223> OTHER INFORMATION: Target sequence in the gene NDNL2

<400> SEQUENCE: 372
cagggagcat attgctgtaa a                                              21

<210> SEQ ID NO 373
<211> LENGTH: 21
<212> TYPE: DNA
<213> ORGANISM: Artificial
<220> FEATURE:
<223> OTHER INFORMATION: Target sequence in the gene NDST1

<400> SEQUENCE: 373
ctcgaactaa ctgctaataa a                                              21

<210> SEQ ID NO 374
<211> LENGTH: 21
<212> TYPE: DNA
<213> ORGANISM: Artificial
<220> FEATURE:
<223> OTHER INFORMATION: Target sequence in the gene NDUFS8

<400> SEQUENCE: 374
caaggagaag ttgctcaaca a                                              21

<210> SEQ ID NO 375
<211> LENGTH: 21
<212> TYPE: DNA
<213> ORGANISM: Artificial
<220> FEATURE:
<223> OTHER INFORMATION: Target sequence in the gene NDUFV1

<400> SEQUENCE: 375
ccgcctcatt gagttctata a                                              21

<210> SEQ ID NO 376
<211> LENGTH: 21
<212> TYPE: DNA
<213> ORGANISM: Artificial
<220> FEATURE:
<223> OTHER INFORMATION: Target sequence in the gene NFATC3

<400> SEQUENCE: 376
tcccagcggt ctgctcaaga a                                              21

<210> SEQ ID NO 377
<211> LENGTH: 21
<212> TYPE: DNA
<213> ORGANISM: Artificial
<220> FEATURE:
<223> OTHER INFORMATION: Target sequence in the gene NIPBL

<400> SEQUENCE: 377
aagcggcaat gtatgatata a                                              21
```

<210> SEQ ID NO 378
<211> LENGTH: 21
<212> TYPE: DNA
<213> ORGANISM: Artificial
<220> FEATURE:
<223> OTHER INFORMATION: Target sequence in the gene NKX2-1

<400> SEQUENCE: 378
ctccgttacg tgtacatcca a                                    21

<210> SEQ ID NO 379
<211> LENGTH: 21
<212> TYPE: DNA
<213> ORGANISM: Artificial
<220> FEATURE:
<223> OTHER INFORMATION: Target sequence in the gene NKX3-2

<400> SEQUENCE: 379
cgccaagaag gtggccgtaa a                                    21

<210> SEQ ID NO 380
<211> LENGTH: 21
<212> TYPE: DNA
<213> ORGANISM: Artificial
<220> FEATURE:
<223> OTHER INFORMATION: Target sequence in the gene NOL4

<400> SEQUENCE: 380
cacattgtcc ttgatccgta a                                    21

<210> SEQ ID NO 381
<211> LENGTH: 21
<212> TYPE: DNA
<213> ORGANISM: Artificial
<220> FEATURE:
<223> OTHER INFORMATION: Target sequence in the gene NOLC1

<400> SEQUENCE: 381
agccttcatg gacgagttat a                                    21

<210> SEQ ID NO 382
<211> LENGTH: 21
<212> TYPE: DNA
<213> ORGANISM: Artificial
<220> FEATURE:
<223> OTHER INFORMATION: Target sequence in the gene NPPB

<400> SEQUENCE: 382
ctgaggcggc attaagagga a                                    21

<210> SEQ ID NO 383
<211> LENGTH: 21
<212> TYPE: DNA
<213> ORGANISM: Artificial
<220> FEATURE:
<223> OTHER INFORMATION: Target sequence in the gene NPS

<400> SEQUENCE: 383
tggagttggc acagggatga a                                    21

<210> SEQ ID NO 384
<211> LENGTH: 21
<212> TYPE: DNA
<213> ORGANISM: Artificial
<220> FEATURE:
<223> OTHER INFORMATION: Target sequence in the gene NSUN3

-continued

```
<400> SEQUENCE: 384
ctccgtgttc aaatgatcga a                                              21

<210> SEQ ID NO 385
<211> LENGTH: 21
<212> TYPE: DNA
<213> ORGANISM: Artificial
<220> FEATURE:
<223> OTHER INFORMATION: Target sequence in the gene NTHL1

<400> SEQUENCE: 385
gagcaaggtg aaatacatca a                                              21

<210> SEQ ID NO 386
<211> LENGTH: 21
<212> TYPE: DNA
<213> ORGANISM: Artificial
<220> FEATURE:
<223> OTHER INFORMATION: Target sequence in the gene NUBPL

<400> SEQUENCE: 386
cgccgggagt gagaccctaa a                                              21

<210> SEQ ID NO 387
<211> LENGTH: 21
<212> TYPE: DNA
<213> ORGANISM: Artificial
<220> FEATURE:
<223> OTHER INFORMATION: Target sequence in the gene NUCB1

<400> SEQUENCE: 387
ccgcgagcac cctaaagtca a                                              21

<210> SEQ ID NO 388
<211> LENGTH: 21
<212> TYPE: DNA
<213> ORGANISM: Artificial
<220> FEATURE:
<223> OTHER INFORMATION: Target sequence in the gene NUDT15

<400> SEQUENCE: 388
cagcagtact cttctcacta a                                              21

<210> SEQ ID NO 389
<211> LENGTH: 21
<212> TYPE: DNA
<213> ORGANISM: Artificial
<220> FEATURE:
<223> OTHER INFORMATION: Target sequence in the gene NUP50

<400> SEQUENCE: 389
cccaaagtag tagttaccga a                                              21

<210> SEQ ID NO 390
<211> LENGTH: 21
<212> TYPE: DNA
<213> ORGANISM: Artificial
<220> FEATURE:
<223> OTHER INFORMATION: Target sequence in the gene NUPL2

<400> SEQUENCE: 390
gacgtggatg gaatacaact a                                              21

<210> SEQ ID NO 391
```

```
<211> LENGTH: 21
<212> TYPE: DNA
<213> ORGANISM: Artificial
<220> FEATURE:
<223> OTHER INFORMATION: Target sequence in the gene NUPL2

<400> SEQUENCE: 391
ttggattgtc tgagaaccca t                                              21

<210> SEQ ID NO 392
<211> LENGTH: 21
<212> TYPE: DNA
<213> ORGANISM: Artificial
<220> FEATURE:
<223> OTHER INFORMATION: Target sequence in the gene NYD-SP21

<400> SEQUENCE: 392
atccctagat atgctatctc a                                              21

<210> SEQ ID NO 393
<211> LENGTH: 21
<212> TYPE: DNA
<213> ORGANISM: Artificial
<220> FEATURE:
<223> OTHER INFORMATION: Target sequence in the gene OAS3

<400> SEQUENCE: 393
caggccggct ccggcgtcaa a                                              21

<210> SEQ ID NO 394
<211> LENGTH: 21
<212> TYPE: DNA
<213> ORGANISM: Artificial
<220> FEATURE:
<223> OTHER INFORMATION: Target sequence in the gene OAZ2

<400> SEQUENCE: 394
tccgatgagg actaatagtc a                                              21

<210> SEQ ID NO 395
<211> LENGTH: 21
<212> TYPE: DNA
<213> ORGANISM: Artificial
<220> FEATURE:
<223> OTHER INFORMATION: Target sequence in the gene OCRL

<400> SEQUENCE: 395
cagcgggagg gtctcatcaa a                                              21

<210> SEQ ID NO 396
<211> LENGTH: 21
<212> TYPE: DNA
<213> ORGANISM: Artificial
<220> FEATURE:
<223> OTHER INFORMATION: Target sequence in the gene OPTC

<400> SEQUENCE: 396
gaggattgac ctctccaaca a                                              21

<210> SEQ ID NO 397
<211> LENGTH: 21
<212> TYPE: DNA
<213> ORGANISM: Artificial
<220> FEATURE:
<223> OTHER INFORMATION: Target sequence in the gene OR2L2

<400> SEQUENCE: 397
```
aaagcgctag gttcatatca a          21

<210> SEQ ID NO 398
<211> LENGTH: 21
<212> TYPE: DNA
<213> ORGANISM: Artificial
<220> FEATURE:
<223> OTHER INFORMATION: Target sequence in the gene OR2T1

<400> SEQUENCE: 398
ctgcaattcc cgggagatta a          21

<210> SEQ ID NO 399
<211> LENGTH: 21
<212> TYPE: DNA
<213> ORGANISM: Artificial
<220> FEATURE:
<223> OTHER INFORMATION: Target sequence in the gene OR4C16

<400> SEQUENCE: 399
cactgttggg taatttgcta a          21

<210> SEQ ID NO 400
<211> LENGTH: 21
<212> TYPE: DNA
<213> ORGANISM: Artificial
<220> FEATURE:
<223> OTHER INFORMATION: Target sequence in the gene OR4D1

<400> SEQUENCE: 400
ctccgaaatc tagctctcat a          21

<210> SEQ ID NO 401
<211> LENGTH: 21
<212> TYPE: DNA
<213> ORGANISM: Artificial
<220> FEATURE:
<223> OTHER INFORMATION: Target sequence in the gene OR4Q3

<400> SEQUENCE: 401
ctgctccaat ctcctatgta t          21

<210> SEQ ID NO 402
<211> LENGTH: 21
<212> TYPE: DNA
<213> ORGANISM: Artificial
<220> FEATURE:
<223> OTHER INFORMATION: Target sequence in the gene OR4Q3

<400> SEQUENCE: 402
gagctgtgtt actgtgccaa a          21

<210> SEQ ID NO 403
<211> LENGTH: 21
<212> TYPE: DNA
<213> ORGANISM: Artificial
<220> FEATURE:
<223> OTHER INFORMATION: Target sequence in the gene OR5M9

<400> SEQUENCE: 403
ctcattgtag tagctgtgct a          21

<210> SEQ ID NO 404
<211> LENGTH: 21
<212> TYPE: DNA

```
<213> ORGANISM: Artificial
<220> FEATURE:
<223> OTHER INFORMATION: Target sequence in the gene OR6T1

<400> SEQUENCE: 404
tcccaagatg cttgtcgtca t                                              21

<210> SEQ ID NO 405
<211> LENGTH: 21
<212> TYPE: DNA
<213> ORGANISM: Artificial
<220> FEATURE:
<223> OTHER INFORMATION: Target sequence in the gene OR8B8

<400> SEQUENCE: 405
caaggtgtct tccctattct a                                              21

<210> SEQ ID NO 406
<211> LENGTH: 21
<212> TYPE: DNA
<213> ORGANISM: Artificial
<220> FEATURE:
<223> OTHER INFORMATION: Target sequence in the gene OR8S1

<400> SEQUENCE: 406
cacccgtata atctctacca t                                              21

<210> SEQ ID NO 407
<211> LENGTH: 21
<212> TYPE: DNA
<213> ORGANISM: Artificial
<220> FEATURE:
<223> OTHER INFORMATION: Target sequence in the gene OSBPL10

<400> SEQUENCE: 407
cagcgtagta taattcttca t                                              21

<210> SEQ ID NO 408
<211> LENGTH: 21
<212> TYPE: DNA
<213> ORGANISM: Artificial
<220> FEATURE:
<223> OTHER INFORMATION: Target sequence in the gene OTP

<400> SEQUENCE: 408
cgccaagtgg aagaagcgca a                                              21

<210> SEQ ID NO 409
<211> LENGTH: 21
<212> TYPE: DNA
<213> ORGANISM: Artificial
<220> FEATURE:
<223> OTHER INFORMATION: Target sequence in the gene P2RX3

<400> SEQUENCE: 409
ctggaccatc gggatcatca a                                              21

<210> SEQ ID NO 410
<211> LENGTH: 21
<212> TYPE: DNA
<213> ORGANISM: Artificial
<220> FEATURE:
<223> OTHER INFORMATION: Target sequence in the gene P2RY11

<400> SEQUENCE: 410
accctaggtg ttgctggaga a                                              21
```

<210> SEQ ID NO 411
<211> LENGTH: 21
<212> TYPE: DNA
<213> ORGANISM: Artificial
<220> FEATURE:
<223> OTHER INFORMATION: Target sequence in the gene PAEP

<400> SEQUENCE: 411
atggtacttg ctggacttga a          21

<210> SEQ ID NO 412
<211> LENGTH: 21
<212> TYPE: DNA
<213> ORGANISM: Artificial
<220> FEATURE:
<223> OTHER INFORMATION: Target sequence in the gene PAGE3

<400> SEQUENCE: 412
caggattata cacctggtca a          21

<210> SEQ ID NO 413
<211> LENGTH: 21
<212> TYPE: DNA
<213> ORGANISM: Artificial
<220> FEATURE:
<223> OTHER INFORMATION: Target sequence in the gene PCDHA1

<400> SEQUENCE: 413
aaggaagtcc tccgatgtca a          21

<210> SEQ ID NO 414
<211> LENGTH: 21
<212> TYPE: DNA
<213> ORGANISM: Artificial
<220> FEATURE:
<223> OTHER INFORMATION: Target sequence in the gene PDZD4

<400> SEQUENCE: 414
ctgcgcaagt ttggcctgca a          21

<210> SEQ ID NO 415
<211> LENGTH: 21
<212> TYPE: DNA
<213> ORGANISM: Artificial
<220> FEATURE:
<223> OTHER INFORMATION: Target sequence in the gene PER3

<400> SEQUENCE: 415
agggttaaag aagttgtact a          21

<210> SEQ ID NO 416
<211> LENGTH: 21
<212> TYPE: DNA
<213> ORGANISM: Artificial
<220> FEATURE:
<223> OTHER INFORMATION: Target sequence in the gene PER4

<400> SEQUENCE: 416
ttccatcatg gagacatagt a          21

<210> SEQ ID NO 417
<211> LENGTH: 21
<212> TYPE: DNA
<213> ORGANISM: Artificial
<220> FEATURE:

```
<223> OTHER INFORMATION: Target sequence in the gene PHYHIPL

<400> SEQUENCE: 417
aacgtgtgac tcattcaaga t                                              21

<210> SEQ ID NO 418
<211> LENGTH: 21
<212> TYPE: DNA
<213> ORGANISM: Artificial
<220> FEATURE:
<223> OTHER INFORMATION: Target sequence in the gene PIK3IP1

<400> SEQUENCE: 418
gcgggtgcgg atgaactcca a                                              21

<210> SEQ ID NO 419
<211> LENGTH: 21
<212> TYPE: DNA
<213> ORGANISM: Artificial
<220> FEATURE:
<223> OTHER INFORMATION: Target sequence in the gene PIP5KL1

<400> SEQUENCE: 419
tccgagaggt atgacatcaa a                                              21

<210> SEQ ID NO 420
<211> LENGTH: 21
<212> TYPE: DNA
<213> ORGANISM: Artificial
<220> FEATURE:
<223> OTHER INFORMATION: Target sequence in the gene PLCB4

<400> SEQUENCE: 420
aacccggtag tctagaacta a                                              21

<210> SEQ ID NO 421
<211> LENGTH: 21
<212> TYPE: DNA
<213> ORGANISM: Artificial
<220> FEATURE:
<223> OTHER INFORMATION: Target sequence in the gene PLEKHA7

<400> SEQUENCE: 421
cagctacttc atcgaccata a                                              21

<210> SEQ ID NO 422
<211> LENGTH: 21
<212> TYPE: DNA
<213> ORGANISM: Artificial
<220> FEATURE:
<223> OTHER INFORMATION: Target sequence in the gene PLXDC2

<400> SEQUENCE: 422
cacagtacat agcacccttta a                                             21

<210> SEQ ID NO 423
<211> LENGTH: 21
<212> TYPE: DNA
<213> ORGANISM: Artificial
<220> FEATURE:
<223> OTHER INFORMATION: Target sequence in the gene POLE4

<400> SEQUENCE: 423
cgggataagc agagatctca t                                              21
```

```
<210> SEQ ID NO 424
<211> LENGTH: 21
<212> TYPE: DNA
<213> ORGANISM: Artificial
<220> FEATURE:
<223> OTHER INFORMATION: Target sequence in the gene POLG

<400> SEQUENCE: 424
cagatgcggg tcacacctaa a                                              21

<210> SEQ ID NO 425
<211> LENGTH: 21
<212> TYPE: DNA
<213> ORGANISM: Artificial
<220> FEATURE:
<223> OTHER INFORMATION: Target sequence in the gene POLQ

<400> SEQUENCE: 425
atcagtgtct atagcatcaa a                                              21

<210> SEQ ID NO 426
<211> LENGTH: 21
<212> TYPE: DNA
<213> ORGANISM: Artificial
<220> FEATURE:
<223> OTHER INFORMATION: Target sequence in the gene POMGNT1

<400> SEQUENCE: 426
caggcctggc tcagaatcta a                                              21

<210> SEQ ID NO 427
<211> LENGTH: 21
<212> TYPE: DNA
<213> ORGANISM: Artificial
<220> FEATURE:
<223> OTHER INFORMATION: Target sequence in the gene POMGNT1

<400> SEQUENCE: 427
ccgcgtgtct cagcactaca a                                              21

<210> SEQ ID NO 428
<211> LENGTH: 21
<212> TYPE: DNA
<213> ORGANISM: Artificial
<220> FEATURE:
<223> OTHER INFORMATION: Target sequence in the gene POP7

<400> SEQUENCE: 428
ccgcaacaac tcagccatcc a                                              21

<210> SEQ ID NO 429
<211> LENGTH: 21
<212> TYPE: DNA
<213> ORGANISM: Artificial
<220> FEATURE:
<223> OTHER INFORMATION: Target sequence in the gene PORCN

<400> SEQUENCE: 429
caccgtgaca tggcacaaga t                                              21

<210> SEQ ID NO 430
<211> LENGTH: 21
<212> TYPE: DNA
<213> ORGANISM: Artificial
<220> FEATURE:
<223> OTHER INFORMATION: Target sequence in the gene POU5F1
```

```
<400> SEQUENCE: 430
tgggattaag ttcttcattc a                                          21

<210> SEQ ID NO 431
<211> LENGTH: 21
<212> TYPE: DNA
<213> ORGANISM: Artificial
<220> FEATURE:
<223> OTHER INFORMATION: Target sequence in the gene PPAN

<400> SEQUENCE: 431
ttccgccact atagcatcaa a                                          21

<210> SEQ ID NO 432
<211> LENGTH: 21
<212> TYPE: DNA
<213> ORGANISM: Artificial
<220> FEATURE:
<223> OTHER INFORMATION: Target sequence in the gene PQLC2

<400> SEQUENCE: 432
ctccgtgctg ttgttcctca t                                          21

<210> SEQ ID NO 433
<211> LENGTH: 21
<212> TYPE: DNA
<213> ORGANISM: Artificial
<220> FEATURE:
<223> OTHER INFORMATION: Target sequence in the gene PRB3

<400> SEQUENCE: 433
aagaaggtgg tcatagctct a                                          21

<210> SEQ ID NO 434
<211> LENGTH: 21
<212> TYPE: DNA
<213> ORGANISM: Artificial
<220> FEATURE:
<223> OTHER INFORMATION: Target sequence in the gene PRKD2

<400> SEQUENCE: 434
ttgggtggtt cattacagca a                                          21

<210> SEQ ID NO 435
<211> LENGTH: 21
<212> TYPE: DNA
<213> ORGANISM: Artificial
<220> FEATURE:
<223> OTHER INFORMATION: Target sequence in the gene PRO0611

<400> SEQUENCE: 435
aagggttaaa ttcagagtga t                                          21

<210> SEQ ID NO 436
<211> LENGTH: 21
<212> TYPE: DNA
<213> ORGANISM: Artificial
<220> FEATURE:
<223> OTHER INFORMATION: Target sequence in the gene PROP1

<400> SEQUENCE: 436
aagcagagaa atctcaagtc a                                          21

<210> SEQ ID NO 437
<211> LENGTH: 21
```

-continued

```
<212> TYPE: DNA
<213> ORGANISM: Artificial
<220> FEATURE:
<223> OTHER INFORMATION: Target sequence in the gene PROX1

<400> SEQUENCE: 437
atggagaagt acgcacgtca a                                              21

<210> SEQ ID NO 438
<211> LENGTH: 21
<212> TYPE: DNA
<213> ORGANISM: Artificial
<220> FEATURE:
<223> OTHER INFORMATION: Target sequence in the gene PRRG3

<400> SEQUENCE: 438
aaggtcaacc cttggttctt a                                              21

<210> SEQ ID NO 439
<211> LENGTH: 21
<212> TYPE: DNA
<213> ORGANISM: Artificial
<220> FEATURE:
<223> OTHER INFORMATION: Target sequence in the gene PSMC3

<400> SEQUENCE: 439
ctgccgaata ttgagagtcc a                                              21

<210> SEQ ID NO 440
<211> LENGTH: 21
<212> TYPE: DNA
<213> ORGANISM: Artificial
<220> FEATURE:
<223> OTHER INFORMATION: Target sequence in the gene PTPRO

<400> SEQUENCE: 440
cacggaagaa cctatagcct a                                              21

<210> SEQ ID NO 441
<211> LENGTH: 21
<212> TYPE: DNA
<213> ORGANISM: Artificial
<220> FEATURE:
<223> OTHER INFORMATION: Target sequence in the gene PTTG2

<400> SEQUENCE: 441
aagctggagt ctagaccttc a                                              21

<210> SEQ ID NO 442
<211> LENGTH: 21
<212> TYPE: DNA
<213> ORGANISM: Artificial
<220> FEATURE:
<223> OTHER INFORMATION: Target sequence in the gene R3HDML

<400> SEQUENCE: 442
ccggtccgta gtggatctca t                                              21

<210> SEQ ID NO 443
<211> LENGTH: 21
<212> TYPE: DNA
<213> ORGANISM: Artificial
<220> FEATURE:
<223> OTHER INFORMATION: Target sequence in the gene RAB6IP1

<400> SEQUENCE: 443
```
cagcatgtct atgtccctat t                                               21

<210> SEQ ID NO 444
<211> LENGTH: 21
<212> TYPE: DNA
<213> ORGANISM: Artificial
<220> FEATURE:
<223> OTHER INFORMATION: Target sequence in the gene RABGGTA

<400> SEQUENCE: 444
ctggacggcg tcaccaacct a                                               21

<210> SEQ ID NO 445
<211> LENGTH: 21
<212> TYPE: DNA
<213> ORGANISM: Artificial
<220> FEATURE:
<223> OTHER INFORMATION: Target sequence in the gene RABL2B

<400> SEQUENCE: 445
cagcgcagtg ggcaaatcca a                                               21

<210> SEQ ID NO 446
<211> LENGTH: 21
<212> TYPE: DNA
<213> ORGANISM: Artificial
<220> FEATURE:
<223> OTHER INFORMATION: Target sequence in the gene RALA

<400> SEQUENCE: 446
cgagctaatg ttgacaaggt a                                               21

<210> SEQ ID NO 447
<211> LENGTH: 21
<212> TYPE: DNA
<213> ORGANISM: Artificial
<220> FEATURE:
<223> OTHER INFORMATION: Target sequence in the gene RALGPS1

<400> SEQUENCE: 447
taacgaagta atagtaatta a                                               21

<210> SEQ ID NO 448
<211> LENGTH: 21
<212> TYPE: DNA
<213> ORGANISM: Artificial
<220> FEATURE:
<223> OTHER INFORMATION: Target sequence in the gene RAMP2

<400> SEQUENCE: 448
cacgagcttc tcaacaacca t                                               21

<210> SEQ ID NO 449
<211> LENGTH: 21
<212> TYPE: DNA
<213> ORGANISM: Artificial
<220> FEATURE:
<223> OTHER INFORMATION: Target sequence in the gene RARA

<400> SEQUENCE: 449
caggaaatgt tggagaactc a                                               21

<210> SEQ ID NO 450
<211> LENGTH: 21
<212> TYPE: DNA
<213> ORGANISM: Artificial

<220> FEATURE:
<223> OTHER INFORMATION: Target sequence in the gene RASSF7

<400> SEQUENCE: 450
ttcactgtgt gtacacagca a                                              21

<210> SEQ ID NO 451
<211> LENGTH: 21
<212> TYPE: DNA
<213> ORGANISM: Artificial
<220> FEATURE:
<223> OTHER INFORMATION: Target sequence in the gene RBJ

<400> SEQUENCE: 451
cagcccgaat tgacacgaca a                                              21

<210> SEQ ID NO 452
<211> LENGTH: 21
<212> TYPE: DNA
<213> ORGANISM: Artificial
<220> FEATURE:
<223> OTHER INFORMATION: Target sequence in the gene RBP1

<400> SEQUENCE: 452
taggaactac atcatggact t                                              21

<210> SEQ ID NO 453
<211> LENGTH: 21
<212> TYPE: DNA
<213> ORGANISM: Artificial
<220> FEATURE:
<223> OTHER INFORMATION: Target sequence in the gene RCCD1

<400> SEQUENCE: 453
ctgcctaagg tcagcatcaa t                                              21

<210> SEQ ID NO 454
<211> LENGTH: 21
<212> TYPE: DNA
<213> ORGANISM: Artificial
<220> FEATURE:
<223> OTHER INFORMATION: Target sequence in the gene RELL2

<400> SEQUENCE: 454
caggccgtgg tcacttctct a                                              21

<210> SEQ ID NO 455
<211> LENGTH: 21
<212> TYPE: DNA
<213> ORGANISM: Artificial
<220> FEATURE:
<223> OTHER INFORMATION: Target sequence in the gene REXO4

<400> SEQUENCE: 455
acgctctgca taatgaccta a                                              21

<210> SEQ ID NO 456
<211> LENGTH: 21
<212> TYPE: DNA
<213> ORGANISM: Artificial
<220> FEATURE:
<223> OTHER INFORMATION: Target sequence in the gene RFFL

<400> SEQUENCE: 456
tcgcaacttt gtcaactaca a                                              21

```
<210> SEQ ID NO 457
<211> LENGTH: 21
<212> TYPE: DNA
<213> ORGANISM: Artificial
<220> FEATURE:
<223> OTHER INFORMATION: Target sequence in the gene RFX4

<400> SEQUENCE: 457
caggcattac ctgacagctt a                                              21

<210> SEQ ID NO 458
<211> LENGTH: 21
<212> TYPE: DNA
<213> ORGANISM: Artificial
<220> FEATURE:
<223> OTHER INFORMATION: Target sequence in the gene RGS3

<400> SEQUENCE: 458
cccgcgggca aggcagacaa a                                              21

<210> SEQ ID NO 459
<211> LENGTH: 21
<212> TYPE: DNA
<213> ORGANISM: Artificial
<220> FEATURE:
<223> OTHER INFORMATION: Target sequence in the gene RGS3

<400> SEQUENCE: 459
cagacggata gacatacgga a                                              21

<210> SEQ ID NO 460
<211> LENGTH: 21
<212> TYPE: DNA
<213> ORGANISM: Artificial
<220> FEATURE:
<223> OTHER INFORMATION: Target sequence in the gene RGS3

<400> SEQUENCE: 460
ccgctgcgac gtcctgagga a                                              21

<210> SEQ ID NO 461
<211> LENGTH: 21
<212> TYPE: DNA
<213> ORGANISM: Artificial
<220> FEATURE:
<223> OTHER INFORMATION: Target sequence in the gene RHBDF1

<400> SEQUENCE: 461
ccacctcatg tggccaataa a                                              21

<210> SEQ ID NO 462
<211> LENGTH: 21
<212> TYPE: DNA
<213> ORGANISM: Artificial
<220> FEATURE:
<223> OTHER INFORMATION: Target sequence in the gene RICS

<400> SEQUENCE: 462
cccgctcaga ttatcatgtc a                                              21

<210> SEQ ID NO 463
<211> LENGTH: 21
<212> TYPE: DNA
<213> ORGANISM: Artificial
<220> FEATURE:
<223> OTHER INFORMATION: Target sequence in the gene RIPK3
```

```
<400> SEQUENCE: 463
cagcctgatg tcgtgcgtca a                                              21

<210> SEQ ID NO 464
<211> LENGTH: 21
<212> TYPE: DNA
<213> ORGANISM: Artificial
<220> FEATURE:
<223> OTHER INFORMATION: Target sequence in the gene RNASEH2B

<400> SEQUENCE: 464
caggctggtc tcggaaacga a                                              21

<210> SEQ ID NO 465
<211> LENGTH: 21
<212> TYPE: DNA
<213> ORGANISM: Artificial
<220> FEATURE:
<223> OTHER INFORMATION: Target sequence in the gene RNF123

<400> SEQUENCE: 465
ctgcgctact attgggatga a                                              21

<210> SEQ ID NO 466
<211> LENGTH: 21
<212> TYPE: DNA
<213> ORGANISM: Artificial
<220> FEATURE:
<223> OTHER INFORMATION: Target sequence in the gene RP6-213H19.1

<400> SEQUENCE: 466
gagctttacc accgtacgaa a                                              21

<210> SEQ ID NO 467
<211> LENGTH: 21
<212> TYPE: DNA
<213> ORGANISM: Artificial
<220> FEATURE:
<223> OTHER INFORMATION: Target sequence in the gene RPL3L

<400> SEQUENCE: 467
ctggtgcatc acagtcgcca a                                              21

<210> SEQ ID NO 468
<211> LENGTH: 21
<212> TYPE: DNA
<213> ORGANISM: Artificial
<220> FEATURE:
<223> OTHER INFORMATION: Target sequence in the gene RSPO1

<400> SEQUENCE: 468
ttggagagta ttgttaccct t                                              21

<210> SEQ ID NO 469
<211> LENGTH: 21
<212> TYPE: DNA
<213> ORGANISM: Artificial
<220> FEATURE:
<223> OTHER INFORMATION: Target sequence in the gene S100A13

<400> SEQUENCE: 469
cagcgtcaac gagttcaaag a                                              21

<210> SEQ ID NO 470
```

```
<211> LENGTH: 21
<212> TYPE: DNA
<213> ORGANISM: Artificial
<220> FEATURE:
<223> OTHER INFORMATION: Target sequence in the gene SAP130

<400> SEQUENCE: 470
ctcaaacatc ccagtcgcca a                                            21

<210> SEQ ID NO 471
<211> LENGTH: 21
<212> TYPE: DNA
<213> ORGANISM: Artificial
<220> FEATURE:
<223> OTHER INFORMATION: Target sequence in the gene SAR1A

<400> SEQUENCE: 471
caggccgtag taagcattaa t                                            21

<210> SEQ ID NO 472
<211> LENGTH: 21
<212> TYPE: DNA
<213> ORGANISM: Artificial
<220> FEATURE:
<223> OTHER INFORMATION: Target sequence in the gene SDCCAG10

<400> SEQUENCE: 472
gtgcctggtt tcatagtcca a                                            21

<210> SEQ ID NO 473
<211> LENGTH: 21
<212> TYPE: DNA
<213> ORGANISM: Artificial
<220> FEATURE:
<223> OTHER INFORMATION: Target sequence in the gene sept-01

<400> SEQUENCE: 473
caccacgatg atggagctac a                                            21

<210> SEQ ID NO 474
<211> LENGTH: 21
<212> TYPE: DNA
<213> ORGANISM: Artificial
<220> FEATURE:
<223> OTHER INFORMATION: Target sequence in the gene SERPINA6

<400> SEQUENCE: 474
cagcagacag atcaacagct a                                            21

<210> SEQ ID NO 475
<211> LENGTH: 21
<212> TYPE: DNA
<213> ORGANISM: Artificial
<220> FEATURE:
<223> OTHER INFORMATION: Target sequence in the gene SERPINB2

<400> SEQUENCE: 475
aacctatgac aaactcaaca a                                            21

<210> SEQ ID NO 476
<211> LENGTH: 21
<212> TYPE: DNA
<213> ORGANISM: Artificial
<220> FEATURE:
<223> OTHER INFORMATION: Target sequence in the gene SET

<400> SEQUENCE: 476
```
aagaagatag gctctcagta a     21

<210> SEQ ID NO 477
<211> LENGTH: 21
<212> TYPE: DNA
<213> ORGANISM: Artificial
<220> FEATURE:
<223> OTHER INFORMATION: Target sequence in the gene SET

<400> SEQUENCE: 477
caggaatctt gctccaataa a     21

<210> SEQ ID NO 478
<211> LENGTH: 21
<212> TYPE: DNA
<213> ORGANISM: Artificial
<220> FEATURE:
<223> OTHER INFORMATION: Target sequence in the gene SFTPB

<400> SEQUENCE: 478
caggatctct ccgagcagca a     21

<210> SEQ ID NO 479
<211> LENGTH: 21
<212> TYPE: DNA
<213> ORGANISM: Artificial
<220> FEATURE:
<223> OTHER INFORMATION: Target sequence in the gene SFTPC

<400> SEQUENCE: 479
cccagtcttg aggctctcaa t     21

<210> SEQ ID NO 480
<211> LENGTH: 21
<212> TYPE: DNA
<213> ORGANISM: Artificial
<220> FEATURE:
<223> OTHER INFORMATION: Target sequence in the gene SGPP2

<400> SEQUENCE: 480
caggcggaga ctggagattg a     21

<210> SEQ ID NO 481
<211> LENGTH: 21
<212> TYPE: DNA
<213> ORGANISM: Artificial
<220> FEATURE:
<223> OTHER INFORMATION: Target sequence in the gene SGSH

<400> SEQUENCE: 481
ccggaaattc ctgcagactc a     21

<210> SEQ ID NO 482
<211> LENGTH: 21
<212> TYPE: DNA
<213> ORGANISM: Artificial
<220> FEATURE:
<223> OTHER INFORMATION: Target sequence in the gene SH3BGRL

<400> SEQUENCE: 482
acgttgtaat ttcttatcgt a     21

<210> SEQ ID NO 483
<211> LENGTH: 21
<212> TYPE: DNA

```
<213> ORGANISM: Artificial
<220> FEATURE:
<223> OTHER INFORMATION: Target sequence in the gene SLC12A5

<400> SEQUENCE: 483
ctgcgggaca agtttggcga a                                              21

<210> SEQ ID NO 484
<211> LENGTH: 21
<212> TYPE: DNA
<213> ORGANISM: Artificial
<220> FEATURE:
<223> OTHER INFORMATION: Target sequence in the gene SLC13A2

<400> SEQUENCE: 484
atgccgtgga atatcgtgtt a                                              21

<210> SEQ ID NO 485
<211> LENGTH: 21
<212> TYPE: DNA
<213> ORGANISM: Artificial
<220> FEATURE:
<223> OTHER INFORMATION: Target sequence in the gene SLC15A3

<400> SEQUENCE: 485
cccgcaagag gacatcgcca a                                              21

<210> SEQ ID NO 486
<211> LENGTH: 21
<212> TYPE: DNA
<213> ORGANISM: Artificial
<220> FEATURE:
<223> OTHER INFORMATION: Target sequence in the gene SLC22A6

<400> SEQUENCE: 486
caccttgatt ggctatgtct a                                              21

<210> SEQ ID NO 487
<211> LENGTH: 21
<212> TYPE: DNA
<213> ORGANISM: Artificial
<220> FEATURE:
<223> OTHER INFORMATION: Target sequence in the gene SLC25A2

<400> SEQUENCE: 487
tacaatttgg tctgtcgtga a                                              21

<210> SEQ ID NO 488
<211> LENGTH: 21
<212> TYPE: DNA
<213> ORGANISM: Artificial
<220> FEATURE:
<223> OTHER INFORMATION: Target sequence in the gene SLC36A1

<400> SEQUENCE: 488
cccgtcggaa ggcctcaaca a                                              21

<210> SEQ ID NO 489
<211> LENGTH: 21
<212> TYPE: DNA
<213> ORGANISM: Artificial
<220> FEATURE:
<223> OTHER INFORMATION: Target sequence in the gene SLC37A3

<400> SEQUENCE: 489
gagccgaatt attcaatcca a                                              21
```

<210> SEQ ID NO 490
<211> LENGTH: 21
<212> TYPE: DNA
<213> ORGANISM: Artificial
<220> FEATURE:
<223> OTHER INFORMATION: Target sequence in the gene SLC39A5

<400> SEQUENCE: 490
cacgcaggac ctggcggact a                                              21

<210> SEQ ID NO 491
<211> LENGTH: 21
<212> TYPE: DNA
<213> ORGANISM: Artificial
<220> FEATURE:
<223> OTHER INFORMATION: Target sequence in the gene SLC44A1

<400> SEQUENCE: 491
ccctatgtag ctacaaccta a                                              21

<210> SEQ ID NO 492
<211> LENGTH: 21
<212> TYPE: DNA
<213> ORGANISM: Artificial
<220> FEATURE:
<223> OTHER INFORMATION: Target sequence in the gene SLC9A6

<400> SEQUENCE: 492
caagttgatg ttgaactcta t                                              21

<210> SEQ ID NO 493
<211> LENGTH: 21
<212> TYPE: DNA
<213> ORGANISM: Artificial
<220> FEATURE:
<223> OTHER INFORMATION: Target sequence in the gene SMG1

<400> SEQUENCE: 493
caccatggta ttacaggttc a                                              21

<210> SEQ ID NO 494
<211> LENGTH: 21
<212> TYPE: DNA
<213> ORGANISM: Artificial
<220> FEATURE:
<223> OTHER INFORMATION: Target sequence in the gene SNORA66

<400> SEQUENCE: 494
ctgcgtgatg tggcagaagc a                                              21

<210> SEQ ID NO 495
<211> LENGTH: 21
<212> TYPE: DNA
<213> ORGANISM: Artificial
<220> FEATURE:
<223> OTHER INFORMATION: Target sequence in the gene SNORA70

<400> SEQUENCE: 495
agcagcttcc ttggtagtgt a                                              21

<210> SEQ ID NO 496
<211> LENGTH: 21
<212> TYPE: DNA
<213> ORGANISM: Artificial
<220> FEATURE:

```
<223> OTHER INFORMATION: Target sequence in the gene SNORD114-1

<400> SEQUENCE: 496
atgatgatga ctggtggcgt a                                            21

<210> SEQ ID NO 497
<211> LENGTH: 21
<212> TYPE: DNA
<213> ORGANISM: Artificial
<220> FEATURE:
<223> OTHER INFORMATION: Target sequence in the gene SNORD114-7

<400> SEQUENCE: 497
atgcctgaga ctctgaggtt a                                            21

<210> SEQ ID NO 498
<211> LENGTH: 21
<212> TYPE: DNA
<213> ORGANISM: Artificial
<220> FEATURE:
<223> OTHER INFORMATION: Target sequence in the gene SNORD9

<400> SEQUENCE: 498
ctgtgatgag ttgccatgct a                                            21

<210> SEQ ID NO 499
<211> LENGTH: 21
<212> TYPE: DNA
<213> ORGANISM: Artificial
<220> FEATURE:
<223> OTHER INFORMATION: Target sequence in the gene SNRK

<400> SEQUENCE: 499
caccactgaa ttggaacgga t                                            21

<210> SEQ ID NO 500
<211> LENGTH: 21
<212> TYPE: DNA
<213> ORGANISM: Artificial
<220> FEATURE:
<223> OTHER INFORMATION: Target sequence in the gene SNX4

<400> SEQUENCE: 500
tggcggcgat atagtgaatt t                                            21

<210> SEQ ID NO 501
<211> LENGTH: 21
<212> TYPE: DNA
<213> ORGANISM: Artificial
<220> FEATURE:
<223> OTHER INFORMATION: Target sequence in the gene SORCS2

<400> SEQUENCE: 501
caccgtcatc gacaatttct a                                            21

<210> SEQ ID NO 502
<211> LENGTH: 21
<212> TYPE: DNA
<213> ORGANISM: Artificial
<220> FEATURE:
<223> OTHER INFORMATION: Target sequence in the gene SORCS2

<400> SEQUENCE: 502
gacgcttata acctacaaca a                                            21
```

```
<210> SEQ ID NO 503
<211> LENGTH: 21
<212> TYPE: DNA
<213> ORGANISM: Artificial
<220> FEATURE:
<223> OTHER INFORMATION: Target sequence in the gene SP1

<400> SEQUENCE: 503
ctaggacgca ataaatttat a                                              21

<210> SEQ ID NO 504
<211> LENGTH: 21
<212> TYPE: DNA
<213> ORGANISM: Artificial
<220> FEATURE:
<223> OTHER INFORMATION: Target sequence in the gene SP100

<400> SEQUENCE: 504
aaggagcgat tcaaacaagg a                                              21

<210> SEQ ID NO 505
<211> LENGTH: 21
<212> TYPE: DNA
<213> ORGANISM: Artificial
<220> FEATURE:
<223> OTHER INFORMATION: Target sequence in the gene SPATS2

<400> SEQUENCE: 505
cacagtgtct cttgcacggt a                                              21

<210> SEQ ID NO 506
<211> LENGTH: 21
<212> TYPE: DNA
<213> ORGANISM: Artificial
<220> FEATURE:
<223> OTHER INFORMATION: Target sequence in the gene SPC25

<400> SEQUENCE: 506
cgggactaag agatacctac a                                              21

<210> SEQ ID NO 507
<211> LENGTH: 21
<212> TYPE: DNA
<213> ORGANISM: Artificial
<220> FEATURE:
<223> OTHER INFORMATION: Target sequence in the gene SPDYA

<400> SEQUENCE: 507
tggagctgtc agaaactaca a                                              21

<210> SEQ ID NO 508
<211> LENGTH: 21
<212> TYPE: DNA
<213> ORGANISM: Artificial
<220> FEATURE:
<223> OTHER INFORMATION: Target sequence in the gene SPINT1

<400> SEQUENCE: 508
cgggaagaag agtgcattct a                                              21

<210> SEQ ID NO 509
<211> LENGTH: 21
<212> TYPE: DNA
<213> ORGANISM: Artificial
<220> FEATURE:
<223> OTHER INFORMATION: Target sequence in the gene SPRED2
```

```
<400> SEQUENCE: 509
aggcgtctag gtaacaagaa a                                              21

<210> SEQ ID NO 510
<211> LENGTH: 21
<212> TYPE: DNA
<213> ORGANISM: Artificial
<220> FEATURE:
<223> OTHER INFORMATION: Target sequence in the gene SPRED3

<400> SEQUENCE: 510
aaccttggag tgtacactga a                                              21

<210> SEQ ID NO 511
<211> LENGTH: 21
<212> TYPE: DNA
<213> ORGANISM: Artificial
<220> FEATURE:
<223> OTHER INFORMATION: Target sequence in the gene SPRED3

<400> SEQUENCE: 511
gccaggcttg gtttacaaca a                                              21

<210> SEQ ID NO 512
<211> LENGTH: 21
<212> TYPE: DNA
<213> ORGANISM: Artificial
<220> FEATURE:
<223> OTHER INFORMATION: Target sequence in the gene SPRR1B

<400> SEQUENCE: 512
cagagtattc ctctcttcac a                                              21

<210> SEQ ID NO 513
<211> LENGTH: 21
<212> TYPE: DNA
<213> ORGANISM: Artificial
<220> FEATURE:
<223> OTHER INFORMATION: Target sequence in the gene SPRYD4

<400> SEQUENCE: 513
aaagctaggc atacagccaa a                                              21

<210> SEQ ID NO 514
<211> LENGTH: 21
<212> TYPE: DNA
<213> ORGANISM: Artificial
<220> FEATURE:
<223> OTHER INFORMATION: Target sequence in the gene SRP14P1

<400> SEQUENCE: 514
cgggctgaga agagggacaa a                                              21

<210> SEQ ID NO 515
<211> LENGTH: 21
<212> TYPE: DNA
<213> ORGANISM: Artificial
<220> FEATURE:
<223> OTHER INFORMATION: Target sequence in the gene SRP9

<400> SEQUENCE: 515
tctgaaagta attgtgacta a                                              21

<210> SEQ ID NO 516
<211> LENGTH: 21
```

```
<212> TYPE: DNA
<213> ORGANISM: Artificial
<220> FEATURE:
<223> OTHER INFORMATION: Target sequence in the gene SRPK3

<400> SEQUENCE: 516
aagatgaggc gcaaacggaa a                                              21

<210> SEQ ID NO 517
<211> LENGTH: 21
<212> TYPE: DNA
<213> ORGANISM: Artificial
<220> FEATURE:
<223> OTHER INFORMATION: Target sequence in the gene SRXN1

<400> SEQUENCE: 517
cagatgtacc atggtgatgt a                                              21

<210> SEQ ID NO 518
<211> LENGTH: 21
<212> TYPE: DNA
<213> ORGANISM: Artificial
<220> FEATURE:
<223> OTHER INFORMATION: Target sequence in the gene STK39

<400> SEQUENCE: 518
ttggagtatt tgtaacttct a                                              21

<210> SEQ ID NO 519
<211> LENGTH: 21
<212> TYPE: DNA
<213> ORGANISM: Artificial
<220> FEATURE:
<223> OTHER INFORMATION: Target sequence in the gene STS

<400> SEQUENCE: 519
cggaagtaat gggatctata a                                              21

<210> SEQ ID NO 520
<211> LENGTH: 21
<212> TYPE: DNA
<213> ORGANISM: Artificial
<220> FEATURE:
<223> OTHER INFORMATION: Target sequence in the gene STXBP6

<400> SEQUENCE: 520
aaggcgaata tttaacttat a                                              21

<210> SEQ ID NO 521
<211> LENGTH: 21
<212> TYPE: DNA
<213> ORGANISM: Artificial
<220> FEATURE:
<223> OTHER INFORMATION: Target sequence in the gene STYXL1

<400> SEQUENCE: 521
caagattcag aaggacttga a                                              21

<210> SEQ ID NO 522
<211> LENGTH: 21
<212> TYPE: DNA
<213> ORGANISM: Artificial
<220> FEATURE:
<223> OTHER INFORMATION: Target sequence in the gene SV2A

<400> SEQUENCE: 522
```

```
caggacgaat attcccgaag a                                           21
```

```
<210> SEQ ID NO 523
<211> LENGTH: 21
<212> TYPE: DNA
<213> ORGANISM: Artificial
<220> FEATURE:
<223> OTHER INFORMATION: Target sequence in the gene SV2C

<400> SEQUENCE: 523
atggacagaa ttgggcgctt a                                           21
```

```
<210> SEQ ID NO 524
<211> LENGTH: 21
<212> TYPE: DNA
<213> ORGANISM: Artificial
<220> FEATURE:
<223> OTHER INFORMATION: Target sequence in the gene SYT2

<400> SEQUENCE: 524
caccttcaag gtgccatacc a                                           21
```

```
<210> SEQ ID NO 525
<211> LENGTH: 21
<212> TYPE: DNA
<213> ORGANISM: Artificial
<220> FEATURE:
<223> OTHER INFORMATION: Target sequence in the gene TARSL2

<400> SEQUENCE: 525
cacggtaata gccaaagtca a                                           21
```

```
<210> SEQ ID NO 526
<211> LENGTH: 21
<212> TYPE: DNA
<213> ORGANISM: Artificial
<220> FEATURE:
<223> OTHER INFORMATION: Target sequence in the gene TAS2R13

<400> SEQUENCE: 526
cagtgtcggt caaattcact a                                           21
```

```
<210> SEQ ID NO 527
<211> LENGTH: 21
<212> TYPE: DNA
<213> ORGANISM: Artificial
<220> FEATURE:
<223> OTHER INFORMATION: Target sequence in the gene TAX1BP1

<400> SEQUENCE: 527
cagatcaatc agctaataat a                                           21
```

```
<210> SEQ ID NO 528
<211> LENGTH: 21
<212> TYPE: DNA
<213> ORGANISM: Artificial
<220> FEATURE:
<223> OTHER INFORMATION: Target sequence in the gene TBC1D13

<400> SEQUENCE: 528
acccttcgta agagagtgga a                                           21
```

```
<210> SEQ ID NO 529
<211> LENGTH: 21
<212> TYPE: DNA
<213> ORGANISM: Artificial
```

```
<220> FEATURE:
<223> OTHER INFORMATION: Target sequence in the gene TBC1D5

<400> SEQUENCE: 529
aggaaggttg ttggccaaca a                                              21

<210> SEQ ID NO 530
<211> LENGTH: 21
<212> TYPE: DNA
<213> ORGANISM: Artificial
<220> FEATURE:
<223> OTHER INFORMATION: Target sequence in the gene TCP11L1

<400> SEQUENCE: 530
cagcagtcag ttgaatacga a                                              21

<210> SEQ ID NO 531
<211> LENGTH: 21
<212> TYPE: DNA
<213> ORGANISM: Artificial
<220> FEATURE:
<223> OTHER INFORMATION: Target sequence in the gene TCTEX1D1

<400> SEQUENCE: 531
cagggctgaa atagcttatt a                                              21

<210> SEQ ID NO 532
<211> LENGTH: 21
<212> TYPE: DNA
<213> ORGANISM: Artificial
<220> FEATURE:
<223> OTHER INFORMATION: Target sequence in the gene TCTEX1D2

<400> SEQUENCE: 532
aagaggtgaa ggagtattca t                                              21

<210> SEQ ID NO 533
<211> LENGTH: 21
<212> TYPE: DNA
<213> ORGANISM: Artificial
<220> FEATURE:
<223> OTHER INFORMATION: Target sequence in the gene TDRD12

<400> SEQUENCE: 533
tggtgggtac ttggtattca a                                              21

<210> SEQ ID NO 534
<211> LENGTH: 21
<212> TYPE: DNA
<213> ORGANISM: Artificial
<220> FEATURE:
<223> OTHER INFORMATION: Target sequence in the gene TG

<400> SEQUENCE: 534
aaaggtgatc ttcgacgcca a                                              21

<210> SEQ ID NO 535
<211> LENGTH: 21
<212> TYPE: DNA
<213> ORGANISM: Artificial
<220> FEATURE:
<223> OTHER INFORMATION: Target sequence in the gene TGFB1

<400> SEQUENCE: 535
cagcatatat atgttcttca a                                              21
```

<210> SEQ ID NO 536
<211> LENGTH: 21
<212> TYPE: DNA
<213> ORGANISM: Artificial
<220> FEATURE:
<223> OTHER INFORMATION: Target sequence in the gene TGIF2LX

<400> SEQUENCE: 536
ctgctagtcg atgcagcagt a                                             21

<210> SEQ ID NO 537
<211> LENGTH: 21
<212> TYPE: DNA
<213> ORGANISM: Artificial
<220> FEATURE:
<223> OTHER INFORMATION: Target sequence in the gene THAP10

<400> SEQUENCE: 537
aagtactaca tttctaacgt a                                             21

<210> SEQ ID NO 538
<211> LENGTH: 21
<212> TYPE: DNA
<213> ORGANISM: Artificial
<220> FEATURE:
<223> OTHER INFORMATION: Target sequence in the gene THBS2

<400> SEQUENCE: 538
agcgttggga tacttcatta a                                             21

<210> SEQ ID NO 539
<211> LENGTH: 21
<212> TYPE: DNA
<213> ORGANISM: Artificial
<220> FEATURE:
<223> OTHER INFORMATION: Target sequence in the gene THSD1P

<400> SEQUENCE: 539
ctggatttag ccagtcctgc a                                             21

<210> SEQ ID NO 540
<211> LENGTH: 21
<212> TYPE: DNA
<213> ORGANISM: Artificial
<220> FEATURE:
<223> OTHER INFORMATION: Target sequence in the gene TMCC3

<400> SEQUENCE: 540
ctgggtttat ctggtgacat a                                             21

<210> SEQ ID NO 541
<211> LENGTH: 21
<212> TYPE: DNA
<213> ORGANISM: Artificial
<220> FEATURE:
<223> OTHER INFORMATION: Target sequence in the gene TMCO3

<400> SEQUENCE: 541
gaggagcagc cagtacatca a                                             21

<210> SEQ ID NO 542
<211> LENGTH: 21
<212> TYPE: DNA
<213> ORGANISM: Artificial
<220> FEATURE:
<223> OTHER INFORMATION: Target sequence in the gene TMED6

-continued

<400> SEQUENCE: 542
ttccgtggag ctgatcgata t                                          21

<210> SEQ ID NO 543
<211> LENGTH: 21
<212> TYPE: DNA
<213> ORGANISM: Artificial
<220> FEATURE:
<223> OTHER INFORMATION: Target sequence in the gene TMEM108

<400> SEQUENCE: 543
cagggagatc cagtcccttg a                                          21

<210> SEQ ID NO 544
<211> LENGTH: 21
<212> TYPE: DNA
<213> ORGANISM: Artificial
<220> FEATURE:
<223> OTHER INFORMATION: Target sequence in the gene TMEM161B

<400> SEQUENCE: 544
cagaagatta tacctcacta t                                          21

<210> SEQ ID NO 545
<211> LENGTH: 21
<212> TYPE: DNA
<213> ORGANISM: Artificial
<220> FEATURE:
<223> OTHER INFORMATION: Target sequence in the gene TMEM188

<400> SEQUENCE: 545
accattagct gtatcactct a                                          21

<210> SEQ ID NO 546
<211> LENGTH: 21
<212> TYPE: DNA
<213> ORGANISM: Artificial
<220> FEATURE:
<223> OTHER INFORMATION: Target sequence in the gene TMEM33

<400> SEQUENCE: 546
cccttcgata ttcgtctcga a                                          21

<210> SEQ ID NO 547
<211> LENGTH: 21
<212> TYPE: DNA
<213> ORGANISM: Artificial
<220> FEATURE:
<223> OTHER INFORMATION: Target sequence in the gene TMEM37

<400> SEQUENCE: 547
caggcttagc cagatgttga t                                          21

<210> SEQ ID NO 548
<211> LENGTH: 21
<212> TYPE: DNA
<213> ORGANISM: Artificial
<220> FEATURE:
<223> OTHER INFORMATION: Target sequence in the gene TMEM45B

<400> SEQUENCE: 548
cagcgtctcg agatcgtcga a                                          21

<210> SEQ ID NO 549

```
<211> LENGTH: 21
<212> TYPE: DNA
<213> ORGANISM: Artificial
<220> FEATURE:
<223> OTHER INFORMATION: Target sequence in the gene TMEM48

<400> SEQUENCE: 549
cagcatcatt tacagaggat a                                              21

<210> SEQ ID NO 550
<211> LENGTH: 21
<212> TYPE: DNA
<213> ORGANISM: Artificial
<220> FEATURE:
<223> OTHER INFORMATION: Target sequence in the gene TMEM49

<400> SEQUENCE: 550
tagggtggaa tgtgatgttc a                                              21

<210> SEQ ID NO 551
<211> LENGTH: 21
<212> TYPE: DNA
<213> ORGANISM: Artificial
<220> FEATURE:
<223> OTHER INFORMATION: Target sequence in the gene TMEM59L

<400> SEQUENCE: 551
ctgcgtggaa gcctatgtga a                                              21

<210> SEQ ID NO 552
<211> LENGTH: 21
<212> TYPE: DNA
<213> ORGANISM: Artificial
<220> FEATURE:
<223> OTHER INFORMATION: Target sequence in the gene TNFAIP8L3

<400> SEQUENCE: 552
aaacctggat gtagactatt a                                              21

<210> SEQ ID NO 553
<211> LENGTH: 21
<212> TYPE: DNA
<213> ORGANISM: Artificial
<220> FEATURE:
<223> OTHER INFORMATION: Target sequence in the gene TNIP1

<400> SEQUENCE: 553
ccggtccatg aagcagcagt a                                              21

<210> SEQ ID NO 554
<211> LENGTH: 21
<212> TYPE: DNA
<213> ORGANISM: Artificial
<220> FEATURE:
<223> OTHER INFORMATION: Target sequence in the gene TNXA

<400> SEQUENCE: 554
cacagcgact tcattgtctg a                                              21

<210> SEQ ID NO 555
<211> LENGTH: 21
<212> TYPE: DNA
<213> ORGANISM: Artificial
<220> FEATURE:
<223> OTHER INFORMATION: Target sequence in the gene TOP1

<400> SEQUENCE: 555
```
gcccgaggat ataatcatca a         21

<210> SEQ ID NO 556
<211> LENGTH: 21
<212> TYPE: DNA
<213> ORGANISM: Artificial
<220> FEATURE:
<223> OTHER INFORMATION: Target sequence in the gene TPRG1

<400> SEQUENCE: 556
aaggatcagc ctgacaatcg a         21

<210> SEQ ID NO 557
<211> LENGTH: 21
<212> TYPE: DNA
<213> ORGANISM: Artificial
<220> FEATURE:
<223> OTHER INFORMATION: Target sequence in the gene TRADD

<400> SEQUENCE: 557
cccgaatgtt aagcaatgat a         21

<210> SEQ ID NO 558
<211> LENGTH: 21
<212> TYPE: DNA
<213> ORGANISM: Artificial
<220> FEATURE:
<223> OTHER INFORMATION: Target sequence in the gene TRH

<400> SEQUENCE: 558
ctggcagatc ccaaggctca a         21

<210> SEQ ID NO 559
<211> LENGTH: 21
<212> TYPE: DNA
<213> ORGANISM: Artificial
<220> FEATURE:
<223> OTHER INFORMATION: Target sequence in the gene TRIM3

<400> SEQUENCE: 559
tagaccggaa tggacatatc a         21

<210> SEQ ID NO 560
<211> LENGTH: 21
<212> TYPE: DNA
<213> ORGANISM: Artificial
<220> FEATURE:
<223> OTHER INFORMATION: Target sequence in the gene TRIM37

<400> SEQUENCE: 560
ctcgaaggtg gtcctactac a         21

<210> SEQ ID NO 561
<211> LENGTH: 21
<212> TYPE: DNA
<213> ORGANISM: Artificial
<220> FEATURE:
<223> OTHER INFORMATION: Target sequence in the gene TRIM48

<400> SEQUENCE: 561
atgcataaag acaatacagc a         21

<210> SEQ ID NO 562
<211> LENGTH: 21
<212> TYPE: DNA

```
<213> ORGANISM: Artificial
<220> FEATURE:
<223> OTHER INFORMATION: Target sequence in the gene TRIM60

<400> SEQUENCE: 562
ttgcgtcagg tcctaagaca a                                              21

<210> SEQ ID NO 563
<211> LENGTH: 21
<212> TYPE: DNA
<213> ORGANISM: Artificial
<220> FEATURE:
<223> OTHER INFORMATION: Target sequence in the gene TRSPAP1

<400> SEQUENCE: 563
ctgagcgtgg caatccctaa a                                              21

<210> SEQ ID NO 564
<211> LENGTH: 21
<212> TYPE: DNA
<213> ORGANISM: Artificial
<220> FEATURE:
<223> OTHER INFORMATION: Target sequence in the gene TSHZ2

<400> SEQUENCE: 564
ccggcctaat ctcaccaaca a                                              21

<210> SEQ ID NO 565
<211> LENGTH: 21
<212> TYPE: DNA
<213> ORGANISM: Artificial
<220> FEATURE:
<223> OTHER INFORMATION: Target sequence in the gene TTC17

<400> SEQUENCE: 565
ctggatctat atgatggcac a                                              21

<210> SEQ ID NO 566
<211> LENGTH: 21
<212> TYPE: DNA
<213> ORGANISM: Artificial
<220> FEATURE:
<223> OTHER INFORMATION: Target sequence in the gene UBR5

<400> SEQUENCE: 566
caggtatgct tgagaaataa t                                              21

<210> SEQ ID NO 567
<211> LENGTH: 21
<212> TYPE: DNA
<213> ORGANISM: Artificial
<220> FEATURE:
<223> OTHER INFORMATION: Target sequence in the gene UBR5

<400> SEQUENCE: 567
ctggtatttc ttcaatgccg a                                              21

<210> SEQ ID NO 568
<211> LENGTH: 21
<212> TYPE: DNA
<213> ORGANISM: Artificial
<220> FEATURE:
<223> OTHER INFORMATION: Target sequence in the gene UBXD5

<400> SEQUENCE: 568
ctcccttagc aagacccgaa a                                              21
```

```
<210> SEQ ID NO 569
<211> LENGTH: 21
<212> TYPE: DNA
<213> ORGANISM: Artificial
<220> FEATURE:
<223> OTHER INFORMATION: Target sequence in the gene UGT1A10

<400> SEQUENCE: 569
acgatacttg ttaagtggct a                                              21

<210> SEQ ID NO 570
<211> LENGTH: 21
<212> TYPE: DNA
<213> ORGANISM: Artificial
<220> FEATURE:
<223> OTHER INFORMATION: Target sequence in the gene USP16

<400> SEQUENCE: 570
acccgtaatg agaaacttcg a                                              21

<210> SEQ ID NO 571
<211> LENGTH: 21
<212> TYPE: DNA
<213> ORGANISM: Artificial
<220> FEATURE:
<223> OTHER INFORMATION: Target sequence in the gene USP20

<400> SEQUENCE: 571
accgtcgtac gtgctcaaga a                                              21

<210> SEQ ID NO 572
<211> LENGTH: 21
<212> TYPE: DNA
<213> ORGANISM: Artificial
<220> FEATURE:
<223> OTHER INFORMATION: Target sequence in the gene USP37

<400> SEQUENCE: 572
atccgggtag aggatcgatt a                                              21

<210> SEQ ID NO 573
<211> LENGTH: 21
<212> TYPE: DNA
<213> ORGANISM: Artificial
<220> FEATURE:
<223> OTHER INFORMATION: Target sequence in the gene VPS37D

<400> SEQUENCE: 573
cgggctgccc tggccatcaa a                                              21

<210> SEQ ID NO 574
<211> LENGTH: 21
<212> TYPE: DNA
<213> ORGANISM: Artificial
<220> FEATURE:
<223> OTHER INFORMATION: Target sequence in the gene VPS54

<400> SEQUENCE: 574
tcagctaagc ttgtagcgat a                                              21

<210> SEQ ID NO 575
<211> LENGTH: 21
<212> TYPE: DNA
<213> ORGANISM: Artificial
<220> FEATURE:
```

<223> OTHER INFORMATION: Target sequence in the gene VPS8

<400> SEQUENCE: 575
cagcagtaca agagacgcca a                                          21

<210> SEQ ID NO 576
<211> LENGTH: 21
<212> TYPE: DNA
<213> ORGANISM: Artificial
<220> FEATURE:
<223> OTHER INFORMATION: Target sequence in the gene VSTM2A

<400> SEQUENCE: 576
caggtgcgag gatagctaca a                                          21

<210> SEQ ID NO 577
<211> LENGTH: 21
<212> TYPE: DNA
<213> ORGANISM: Artificial
<220> FEATURE:
<223> OTHER INFORMATION: Target sequence in the gene VWCE

<400> SEQUENCE: 577
aggctgctct cttgacgaca a                                          21

<210> SEQ ID NO 578
<211> LENGTH: 21
<212> TYPE: DNA
<213> ORGANISM: Artificial
<220> FEATURE:
<223> OTHER INFORMATION: Target sequence in the gene WDR17

<400> SEQUENCE: 578
caccgttata atgaattcaa a                                          21

<210> SEQ ID NO 579
<211> LENGTH: 21
<212> TYPE: DNA
<213> ORGANISM: Artificial
<220> FEATURE:
<223> OTHER INFORMATION: Target sequence in the gene WDR38

<400> SEQUENCE: 579
cagcctgctt atccaactga a                                          21

<210> SEQ ID NO 580
<211> LENGTH: 21
<212> TYPE: DNA
<213> ORGANISM: Artificial
<220> FEATURE:
<223> OTHER INFORMATION: Target sequence in the gene WFDC5

<400> SEQUENCE: 580
cagcccaacc atccagaatg a                                          21

<210> SEQ ID NO 581
<211> LENGTH: 21
<212> TYPE: DNA
<213> ORGANISM: Artificial
<220> FEATURE:
<223> OTHER INFORMATION: Target sequence in the gene WWP2

<400> SEQUENCE: 581
ctcacctact ttcgctttat a                                          21

```
<210> SEQ ID NO 582
<211> LENGTH: 21
<212> TYPE: DNA
<213> ORGANISM: Artificial
<220> FEATURE:
<223> OTHER INFORMATION: Target sequence in the gene XIRP1

<400> SEQUENCE: 582
atccaggacg gtcttcggaa a                                               21

<210> SEQ ID NO 583
<211> LENGTH: 21
<212> TYPE: DNA
<213> ORGANISM: Artificial
<220> FEATURE:
<223> OTHER INFORMATION: Target sequence in the gene XIRP1

<400> SEQUENCE: 583
aagggcaacc ctgatgtctc a                                               21

<210> SEQ ID NO 584
<211> LENGTH: 21
<212> TYPE: DNA
<213> ORGANISM: Artificial
<220> FEATURE:
<223> OTHER INFORMATION: Target sequence in the gene XIST

<400> SEQUENCE: 584
taagtgcttg aaagacgtaa a                                               21

<210> SEQ ID NO 585
<211> LENGTH: 21
<212> TYPE: DNA
<213> ORGANISM: Artificial
<220> FEATURE:
<223> OTHER INFORMATION: Target sequence in the gene XPO7

<400> SEQUENCE: 585
caagcttgta tcacgcacaa a                                               21

<210> SEQ ID NO 586
<211> LENGTH: 21
<212> TYPE: DNA
<213> ORGANISM: Artificial
<220> FEATURE:
<223> OTHER INFORMATION: Target sequence in the gene ZC3H12D

<400> SEQUENCE: 586
ccgggctcgc atcgcgctct a                                               21

<210> SEQ ID NO 587
<211> LENGTH: 21
<212> TYPE: DNA
<213> ORGANISM: Artificial
<220> FEATURE:
<223> OTHER INFORMATION: Target sequence in the gene ZC3HC1

<400> SEQUENCE: 587
gagtgtggga ttaacagact a                                               21

<210> SEQ ID NO 588
<211> LENGTH: 21
<212> TYPE: DNA
<213> ORGANISM: Artificial
<220> FEATURE:
<223> OTHER INFORMATION: Target sequence in the gene ZCCHC7
```

```
<400> SEQUENCE: 588
cagatagcta ataaccgaac a                                              21

<210> SEQ ID NO 589
<211> LENGTH: 21
<212> TYPE: DNA
<213> ORGANISM: Artificial
<220> FEATURE:
<223> OTHER INFORMATION: Target sequence in the gene ZDHHC22

<400> SEQUENCE: 589
cccgctgata gctgcgcaac a                                              21

<210> SEQ ID NO 590
<211> LENGTH: 21
<212> TYPE: DNA
<213> ORGANISM: Artificial
<220> FEATURE:
<223> OTHER INFORMATION: Target sequence in the gene ZDHHC4

<400> SEQUENCE: 590
ttgagctgta gttcccgttt a                                              21

<210> SEQ ID NO 591
<211> LENGTH: 21
<212> TYPE: DNA
<213> ORGANISM: Artificial
<220> FEATURE:
<223> OTHER INFORMATION: Target sequence in the gene ZFP106

<400> SEQUENCE: 591
cccgccgcat tcgcaatatt a                                              21

<210> SEQ ID NO 592
<211> LENGTH: 21
<212> TYPE: DNA
<213> ORGANISM: Artificial
<220> FEATURE:
<223> OTHER INFORMATION: Target sequence in the gene ZFP30

<400> SEQUENCE: 592
cagcgctggc ataaacaata a                                              21

<210> SEQ ID NO 593
<211> LENGTH: 21
<212> TYPE: DNA
<213> ORGANISM: Artificial
<220> FEATURE:
<223> OTHER INFORMATION: Target sequence in the gene ZFX

<400> SEQUENCE: 593
gaggacgttg ttatagaaga t                                              21

<210> SEQ ID NO 594
<211> LENGTH: 21
<212> TYPE: DNA
<213> ORGANISM: Artificial
<220> FEATURE:
<223> OTHER INFORMATION: Target sequence in the gene ZMAT5

<400> SEQUENCE: 594
ctccgcactg gaagacttga a                                              21

<210> SEQ ID NO 595
<211> LENGTH: 21
```

```
<212> TYPE: DNA
<213> ORGANISM: Artificial
<220> FEATURE:
<223> OTHER INFORMATION: Target sequence in the gene ZNF223

<400> SEQUENCE: 595
cagaggttta gaggcacaat t                                        21

<210> SEQ ID NO 596
<211> LENGTH: 21
<212> TYPE: DNA
<213> ORGANISM: Artificial
<220> FEATURE:
<223> OTHER INFORMATION: Target sequence in the gene ZNF233

<400> SEQUENCE: 596
aatgagatag ataccttca a                                         21

<210> SEQ ID NO 597
<211> LENGTH: 21
<212> TYPE: DNA
<213> ORGANISM: Artificial
<220> FEATURE:
<223> OTHER INFORMATION: Target sequence in the gene ZNF236

<400> SEQUENCE: 597
cacgctgaca gcgcacatca a                                        21

<210> SEQ ID NO 598
<211> LENGTH: 21
<212> TYPE: DNA
<213> ORGANISM: Artificial
<220> FEATURE:
<223> OTHER INFORMATION: Target sequence in the gene ZNF285A

<400> SEQUENCE: 598
cagggacact gccatcgata a                                        21

<210> SEQ ID NO 599
<211> LENGTH: 21
<212> TYPE: DNA
<213> ORGANISM: Artificial
<220> FEATURE:
<223> OTHER INFORMATION: Target sequence in the gene ZNF319

<400> SEQUENCE: 599
ctggtcttga aagaagacta a                                        21

<210> SEQ ID NO 600
<211> LENGTH: 21
<212> TYPE: DNA
<213> ORGANISM: Artificial
<220> FEATURE:
<223> OTHER INFORMATION: Target sequence in the gene ZNF319

<400> SEQUENCE: 600
tacaaccgtc ccaactgcta a                                        21

<210> SEQ ID NO 601
<211> LENGTH: 21
<212> TYPE: DNA
<213> ORGANISM: Artificial
<220> FEATURE:
<223> OTHER INFORMATION: Target sequence in the gene ZNF321

<400> SEQUENCE: 601
```
caagtgtagt gagcataaca a                                          21

<210> SEQ ID NO 602
<211> LENGTH: 21
<212> TYPE: DNA
<213> ORGANISM: Artificial
<220> FEATURE:
<223> OTHER INFORMATION: Target sequence in the gene ZNF500

<400> SEQUENCE: 602
cccgttgaga atggagtggt a                                          21

<210> SEQ ID NO 603
<211> LENGTH: 21
<212> TYPE: DNA
<213> ORGANISM: Artificial
<220> FEATURE:
<223> OTHER INFORMATION: Target sequence in the gene ZNF559

<400> SEQUENCE: 603
tcccgagaga tggctaatga a                                          21

<210> SEQ ID NO 604
<211> LENGTH: 21
<212> TYPE: DNA
<213> ORGANISM: Artificial
<220> FEATURE:
<223> OTHER INFORMATION: Target sequence in the gene ZNF648

<400> SEQUENCE: 604
ccagcgcaac atgcacagca a                                          21

<210> SEQ ID NO 605
<211> LENGTH: 21
<212> TYPE: DNA
<213> ORGANISM: Artificial
<220> FEATURE:
<223> OTHER INFORMATION: Target sequence in the gene ZNF684

<400> SEQUENCE: 605
tagccggtat tcaatcttca a                                          21

<210> SEQ ID NO 606
<211> LENGTH: 21
<212> TYPE: DNA
<213> ORGANISM: Artificial
<220> FEATURE:
<223> OTHER INFORMATION: Target sequence in the gene ZNF70

<400> SEQUENCE: 606
caagccctgt tcagcatcaa a                                          21

<210> SEQ ID NO 607
<211> LENGTH: 21
<212> TYPE: DNA
<213> ORGANISM: Artificial
<220> FEATURE:
<223> OTHER INFORMATION: Target sequence in the gene ZNF701

<400> SEQUENCE: 607
aaggatttcg ggtgtgattc a                                          21

<210> SEQ ID NO 608
<211> LENGTH: 21
<212> TYPE: DNA
<213> ORGANISM: Artificial

```
<220> FEATURE:
<223> OTHER INFORMATION: Target sequence in the gene ZNF701

<400> SEQUENCE: 608
aaggtgtgaa attctcagtt t                                              21

<210> SEQ ID NO 609
<211> LENGTH: 21
<212> TYPE: DNA
<213> ORGANISM: Artificial
<220> FEATURE:
<223> OTHER INFORMATION: Target sequence in the gene ZNF75A

<400> SEQUENCE: 609
atggatcgtc acaagaaaga t                                              21

<210> SEQ ID NO 610
<211> LENGTH: 21
<212> TYPE: DNA
<213> ORGANISM: Artificial
<220> FEATURE:
<223> OTHER INFORMATION: Target sequence in the gene ZNF786

<400> SEQUENCE: 610
tagggcctgg gagaaattca a                                              21

<210> SEQ ID NO 611
<211> LENGTH: 21
<212> TYPE: DNA
<213> ORGANISM: Artificial
<220> FEATURE:
<223> OTHER INFORMATION: Target sequence in the gene ZSCAN1

<400> SEQUENCE: 611
cacaccaaag gtggtaccca a                                              21

<210> SEQ ID NO 612
<211> LENGTH: 21
<212> TYPE: DNA
<213> ORGANISM: Artificial
<220> FEATURE:
<223> OTHER INFORMATION: Target sequence in the gene ABCA10

<400> SEQUENCE: 612
taccatacct tcagagtgtt a                                              21

<210> SEQ ID NO 613
<211> LENGTH: 21
<212> TYPE: DNA
<213> ORGANISM: Artificial
<220> FEATURE:
<223> OTHER INFORMATION: Target sequence in the gene ABCG1

<400> SEQUENCE: 613
caagctgtac ctggacttca t                                              21

<210> SEQ ID NO 614
<211> LENGTH: 21
<212> TYPE: DNA
<213> ORGANISM: Artificial
<220> FEATURE:
<223> OTHER INFORMATION: Target sequence in the gene ABHD2

<400> SEQUENCE: 614
acgatccgtt ggtgcatgaa a                                              21
```

```
<210> SEQ ID NO 615
<211> LENGTH: 21
<212> TYPE: DNA
<213> ORGANISM: Artificial
<220> FEATURE:
<223> OTHER INFORMATION: Target sequence in the gene ACOT12

<400> SEQUENCE: 615
atgcatcgta tcttacttta a                                              21

<210> SEQ ID NO 616
<211> LENGTH: 21
<212> TYPE: DNA
<213> ORGANISM: Artificial
<220> FEATURE:
<223> OTHER INFORMATION: Target sequence in the gene ACRV1

<400> SEQUENCE: 616
tccatagatc atcaaacttc a                                              21

<210> SEQ ID NO 617
<211> LENGTH: 21
<212> TYPE: DNA
<213> ORGANISM: Artificial
<220> FEATURE:
<223> OTHER INFORMATION: Target sequence in the gene ADAM2

<400> SEQUENCE: 617
ctgttggtta gtagacacta a                                              21

<210> SEQ ID NO 618
<211> LENGTH: 21
<212> TYPE: DNA
<213> ORGANISM: Artificial
<220> FEATURE:
<223> OTHER INFORMATION: Target sequence in the gene ADCY10

<400> SEQUENCE: 618
ctggcacaac tttaccggca a                                              21

<210> SEQ ID NO 619
<211> LENGTH: 21
<212> TYPE: DNA
<213> ORGANISM: Artificial
<220> FEATURE:
<223> OTHER INFORMATION: Target sequence in the gene AGBL2

<400> SEQUENCE: 619
cagcctacca tccagaagta a                                              21

<210> SEQ ID NO 620
<211> LENGTH: 21
<212> TYPE: DNA
<213> ORGANISM: Artificial
<220> FEATURE:
<223> OTHER INFORMATION: Target sequence in the gene AGXT2L1

<400> SEQUENCE: 620
cacgacaaca ttgttgagta t                                              21

<210> SEQ ID NO 621
<211> LENGTH: 21
<212> TYPE: DNA
<213> ORGANISM: Artificial
<220> FEATURE:
<223> OTHER INFORMATION: Target sequence in the gene AIM1
```

```
<400> SEQUENCE: 621
aacgtttgtt gggagggcaa a                                         21

<210> SEQ ID NO 622
<211> LENGTH: 21
<212> TYPE: DNA
<213> ORGANISM: Artificial
<220> FEATURE:
<223> OTHER INFORMATION: Target sequence in the gene AMTN

<400> SEQUENCE: 622
tgcctcgaat ttggtgatac a                                         21

<210> SEQ ID NO 623
<211> LENGTH: 21
<212> TYPE: DNA
<213> ORGANISM: Artificial
<220> FEATURE:
<223> OTHER INFORMATION: Target sequence in the gene ANGEL2

<400> SEQUENCE: 623
ctgacgcaat tggcaatgct a                                         21

<210> SEQ ID NO 624
<211> LENGTH: 21
<212> TYPE: DNA
<213> ORGANISM: Artificial
<220> FEATURE:
<223> OTHER INFORMATION: Target sequence in the gene ANKFN1

<400> SEQUENCE: 624
caggacagaa taatccttac a                                         21

<210> SEQ ID NO 625
<211> LENGTH: 21
<212> TYPE: DNA
<213> ORGANISM: Artificial
<220> FEATURE:
<223> OTHER INFORMATION: Target sequence in the gene ANP32A

<400> SEQUENCE: 625
ttgagccttc aaagtcctaa a                                         21

<210> SEQ ID NO 626
<211> LENGTH: 21
<212> TYPE: DNA
<213> ORGANISM: Artificial
<220> FEATURE:
<223> OTHER INFORMATION: Target sequence in the gene AP1G1

<400> SEQUENCE: 626
taggctgtgc atagtgatca t                                         21

<210> SEQ ID NO 627
<211> LENGTH: 21
<212> TYPE: DNA
<213> ORGANISM: Artificial
<220> FEATURE:
<223> OTHER INFORMATION: Target sequence in the gene APOA1

<400> SEQUENCE: 627
cggcgccaga ctggccgagt a                                         21

<210> SEQ ID NO 628
```

```
<211> LENGTH: 21
<212> TYPE: DNA
<213> ORGANISM: Artificial
<220> FEATURE:
<223> OTHER INFORMATION: Target sequence in the gene APOA2

<400> SEQUENCE: 628
aggccaagtc ttactttgaa a                                              21

<210> SEQ ID NO 629
<211> LENGTH: 21
<212> TYPE: DNA
<213> ORGANISM: Artificial
<220> FEATURE:
<223> OTHER INFORMATION: Target sequence in the gene APP

<400> SEQUENCE: 629
ctggtcttca attaccaaga a                                              21

<210> SEQ ID NO 630
<211> LENGTH: 21
<212> TYPE: DNA
<213> ORGANISM: Artificial
<220> FEATURE:
<223> OTHER INFORMATION: Target sequence in the gene AQP1

<400> SEQUENCE: 630
cagcatggcc agcgagttca a                                              21

<210> SEQ ID NO 631
<211> LENGTH: 21
<212> TYPE: DNA
<213> ORGANISM: Artificial
<220> FEATURE:
<223> OTHER INFORMATION: Target sequence in the gene ARHGEF12

<400> SEQUENCE: 631
accgagagtc accaacagat a                                              21

<210> SEQ ID NO 632
<211> LENGTH: 21
<212> TYPE: DNA
<213> ORGANISM: Artificial
<220> FEATURE:
<223> OTHER INFORMATION: Target sequence in the gene ARL15

<400> SEQUENCE: 632
ctggtaattc tccagaagat a                                              21

<210> SEQ ID NO 633
<211> LENGTH: 21
<212> TYPE: DNA
<213> ORGANISM: Artificial
<220> FEATURE:
<223> OTHER INFORMATION: Target sequence in the gene ARMCX2

<400> SEQUENCE: 633
caccatgacc tcttagtgaa a                                              21

<210> SEQ ID NO 634
<211> LENGTH: 21
<212> TYPE: DNA
<213> ORGANISM: Artificial
<220> FEATURE:
<223> OTHER INFORMATION: Target sequence in the gene ARPC5L

<400> SEQUENCE: 634
```
cggcgttgac ttgttaatga a                                              21

<210> SEQ ID NO 635
<211> LENGTH: 21
<212> TYPE: DNA
<213> ORGANISM: Artificial
<220> FEATURE:
<223> OTHER INFORMATION: Target sequence in the gene ASCC3L1

<400> SEQUENCE: 635
cgccagcgta agggctatga a                                              21

<210> SEQ ID NO 636
<211> LENGTH: 21
<212> TYPE: DNA
<213> ORGANISM: Artificial
<220> FEATURE:
<223> OTHER INFORMATION: Target sequence in the gene ATP2A1

<400> SEQUENCE: 636
caccaacatt gcagccggca a                                              21

<210> SEQ ID NO 637
<211> LENGTH: 21
<212> TYPE: DNA
<213> ORGANISM: Artificial
<220> FEATURE:
<223> OTHER INFORMATION: Target sequence in the gene ATXN1

<400> SEQUENCE: 637
aaccaagagc ggagcaacga a                                              21

<210> SEQ ID NO 638
<211> LENGTH: 21
<212> TYPE: DNA
<213> ORGANISM: Artificial
<220> FEATURE:
<223> OTHER INFORMATION: Target sequence in the gene AXIN1

<400> SEQUENCE: 638
ctggatacct gccgacctta a                                              21

<210> SEQ ID NO 639
<211> LENGTH: 21
<212> TYPE: DNA
<213> ORGANISM: Artificial
<220> FEATURE:
<223> OTHER INFORMATION: Target sequence in the gene B3GALNT2

<400> SEQUENCE: 639
atcgttatta ccagtcttgg a                                              21

<210> SEQ ID NO 640
<211> LENGTH: 21
<212> TYPE: DNA
<213> ORGANISM: Artificial
<220> FEATURE:
<223> OTHER INFORMATION: Target sequence in the gene B4GALNT3

<400> SEQUENCE: 640
caccggtgac ccacacttca a                                              21

<210> SEQ ID NO 641
<211> LENGTH: 21
<212> TYPE: DNA

<213> ORGANISM: Artificial
<220> FEATURE:
<223> OTHER INFORMATION: Target sequence in the gene BFSP1

<400> SEQUENCE: 641
caagatgata tcagtgcggc a                                              21

<210> SEQ ID NO 642
<211> LENGTH: 21
<212> TYPE: DNA
<213> ORGANISM: Artificial
<220> FEATURE:
<223> OTHER INFORMATION: Target sequence in the gene BPIL3

<400> SEQUENCE: 642
cccggacttt ctggccatga a                                              21

<210> SEQ ID NO 643
<211> LENGTH: 21
<212> TYPE: DNA
<213> ORGANISM: Artificial
<220> FEATURE:
<223> OTHER INFORMATION: Target sequence in the gene BRUNOL4

<400> SEQUENCE: 643
cccgtcgacc attcccatga a                                              21

<210> SEQ ID NO 644
<211> LENGTH: 21
<212> TYPE: DNA
<213> ORGANISM: Artificial
<220> FEATURE:
<223> OTHER INFORMATION: Target sequence in the gene BTK

<400> SEQUENCE: 644
cagctcgaaa ctgtttggta a                                              21

<210> SEQ ID NO 645
<211> LENGTH: 21
<212> TYPE: DNA
<213> ORGANISM: Artificial
<220> FEATURE:
<223> OTHER INFORMATION: Target sequence in the gene C11orf47

<400> SEQUENCE: 645
cagagggtac agcacaagca a                                              21

<210> SEQ ID NO 646
<211> LENGTH: 21
<212> TYPE: DNA
<213> ORGANISM: Artificial
<220> FEATURE:
<223> OTHER INFORMATION: Target sequence in the gene C14orf145

<400> SEQUENCE: 646
ctcgaaggtt attgaatcaa t                                              21

<210> SEQ ID NO 647
<211> LENGTH: 21
<212> TYPE: DNA
<213> ORGANISM: Artificial
<220> FEATURE:
<223> OTHER INFORMATION: Target sequence in the gene C14orf45

<400> SEQUENCE: 647
ttccgtcttc caagttacca a                                              21

<210> SEQ ID NO 648
<211> LENGTH: 21
<212> TYPE: DNA
<213> ORGANISM: Artificial
<220> FEATURE:
<223> OTHER INFORMATION: Target sequence in the gene C15orf15

<400> SEQUENCE: 648
cggcatgatg ttcgtccgca a                                         21

<210> SEQ ID NO 649
<211> LENGTH: 21
<212> TYPE: DNA
<213> ORGANISM: Artificial
<220> FEATURE:
<223> OTHER INFORMATION: Target sequence in the gene C1orf216

<400> SEQUENCE: 649
caggctgtgc agcacttaca a                                         21

<210> SEQ ID NO 650
<211> LENGTH: 21
<212> TYPE: DNA
<213> ORGANISM: Artificial
<220> FEATURE:
<223> OTHER INFORMATION: Target sequence in the gene C1orf63

<400> SEQUENCE: 650
caggcgctac tcgcggtcat a                                         21

<210> SEQ ID NO 651
<211> LENGTH: 21
<212> TYPE: DNA
<213> ORGANISM: Artificial
<220> FEATURE:
<223> OTHER INFORMATION: Target sequence in the gene C20orf19

<400> SEQUENCE: 651
aaggctcata ctcgaaacca a                                         21

<210> SEQ ID NO 652
<211> LENGTH: 21
<212> TYPE: DNA
<213> ORGANISM: Artificial
<220> FEATURE:
<223> OTHER INFORMATION: Target sequence in the gene C2orf30

<400> SEQUENCE: 652
ctgcaagtag ttaaactaga a                                         21

<210> SEQ ID NO 653
<211> LENGTH: 21
<212> TYPE: DNA
<213> ORGANISM: Artificial
<220> FEATURE:
<223> OTHER INFORMATION: Target sequence in the gene C2orf49

<400> SEQUENCE: 653
cagaaccatg acttaacgca t                                         21

<210> SEQ ID NO 654
<211> LENGTH: 21
<212> TYPE: DNA
<213> ORGANISM: Artificial
<220> FEATURE:

<223> OTHER INFORMATION: Target sequence in the gene C3orf54

<400> SEQUENCE: 654
ctcggcttga cagcttcctt a                                    21

<210> SEQ ID NO 655
<211> LENGTH: 21
<212> TYPE: DNA
<213> ORGANISM: Artificial
<220> FEATURE:
<223> OTHER INFORMATION: Target sequence in the gene C3orf59

<400> SEQUENCE: 655
aagggcaagt aacgtgttca t                                    21

<210> SEQ ID NO 656
<211> LENGTH: 21
<212> TYPE: DNA
<213> ORGANISM: Artificial
<220> FEATURE:
<223> OTHER INFORMATION: Target sequence in the gene C5

<400> SEQUENCE: 656
gcctgcgtta ataatgatga a                                    21

<210> SEQ ID NO 657
<211> LENGTH: 21
<212> TYPE: DNA
<213> ORGANISM: Artificial
<220> FEATURE:
<223> OTHER INFORMATION: Target sequence in the gene C5orf37

<400> SEQUENCE: 657
atgagctcag ttgttgtgga a                                    21

<210> SEQ ID NO 658
<211> LENGTH: 21
<212> TYPE: DNA
<213> ORGANISM: Artificial
<220> FEATURE:
<223> OTHER INFORMATION: Target sequence in the gene C6orf10

<400> SEQUENCE: 658
ctcgatcaag tattggtagt a                                    21

<210> SEQ ID NO 659
<211> LENGTH: 21
<212> TYPE: DNA
<213> ORGANISM: Artificial
<220> FEATURE:
<223> OTHER INFORMATION: Target sequence in the gene C8orf32

<400> SEQUENCE: 659
ccctctcaga cttgagcgtt a                                    21

<210> SEQ ID NO 660
<211> LENGTH: 21
<212> TYPE: DNA
<213> ORGANISM: Artificial
<220> FEATURE:
<223> OTHER INFORMATION: Target sequence in the gene C8orf76

<400> SEQUENCE: 660
ttgctaatca tggagtataa a                                    21

```
<210> SEQ ID NO 661
<211> LENGTH: 21
<212> TYPE: DNA
<213> ORGANISM: Artificial
<220> FEATURE:
<223> OTHER INFORMATION: Target sequence in the gene C9orf100

<400> SEQUENCE: 661
accgagcggc gctaccaaga a                                              21

<210> SEQ ID NO 662
<211> LENGTH: 21
<212> TYPE: DNA
<213> ORGANISM: Artificial
<220> FEATURE:
<223> OTHER INFORMATION: Target sequence in the gene CACNA1F

<400> SEQUENCE: 662
ctggcctgca ctgctataca a                                              21

<210> SEQ ID NO 663
<211> LENGTH: 21
<212> TYPE: DNA
<213> ORGANISM: Artificial
<220> FEATURE:
<223> OTHER INFORMATION: Target sequence in the gene CAMK4

<400> SEQUENCE: 663
ttgcaagtta acacaacgta a                                              21

<210> SEQ ID NO 664
<211> LENGTH: 21
<212> TYPE: DNA
<213> ORGANISM: Artificial
<220> FEATURE:
<223> OTHER INFORMATION: Target sequence in the gene CAP2

<400> SEQUENCE: 664
cagggtctta aaggactaca a                                              21

<210> SEQ ID NO 665
<211> LENGTH: 21
<212> TYPE: DNA
<213> ORGANISM: Artificial
<220> FEATURE:
<223> OTHER INFORMATION: Target sequence in the gene CARS2

<400> SEQUENCE: 665
cagcaccaag agggccgtga a                                              21

<210> SEQ ID NO 666
<211> LENGTH: 21
<212> TYPE: DNA
<213> ORGANISM: Artificial
<220> FEATURE:
<223> OTHER INFORMATION: Target sequence in the gene CASP1

<400> SEQUENCE: 666
tacctcttcc caggacatta a                                              21

<210> SEQ ID NO 667
<211> LENGTH: 21
<212> TYPE: DNA
<213> ORGANISM: Artificial
<220> FEATURE:
<223> OTHER INFORMATION: Target sequence in the gene CCDC85A
```

<400> SEQUENCE: 667
tgggagtaac agttcaccca a                                              21

<210> SEQ ID NO 668
<211> LENGTH: 21
<212> TYPE: DNA
<213> ORGANISM: Artificial
<220> FEATURE:
<223> OTHER INFORMATION: Target sequence in the gene CD160

<400> SEQUENCE: 668
ctcagttgat gttcaccata a                                              21

<210> SEQ ID NO 669
<211> LENGTH: 21
<212> TYPE: DNA
<213> ORGANISM: Artificial
<220> FEATURE:
<223> OTHER INFORMATION: Target sequence in the gene CD19

<400> SEQUENCE: 669
cggccagaga tatgtgggta a                                              21

<210> SEQ ID NO 670
<211> LENGTH: 21
<212> TYPE: DNA
<213> ORGANISM: Artificial
<220> FEATURE:
<223> OTHER INFORMATION: Target sequence in the gene CD47

<400> SEQUENCE: 670
cacgataagt ttactcctcc a                                              21

<210> SEQ ID NO 671
<211> LENGTH: 21
<212> TYPE: DNA
<213> ORGANISM: Artificial
<220> FEATURE:
<223> OTHER INFORMATION: Target sequence in the gene CD5L

<400> SEQUENCE: 671
ccctttgact tgagactagt a                                              21

<210> SEQ ID NO 672
<211> LENGTH: 21
<212> TYPE: DNA
<213> ORGANISM: Artificial
<220> FEATURE:
<223> OTHER INFORMATION: Target sequence in the gene CD68

<400> SEQUENCE: 672
cacggttcat ccaacaagca a                                              21

<210> SEQ ID NO 673
<211> LENGTH: 21
<212> TYPE: DNA
<213> ORGANISM: Artificial
<220> FEATURE:
<223> OTHER INFORMATION: Target sequence in the gene CD8B

<400> SEQUENCE: 673
cagcaatact acaacctcac a                                              21

<210> SEQ ID NO 674
<211> LENGTH: 21

```
<212> TYPE: DNA
<213> ORGANISM: Artificial
<220> FEATURE:
<223> OTHER INFORMATION: Target sequence in the gene CDK2

<400> SEQUENCE: 674
cacgttagat ttgccgtacc a                                           21

<210> SEQ ID NO 675
<211> LENGTH: 21
<212> TYPE: DNA
<213> ORGANISM: Artificial
<220> FEATURE:
<223> OTHER INFORMATION: Target sequence in the gene CDKN1B

<400> SEQUENCE: 675
accgacgatt cttctactca a                                           21

<210> SEQ ID NO 676
<211> LENGTH: 21
<212> TYPE: DNA
<213> ORGANISM: Artificial
<220> FEATURE:
<223> OTHER INFORMATION: Target sequence in the gene CENPE

<400> SEQUENCE: 676
cacgatactg ttaacatgaa t                                           21

<210> SEQ ID NO 677
<211> LENGTH: 21
<212> TYPE: DNA
<213> ORGANISM: Artificial
<220> FEATURE:
<223> OTHER INFORMATION: Target sequence in the gene CENPE

<400> SEQUENCE: 677
caggttaatc ctaccacaca a                                           21

<210> SEQ ID NO 678
<211> LENGTH: 21
<212> TYPE: DNA
<213> ORGANISM: Artificial
<220> FEATURE:
<223> OTHER INFORMATION: Target sequence in the gene CENPO

<400> SEQUENCE: 678
ctccggatac atcaccattc a                                           21

<210> SEQ ID NO 679
<211> LENGTH: 21
<212> TYPE: DNA
<213> ORGANISM: Artificial
<220> FEATURE:
<223> OTHER INFORMATION: Target sequence in the gene CEP72

<400> SEQUENCE: 679
cccgcagttg gtacagtacc a                                           21

<210> SEQ ID NO 680
<211> LENGTH: 21
<212> TYPE: DNA
<213> ORGANISM: Artificial
<220> FEATURE:
<223> OTHER INFORMATION: Target sequence in the gene CHAC2

<400> SEQUENCE: 680
```

```
cccggcaagc ctggaagagt t                                              21
```

<210> SEQ ID NO 681
<211> LENGTH: 21
<212> TYPE: DNA
<213> ORGANISM: Artificial
<220> FEATURE:
<223> OTHER INFORMATION: Target sequence in the gene CIR

<400> SEQUENCE: 681

```
cagtagtgag agtgagagta a                                              21
```

<210> SEQ ID NO 682
<211> LENGTH: 21
<212> TYPE: DNA
<213> ORGANISM: Artificial
<220> FEATURE:
<223> OTHER INFORMATION: Target sequence in the gene CIRH1A

<400> SEQUENCE: 682

```
ctctatcggc tgaattatga a                                              21
```

<210> SEQ ID NO 683
<211> LENGTH: 21
<212> TYPE: DNA
<213> ORGANISM: Artificial
<220> FEATURE:
<223> OTHER INFORMATION: Target sequence in the gene CKAP5

<400> SEQUENCE: 683

```
aagggtcgac tcaatgattc a                                              21
```

<210> SEQ ID NO 684
<211> LENGTH: 21
<212> TYPE: DNA
<213> ORGANISM: Artificial
<220> FEATURE:
<223> OTHER INFORMATION: Target sequence in the gene CLIP2

<400> SEQUENCE: 684

```
cacggagacc tcttcacgct a                                              21
```

<210> SEQ ID NO 685
<211> LENGTH: 21
<212> TYPE: DNA
<213> ORGANISM: Artificial
<220> FEATURE:
<223> OTHER INFORMATION: Target sequence in the gene CMKLR1

<400> SEQUENCE: 685

```
cagccttgga ctagcaattt a                                              21
```

<210> SEQ ID NO 686
<211> LENGTH: 21
<212> TYPE: DNA
<213> ORGANISM: Artificial
<220> FEATURE:
<223> OTHER INFORMATION: Target sequence in the gene CNOT7

<400> SEQUENCE: 686

```
cagcggcaac tgtagatcat a                                              21
```

<210> SEQ ID NO 687
<211> LENGTH: 21
<212> TYPE: DNA
<213> ORGANISM: Artificial

-continued

```
<220> FEATURE:
<223> OTHER INFORMATION: Target sequence in the gene CNR1

<400> SEQUENCE: 687
ttccatagtt taggtactca a                                              21

<210> SEQ ID NO 688
<211> LENGTH: 21
<212> TYPE: DNA
<213> ORGANISM: Artificial
<220> FEATURE:
<223> OTHER INFORMATION: Target sequence in the gene CNTF

<400> SEQUENCE: 688
gaccagtata gacagaagta a                                              21

<210> SEQ ID NO 689
<211> LENGTH: 21
<212> TYPE: DNA
<213> ORGANISM: Artificial
<220> FEATURE:
<223> OTHER INFORMATION: Target sequence in the gene CNTF

<400> SEQUENCE: 689
gaccagtata gacagaagta a                                              21

<210> SEQ ID NO 690
<211> LENGTH: 21
<212> TYPE: DNA
<213> ORGANISM: Artificial
<220> FEATURE:
<223> OTHER INFORMATION: Target sequence in the gene CNTN6

<400> SEQUENCE: 690
tacaagattc tgtaccggca a                                              21

<210> SEQ ID NO 691
<211> LENGTH: 21
<212> TYPE: DNA
<213> ORGANISM: Artificial
<220> FEATURE:
<223> OTHER INFORMATION: Target sequence in the gene CPLX3

<400> SEQUENCE: 691
tccgcgaaac ctagtgctga a                                              21

<210> SEQ ID NO 692
<211> LENGTH: 21
<212> TYPE: DNA
<213> ORGANISM: Artificial
<220> FEATURE:
<223> OTHER INFORMATION: Target sequence in the gene CPNE7

<400> SEQUENCE: 692
cccggtgtgg gaggccttca a                                              21

<210> SEQ ID NO 693
<211> LENGTH: 21
<212> TYPE: DNA
<213> ORGANISM: Artificial
<220> FEATURE:
<223> OTHER INFORMATION: Target sequence in the gene CRYGC

<400> SEQUENCE: 693
gcggagagtg gtggatttgt a                                              21
```

```
<210> SEQ ID NO 694
<211> LENGTH: 21
<212> TYPE: DNA
<213> ORGANISM: Artificial
<220> FEATURE:
<223> OTHER INFORMATION: Target sequence in the gene CTRB1

<400> SEQUENCE: 694
cagcattctg accgtgaaca a                                             21

<210> SEQ ID NO 695
<211> LENGTH: 21
<212> TYPE: DNA
<213> ORGANISM: Artificial
<220> FEATURE:
<223> OTHER INFORMATION: Target sequence in the gene CYP2A13

<400> SEQUENCE: 695
ccagcacttc ctggataaga a                                             21

<210> SEQ ID NO 696
<211> LENGTH: 21
<212> TYPE: DNA
<213> ORGANISM: Artificial
<220> FEATURE:
<223> OTHER INFORMATION: Target sequence in the gene DAD1

<400> SEQUENCE: 696
cagatttgac acttactgct a                                             21

<210> SEQ ID NO 697
<211> LENGTH: 21
<212> TYPE: DNA
<213> ORGANISM: Artificial
<220> FEATURE:
<223> OTHER INFORMATION: Target sequence in the gene DAGLB

<400> SEQUENCE: 697
caggacagtt gtaaacggca t                                             21

<210> SEQ ID NO 698
<211> LENGTH: 21
<212> TYPE: DNA
<213> ORGANISM: Artificial
<220> FEATURE:
<223> OTHER INFORMATION: Target sequence in the gene DCUN1D3

<400> SEQUENCE: 698
tgcacccatg ttgtcactta a                                             21

<210> SEQ ID NO 699
<211> LENGTH: 21
<212> TYPE: DNA
<213> ORGANISM: Artificial
<220> FEATURE:
<223> OTHER INFORMATION: Target sequence in the gene DDR2

<400> SEQUENCE: 699
ccggttcatt ccagtcaccg a                                             21

<210> SEQ ID NO 700
<211> LENGTH: 21
<212> TYPE: DNA
<213> ORGANISM: Artificial
<220> FEATURE:
<223> OTHER INFORMATION: Target sequence in the gene DFFB
```

-continued

```
<400> SEQUENCE: 700
acgggtcagt agggataaga a                                              21

<210> SEQ ID NO 701
<211> LENGTH: 21
<212> TYPE: DNA
<213> ORGANISM: Artificial
<220> FEATURE:
<223> OTHER INFORMATION: Target sequence in the gene DHDDS

<400> SEQUENCE: 701
aagaactatg tcatggatca a                                              21

<210> SEQ ID NO 702
<211> LENGTH: 21
<212> TYPE: DNA
<213> ORGANISM: Artificial
<220> FEATURE:
<223> OTHER INFORMATION: Target sequence in the gene DHRS4

<400> SEQUENCE: 702
accctgcgga taagaaggtt a                                              21

<210> SEQ ID NO 703
<211> LENGTH: 21
<212> TYPE: DNA
<213> ORGANISM: Artificial
<220> FEATURE:
<223> OTHER INFORMATION: Target sequence in the gene DHX32

<400> SEQUENCE: 703
atggatcagg taactactta a                                              21

<210> SEQ ID NO 704
<211> LENGTH: 21
<212> TYPE: DNA
<213> ORGANISM: Artificial
<220> FEATURE:
<223> OTHER INFORMATION: Target sequence in the gene DHX8

<400> SEQUENCE: 704
ctccctaagg tggatgatga a                                              21

<210> SEQ ID NO 705
<211> LENGTH: 21
<212> TYPE: DNA
<213> ORGANISM: Artificial
<220> FEATURE:
<223> OTHER INFORMATION: Target sequence in the gene DHX8

<400> SEQUENCE: 705
cgcgatcatc atgttggacg a                                              21

<210> SEQ ID NO 706
<211> LENGTH: 21
<212> TYPE: DNA
<213> ORGANISM: Artificial
<220> FEATURE:
<223> OTHER INFORMATION: Target sequence in the gene DIS3

<400> SEQUENCE: 706
caggtagagt tgtaggaata a                                              21

<210> SEQ ID NO 707
```

```
<211> LENGTH: 21
<212> TYPE: DNA
<213> ORGANISM: Artificial
<220> FEATURE:
<223> OTHER INFORMATION: Target sequence in the gene DIS3L

<400> SEQUENCE: 707
tacggtcttg cattagataa a                                              21

<210> SEQ ID NO 708
<211> LENGTH: 21
<212> TYPE: DNA
<213> ORGANISM: Artificial
<220> FEATURE:
<223> OTHER INFORMATION: Target sequence in the gene DMBT1

<400> SEQUENCE: 708
tccgtgtacc tgcgttgtaa a                                              21

<210> SEQ ID NO 709
<211> LENGTH: 21
<212> TYPE: DNA
<213> ORGANISM: Artificial
<220> FEATURE:
<223> OTHER INFORMATION: Target sequence in the gene DNAH3

<400> SEQUENCE: 709
cagggctgaa ctgcccgaca a                                              21

<210> SEQ ID NO 710
<211> LENGTH: 21
<212> TYPE: DNA
<213> ORGANISM: Artificial
<220> FEATURE:
<223> OTHER INFORMATION: Target sequence in the gene DPH1

<400> SEQUENCE: 710
ccctctcagg agagtgtgca a                                              21

<210> SEQ ID NO 711
<211> LENGTH: 21
<212> TYPE: DNA
<213> ORGANISM: Artificial
<220> FEATURE:
<223> OTHER INFORMATION: Target sequence in the gene E2F1

<400> SEQUENCE: 711
cagatggtta tggtgatcaa a                                              21

<210> SEQ ID NO 712
<211> LENGTH: 21
<212> TYPE: DNA
<213> ORGANISM: Artificial
<220> FEATURE:
<223> OTHER INFORMATION: Target sequence in the gene E2F6

<400> SEQUENCE: 712
aatgttgaga ttacttacga a                                              21

<210> SEQ ID NO 713
<211> LENGTH: 21
<212> TYPE: DNA
<213> ORGANISM: Artificial
<220> FEATURE:
<223> OTHER INFORMATION: Target sequence in the gene EFHA1

<400> SEQUENCE: 713
```
tcgaggttta tgggtaccac a                                              21

<210> SEQ ID NO 714
<211> LENGTH: 21
<212> TYPE: DNA
<213> ORGANISM: Artificial
<220> FEATURE:
<223> OTHER INFORMATION: Target sequence in the gene EGLN1

<400> SEQUENCE: 714
cagatgagag agcacgagct a                                              21

<210> SEQ ID NO 715
<211> LENGTH: 21
<212> TYPE: DNA
<213> ORGANISM: Artificial
<220> FEATURE:
<223> OTHER INFORMATION: Target sequence in the gene EID2B

<400> SEQUENCE: 715
tccggtcaga ttactacggg a                                              21

<210> SEQ ID NO 716
<211> LENGTH: 21
<212> TYPE: DNA
<213> ORGANISM: Artificial
<220> FEATURE:
<223> OTHER INFORMATION: Target sequence in the gene ELOVL7

<400> SEQUENCE: 716
gacggagatc catgtgataa a                                              21

<210> SEQ ID NO 717
<211> LENGTH: 21
<212> TYPE: DNA
<213> ORGANISM: Artificial
<220> FEATURE:
<223> OTHER INFORMATION: Target sequence in the gene ELP2

<400> SEQUENCE: 717
caggttcgag taggtgaagt a                                              21

<210> SEQ ID NO 718
<211> LENGTH: 21
<212> TYPE: DNA
<213> ORGANISM: Artificial
<220> FEATURE:
<223> OTHER INFORMATION: Target sequence in the gene ENTPD7

<400> SEQUENCE: 718
atgtaccaag tcttacatga a                                              21

<210> SEQ ID NO 719
<211> LENGTH: 21
<212> TYPE: DNA
<213> ORGANISM: Artificial
<220> FEATURE:
<223> OTHER INFORMATION: Target sequence in the gene EPDR1

<400> SEQUENCE: 719
caggactaga gttccctcgt a                                              21

<210> SEQ ID NO 720
<211> LENGTH: 21
<212> TYPE: DNA

<213> ORGANISM: Artificial
<220> FEATURE:
<223> OTHER INFORMATION: Target sequence in the gene EPHB3

<400> SEQUENCE: 720
ccgcagctga ccgccagatt a                                              21

<210> SEQ ID NO 721
<211> LENGTH: 21
<212> TYPE: DNA
<213> ORGANISM: Artificial
<220> FEATURE:
<223> OTHER INFORMATION: Target sequence in the gene EPS8L3

<400> SEQUENCE: 721
cagcttagac acctccaaga a                                              21

<210> SEQ ID NO 722
<211> LENGTH: 21
<212> TYPE: DNA
<213> ORGANISM: Artificial
<220> FEATURE:
<223> OTHER INFORMATION: Target sequence in the gene ESF1

<400> SEQUENCE: 722
ctgggataga ttaaaggcaa a                                              21

<210> SEQ ID NO 723
<211> LENGTH: 21
<212> TYPE: DNA
<213> ORGANISM: Artificial
<220> FEATURE:
<223> OTHER INFORMATION: Target sequence in the gene ESPL1

<400> SEQUENCE: 723
ctccaggaag atcgtttcct a                                              21

<210> SEQ ID NO 724
<211> LENGTH: 21
<212> TYPE: DNA
<213> ORGANISM: Artificial
<220> FEATURE:
<223> OTHER INFORMATION: Target sequence in the gene ESSPL

<400> SEQUENCE: 724
cagcctacac tttgaccaca a                                              21

<210> SEQ ID NO 725
<211> LENGTH: 21
<212> TYPE: DNA
<213> ORGANISM: Artificial
<220> FEATURE:
<223> OTHER INFORMATION: Target sequence in the gene EVI5L

<400> SEQUENCE: 725
cccgttgtct ctgctgaatc a                                              21

<210> SEQ ID NO 726
<211> LENGTH: 21
<212> TYPE: DNA
<213> ORGANISM: Artificial
<220> FEATURE:
<223> OTHER INFORMATION: Target sequence in the gene EXOC3

<400> SEQUENCE: 726
caggcgcata cttgaccgga a                                              21

<210> SEQ ID NO 727
<211> LENGTH: 21
<212> TYPE: DNA
<213> ORGANISM: Artificial
<220> FEATURE:
<223> OTHER INFORMATION: Target sequence in the gene FAM105B

<400> SEQUENCE: 727
aagcggaagc atacgggaat a                                              21

<210> SEQ ID NO 728
<211> LENGTH: 21
<212> TYPE: DNA
<213> ORGANISM: Artificial
<220> FEATURE:
<223> OTHER INFORMATION: Target sequence in the gene FAM120B

<400> SEQUENCE: 728
acctcgcagc ttgtaaatct a                                              21

<210> SEQ ID NO 729
<211> LENGTH: 21
<212> TYPE: DNA
<213> ORGANISM: Artificial
<220> FEATURE:
<223> OTHER INFORMATION: Target sequence in the gene FAM13A1

<400> SEQUENCE: 729
aaggagcagg atgaagttcg a                                              21

<210> SEQ ID NO 730
<211> LENGTH: 21
<212> TYPE: DNA
<213> ORGANISM: Artificial
<220> FEATURE:
<223> OTHER INFORMATION: Target sequence in the gene FAM80B

<400> SEQUENCE: 730
ctgcggatca atggagagct a                                              21

<210> SEQ ID NO 731
<211> LENGTH: 21
<212> TYPE: DNA
<213> ORGANISM: Artificial
<220> FEATURE:
<223> OTHER INFORMATION: Target sequence in the gene FANCB

<400> SEQUENCE: 731
ccggctatgc cctgaattca a                                              21

<210> SEQ ID NO 732
<211> LENGTH: 21
<212> TYPE: DNA
<213> ORGANISM: Artificial
<220> FEATURE:
<223> OTHER INFORMATION: Target sequence in the gene FCF1

<400> SEQUENCE: 732
actgcttagt acagagagta a                                              21

<210> SEQ ID NO 733
<211> LENGTH: 21
<212> TYPE: DNA
<213> ORGANISM: Artificial
<220> FEATURE:

```
<223> OTHER INFORMATION: Target sequence in the gene FEN1

<400> SEQUENCE: 733
taagtccatt gttacatgaa a                                              21

<210> SEQ ID NO 734
<211> LENGTH: 21
<212> TYPE: DNA
<213> ORGANISM: Artificial
<220> FEATURE:
<223> OTHER INFORMATION: Target sequence in the gene FEZF2

<400> SEQUENCE: 734
aacacggaat atatacatat a                                              21

<210> SEQ ID NO 735
<211> LENGTH: 21
<212> TYPE: DNA
<213> ORGANISM: Artificial
<220> FEATURE:
<223> OTHER INFORMATION: Target sequence in the gene FFAR3

<400> SEQUENCE: 735
gtggatcatc agagacattt a                                              21

<210> SEQ ID NO 736
<211> LENGTH: 21
<212> TYPE: DNA
<213> ORGANISM: Artificial
<220> FEATURE:
<223> OTHER INFORMATION: Target sequence in the gene FLCN

<400> SEQUENCE: 736
ccgggatata tcagccatga t                                              21

<210> SEQ ID NO 737
<211> LENGTH: 21
<212> TYPE: DNA
<213> ORGANISM: Artificial
<220> FEATURE:
<223> OTHER INFORMATION: Target sequence in the gene FLJ20254

<400> SEQUENCE: 737
cccgattccg tgaatcagct a                                              21

<210> SEQ ID NO 738
<211> LENGTH: 21
<212> TYPE: DNA
<213> ORGANISM: Artificial
<220> FEATURE:
<223> OTHER INFORMATION: Target sequence in the gene FLT3LG

<400> SEQUENCE: 738
ctcctccgac ttcgctgtca a                                              21

<210> SEQ ID NO 739
<211> LENGTH: 21
<212> TYPE: DNA
<213> ORGANISM: Artificial
<220> FEATURE:
<223> OTHER INFORMATION: Target sequence in the gene FOXN1

<400> SEQUENCE: 739
cagcgtttgc ctggtctgga a                                              21
```

```
<210> SEQ ID NO 740
<211> LENGTH: 21
<212> TYPE: DNA
<213> ORGANISM: Artificial
<220> FEATURE:
<223> OTHER INFORMATION: Target sequence in the gene FTH1

<400> SEQUENCE: 740
ttgggatgaa tcagaaatct a                                              21

<210> SEQ ID NO 741
<211> LENGTH: 21
<212> TYPE: DNA
<213> ORGANISM: Artificial
<220> FEATURE:
<223> OTHER INFORMATION: Target sequence in the gene FTH1

<400> SEQUENCE: 741
cgccatcaac cgccagatca a                                              21

<210> SEQ ID NO 742
<211> LENGTH: 21
<212> TYPE: DNA
<213> ORGANISM: Artificial
<220> FEATURE:
<223> OTHER INFORMATION: Target sequence in the gene FZR1

<400> SEQUENCE: 742
cgggtcgatc ttccacattc a                                              21

<210> SEQ ID NO 743
<211> LENGTH: 21
<212> TYPE: DNA
<213> ORGANISM: Artificial
<220> FEATURE:
<223> OTHER INFORMATION: Target sequence in the gene GAB3

<400> SEQUENCE: 743
ttctgcgatg ttcaactgga a                                              21

<210> SEQ ID NO 744
<211> LENGTH: 21
<212> TYPE: DNA
<213> ORGANISM: Artificial
<220> FEATURE:
<223> OTHER INFORMATION: Target sequence in the gene GABRD

<400> SEQUENCE: 744
caccttcatc gtgaacgcca a                                              21

<210> SEQ ID NO 745
<211> LENGTH: 21
<212> TYPE: DNA
<213> ORGANISM: Artificial
<220> FEATURE:
<223> OTHER INFORMATION: Target sequence in the gene GALNS

<400> SEQUENCE: 745
cagggccatt gatggcctca a                                              21

<210> SEQ ID NO 746
<211> LENGTH: 21
<212> TYPE: DNA
<213> ORGANISM: Artificial
<220> FEATURE:
<223> OTHER INFORMATION: Target sequence in the gene GALNT8
```

```
<400> SEQUENCE: 746
ctcgattgtt gaaggaaatc a                                             21

<210> SEQ ID NO 747
<211> LENGTH: 21
<212> TYPE: DNA
<213> ORGANISM: Artificial
<220> FEATURE:
<223> OTHER INFORMATION: Target sequence in the gene GBP1

<400> SEQUENCE: 747
atgggacact ttagaccatt a                                             21

<210> SEQ ID NO 748
<211> LENGTH: 21
<212> TYPE: DNA
<213> ORGANISM: Artificial
<220> FEATURE:
<223> OTHER INFORMATION: Target sequence in the gene GDNF

<400> SEQUENCE: 748
aggctggtga gtgacaaagt a                                             21

<210> SEQ ID NO 749
<211> LENGTH: 21
<212> TYPE: DNA
<213> ORGANISM: Artificial
<220> FEATURE:
<223> OTHER INFORMATION: Target sequence in the gene GINS1

<400> SEQUENCE: 749
cgctgtagga ctagaacgaa a                                             21

<210> SEQ ID NO 750
<211> LENGTH: 21
<212> TYPE: DNA
<213> ORGANISM: Artificial
<220> FEATURE:
<223> OTHER INFORMATION: Target sequence in the gene GMFG

<400> SEQUENCE: 750
cagctacaag tacgtgcatg a                                             21

<210> SEQ ID NO 751
<211> LENGTH: 21
<212> TYPE: DNA
<213> ORGANISM: Artificial
<220> FEATURE:
<223> OTHER INFORMATION: Target sequence in the gene GNB2L1

<400> SEQUENCE: 751
cccgcagttc ccggacatga t                                             21

<210> SEQ ID NO 752
<211> LENGTH: 21
<212> TYPE: DNA
<213> ORGANISM: Artificial
<220> FEATURE:
<223> OTHER INFORMATION: Target sequence in the gene GPIHBP1

<400> SEQUENCE: 752
ccagatgact acgacgagga a                                             21

<210> SEQ ID NO 753
<211> LENGTH: 21
```

```
<212> TYPE: DNA
<213> ORGANISM: Artificial
<220> FEATURE:
<223> OTHER INFORMATION: Target sequence in the gene GPR152

<400> SEQUENCE: 753
caaatggaca ctaccatgga a                                            21

<210> SEQ ID NO 754
<211> LENGTH: 21
<212> TYPE: DNA
<213> ORGANISM: Artificial
<220> FEATURE:
<223> OTHER INFORMATION: Target sequence in the gene GPR39

<400> SEQUENCE: 754
cgggcagtga ctgctcccaa a                                            21

<210> SEQ ID NO 755
<211> LENGTH: 21
<212> TYPE: DNA
<213> ORGANISM: Artificial
<220> FEATURE:
<223> OTHER INFORMATION: Target sequence in the gene GPR92

<400> SEQUENCE: 755
ccggaggtga atgccatgcc a                                            21

<210> SEQ ID NO 756
<211> LENGTH: 21
<212> TYPE: DNA
<213> ORGANISM: Artificial
<220> FEATURE:
<223> OTHER INFORMATION: Target sequence in the gene GRIA3

<400> SEQUENCE: 756
agcgaataag agagagagta a                                            21

<210> SEQ ID NO 757
<211> LENGTH: 21
<212> TYPE: DNA
<213> ORGANISM: Artificial
<220> FEATURE:
<223> OTHER INFORMATION: Target sequence in the gene GRIK3

<400> SEQUENCE: 757
ccggatcgga ggaatcttcg a                                            21

<210> SEQ ID NO 758
<211> LENGTH: 21
<212> TYPE: DNA
<213> ORGANISM: Artificial
<220> FEATURE:
<223> OTHER INFORMATION: Target sequence in the gene GRIN2C

<400> SEQUENCE: 758
ctggacgaga tcagcagggt a                                            21

<210> SEQ ID NO 759
<211> LENGTH: 21
<212> TYPE: DNA
<213> ORGANISM: Artificial
<220> FEATURE:
<223> OTHER INFORMATION: Target sequence in the gene GRK1

<400> SEQUENCE: 759
```
ccagatgaag gcgaccggca a                                              21

<210> SEQ ID NO 760
<211> LENGTH: 21
<212> TYPE: DNA
<213> ORGANISM: Artificial
<220> FEATURE:
<223> OTHER INFORMATION: Target sequence in the gene GRK4

<400> SEQUENCE: 760
caggatgtta ctcaccaaga a                                              21

<210> SEQ ID NO 761
<211> LENGTH: 21
<212> TYPE: DNA
<213> ORGANISM: Artificial
<220> FEATURE:
<223> OTHER INFORMATION: Target sequence in the gene GZF1

<400> SEQUENCE: 761
cggacggaca ttcaccgaca a                                              21

<210> SEQ ID NO 762
<211> LENGTH: 21
<212> TYPE: DNA
<213> ORGANISM: Artificial
<220> FEATURE:
<223> OTHER INFORMATION: Target sequence in the gene HEMGN

<400> SEQUENCE: 762
taacgaaatt attgtgccta a                                              21

<210> SEQ ID NO 763
<211> LENGTH: 21
<212> TYPE: DNA
<213> ORGANISM: Artificial
<220> FEATURE:
<223> OTHER INFORMATION: Target sequence in the gene HIAT1

<400> SEQUENCE: 763
acggcttaat tcaaggagta a                                              21

<210> SEQ ID NO 764
<211> LENGTH: 21
<212> TYPE: DNA
<213> ORGANISM: Artificial
<220> FEATURE:
<223> OTHER INFORMATION: Target sequence in the gene HSD17B8

<400> SEQUENCE: 764
caggaatgct gaatatggga a                                              21

<210> SEQ ID NO 765
<211> LENGTH: 21
<212> TYPE: DNA
<213> ORGANISM: Artificial
<220> FEATURE:
<223> OTHER INFORMATION: Target sequence in the gene HSPA5

<400> SEQUENCE: 765
caagcccaat acagccatta a                                              21

<210> SEQ ID NO 766
<211> LENGTH: 21
<212> TYPE: DNA
<213> ORGANISM: Artificial

```
<220> FEATURE:
<223> OTHER INFORMATION: Target sequence in the gene HTATIP

<400> SEQUENCE: 766
ctgatcgagt tcagctatga a                                       21

<210> SEQ ID NO 767
<211> LENGTH: 21
<212> TYPE: DNA
<213> ORGANISM: Artificial
<220> FEATURE:
<223> OTHER INFORMATION: Target sequence in the gene ID3

<400> SEQUENCE: 767
tccggaactt gtcatctcca a                                       21

<210> SEQ ID NO 768
<211> LENGTH: 21
<212> TYPE: DNA
<213> ORGANISM: Artificial
<220> FEATURE:
<223> OTHER INFORMATION: Target sequence in the gene IFNB1

<400> SEQUENCE: 768
caaggacagg atgaactttg a                                       21

<210> SEQ ID NO 769
<211> LENGTH: 21
<212> TYPE: DNA
<213> ORGANISM: Artificial
<220> FEATURE:
<223> OTHER INFORMATION: Target sequence in the gene IHH

<400> SEQUENCE: 769
ccgcctgaac tcgctggcta t                                       21

<210> SEQ ID NO 770
<211> LENGTH: 21
<212> TYPE: DNA
<213> ORGANISM: Artificial
<220> FEATURE:
<223> OTHER INFORMATION: Target sequence in the gene IL17B

<400> SEQUENCE: 770
ttgcaccttt gtgccaagaa a                                       21

<210> SEQ ID NO 771
<211> LENGTH: 21
<212> TYPE: DNA
<213> ORGANISM: Artificial
<220> FEATURE:
<223> OTHER INFORMATION: Target sequence in the gene INSL4

<400> SEQUENCE: 771
atccattctg ttgtgaagta a                                       21

<210> SEQ ID NO 772
<211> LENGTH: 21
<212> TYPE: DNA
<213> ORGANISM: Artificial
<220> FEATURE:
<223> OTHER INFORMATION: Target sequence in the gene INTS6

<400> SEQUENCE: 772
cgcggtagag accttcatga a                                       21
```

```
<210> SEQ ID NO 773
<211> LENGTH: 21
<212> TYPE: DNA
<213> ORGANISM: Artificial
<220> FEATURE:
<223> OTHER INFORMATION: Target sequence in the gene ITK

<400> SEQUENCE: 773
caggacttta gtagagactg a                                            21

<210> SEQ ID NO 774
<211> LENGTH: 21
<212> TYPE: DNA
<213> ORGANISM: Artificial
<220> FEATURE:
<223> OTHER INFORMATION: Target sequence in the gene KCNIP1

<400> SEQUENCE: 774
tccagaaacg aggaccaata a                                            21

<210> SEQ ID NO 775
<211> LENGTH: 21
<212> TYPE: DNA
<213> ORGANISM: Artificial
<220> FEATURE:
<223> OTHER INFORMATION: Target sequence in the gene KCNK3

<400> SEQUENCE: 775
cgccgacgtg tccatggcca a                                            21

<210> SEQ ID NO 776
<211> LENGTH: 21
<212> TYPE: DNA
<213> ORGANISM: Artificial
<220> FEATURE:
<223> OTHER INFORMATION: Target sequence in the gene KCNQ4

<400> SEQUENCE: 776
cgggcatctc tgagactcaa a                                            21

<210> SEQ ID NO 777
<211> LENGTH: 21
<212> TYPE: DNA
<213> ORGANISM: Artificial
<220> FEATURE:
<223> OTHER INFORMATION: Target sequence in the gene KCNQ4

<400> SEQUENCE: 777
cgggcatctc tgagactcaa a                                            21

<210> SEQ ID NO 778
<211> LENGTH: 21
<212> TYPE: DNA
<213> ORGANISM: Artificial
<220> FEATURE:
<223> OTHER INFORMATION: Target sequence in the gene KHDRBS3

<400> SEQUENCE: 778
ctgcgcctgg tgaaccaaga a                                            21

<210> SEQ ID NO 779
<211> LENGTH: 21
<212> TYPE: DNA
<213> ORGANISM: Artificial
<220> FEATURE:
<223> OTHER INFORMATION: Target sequence in the gene KIAA0391
```

```
<400> SEQUENCE: 779
ctcgtggcac ataccatatg a                                              21

<210> SEQ ID NO 780
<211> LENGTH: 21
<212> TYPE: DNA
<213> ORGANISM: Artificial
<220> FEATURE:
<223> OTHER INFORMATION: Target sequence in the gene KIAA1683

<400> SEQUENCE: 780
cccagtgagt ttggacgcaa a                                              21

<210> SEQ ID NO 781
<211> LENGTH: 21
<212> TYPE: DNA
<213> ORGANISM: Artificial
<220> FEATURE:
<223> OTHER INFORMATION: Target sequence in the gene KIAA1797

<400> SEQUENCE: 781
gtcgtcgtat ctagacatga a                                              21

<210> SEQ ID NO 782
<211> LENGTH: 21
<212> TYPE: DNA
<213> ORGANISM: Artificial
<220> FEATURE:
<223> OTHER INFORMATION: Target sequence in the gene KLF5

<400> SEQUENCE: 782
cagtatcaac atgaacgtct t                                              21

<210> SEQ ID NO 783
<211> LENGTH: 21
<212> TYPE: DNA
<213> ORGANISM: Artificial
<220> FEATURE:
<223> OTHER INFORMATION: Target sequence in the gene KLK14

<400> SEQUENCE: 783
cccggatgag gtgtgccaga a                                              21

<210> SEQ ID NO 784
<211> LENGTH: 21
<212> TYPE: DNA
<213> ORGANISM: Artificial
<220> FEATURE:
<223> OTHER INFORMATION: Target sequence in the gene KLKB1

<400> SEQUENCE: 784
cgctataaag gtgctgagta a                                              21

<210> SEQ ID NO 785
<211> LENGTH: 21
<212> TYPE: DNA
<213> ORGANISM: Artificial
<220> FEATURE:
<223> OTHER INFORMATION: Target sequence in the gene KRTAP10-10

<400> SEQUENCE: 785
ctgctctaag tccgtctgct a                                              21

<210> SEQ ID NO 786
```

```
<211> LENGTH: 21
<212> TYPE: DNA
<213> ORGANISM: Artificial
<220> FEATURE:
<223> OTHER INFORMATION: Target sequence in the gene KRTAP5-8

<400> SEQUENCE: 786
cccaatttgc tgccagtgca a                                          21

<210> SEQ ID NO 787
<211> LENGTH: 21
<212> TYPE: DNA
<213> ORGANISM: Artificial
<220> FEATURE:
<223> OTHER INFORMATION: Target sequence in the gene L3MBTL4

<400> SEQUENCE: 787
ctgcccgtat tcagacatga a                                          21

<210> SEQ ID NO 788
<211> LENGTH: 21
<212> TYPE: DNA
<213> ORGANISM: Artificial
<220> FEATURE:
<223> OTHER INFORMATION: Target sequence in the gene LINS1

<400> SEQUENCE: 788
aacccggata ttgtctgtca a                                          21

<210> SEQ ID NO 789
<211> LENGTH: 21
<212> TYPE: DNA
<213> ORGANISM: Artificial
<220> FEATURE:
<223> OTHER INFORMATION: Target sequence in the gene LMO2

<400> SEQUENCE: 789
cagcccatcc atagtaactg a                                          21

<210> SEQ ID NO 790
<211> LENGTH: 21
<212> TYPE: DNA
<213> ORGANISM: Artificial
<220> FEATURE:
<223> OTHER INFORMATION: Target sequence in the gene LOC374443

<400> SEQUENCE: 790
cccatcgcat ttggaaatgg a                                          21

<210> SEQ ID NO 791
<211> LENGTH: 21
<212> TYPE: DNA
<213> ORGANISM: Artificial
<220> FEATURE:
<223> OTHER INFORMATION: Target sequence in the gene LOC400301

<400> SEQUENCE: 791
ctgctgggat gaagacatga a                                          21

<210> SEQ ID NO 792
<211> LENGTH: 21
<212> TYPE: DNA
<213> ORGANISM: Artificial
<220> FEATURE:
<223> OTHER INFORMATION: Target sequence in the gene LOC400804

<400> SEQUENCE: 792
```
ctctgcgtct attaagaaca a                           21

<210> SEQ ID NO 793
<211> LENGTH: 21
<212> TYPE: DNA
<213> ORGANISM: Artificial
<220> FEATURE:
<223> OTHER INFORMATION: Target sequence in the gene LOC402641

<400> SEQUENCE: 793
atccaactga caagaccttta a                          21

<210> SEQ ID NO 794
<211> LENGTH: 21
<212> TYPE: DNA
<213> ORGANISM: Artificial
<220> FEATURE:
<223> OTHER INFORMATION: Target sequence in the gene LOC729747

<400> SEQUENCE: 794
aaggatcttc gaatacatga a                           21

<210> SEQ ID NO 795
<211> LENGTH: 21
<212> TYPE: DNA
<213> ORGANISM: Artificial
<220> FEATURE:
<223> OTHER INFORMATION: Target sequence in the gene LOC790955

<400> SEQUENCE: 795
ccggaccgag ataccatgcc a                           21

<210> SEQ ID NO 796
<211> LENGTH: 21
<212> TYPE: DNA
<213> ORGANISM: Artificial
<220> FEATURE:
<223> OTHER INFORMATION: Target sequence in the gene LONRF1

<400> SEQUENCE: 796
caactaggat ttagaccact a                           21

<210> SEQ ID NO 797
<211> LENGTH: 21
<212> TYPE: DNA
<213> ORGANISM: Artificial
<220> FEATURE:
<223> OTHER INFORMATION: Target sequence in the gene LOXL2

<400> SEQUENCE: 797
ccggagttgc ctgctcagaa a                           21

<210> SEQ ID NO 798
<211> LENGTH: 21
<212> TYPE: DNA
<213> ORGANISM: Artificial
<220> FEATURE:
<223> OTHER INFORMATION: Target sequence in the gene LTB4R

<400> SEQUENCE: 798
aaggcccatg gtcagattga a                           21

<210> SEQ ID NO 799
<211> LENGTH: 21
<212> TYPE: DNA

<213> ORGANISM: Artificial
<220> FEATURE:
<223> OTHER INFORMATION: Target sequence in the gene MAD2L1BP

<400> SEQUENCE: 799
ctgggtcagg catttctatt a       21

<210> SEQ ID NO 800
<211> LENGTH: 21
<212> TYPE: DNA
<213> ORGANISM: Artificial
<220> FEATURE:
<223> OTHER INFORMATION: Target sequence in the gene MARCH2

<400> SEQUENCE: 800
cacgctgggt gccgtgcata a       21

<210> SEQ ID NO 801
<211> LENGTH: 21
<212> TYPE: DNA
<213> ORGANISM: Artificial
<220> FEATURE:
<223> OTHER INFORMATION: Target sequence in the gene MAT1A

<400> SEQUENCE: 801
ttggctcaca ctcgacatga a       21

<210> SEQ ID NO 802
<211> LENGTH: 21
<212> TYPE: DNA
<213> ORGANISM: Artificial
<220> FEATURE:
<223> OTHER INFORMATION: Target sequence in the gene MED16

<400> SEQUENCE: 802
cacccggatc ctggccatga a       21

<210> SEQ ID NO 803
<211> LENGTH: 21
<212> TYPE: DNA
<213> ORGANISM: Artificial
<220> FEATURE:
<223> OTHER INFORMATION: Target sequence in the gene METTL10

<400> SEQUENCE: 803
cagcgataca tgcacaaaga t       21

<210> SEQ ID NO 804
<211> LENGTH: 21
<212> TYPE: DNA
<213> ORGANISM: Artificial
<220> FEATURE:
<223> OTHER INFORMATION: Target sequence in the gene METTL5

<400> SEQUENCE: 804
aagaaatcag tggacattga a       21

<210> SEQ ID NO 805
<211> LENGTH: 21
<212> TYPE: DNA
<213> ORGANISM: Artificial
<220> FEATURE:
<223> OTHER INFORMATION: Target sequence in the gene MGLL

<400> SEQUENCE: 805
aagacagagg tcgacattta t       21

<210> SEQ ID NO 806
<211> LENGTH: 21
<212> TYPE: DNA
<213> ORGANISM: Artificial
<220> FEATURE:
<223> OTHER INFORMATION: Target sequence in the gene MIST

<400> SEQUENCE: 806
tggtccgaga ttgttccaca a					21

<210> SEQ ID NO 807
<211> LENGTH: 21
<212> TYPE: DNA
<213> ORGANISM: Artificial
<220> FEATURE:
<223> OTHER INFORMATION: Target sequence in the gene MMP14

<400> SEQUENCE: 807
tggcgggtga ggaataacca a					21

<210> SEQ ID NO 808
<211> LENGTH: 21
<212> TYPE: DNA
<213> ORGANISM: Artificial
<220> FEATURE:
<223> OTHER INFORMATION: Target sequence in the gene MMP3

<400> SEQUENCE: 808
agggattgac tcaaagattg a					21

<210> SEQ ID NO 809
<211> LENGTH: 21
<212> TYPE: DNA
<213> ORGANISM: Artificial
<220> FEATURE:
<223> OTHER INFORMATION: Target sequence in the gene MMP7

<400> SEQUENCE: 809
acccatttga tgggccagga a					21

<210> SEQ ID NO 810
<211> LENGTH: 21
<212> TYPE: DNA
<213> ORGANISM: Artificial
<220> FEATURE:
<223> OTHER INFORMATION: Target sequence in the gene MOBKL3

<400> SEQUENCE: 810
cacaatggta aggcacataa a					21

<210> SEQ ID NO 811
<211> LENGTH: 21
<212> TYPE: DNA
<213> ORGANISM: Artificial
<220> FEATURE:
<223> OTHER INFORMATION: Target sequence in the gene MPHOSPH1

<400> SEQUENCE: 811
cacaaggtgt tacttgctat a					21

<210> SEQ ID NO 812
<211> LENGTH: 21
<212> TYPE: DNA
<213> ORGANISM: Artificial
<220> FEATURE:

```
<223> OTHER INFORMATION: Target sequence in the gene MRPS17

<400> SEQUENCE: 812
caggcttgtt ctggatccct a                                              21

<210> SEQ ID NO 813
<211> LENGTH: 21
<212> TYPE: DNA
<213> ORGANISM: Artificial
<220> FEATURE:
<223> OTHER INFORMATION: Target sequence in the gene MSH5

<400> SEQUENCE: 813
cccgggacta tggctactca a                                              21

<210> SEQ ID NO 814
<211> LENGTH: 21
<212> TYPE: DNA
<213> ORGANISM: Artificial
<220> FEATURE:
<223> OTHER INFORMATION: Target sequence in the gene MSH5

<400> SEQUENCE: 814
cccgggacta tggctactca a                                              21

<210> SEQ ID NO 815
<211> LENGTH: 21
<212> TYPE: DNA
<213> ORGANISM: Artificial
<220> FEATURE:
<223> OTHER INFORMATION: Target sequence in the gene MSLN

<400> SEQUENCE: 815
ctggacgtcc taaagcataa a                                              21

<210> SEQ ID NO 816
<211> LENGTH: 21
<212> TYPE: DNA
<213> ORGANISM: Artificial
<220> FEATURE:
<223> OTHER INFORMATION: Target sequence in the gene MYBBP1A

<400> SEQUENCE: 816
ccactcgttc tttgtcacaa a                                              21

<210> SEQ ID NO 817
<211> LENGTH: 21
<212> TYPE: DNA
<213> ORGANISM: Artificial
<220> FEATURE:
<223> OTHER INFORMATION: Target sequence in the gene MYOZ3

<400> SEQUENCE: 817
tagccggatg aacttgagca a                                              21

<210> SEQ ID NO 818
<211> LENGTH: 21
<212> TYPE: DNA
<213> ORGANISM: Artificial
<220> FEATURE:
<223> OTHER INFORMATION: Target sequence in the gene MYST3

<400> SEQUENCE: 818
tgggcgaata gcacttccta a                                              21
```

```
<210> SEQ ID NO 819
<211> LENGTH: 21
<212> TYPE: DNA
<213> ORGANISM: Artificial
<220> FEATURE:
<223> OTHER INFORMATION: Target sequence in the gene MYST3

<400> SEQUENCE: 819
tgggcgaata gcacttccta a                                            21

<210> SEQ ID NO 820
<211> LENGTH: 21
<212> TYPE: DNA
<213> ORGANISM: Artificial
<220> FEATURE:
<223> OTHER INFORMATION: Target sequence in the gene NDRG1

<400> SEQUENCE: 820
aacgtgaacc cttgtgcgga a                                            21

<210> SEQ ID NO 821
<211> LENGTH: 21
<212> TYPE: DNA
<213> ORGANISM: Artificial
<220> FEATURE:
<223> OTHER INFORMATION: Target sequence in the gene NDST2

<400> SEQUENCE: 821
ctgcctggac cttgaccgct a                                            21

<210> SEQ ID NO 822
<211> LENGTH: 21
<212> TYPE: DNA
<213> ORGANISM: Artificial
<220> FEATURE:
<223> OTHER INFORMATION: Target sequence in the gene NEFH

<400> SEQUENCE: 822
aagaaggaac ctgctgtcga a                                            21

<210> SEQ ID NO 823
<211> LENGTH: 21
<212> TYPE: DNA
<213> ORGANISM: Artificial
<220> FEATURE:
<223> OTHER INFORMATION: Target sequence in the gene NLGN4Y

<400> SEQUENCE: 823
cacctagtcc cttatgtatc a                                            21

<210> SEQ ID NO 824
<211> LENGTH: 21
<212> TYPE: DNA
<213> ORGANISM: Artificial
<220> FEATURE:
<223> OTHER INFORMATION: Target sequence in the gene NRGN

<400> SEQUENCE: 824
aacaataaag aggaatgtcc a                                            21

<210> SEQ ID NO 825
<211> LENGTH: 21
<212> TYPE: DNA
<213> ORGANISM: Artificial
<220> FEATURE:
<223> OTHER INFORMATION: Target sequence in the gene NUDCD1
```

<400> SEQUENCE: 825
aagcgtgata ttctccgtgg a                                              21

<210> SEQ ID NO 826
<211> LENGTH: 21
<212> TYPE: DNA
<213> ORGANISM: Artificial
<220> FEATURE:
<223> OTHER INFORMATION: Target sequence in the gene NUDT6

<400> SEQUENCE: 826
cacgcagaat cggattcatc a                                              21

<210> SEQ ID NO 827
<211> LENGTH: 21
<212> TYPE: DNA
<213> ORGANISM: Artificial
<220> FEATURE:
<223> OTHER INFORMATION: Target sequence in the gene OBFC1

<400> SEQUENCE: 827
tcagcttaac ctcacaactt a                                              21

<210> SEQ ID NO 828
<211> LENGTH: 21
<212> TYPE: DNA
<213> ORGANISM: Artificial
<220> FEATURE:
<223> OTHER INFORMATION: Target sequence in the gene OGDH

<400> SEQUENCE: 828
caggatcaat cgtgtcaccg a                                              21

<210> SEQ ID NO 829
<211> LENGTH: 21
<212> TYPE: DNA
<213> ORGANISM: Artificial
<220> FEATURE:
<223> OTHER INFORMATION: Target sequence in the gene OGDH

<400> SEQUENCE: 829
gagaagcgct ttggtctaga a                                              21

<210> SEQ ID NO 830
<211> LENGTH: 21
<212> TYPE: DNA
<213> ORGANISM: Artificial
<220> FEATURE:
<223> OTHER INFORMATION: Target sequence in the gene ONECUT3

<400> SEQUENCE: 830
cgccacggcc actttctcca a                                              21

<210> SEQ ID NO 831
<211> LENGTH: 21
<212> TYPE: DNA
<213> ORGANISM: Artificial
<220> FEATURE:
<223> OTHER INFORMATION: Target sequence in the gene OR2B2

<400> SEQUENCE: 831
ctggattagt ggctttagca a                                              21

<210> SEQ ID NO 832
<211> LENGTH: 21

```
<212> TYPE: DNA
<213> ORGANISM: Artificial
<220> FEATURE:
<223> OTHER INFORMATION: Target sequence in the gene OR5AS1

<400> SEQUENCE: 832
atgaatggta tttaaatcgt t                                              21

<210> SEQ ID NO 833
<211> LENGTH: 21
<212> TYPE: DNA
<213> ORGANISM: Artificial
<220> FEATURE:
<223> OTHER INFORMATION: Target sequence in the gene OR6C3

<400> SEQUENCE: 833
tcacgtatat attaagtgtt a                                              21

<210> SEQ ID NO 834
<211> LENGTH: 21
<212> TYPE: DNA
<213> ORGANISM: Artificial
<220> FEATURE:
<223> OTHER INFORMATION: Target sequence in the gene OR6C3

<400> SEQUENCE: 834
tcccgtctgc cagtcaaaga a                                              21

<210> SEQ ID NO 835
<211> LENGTH: 21
<212> TYPE: DNA
<213> ORGANISM: Artificial
<220> FEATURE:
<223> OTHER INFORMATION: Target sequence in the gene OR6F1

<400> SEQUENCE: 835
acgcttcgta ataaggaagt a                                              21

<210> SEQ ID NO 836
<211> LENGTH: 21
<212> TYPE: DNA
<213> ORGANISM: Artificial
<220> FEATURE:
<223> OTHER INFORMATION: Target sequence in the gene ORC4L

<400> SEQUENCE: 836
cagtcgtaaa tcaaagagta a                                              21

<210> SEQ ID NO 837
<211> LENGTH: 21
<212> TYPE: DNA
<213> ORGANISM: Artificial
<220> FEATURE:
<223> OTHER INFORMATION: Target sequence in the gene OSBPL11

<400> SEQUENCE: 837
ccaggatctc ttaatgctca a                                              21

<210> SEQ ID NO 838
<211> LENGTH: 21
<212> TYPE: DNA
<213> ORGANISM: Artificial
<220> FEATURE:
<223> OTHER INFORMATION: Target sequence in the gene PAPD5

<400> SEQUENCE: 838
```
taggtagaat aattagagta a                                         21

<210> SEQ ID NO 839
<211> LENGTH: 21
<212> TYPE: DNA
<213> ORGANISM: Artificial
<220> FEATURE:
<223> OTHER INFORMATION: Target sequence in the gene PCGF3

<400> SEQUENCE: 839
cagcagcgta cggcagacga a                                         21

<210> SEQ ID NO 840
<211> LENGTH: 21
<212> TYPE: DNA
<213> ORGANISM: Artificial
<220> FEATURE:
<223> OTHER INFORMATION: Target sequence in the gene PDCD11

<400> SEQUENCE: 840
ctgcattgtg aagttctaca a                                         21

<210> SEQ ID NO 841
<211> LENGTH: 21
<212> TYPE: DNA
<213> ORGANISM: Artificial
<220> FEATURE:
<223> OTHER INFORMATION: Target sequence in the gene PDE11A

<400> SEQUENCE: 841
tcggatggtt ctataccaca a                                         21

<210> SEQ ID NO 842
<211> LENGTH: 21
<212> TYPE: DNA
<213> ORGANISM: Artificial
<220> FEATURE:
<223> OTHER INFORMATION: Target sequence in the gene PDE6B

<400> SEQUENCE: 842
cacgctgctc atgaccggca a                                         21

<210> SEQ ID NO 843
<211> LENGTH: 21
<212> TYPE: DNA
<213> ORGANISM: Artificial
<220> FEATURE:
<223> OTHER INFORMATION: Target sequence in the gene PDLIM5

<400> SEQUENCE: 843
ctctgacaat ctctagtcta a                                         21

<210> SEQ ID NO 844
<211> LENGTH: 21
<212> TYPE: DNA
<213> ORGANISM: Artificial
<220> FEATURE:
<223> OTHER INFORMATION: Target sequence in the gene PER1

<400> SEQUENCE: 844
cccggactct ccactgttca a                                         21

<210> SEQ ID NO 845
<211> LENGTH: 21
<212> TYPE: DNA
<213> ORGANISM: Artificial

```
<220> FEATURE:
<223> OTHER INFORMATION: Target sequence in the gene PFKFB2

<400> SEQUENCE: 845
ccagagcaag atagtctact a                                              21

<210> SEQ ID NO 846
<211> LENGTH: 21
<212> TYPE: DNA
<213> ORGANISM: Artificial
<220> FEATURE:
<223> OTHER INFORMATION: Target sequence in the gene PFKFB4

<400> SEQUENCE: 846
acggagagcg accatcttta a                                              21

<210> SEQ ID NO 847
<211> LENGTH: 21
<212> TYPE: DNA
<213> ORGANISM: Artificial
<220> FEATURE:
<223> OTHER INFORMATION: Target sequence in the gene PHOX2B

<400> SEQUENCE: 847
tacgccgcag ttccttacaa a                                              21

<210> SEQ ID NO 848
<211> LENGTH: 21
<212> TYPE: DNA
<213> ORGANISM: Artificial
<220> FEATURE:
<223> OTHER INFORMATION: Target sequence in the gene PLCE1

<400> SEQUENCE: 848
ccgcggtaca attcccaaga a                                              21

<210> SEQ ID NO 849
<211> LENGTH: 21
<212> TYPE: DNA
<213> ORGANISM: Artificial
<220> FEATURE:
<223> OTHER INFORMATION: Target sequence in the gene PLEKHG2

<400> SEQUENCE: 849
caggttcagc cagaccctca a                                              21

<210> SEQ ID NO 850
<211> LENGTH: 21
<212> TYPE: DNA
<213> ORGANISM: Artificial
<220> FEATURE:
<223> OTHER INFORMATION: Target sequence in the gene PLEKHG7

<400> SEQUENCE: 850
caccgctttg ggatagagat a                                              21

<210> SEQ ID NO 851
<211> LENGTH: 21
<212> TYPE: DNA
<213> ORGANISM: Artificial
<220> FEATURE:
<223> OTHER INFORMATION: Target sequence in the gene PLOD3

<400> SEQUENCE: 851
caccgtggac atccacatga a                                              21
```

```
<210> SEQ ID NO 852
<211> LENGTH: 21
<212> TYPE: DNA
<213> ORGANISM: Artificial
<220> FEATURE:
<223> OTHER INFORMATION: Target sequence in the gene PNPLA6

<400> SEQUENCE: 852
ccggcggtct acagacctta a                                              21

<210> SEQ ID NO 853
<211> LENGTH: 21
<212> TYPE: DNA
<213> ORGANISM: Artificial
<220> FEATURE:
<223> OTHER INFORMATION: Target sequence in the gene PRCC

<400> SEQUENCE: 853
cgccgtcaga cccaagccaa a                                              21

<210> SEQ ID NO 854
<211> LENGTH: 21
<212> TYPE: DNA
<213> ORGANISM: Artificial
<220> FEATURE:
<223> OTHER INFORMATION: Target sequence in the gene PRIMA1

<400> SEQUENCE: 854
ccctgccggc ctagtatttg a                                              21

<210> SEQ ID NO 855
<211> LENGTH: 21
<212> TYPE: DNA
<213> ORGANISM: Artificial
<220> FEATURE:
<223> OTHER INFORMATION: Target sequence in the gene PRL

<400> SEQUENCE: 855
cagcgaattc gataaacggt a                                              21

<210> SEQ ID NO 856
<211> LENGTH: 21
<212> TYPE: DNA
<213> ORGANISM: Artificial
<220> FEATURE:
<223> OTHER INFORMATION: Target sequence in the gene PROKR1

<400> SEQUENCE: 856
ccgctacaag aaactgcgca a                                              21

<210> SEQ ID NO 857
<211> LENGTH: 21
<212> TYPE: DNA
<213> ORGANISM: Artificial
<220> FEATURE:
<223> OTHER INFORMATION: Target sequence in the gene PRPH2

<400> SEQUENCE: 857
gaggagcgat gtgatgaata a                                              21

<210> SEQ ID NO 858
<211> LENGTH: 21
<212> TYPE: DNA
<213> ORGANISM: Artificial
<220> FEATURE:
<223> OTHER INFORMATION: Target sequence in the gene PSD3
```

-continued

```
<400> SEQUENCE: 858
aaggacgtcg atgagtacaa a                                            21

<210> SEQ ID NO 859
<211> LENGTH: 21
<212> TYPE: DNA
<213> ORGANISM: Artificial
<220> FEATURE:
<223> OTHER INFORMATION: Target sequence in the gene PSMD1

<400> SEQUENCE: 859
cagtttcgga ataaagtact a                                            21

<210> SEQ ID NO 860
<211> LENGTH: 21
<212> TYPE: DNA
<213> ORGANISM: Artificial
<220> FEATURE:
<223> OTHER INFORMATION: Target sequence in the gene PSMD1

<400> SEQUENCE: 860
aaagaccata ctggagtcga a                                            21

<210> SEQ ID NO 861
<211> LENGTH: 21
<212> TYPE: DNA
<213> ORGANISM: Artificial
<220> FEATURE:
<223> OTHER INFORMATION: Target sequence in the gene PTGES

<400> SEQUENCE: 861
ttgggtgacc agccactcaa a                                            21

<210> SEQ ID NO 862
<211> LENGTH: 21
<212> TYPE: DNA
<213> ORGANISM: Artificial
<220> FEATURE:
<223> OTHER INFORMATION: Target sequence in the gene PTGIS

<400> SEQUENCE: 862
ctcgagagta tcctttggca a                                            21

<210> SEQ ID NO 863
<211> LENGTH: 21
<212> TYPE: DNA
<213> ORGANISM: Artificial
<220> FEATURE:
<223> OTHER INFORMATION: Target sequence in the gene PUS10

<400> SEQUENCE: 863
tgcgctgttc ttgaaattga a                                            21

<210> SEQ ID NO 864
<211> LENGTH: 21
<212> TYPE: DNA
<213> ORGANISM: Artificial
<220> FEATURE:
<223> OTHER INFORMATION: Target sequence in the gene RAB17

<400> SEQUENCE: 864
aagtgagatc ctggaagtga a                                            21

<210> SEQ ID NO 865
```

```
<211> LENGTH: 21
<212> TYPE: DNA
<213> ORGANISM: Artificial
<220> FEATURE:
<223> OTHER INFORMATION: Target sequence in the gene RAB34

<400> SEQUENCE: 865
ccgcgtaatc gtaggaacta t                                              21

<210> SEQ ID NO 866
<211> LENGTH: 21
<212> TYPE: DNA
<213> ORGANISM: Artificial
<220> FEATURE:
<223> OTHER INFORMATION: Target sequence in the gene RABL2B

<400> SEQUENCE: 866
caggacttca tggatgagat t                                              21

<210> SEQ ID NO 867
<211> LENGTH: 21
<212> TYPE: DNA
<213> ORGANISM: Artificial
<220> FEATURE:
<223> OTHER INFORMATION: Target sequence in the gene RAET1E

<400> SEQUENCE: 867
agcgcaggtc ttcttgaata a                                              21

<210> SEQ ID NO 868
<211> LENGTH: 21
<212> TYPE: DNA
<213> ORGANISM: Artificial
<220> FEATURE:
<223> OTHER INFORMATION: Target sequence in the gene REPS2

<400> SEQUENCE: 868
cccggtacgg atagagagta t                                              21

<210> SEQ ID NO 869
<211> LENGTH: 21
<212> TYPE: DNA
<213> ORGANISM: Artificial
<220> FEATURE:
<223> OTHER INFORMATION: Target sequence in the gene RFC1

<400> SEQUENCE: 869
ttggagtaat accaagtgga a                                              21

<210> SEQ ID NO 870
<211> LENGTH: 21
<212> TYPE: DNA
<213> ORGANISM: Artificial
<220> FEATURE:
<223> OTHER INFORMATION: Target sequence in the gene RGL4

<400> SEQUENCE: 870
cccggacgac ctggatggca a                                              21

<210> SEQ ID NO 871
<211> LENGTH: 21
<212> TYPE: DNA
<213> ORGANISM: Artificial
<220> FEATURE:
<223> OTHER INFORMATION: Target sequence in the gene RHEB

<400> SEQUENCE: 871
```
cagggctatt tctaatacgt a                                               21

<210> SEQ ID NO 872
<211> LENGTH: 21
<212> TYPE: DNA
<213> ORGANISM: Artificial
<220> FEATURE:
<223> OTHER INFORMATION: Target sequence in the gene RNF111

<400> SEQUENCE: 872
caggcaaggt tagctgcttt a                                               21

<210> SEQ ID NO 873
<211> LENGTH: 21
<212> TYPE: DNA
<213> ORGANISM: Artificial
<220> FEATURE:
<223> OTHER INFORMATION: Target sequence in the gene RNF128

<400> SEQUENCE: 873
cagggcctag tttctattaa t                                               21

<210> SEQ ID NO 874
<211> LENGTH: 21
<212> TYPE: DNA
<213> ORGANISM: Artificial
<220> FEATURE:
<223> OTHER INFORMATION: Target sequence in the gene RPL27

<400> SEQUENCE: 874
cacaaggtac tctgtggata t                                               21

<210> SEQ ID NO 875
<211> LENGTH: 21
<212> TYPE: DNA
<213> ORGANISM: Artificial
<220> FEATURE:
<223> OTHER INFORMATION: Target sequence in the gene RPL32P3

<400> SEQUENCE: 875
cccggcctga gtgagtctta a                                               21

<210> SEQ ID NO 876
<211> LENGTH: 21
<212> TYPE: DNA
<213> ORGANISM: Artificial
<220> FEATURE:
<223> OTHER INFORMATION: Target sequence in the gene RPL35

<400> SEQUENCE: 876
ccgtgttctc acagttatta a                                               21

<210> SEQ ID NO 877
<211> LENGTH: 21
<212> TYPE: DNA
<213> ORGANISM: Artificial
<220> FEATURE:
<223> OTHER INFORMATION: Target sequence in the gene RPL36

<400> SEQUENCE: 877
cgggaggagc tgagcaacgt a                                               21

<210> SEQ ID NO 878
<211> LENGTH: 21
<212> TYPE: DNA

```
<213> ORGANISM: Artificial
<220> FEATURE:
<223> OTHER INFORMATION: Target sequence in the gene RPS12

<400> SEQUENCE: 878
tggaggtgta atggacgtta a                                              21

<210> SEQ ID NO 879
<211> LENGTH: 21
<212> TYPE: DNA
<213> ORGANISM: Artificial
<220> FEATURE:
<223> OTHER INFORMATION: Target sequence in the gene RPS19

<400> SEQUENCE: 879
taccgtcaag ctggccaagc a                                              21

<210> SEQ ID NO 880
<211> LENGTH: 21
<212> TYPE: DNA
<213> ORGANISM: Artificial
<220> FEATURE:
<223> OTHER INFORMATION: Target sequence in the gene RPS6

<400> SEQUENCE: 880
aagaagcagc gtaccaagaa a                                              21

<210> SEQ ID NO 881
<211> LENGTH: 21
<212> TYPE: DNA
<213> ORGANISM: Artificial
<220> FEATURE:
<223> OTHER INFORMATION: Target sequence in the gene RPS6KB1

<400> SEQUENCE: 881
cacctgcgta tgaatctatg a                                              21

<210> SEQ ID NO 882
<211> LENGTH: 21
<212> TYPE: DNA
<213> ORGANISM: Artificial
<220> FEATURE:
<223> OTHER INFORMATION: Target sequence in the gene RPS7

<400> SEQUENCE: 882
ttcgagcgcc aagatcgtga a                                              21

<210> SEQ ID NO 883
<211> LENGTH: 21
<212> TYPE: DNA
<213> ORGANISM: Artificial
<220> FEATURE:
<223> OTHER INFORMATION: Target sequence in the gene RTN3

<400> SEQUENCE: 883
caggatctac aagtccgtca t                                              21

<210> SEQ ID NO 884
<211> LENGTH: 21
<212> TYPE: DNA
<213> ORGANISM: Artificial
<220> FEATURE:
<223> OTHER INFORMATION: Target sequence in the gene SBF2

<400> SEQUENCE: 884
aaccgtggac cttaaagaag a                                              21
```

<210> SEQ ID NO 885
<211> LENGTH: 21
<212> TYPE: DNA
<213> ORGANISM: Artificial
<220> FEATURE:
<223> OTHER INFORMATION: Target sequence in the gene SCNN1A

<400> SEQUENCE: 885
cccgatgtat ggaaactgct a         21

<210> SEQ ID NO 886
<211> LENGTH: 21
<212> TYPE: DNA
<213> ORGANISM: Artificial
<220> FEATURE:
<223> OTHER INFORMATION: Target sequence in the gene SEC22A

<400> SEQUENCE: 886
tggcttaatc tgtctatgca a         21

<210> SEQ ID NO 887
<211> LENGTH: 21
<212> TYPE: DNA
<213> ORGANISM: Artificial
<220> FEATURE:
<223> OTHER INFORMATION: Target sequence in the gene SELPLG

<400> SEQUENCE: 887
atggagatac agaccactca a         21

<210> SEQ ID NO 888
<211> LENGTH: 21
<212> TYPE: DNA
<213> ORGANISM: Artificial
<220> FEATURE:
<223> OTHER INFORMATION: Target sequence in the gene SEMA6C

<400> SEQUENCE: 888
ccgcgtagcc cgagtatgta a         21

<210> SEQ ID NO 889
<211> LENGTH: 21
<212> TYPE: DNA
<213> ORGANISM: Artificial
<220> FEATURE:
<223> OTHER INFORMATION: Target sequence in the gene SEMA6D

<400> SEQUENCE: 889
cacggccttg ccgaagctta t         21

<210> SEQ ID NO 890
<211> LENGTH: 21
<212> TYPE: DNA
<213> ORGANISM: Artificial
<220> FEATURE:
<223> OTHER INFORMATION: Target sequence in the gene sept-12

<400> SEQUENCE: 890
ctgggctaca tcaacgagca a         21

<210> SEQ ID NO 891
<211> LENGTH: 21
<212> TYPE: DNA
<213> ORGANISM: Artificial
<220> FEATURE:

<223> OTHER INFORMATION: Target sequence in the gene SERINC4

<400> SEQUENCE: 891
caccagatat ctctctagca a                                              21

<210> SEQ ID NO 892
<211> LENGTH: 21
<212> TYPE: DNA
<213> ORGANISM: Artificial
<220> FEATURE:
<223> OTHER INFORMATION: Target sequence in the gene SGEF

<400> SEQUENCE: 892
tccgaagtat gaagtctgca a                                              21

<210> SEQ ID NO 893
<211> LENGTH: 21
<212> TYPE: DNA
<213> ORGANISM: Artificial
<220> FEATURE:
<223> OTHER INFORMATION: Target sequence in the gene SH3RF2

<400> SEQUENCE: 893
cccgatgagc tggacctgca a                                              21

<210> SEQ ID NO 894
<211> LENGTH: 21
<212> TYPE: DNA
<213> ORGANISM: Artificial
<220> FEATURE:
<223> OTHER INFORMATION: Target sequence in the gene SHBG

<400> SEQUENCE: 894
caggcagaat tcaatctccg a                                              21

<210> SEQ ID NO 895
<211> LENGTH: 21
<212> TYPE: DNA
<213> ORGANISM: Artificial
<220> FEATURE:
<223> OTHER INFORMATION: Target sequence in the gene SHFM1

<400> SEQUENCE: 895
gacagtcgag atgtcagaga a                                              21

<210> SEQ ID NO 896
<211> LENGTH: 21
<212> TYPE: DNA
<213> ORGANISM: Artificial
<220> FEATURE:
<223> OTHER INFORMATION: Target sequence in the gene SIGLEC9

<400> SEQUENCE: 896
caggctttag agtcaaagta t                                              21

<210> SEQ ID NO 897
<211> LENGTH: 21
<212> TYPE: DNA
<213> ORGANISM: Artificial
<220> FEATURE:
<223> OTHER INFORMATION: Target sequence in the gene SIPA1L2

<400> SEQUENCE: 897
cagaccgacc ttcggaagga a                                              21

```
<210> SEQ ID NO 898
<211> LENGTH: 21
<212> TYPE: DNA
<213> ORGANISM: Artificial
<220> FEATURE:
<223> OTHER INFORMATION: Target sequence in the gene SIVA1

<400> SEQUENCE: 898
cacgccgtgc atggcagcct t                                              21

<210> SEQ ID NO 899
<211> LENGTH: 21
<212> TYPE: DNA
<213> ORGANISM: Artificial
<220> FEATURE:
<223> OTHER INFORMATION: Target sequence in the gene SLAMF6

<400> SEQUENCE: 899
ctccattgtt tgagccaaga a                                              21

<210> SEQ ID NO 900
<211> LENGTH: 21
<212> TYPE: DNA
<213> ORGANISM: Artificial
<220> FEATURE:
<223> OTHER INFORMATION: Target sequence in the gene SLAMF9

<400> SEQUENCE: 900
caggcatgga tatgacctac a                                              21

<210> SEQ ID NO 901
<211> LENGTH: 21
<212> TYPE: DNA
<213> ORGANISM: Artificial
<220> FEATURE:
<223> OTHER INFORMATION: Target sequence in the gene SLC17A6

<400> SEQUENCE: 901
ctgccatact tcttacctct a                                              21

<210> SEQ ID NO 902
<211> LENGTH: 21
<212> TYPE: DNA
<213> ORGANISM: Artificial
<220> FEATURE:
<223> OTHER INFORMATION: Target sequence in the gene SLC25A36

<400> SEQUENCE: 902
ccggacctct tcattgccta a                                              21

<210> SEQ ID NO 903
<211> LENGTH: 21
<212> TYPE: DNA
<213> ORGANISM: Artificial
<220> FEATURE:
<223> OTHER INFORMATION: Target sequence in the gene SLC30A8

<400> SEQUENCE: 903
aacactatct gtggagagta a                                              21

<210> SEQ ID NO 904
<211> LENGTH: 21
<212> TYPE: DNA
<213> ORGANISM: Artificial
<220> FEATURE:
<223> OTHER INFORMATION: Target sequence in the gene SLC47A2
```

<400> SEQUENCE: 904
caccacggtc tgccctgcaa a					21

<210> SEQ ID NO 905
<211> LENGTH: 21
<212> TYPE: DNA
<213> ORGANISM: Artificial
<220> FEATURE:
<223> OTHER INFORMATION: Target sequence in the gene SLCO4C1

<400> SEQUENCE: 905
atgattgtta agtaagcttg a					21

<210> SEQ ID NO 906
<211> LENGTH: 21
<212> TYPE: DNA
<213> ORGANISM: Artificial
<220> FEATURE:
<223> OTHER INFORMATION: Target sequence in the gene SLU7

<400> SEQUENCE: 906
aagactatgt ggagtactca a					21

<210> SEQ ID NO 907
<211> LENGTH: 21
<212> TYPE: DNA
<213> ORGANISM: Artificial
<220> FEATURE:
<223> OTHER INFORMATION: Target sequence in the gene SMARCC1

<400> SEQUENCE: 907
cagcggattt caaccaagaa t					21

<210> SEQ ID NO 908
<211> LENGTH: 21
<212> TYPE: DNA
<213> ORGANISM: Artificial
<220> FEATURE:
<223> OTHER INFORMATION: Target sequence in the gene SMCR8

<400> SEQUENCE: 908
ctcgtaggtg ttgctgcaca a					21

<210> SEQ ID NO 909
<211> LENGTH: 21
<212> TYPE: DNA
<213> ORGANISM: Artificial
<220> FEATURE:
<223> OTHER INFORMATION: Target sequence in the gene SMEK2

<400> SEQUENCE: 909
taccatctat attgcgtagt a					21

<210> SEQ ID NO 910
<211> LENGTH: 21
<212> TYPE: DNA
<213> ORGANISM: Artificial
<220> FEATURE:
<223> OTHER INFORMATION: Target sequence in the gene SNRPE

<400> SEQUENCE: 910
taccctcgtg ttactacaag a					21

<210> SEQ ID NO 911
<211> LENGTH: 21

```
<212> TYPE: DNA
<213> ORGANISM: Artificial
<220> FEATURE:
<223> OTHER INFORMATION: Target sequence in the gene SNX29

<400> SEQUENCE: 911
tggcgagctg attgagttca a                                              21

<210> SEQ ID NO 912
<211> LENGTH: 21
<212> TYPE: DNA
<213> ORGANISM: Artificial
<220> FEATURE:
<223> OTHER INFORMATION: Target sequence in the gene SOX21

<400> SEQUENCE: 912
ctgctcgacc tgggctccaa a                                              21

<210> SEQ ID NO 913
<211> LENGTH: 21
<212> TYPE: DNA
<213> ORGANISM: Artificial
<220> FEATURE:
<223> OTHER INFORMATION: Target sequence in the gene SPACA1

<400> SEQUENCE: 913
cagcgagacc gcggagaact a                                              21

<210> SEQ ID NO 914
<211> LENGTH: 21
<212> TYPE: DNA
<213> ORGANISM: Artificial
<220> FEATURE:
<223> OTHER INFORMATION: Target sequence in the gene SPATA5L1

<400> SEQUENCE: 914
acccgggaga tttgaccgag a                                              21

<210> SEQ ID NO 915
<211> LENGTH: 21
<212> TYPE: DNA
<213> ORGANISM: Artificial
<220> FEATURE:
<223> OTHER INFORMATION: Target sequence in the gene SPECC1L

<400> SEQUENCE: 915
ccgggtatac aattacatga a                                              21

<210> SEQ ID NO 916
<211> LENGTH: 21
<212> TYPE: DNA
<213> ORGANISM: Artificial
<220> FEATURE:
<223> OTHER INFORMATION: Target sequence in the gene SPEN

<400> SEQUENCE: 916
cccgtggata tggttcaact t                                              21

<210> SEQ ID NO 917
<211> LENGTH: 21
<212> TYPE: DNA
<213> ORGANISM: Artificial
<220> FEATURE:
<223> OTHER INFORMATION: Target sequence in the gene SPSB2

<400> SEQUENCE: 917
```

```
caaggctatg acagtctgct a                                              21

<210> SEQ ID NO 918
<211> LENGTH: 21
<212> TYPE: DNA
<213> ORGANISM: Artificial
<220> FEATURE:
<223> OTHER INFORMATION: Target sequence in the gene SRP68

<400> SEQUENCE: 918
cagagagatt atatccttga a                                              21

<210> SEQ ID NO 919
<211> LENGTH: 21
<212> TYPE: DNA
<213> ORGANISM: Artificial
<220> FEATURE:
<223> OTHER INFORMATION: Target sequence in the gene SSR1

<400> SEQUENCE: 919
aaagatttga acggcaatgt a                                              21

<210> SEQ ID NO 920
<211> LENGTH: 21
<212> TYPE: DNA
<213> ORGANISM: Artificial
<220> FEATURE:
<223> OTHER INFORMATION: Target sequence in the gene ST8SIA4

<400> SEQUENCE: 920
cacccaagat gcgctccatt a                                              21

<210> SEQ ID NO 921
<211> LENGTH: 21
<212> TYPE: DNA
<213> ORGANISM: Artificial
<220> FEATURE:
<223> OTHER INFORMATION: Target sequence in the gene STX10

<400> SEQUENCE: 921
cagagagata ctcgcaggca a                                              21

<210> SEQ ID NO 922
<211> LENGTH: 21
<212> TYPE: DNA
<213> ORGANISM: Artificial
<220> FEATURE:
<223> OTHER INFORMATION: Target sequence in the gene SULT1A2

<400> SEQUENCE: 922
cacgtcgttc aaggagatga a                                              21

<210> SEQ ID NO 923
<211> LENGTH: 21
<212> TYPE: DNA
<213> ORGANISM: Artificial
<220> FEATURE:
<223> OTHER INFORMATION: Target sequence in the gene SYDE1

<400> SEQUENCE: 923
cgccggcgag atctggtaca a                                              21

<210> SEQ ID NO 924
<211> LENGTH: 21
<212> TYPE: DNA
<213> ORGANISM: Artificial
```

```
<220> FEATURE:
<223> OTHER INFORMATION: Target sequence in the gene SYN3

<400> SEQUENCE: 924
cacgctcaag acccgccctt a                                              21

<210> SEQ ID NO 925
<211> LENGTH: 21
<212> TYPE: DNA
<213> ORGANISM: Artificial
<220> FEATURE:
<223> OTHER INFORMATION: Target sequence in the gene SYT14

<400> SEQUENCE: 925
tatggtgtac atcgcatgaa a                                              21

<210> SEQ ID NO 926
<211> LENGTH: 21
<212> TYPE: DNA
<213> ORGANISM: Artificial
<220> FEATURE:
<223> OTHER INFORMATION: Target sequence in the gene TACR2

<400> SEQUENCE: 926
cgcggtgatg tttgtagcct a                                              21

<210> SEQ ID NO 927
<211> LENGTH: 21
<212> TYPE: DNA
<213> ORGANISM: Artificial
<220> FEATURE:
<223> OTHER INFORMATION: Target sequence in the gene TAF3

<400> SEQUENCE: 927
cagcgggatg tgcgagagtt a                                              21

<210> SEQ ID NO 928
<211> LENGTH: 21
<212> TYPE: DNA
<213> ORGANISM: Artificial
<220> FEATURE:
<223> OTHER INFORMATION: Target sequence in the gene TAF8

<400> SEQUENCE: 928
cagaggctat actcttataa t                                              21

<210> SEQ ID NO 929
<211> LENGTH: 21
<212> TYPE: DNA
<213> ORGANISM: Artificial
<220> FEATURE:
<223> OTHER INFORMATION: Target sequence in the gene TAF8

<400> SEQUENCE: 929
tcccgtcggc atttgacgaa a                                              21

<210> SEQ ID NO 930
<211> LENGTH: 21
<212> TYPE: DNA
<213> ORGANISM: Artificial
<220> FEATURE:
<223> OTHER INFORMATION: Target sequence in the gene TBX15

<400> SEQUENCE: 930
aagcggttcc atgatattgg a                                              21
```

<210> SEQ ID NO 931
<211> LENGTH: 21
<212> TYPE: DNA
<213> ORGANISM: Artificial
<220> FEATURE:
<223> OTHER INFORMATION: Target sequence in the gene TCEB3B

<400> SEQUENCE: 931
ctcgttagag agacagacga a                                            21

<210> SEQ ID NO 932
<211> LENGTH: 21
<212> TYPE: DNA
<213> ORGANISM: Artificial
<220> FEATURE:
<223> OTHER INFORMATION: Target sequence in the gene TFPI

<400> SEQUENCE: 932
cagcgacttt aggctggata a                                            21

<210> SEQ ID NO 933
<211> LENGTH: 21
<212> TYPE: DNA
<213> ORGANISM: Artificial
<220> FEATURE:
<223> OTHER INFORMATION: Target sequence in the gene THOC4

<400> SEQUENCE: 933
cagaggtggc atgactagaa a                                            21

<210> SEQ ID NO 934
<211> LENGTH: 21
<212> TYPE: DNA
<213> ORGANISM: Artificial
<220> FEATURE:
<223> OTHER INFORMATION: Target sequence in the gene TIAM1

<400> SEQUENCE: 934
aacggaaatg gtagagtttc a                                            21

<210> SEQ ID NO 935
<211> LENGTH: 21
<212> TYPE: DNA
<213> ORGANISM: Artificial
<220> FEATURE:
<223> OTHER INFORMATION: Target sequence in the gene TM2D2

<400> SEQUENCE: 935
atggccgtgg attgtaatac a                                            21

<210> SEQ ID NO 936
<211> LENGTH: 21
<212> TYPE: DNA
<213> ORGANISM: Artificial
<220> FEATURE:
<223> OTHER INFORMATION: Target sequence in the gene TM2D2

<400> SEQUENCE: 936
ttggtggttt gttgacctta t                                            21

<210> SEQ ID NO 937
<211> LENGTH: 21
<212> TYPE: DNA
<213> ORGANISM: Artificial
<220> FEATURE:
<223> OTHER INFORMATION: Target sequence in the gene TM4SF20

```
<400> SEQUENCE: 937
aagcacgttg taaatgcata a                                             21

<210> SEQ ID NO 938
<211> LENGTH: 21
<212> TYPE: DNA
<213> ORGANISM: Artificial
<220> FEATURE:
<223> OTHER INFORMATION: Target sequence in the gene TMBIM4

<400> SEQUENCE: 938
tagtagagtc tttaccatta t                                             21

<210> SEQ ID NO 939
<211> LENGTH: 21
<212> TYPE: DNA
<213> ORGANISM: Artificial
<220> FEATURE:
<223> OTHER INFORMATION: Target sequence in the gene TMEM16J

<400> SEQUENCE: 939
ccctcagtcg gtgaagaaca a                                             21

<210> SEQ ID NO 940
<211> LENGTH: 21
<212> TYPE: DNA
<213> ORGANISM: Artificial
<220> FEATURE:
<223> OTHER INFORMATION: Target sequence in the gene TMEM24

<400> SEQUENCE: 940
agccgggagc tgaccctcaa a                                             21

<210> SEQ ID NO 941
<211> LENGTH: 21
<212> TYPE: DNA
<213> ORGANISM: Artificial
<220> FEATURE:
<223> OTHER INFORMATION: Target sequence in the gene TNNC2

<400> SEQUENCE: 941
cagcggcacc atcgacttcg a                                             21

<210> SEQ ID NO 942
<211> LENGTH: 21
<212> TYPE: DNA
<213> ORGANISM: Artificial
<220> FEATURE:
<223> OTHER INFORMATION: Target sequence in the gene TNS4

<400> SEQUENCE: 942
cagcaatgac ctcatccgac a                                             21

<210> SEQ ID NO 943
<211> LENGTH: 21
<212> TYPE: DNA
<213> ORGANISM: Artificial
<220> FEATURE:
<223> OTHER INFORMATION: Target sequence in the gene TOB2

<400> SEQUENCE: 943
tgggtcgcaa gtccttattt a                                             21

<210> SEQ ID NO 944
```

```
<211> LENGTH: 21
<212> TYPE: DNA
<213> ORGANISM: Artificial
<220> FEATURE:
<223> OTHER INFORMATION: Target sequence in the gene TOR1B

<400> SEQUENCE: 944
cgggatcatt gacgcaatca a                                              21

<210> SEQ ID NO 945
<211> LENGTH: 21
<212> TYPE: DNA
<213> ORGANISM: Artificial
<220> FEATURE:
<223> OTHER INFORMATION: Target sequence in the gene TRIM17

<400> SEQUENCE: 945
cagggacaac gtgagccgga a                                              21

<210> SEQ ID NO 946
<211> LENGTH: 21
<212> TYPE: DNA
<213> ORGANISM: Artificial
<220> FEATURE:
<223> OTHER INFORMATION: Target sequence in the gene TRIM17

<400> SEQUENCE: 946
cccggacaga ttgaagtgct a                                              21

<210> SEQ ID NO 947
<211> LENGTH: 21
<212> TYPE: DNA
<213> ORGANISM: Artificial
<220> FEATURE:
<223> OTHER INFORMATION: Target sequence in the gene TRIM61

<400> SEQUENCE: 947
cagctgggta gtttgactga a                                              21

<210> SEQ ID NO 948
<211> LENGTH: 21
<212> TYPE: DNA
<213> ORGANISM: Artificial
<220> FEATURE:
<223> OTHER INFORMATION: Target sequence in the gene TRPV5

<400> SEQUENCE: 948
cccgggagcc aactccagaa a                                              21

<210> SEQ ID NO 949
<211> LENGTH: 21
<212> TYPE: DNA
<213> ORGANISM: Artificial
<220> FEATURE:
<223> OTHER INFORMATION: Target sequence in the gene TTPA

<400> SEQUENCE: 949
acgtatttcg agtaagtcta a                                              21

<210> SEQ ID NO 950
<211> LENGTH: 21
<212> TYPE: DNA
<213> ORGANISM: Artificial
<220> FEATURE:
<223> OTHER INFORMATION: Target sequence in the gene TUG1

<400> SEQUENCE: 950
```
caccgtgagg actacagtca a    21

<210> SEQ ID NO 951
<211> LENGTH: 21
<212> TYPE: DNA
<213> ORGANISM: Artificial
<220> FEATURE:
<223> OTHER INFORMATION: Target sequence in the gene UPK3B

<400> SEQUENCE: 951
cccggagaca ctggctgaca t    21

<210> SEQ ID NO 952
<211> LENGTH: 21
<212> TYPE: DNA
<213> ORGANISM: Artificial
<220> FEATURE:
<223> OTHER INFORMATION: Target sequence in the gene USP43

<400> SEQUENCE: 952
ctccgtcgag ttggtggagt a    21

<210> SEQ ID NO 953
<211> LENGTH: 21
<212> TYPE: DNA
<213> ORGANISM: Artificial
<220> FEATURE:
<223> OTHER INFORMATION: Target sequence in the gene VAMP4

<400> SEQUENCE: 953
tggaacgttg agaatgtcca a    21

<210> SEQ ID NO 954
<211> LENGTH: 21
<212> TYPE: DNA
<213> ORGANISM: Artificial
<220> FEATURE:
<223> OTHER INFORMATION: Target sequence in the gene VPRBP

<400> SEQUENCE: 954
accgatgatt tagatgagct t    21

<210> SEQ ID NO 955
<211> LENGTH: 21
<212> TYPE: DNA
<213> ORGANISM: Artificial
<220> FEATURE:
<223> OTHER INFORMATION: Target sequence in the gene VPS18

<400> SEQUENCE: 955
ccgggtgcat tacgacctca a    21

<210> SEQ ID NO 956
<211> LENGTH: 21
<212> TYPE: DNA
<213> ORGANISM: Artificial
<220> FEATURE:
<223> OTHER INFORMATION: Target sequence in the gene WDFY2

<400> SEQUENCE: 956
tccctcactc gtaacaatga a    21

<210> SEQ ID NO 957
<211> LENGTH: 21
<212> TYPE: DNA

```
<213> ORGANISM: Artificial
<220> FEATURE:
<223> OTHER INFORMATION: Target sequence in the gene ZC3H18

<400> SEQUENCE: 957
cgggctcgaa ggcgtcggaa a                                              21

<210> SEQ ID NO 958
<211> LENGTH: 21
<212> TYPE: DNA
<213> ORGANISM: Artificial
<220> FEATURE:
<223> OTHER INFORMATION: Target sequence in the gene ZNF10

<400> SEQUENCE: 958
atccgtgtaa tggaagatta t                                              21

<210> SEQ ID NO 959
<211> LENGTH: 21
<212> TYPE: DNA
<213> ORGANISM: Artificial
<220> FEATURE:
<223> OTHER INFORMATION: Target sequence in the gene ZNF254

<400> SEQUENCE: 959
aagaatataa caaatctcct a                                              21

<210> SEQ ID NO 960
<211> LENGTH: 21
<212> TYPE: DNA
<213> ORGANISM: Artificial
<220> FEATURE:
<223> OTHER INFORMATION: Target sequence in the gene ZNF26

<400> SEQUENCE: 960
caggagactt cggataatat a                                              21

<210> SEQ ID NO 961
<211> LENGTH: 21
<212> TYPE: DNA
<213> ORGANISM: Artificial
<220> FEATURE:
<223> OTHER INFORMATION: Target sequence in the gene ZNF277

<400> SEQUENCE: 961
tggctgccat gtgaagttca a                                              21

<210> SEQ ID NO 962
<211> LENGTH: 21
<212> TYPE: DNA
<213> ORGANISM: Artificial
<220> FEATURE:
<223> OTHER INFORMATION: Target sequence in the gene ZNF334

<400> SEQUENCE: 962
aacaaccgtt tgactataat a                                              21

<210> SEQ ID NO 963
<211> LENGTH: 21
<212> TYPE: DNA
<213> ORGANISM: Artificial
<220> FEATURE:
<223> OTHER INFORMATION: Target sequence in the gene ZNF438

<400> SEQUENCE: 963
caccttcgag accacatgaa t                                              21
```

<210> SEQ ID NO 964
<211> LENGTH: 21
<212> TYPE: DNA
<213> ORGANISM: Artificial
<220> FEATURE:
<223> OTHER INFORMATION: Target sequence in the gene ZNF503

<400> SEQUENCE: 964
caagtcgagt ttcaagccgt a                                    21

<210> SEQ ID NO 965
<211> LENGTH: 21
<212> TYPE: DNA
<213> ORGANISM: Artificial
<220> FEATURE:
<223> OTHER INFORMATION: Target sequence in the gene ZNF697

<400> SEQUENCE: 965
ctggtctttg tcgcctaatt a                                    21

<210> SEQ ID NO 966
<211> LENGTH: 21
<212> TYPE: DNA
<213> ORGANISM: Artificial
<220> FEATURE:
<223> OTHER INFORMATION: Target sequence in the gene ZNF804B

<400> SEQUENCE: 966
cacgactcta ttgatgagac a                                    21

<210> SEQ ID NO 967
<211> LENGTH: 25
<212> TYPE: DNA
<213> ORGANISM: Artificial
<220> FEATURE:
<223> OTHER INFORMATION: Target sequence in the gene RAD51

<400> SEQUENCE: 967
gcgactcgct gatgagtttg gtgta                                25

<210> SEQ ID NO 968
<211> LENGTH: 25
<212> TYPE: DNA
<213> ORGANISM: Artificial
<220> FEATURE:
<223> OTHER INFORMATION: Target sequence in the gene GFP

<400> SEQUENCE: 968
gggcacaagc tggagtacaa ctaca                                25

<210> SEQ ID NO 969
<211> LENGTH: 25
<212> TYPE: DNA
<213> ORGANISM: Artificial
<220> FEATURE:
<223> OTHER INFORMATION: Target sequence in the gene LIFR

<400> SEQUENCE: 969
ccagtggctg ttatcaacat ttatt                                25

<210> SEQ ID NO 970
<211> LENGTH: 25
<212> TYPE: DNA
<213> ORGANISM: Artificial
<220> FEATURE:

```
<223> OTHER INFORMATION: Target sequence in the gene LIFR

<400> SEQUENCE: 970
ccaaataatg ttgaggttct ggaaa                                              25

<210> SEQ ID NO 971
<211> LENGTH: 25
<212> TYPE: DNA
<213> ORGANISM: Artificial
<220> FEATURE:
<223> OTHER INFORMATION: Target sequence in the gene CCL19

<400> SEQUENCE: 971
ggaacttcca ctaccttctc atcaa                                              25

<210> SEQ ID NO 972
<211> LENGTH: 25
<212> TYPE: DNA
<213> ORGANISM: Artificial
<220> FEATURE:
<223> OTHER INFORMATION: Target sequence in the gene CCL19

<400> SEQUENCE: 972
cctgctgtag tgttcaccac actga                                              25

<210> SEQ ID NO 973
<211> LENGTH: 25
<212> TYPE: DNA
<213> ORGANISM: Artificial
<220> FEATURE:
<223> OTHER INFORMATION: Target sequence in the gene ATR

<400> SEQUENCE: 973
cagctcgtct ctaaacccTT ctaaa                                              25

<210> SEQ ID NO 974
<211> LENGTH: 25
<212> TYPE: DNA
<213> ORGANISM: Artificial
<220> FEATURE:
<223> OTHER INFORMATION: Target sequence in the gene FBXO34

<400> SEQUENCE: 974
caccaagagt ttagtggccc ttaaa                                              25

<210> SEQ ID NO 975
<211> LENGTH: 25
<212> TYPE: DNA
<213> ORGANISM: Artificial
<220> FEATURE:
<223> OTHER INFORMATION: Target sequence in the gene DNAJB7

<400> SEQUENCE: 975
aagcttatca taaagtggca cttaa                                              25

<210> SEQ ID NO 976
<211> LENGTH: 25
<212> TYPE: DNA
<213> ORGANISM: Artificial
<220> FEATURE:
<223> OTHER INFORMATION: Target sequence in the gene DNAJB7

<400> SEQUENCE: 976
caaatgatga gaaacgggac attta                                              25
```

```
<210> SEQ ID NO 977
<211> LENGTH: 25
<212> TYPE: DNA
<213> ORGANISM: Artificial
<220> FEATURE:
<223> OTHER INFORMATION: Target sequence in the gene OCRL

<400> SEQUENCE: 977
cccagcttcc gagatgccat agaaa                                              25

<210> SEQ ID NO 978
<211> LENGTH: 25
<212> TYPE: DNA
<213> ORGANISM: Artificial
<220> FEATURE:
<223> OTHER INFORMATION: Target sequence in the gene OCRL

<400> SEQUENCE: 978
ccaaggagat ctggcttcta gtaga                                              25

<210> SEQ ID NO 979
<211> LENGTH: 25
<212> TYPE: DNA
<213> ORGANISM: Artificial
<220> FEATURE:
<223> OTHER INFORMATION: Target sequence in the gene POLQ

<400> SEQUENCE: 979
ccttaagact gtaggtacta tgaaa                                              25

<210> SEQ ID NO 980
<211> LENGTH: 25
<212> TYPE: DNA
<213> ORGANISM: Artificial
<220> FEATURE:
<223> OTHER INFORMATION: Target sequence in the gene POLQ

<400> SEQUENCE: 980
gcttcagtga tgactatcta gtaaa                                              25

<210> SEQ ID NO 981
<211> LENGTH: 25
<212> TYPE: DNA
<213> ORGANISM: Artificial
<220> FEATURE:
<223> OTHER INFORMATION: Target sequence in the gene KCNJ3

<400> SEQUENCE: 981
ccctcacaat ttgccacgtg atcga                                              25

<210> SEQ ID NO 982
<211> LENGTH: 25
<212> TYPE: DNA
<213> ORGANISM: Artificial
<220> FEATURE:
<223> OTHER INFORMATION: Target sequence in the gene MRC2

<400> SEQUENCE: 982
ggtggagcag gagcctttga tgtat                                              25

<210> SEQ ID NO 983
<211> LENGTH: 25
<212> TYPE: DNA
<213> ORGANISM: Artificial
<220> FEATURE:
<223> OTHER INFORMATION: Target sequence in the gene MRC2
```

```
<400> SEQUENCE: 983
cccttcaaat atgacaacca gtggt                                          25

<210> SEQ ID NO 984
<211> LENGTH: 25
<212> TYPE: DNA
<213> ORGANISM: Artificial
<220> FEATURE:
<223> OTHER INFORMATION: Target sequence in the gene SERPINB2

<400> SEQUENCE: 984
aaattggccc gtcccttgtt gaagg                                          25

<210> SEQ ID NO 985
<211> LENGTH: 25
<212> TYPE: DNA
<213> ORGANISM: Artificial
<220> FEATURE:
<223> OTHER INFORMATION: Target sequence in the gene EP300

<400> SEQUENCE: 985
caggtatgat gaacagtcca gtaaa                                          25

<210> SEQ ID NO 986
<211> LENGTH: 25
<212> TYPE: DNA
<213> ORGANISM: Artificial
<220> FEATURE:
<223> OTHER INFORMATION: Target sequence in the gene ATF7IP

<400> SEQUENCE: 986
ccagcagaag tagaaagtaa tgaaa                                          25

<210> SEQ ID NO 987
<211> LENGTH: 25
<212> TYPE: DNA
<213> ORGANISM: Artificial
<220> FEATURE:
<223> OTHER INFORMATION: Target sequence in the gene DCDC2

<400> SEQUENCE: 987
ccagaaagtc taagggagt ggaaa                                           25

<210> SEQ ID NO 988
<211> LENGTH: 25
<212> TYPE: DNA
<213> ORGANISM: Artificial
<220> FEATURE:
<223> OTHER INFORMATION: Target sequence in the gene PROP1

<400> SEQUENCE: 988
caccagtctg aggactggta cccta                                          25

<210> SEQ ID NO 989
<211> LENGTH: 25
<212> TYPE: DNA
<213> ORGANISM: Artificial
<220> FEATURE:
<223> OTHER INFORMATION: Target sequence in the gene CCL1

<400> SEQUENCE: 989
acagcaagag catgcaggta ccctt                                          25

<210> SEQ ID NO 990
<211> LENGTH: 21
```

```
<212> TYPE: DNA
<213> ORGANISM: Artificial
<220> FEATURE:
<223> OTHER INFORMATION: Target sequence in the gene SERPINB2

<400> SEQUENCE: 990
cagaagggta gttatcctga t                                          21

<210> SEQ ID NO 991
<211> LENGTH: 21
<212> TYPE: DNA
<213> ORGANISM: Artificial
<220> FEATURE:
<223> OTHER INFORMATION: Target sequence in the gene LIFR

<400> SEQUENCE: 991
ttggaagcct ttacccatta a                                          21

<210> SEQ ID NO 992
<211> LENGTH: 21
<212> TYPE: DNA
<213> ORGANISM: Artificial
<220> FEATURE:
<223> OTHER INFORMATION: Target sequence in the gene GJB1

<400> SEQUENCE: 992
tggcatctgc atcatcctca a                                          21

<210> SEQ ID NO 993
<211> LENGTH: 21
<212> TYPE: DNA
<213> ORGANISM: Artificial
<220> FEATURE:
<223> OTHER INFORMATION: Target sequence in the gene NDUFV1

<400> SEQUENCE: 993
ccgctcgacg gacatcgtga a                                          21

<210> SEQ ID NO 994
<211> LENGTH: 21
<212> TYPE: DNA
<213> ORGANISM: Artificial
<220> FEATURE:
<223> OTHER INFORMATION: Target sequence in the gene ATR

<400> SEQUENCE: 994
aaggacatgt gcattacctt a                                          21

<210> SEQ ID NO 995
<211> LENGTH: 7579
<212> TYPE: DNA
<213> ORGANISM: Artificial
<220> FEATURE:
<223> OTHER INFORMATION: pCLS1969

<400> SEQUENCE: 995
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
aatattaaac ttgatgagct ctagagatgg tcatgcattt taaaagaat tactcaaaat    300 attgtcttgg aataccagag agcaagtgct ttaagtatag gctgggaagt aaaatgctaa    360
```

```
aggaatgaga aggcatttgg ggttgagttc aacctaagag gcaggggagc cacagggaaa    420
gacctagcac ctgccacaga agagaattag gaagcagaat tgaactataa gcaattttga    480
ggtgttcgtt gggctgcagt tgaaatattt tttgaggtta atgagacatt tgaaatggcc    540
gtgtattgtt taactcttgc atagtcctgc atagggaaca atctaatagg atttctctgt    600
gaatcaagtc ttagaaattt gcttttaatt tttatgaaaa acgcccattt ctttgttttt    660
gagacagagt cctgctctgt catccaggct gggttgcagt ggcgtgatct tggcccactg    720
caatctctgc ctcctgggtt caggcaattt tcctgtctca gcctcccgag tagctgggat    780
ttcaagtgcc tgccaccatg cccggctaaa ttttttttgta tttttggtac agatggagta    840
tcaccatgtt ggccaggctg gtctcgaact cctgacctca agtgattcac cagccttgac    900
ctcccaaagt gttgggatca caggcatgag ccactgtgcc tgtgcccaa acaccaatt     960 tctgatgtgt gatgcatgta agatagaaca aacttcagta aagcgggac ttgaaaagag    1020 gctttggtaa cagctgtcag cattaaccct tgcccctccg tacctcctaa tcccacccct    1080
gctcaaagta tgttcatctg agaatttgtc tccataacta tgtgactata aaaattctca    1140
tcgattttgt tagttgatca attgagggaa aaacatatgt tacttgatat aactggtggg    1200
tcaaaagaat taacccaggc aaatttgaga taggtggatg ggatgatgga ttgaaaatac    1260
agctgctctc tttccaatca tgtactaagt aatttgggaa agattgatct aattgggtct    1320
agagagtaca cttcacatgg cattgtttga cttttttttct gcatcgctag cgatctgtgc    1380
attacaactc aaatcagtcg ggtttcctgg catatgtaat tgccaatgtt ttttaccaga    1440
agagaaacat tactcccacc tcttcttatt atgttacaaa ctatagtgct aatgaccatc    1500
gaccaacagt gactttcagg atgacctgtg tgagttttat ctgaaaccat gtgaatttt     1560 catcttaaaa gtcccttaga atctcagtct atgtacactc aggtttgttg caggtttaga    1620
gttccgtgtt ttttgtttct aatgtagaca cagccttata atttacaaca gcattcacta    1680
attaaaattg taagcataat tactatccac gatacttatt attagtttgc attcataaag    1740
ctcaaaattc acttcatcct ttcaagtagt gaataattag tttctttggg tttgcagctt    1800
tatcatcctt ttatgaccca tttggaagaa ataaacaacc aacccctgg aagactgctt     1860 taaaaagctg gaaatacatt gtccagctag tacaatgagg ctaatacaat gtggaaaata    1920 ttactttttct ttgattttag tagcctgttt atctttacat ttactgaaca aataactatt    1980
gagcacctaa tgtatactgg gacccttggg gaggcaaaga tgaatcaaag attctgtcct    2040
taaagacctt aaggttttg tggaaggaaa taaaacttta catgtatata tttaagcact     2100
tatatgtgtg taacaggtat aagtaaccat aaacactgtc agaagaggaa ataactctat    2160
gatcagcacc taacatgata tattaaggta gaagatttaa tacatatctt ttggaataca    2220
tgaataaata attgaatgta tttatttta ttatttataa gatacatcag tgggatattg      2280
atattggtct taatatgact tgttttcatt gttctcgaat tcggtgtgga aagtccccag    2340
gctccccagc aggcagaagt atgcaaagca tgcatctcaa ttagtcagca accaggtgtg    2400
gaaagtcccc aggctcccca gcaggcagaa gtatgcaaag catgcatctc aattagtcag    2460
caaccatagt cccgcccta actccgccca tcccgcccct aactccgccc agttccgccc     2520
attctccgcc ccatggctga ctaattttttt ttatttatgc agaggccgag gccgcctcgg    2580
cctctgagct attccagaag tagtgaggag gctttttgg aggcctaggc ttttgcaaaa      2640
agctcccggg agcttgtata tccatttttcg gatctgatca agagacagga tgaggatcgt    2700
ttcgcatgat tgaacaagat ggattgcacg caggttctcc ggccgcttgg gtggagaggc    2760
```

```
tattcggcta tgactgggca caacagacaa tcggctgctc tgatgccgcc gtgttccggc    2820
tgtcagcgca ggggcgcccg gttcttttg tcaagaccga cctgtccggt gccctgaatg     2880
aactgcagga cgaggcagcg cggctatcgt ggctggccac gacgggcgtt ccttgcgcag    2940
ctgtgctcga cgttgtcact gaagcgggaa gggactggct gctattgggc gaagtgccgg    3000
ggcaggatct cctgtcatct caccttgctc ctgccgagaa agtatccatc atggctgatg    3060
caatgcggcg gctgcatacg cttgatccgg ctacctgccc attcgaccac caagcgaaac    3120
atcgcatcga gcgagcacgt actcggatgg aagccggtct tgtcgatcag gatgatctgg    3180
acgaagagca tcaggggctc gcgccagccg aactgttcgc caggctcaag gcgcgcatgc    3240
ccgacggcga ggatctcgtc gtgacccatg gcgatgcctg cttgccgaat atcatggtgg    3300
aaaatggccg cttttctgga ttcatcgact gtggccggct gggtgtggcg gaccgctatc    3360
aggacatagc gttggctacc cgtgatattg ctgaagagct tggcggcgaa tgggctgacc    3420
gcttcctcgt gctttacggt atcgccgctc ccgattcgca gcgcatcgcc ttctatcgcc    3480
ttcttgacga gttcttctga ttaattaagc ccctctccct cccccccccc taacgttact    3540
ggccgaagcc gcttggaata aggccggtgt gcgtttgtct atatgttatt ttccaccata    3600
ttgccgtctt ttggcaatgt gagggcccgg aaacctggcc ctgtcttctt gacgagcatt    3660
cctaggggtc tttcccctct cgccaaagga atgcaaggtc tgttgaatgt cgtgaaggaa    3720
gcagttcctc tggaagcttc ttgaagacaa acaacgtctg tagcgaccct tgcaggcag    3780 cggaaccccc cacctggcga caggtgcctc tgcggccaaa agccacgtgt ataagataca    3840
cctgcaaagg cggcacaacc ccagtgccac gttgtgagtt ggatagttgt ggaaagagtc    3900
aaatggctct cctcaagcgt attcaacaag ggctgaagg atgccagaa ggtaccccat     3960 tgtatgggat ctgatctggg gcctcggtgc acatgcttta catgtgttta gtcgaggtta    4020
aaaaaacgtc taggccccc gaaccacggg gacgtggttt tcctttgaaa aacacgatga     4080
taatatggcc acaaccatgg gttctgagca gaaactgatt tccgaagagg atctgggatc    4140
cgcagcctct ttcccaccca ccttgggact cagttctgcc ccagatgaaa ttcagcaccc    4200
acatattaaa ttttcagaat ggaaatttaa gctgttccgg gtgagatcct ttgaaaagac    4260
acctgaagaa gctcaaaagg aaaagaagga ttcctttgag gggaaaccct ctctggagca    4320
atctccagca gtcctggaca aggctgatgg tcagaagcca gtcccaactc agccattgtt    4380
aaaagcccac cctaagtttt cgaagaaatt tcacgacaac gagaaagcaa gaggcaaagc    4440
gatccatcaa gccaaccttc gacatctctg ccgcatctgt gggaattctt ttagagctga    4500
tgagcacaac aggagatatc cagtccatgg tcctgtggat ggtaaaaccc taggccttt     4560 acgaaagaag gaaaagagag ctacttcctg gccggacctc attgccaagg ttttccggat    4620
cgatgtgaag gcagatgttg actcgatcca ccccactgag ttctgccata actgctggag    4680
catcatgcac aggaagtta gcagtgcccc atgtgaggtt tacttcccga ggaacgtgac     4740
catggagtgg cacccccaca caccatcctg tgacatctgc aacactgccc gtcggggact    4800
caagaggaag agtcttcagc caaacttgca gctcagcaaa aaactcaaaa ctgtgcttga    4860
ccaagcaaga caagcccgtc agcacaagag aagagctcag gcaaggatca gcagcaagga    4920
tgtcatgaag aagatcgcca actgcagtaa gatacatctt agtaccaagc tccttgcagt    4980
ggacttccca gagcactttg tgaaatccat ctcctgccag atctgtgaac acattctggc    5040
tgaccctgtg gagaccaact gtaagcatgt cttttgccgg gtctgcattc tcagatgcct    5100
```

```
caaagtcatg ggcagctatt gtccctcttg ccgatatcca tgcttcccta ctgacctgga    5160
gagtccagtg aagtcctttc tgagcgtctt gaattccctg atggtgaaat gtccagcaaa    5220
agagtgcaat gaggaggtca gtttggaaaa atataatcac cacatctcaa gtcacaagga    5280
atcaaaagag attttttgtgc acattaataa aggggtcga gtaacgcgtg caggcatgca    5340
agcttggcgt aatcatggtc atagctgttt cctgtgtgaa attgttatcc gctcacaatt    5400
ccacacaaca tacgagccgg aagcataaag tgtaaagcct ggggtgccta atgagtgagc    5460
taactcacat taattgcgtt gcgctcactg cccgctttcc agtcgggaaa cctgtcgtgc    5520
cagctgcatt aatgaatcgg ccaacgcgcg gggagaggcg gtttgcgtat tgggcgctct    5580
tccgcttcct cgctcactga ctcgctgcgc tcggtcgttc ggctgcggcg agcggtatca    5640
gctcactcaa aggcggtaat acggttatcc acagaatcag gggataacgc aggaaagaac    5700
atgtgagcaa aaggccagca aaaggccagg aaccgtaaaa aggccgcgtt gctggcgttt    5760
ttccataggc tccgcccccc tgacgagcat cacaaaaatc gacgctcaag tcagaggtgg    5820
cgaaacccga caggactata aagataccag gcgtttcccc ctggaagctc cctcgtgcgc    5880
tctcctgttc cgaccctgcc gcttaccgga tacctgtccg cctttctccc ttcgggaagc    5940
gtggcgcttt ctcatagctc acgctgtagg tatctcagtt cggtgtaggt cgttcgctcc    6000
aagctgggct gtgtgcacga accccccgtt cagcccgacc gctgcgcctt atccggtaac    6060
tatcgtcttg agtccaaccc ggtaagacac gacttatcgc cactggcagc agccactggt    6120
aacaggatta gcagagcgag gtatgtaggc ggtgctacag agttcttgaa gtggtggcct    6180
aactacggct acactagaag gacagtattt ggtatctgcg ctctgctgaa gccagttacc    6240
ttcggaaaaa gagttggtag ctcttgatcc ggcaaacaaa ccaccgctgg tagcggtggt    6300
ttttttgttt gcaagcagca gattacgcgc agaaaaaaag gatctcaaga agatcctttg    6360
atcttttcta cggggtctga cgctcagtgg aacgaaaact cacgttaagg gattttggtc    6420
atgagattat caaaaaggat cttcacctag atccttttaa attaaaaatg aagttttaaa    6480
tcaatctaaa gtatatatga gtaaacttgg tctgacagtt accaatgctt aatcagtgag    6540
gcacctatct cagcgatctg tctatttcgt tcatccatag ttgcctgact ccccgtcgtg    6600
tagataacta cgatacggga gggcttacca tctggcccca gtgctgcaat gataccgcga    6660
gacccacgct caccggctcc agatttatca gcaataaacc agccagccgg aagggccgag    6720
cgcagaagtg gtcctgcaac tttatccgcc tccatccagt ctattaattg ttgccgggaa    6780
gctagagtaa gtagttcgcc agttaatagt ttgcgcaacg ttgttgccat tgctacaggc    6840
atcgtggtgt cacgctcgtc gtttggtatg gcttcattca gctccggttc ccaacgatca    6900
aggcgagtta catgatcccc catgttgtgc aaaaaagcgg ttagctcctt cggtcctccg    6960
atcgttgtca agtaagtt ggccgcagtg ttatcactca tggttatggc agcactgcat    7020
aattctctta ctgtcatgcc atccgtaaga tgcttttctg tgactggtga gtactcaacc    7080
aagtcattct gagaatagtg tatgcggcga ccgagttgct cttgcccggc gtcaatacgg    7140
gataataccg cgccacatag cagaacttta aaagtgctca tcattggaaa acgttcttcg    7200
gggcgaaaac tctcaaggat cttaccgctg ttgagatcca gttcgatgta acccactcgt    7260
gcacccaact gatcttcagc atcttttact ttcaccagcg tttctgggtg agcaaaaaca    7320
ggaaggcaaa atgccgcaaa aaagggaata agggcgacac ggaaatgttg aatactcata    7380
ctcttccttt ttcaatatta ttgaagcatt tatcagggtt attgtctcat gagcggatac    7440
atatttgaat gtatttagaa aaataaacaa ataggggttc cgcgcacatt tccccgaaaa    7500
```

-continued

```
gtgccacctg acgtctaaga aaccattatt atcatgacat taacctataa aaataggcgt    7560
atcacgaggc cctttcgtc                                                 7579
```

<210> SEQ ID NO 996
<211> LENGTH: 6098
<212> TYPE: DNA
<213> ORGANISM: Artificial
<220> FEATURE:
<223> OTHER INFORMATION: pCLS2162

<400> SEQUENCE: 996

```
atggccaata ccaaatataa cgaagagttc ctgctgtacc tggccggctt tgtggacggt      60
gacggtagca tcatcgctca gattaatcca aaccagtctt ctaagtttaa acatcgtcta     120
cgtttgacct tttatgtgac tcaaaagacc cagcgccgtt ggtttctgga caaactagtg     180
gatgaaattg gcgttggtta cgtacgtgat tctggatccg tttcccagta cgttttaagc     240
gaaatcaagc cgctgcacaa cttcctgact caactgcagc cgtttctgga actgaaacag     300
aaacaggcaa acctggttct gaaaattatc gaacagctgc cgtctgcaaa agaatccccg     360
gacaaattcc tggaagtttg tacctgggtg atcagattg cagctctgaa cgattctaag     420
acgcgtaaaa ccacttctga aaccgttcgt gctgtgctgg acagcctgag cgggaagaag     480
aaatcctccc cggcggccgg tggatctgat aagtataatc aggctctgtc taaatacaac     540
caagcactgt ccaagtacaa tcaggccctg tctggtggag gcggttccaa caaaaagttc     600
ctgctgtacc tggccggctt tgtggactct gacggtagca tcatcgctca gattaaacca     660
cgtcagtcta ataagtttaa acatcagcta agcttgacct ttgctgtgac tcaaaagacc     720
cagcgccgtt ggtttctgga caaactagtg gatcgtattg gcgttggtta cgtatatgat     780
tctggatccg tttccgatta ccgtttaagc gaaatcaagc cgctgcacaa cttcctgact     840
caactgcagc cgtttctgaa actgaaacag aaacaggcaa acctggttct gaaaattatc     900
gaacagctgc cgtctgcaaa agaatccccg gacaaattcc tggaagtttg tacctgggtg     960
gatcagattg cagctctgaa cgattctaag acgcgtaaaa ccacttctga aaccgttcgt    1020
gctgtgctgg acagcctgag cgagaagaag aaatcctccc cggcggccga ctaatctaga    1080
gggcccgcgg ttcgaaggta agcctatccc taaccctctc ctcggtctcg attctacgcg    1140
taccggttag taatgagttt aaacggggga ggctaactga acacggaag gagacaatac    1200 cggaaggaac ccgcgctatg acggcaataa aagacagaa taaaacgcac gggtgttggg    1260
tcgtttgttc ataaacgcgg ggttcggtcc cagggctggc actctgtcga taccccaccg    1320
agaccccatt ggggccaata cgcccgcgtt tcttcctttt ccccacccca cccccaagt    1380 tcgggtgaag gcccagggct cgcagccaac gtcgggcgg caggccctgc catagcagat    1440
ctgcgcagct ggggctctag ggggtatccc cacgcgccct gtagcggcgc attaagcgcg    1500
gcgggtgtgg tggttacgcg cagcgtgacc gctacacttg ccagcgccct agcgcccgct    1560
cctttcgctt tcttcccttc ctttctcgcc acgttcgccg gctttccccg tcaagctcta    1620
aatcggggca tccctttagg gttccgattt agtgctttac ggcacctcga ccccaaaaaa    1680
cttgattagg gtgatggttc acgtagtggg ccatcgccct gatagacggt ttttcgccct    1740
ttgacgttgg agtccacgtt ctttaatagt ggactcttgt tccaaactgg aacaacactc    1800
aaccctatct cggtctattc ttttgattta agggattg tgggattc ggcctattgg    1860 ttaaaaaatg agctgattta acaaaaattt aacgcgaatt aattctgtgg aatgtgtgtc    1920
```

-continued

```
agttagggtg tggaaagtcc ccaggctccc cagcaggcag aagtatgcaa agcatgcatc   1980
tcaattagtc agcaaccagg tgtggaaagt ccccaggctc cccagcaggc agaagtatgc   2040
aaagcatgca tctcaattag tcagcaacca tagtcccgcc cctaactccg cccatcccgc   2100
ccctaactcc gcccagttcc gcccattctc cgccccatgg ctgactaatt ttttttattt   2160
atgcagaggc cgaggccgcc tctgcctctg agctattcca gaagtagtga ggaggctttt   2220
ttggaggcct aggcttttgc aaaaagctcc cgggagcttg tatatccatt ttcggatctg   2280
atcagcacgt gttgacaatt aatcatcggc atagtatatc ggcatagtat aatacgacaa   2340
ggtgaggaac taaaccatgg ccaagccttt gtctcaagaa gaatccaccc tcattgaaag   2400
agcaacggct acaatcaaca gcatccccat ctctgaagac tacagcgtcg ccagcgcagc   2460
tctctctagc gacggccgca tcttcactgg tgtcaatgta tatcatttta ctggggtgacc   2520 ttgtgcagaa ctcgtggtgc tgggcactgc tgctgctgcg gcagctggca acctgacttg   2580
tatcgtcgcg atcggaaatg agaacagggg catcttgagc ccctgcggac ggtgccgaca   2640
ggtgcttctc gatctgcatc ctgggatcaa agccatagtc aaggacagtg atggacagcc   2700
gacggcagtt gggattcgtg aattgctgcc ctctggttat gtgtgggagg gctaagcact   2760
tcgtggccga ggagcaggac tgacacgtgc tacgagattt cgattccacc gccgccttct   2820
atgaaaggtt gggcttcgga atcgttttcc gggacgccgg ctggatgatc ctccagcgcg   2880
gggatctcat gctggagttc ttcgcccacc ccaacttgtt tattgcagct tataatggtt   2940
acaaataaag caatagcatc acaaatttca caaataaagc atttttttca ctgcattcta   3000
gttgtggttt gtccaaactc atcaatgtat cttatcatgt ctgtataccg tcgacctcta   3060
gctagagctt ggcgtaatca tggtcatagc tgtttcctgt gtgaaattgt tatccgctca   3120
caattccaca acatacga gccggaagca taaagtgtaa agcctggggt gcctaatgag   3180
tgagctaact cacattaatt gcgttgcgct cactgcccgc tttccagtcg ggaaacctgt   3240
cgtgccagct gcattaatga atcggccaac gcgcggggag aggcggtttg cgtattgggc   3300
gctcttccgc ttcctcgctc actgactcgc tgcgctcggt cgttcggctg cggcgagcgg   3360
tatcagctca ctcaaaggcg gtaatacggt tatccacaga atcaggggat aacgcaggaa   3420
agaacatgtg agcaaaaggc cagcaaaagg ccaggaaccg taaaaaggcc gcgttgctgg   3480
cgtttttcca taggctccgc cccctgacg agcatcacaa aaatcgacgc tcaagtcaga   3540
ggtggcgaaa cccgacagga ctataaagat accaggcgtt tccccctgga agctccctcg   3600
tgcgctctcc tgttccgacc ctgccgctta ccggatacct gtccgccttt ctcccttcgg   3660
gaagcgtggc gctttctcat agctcacgct gtaggtatct cagttcggtg taggtcgttc   3720
gctccaagct gggctgtgtg cacgaacccc ccgttcagcc cgaccgctgc gccttatccg   3780
gtaactatcg tcttgagtcc aacccggtaa gacacgactt atcgccactg gcagcagcca   3840
ctggtaacag gattagcaga gcgaggtatg taggcggtgc tacagagttc ttgaagtggt   3900
ggcctaacta cggctacact agaagaacag tatttggtat ctgcgctctg ctgaagccag   3960
ttaccttcgg aaaaagagtt ggtagctctt gatccggcaa acaaaccacc gctggtagcg   4020 gttttttgt ttgcaagcag cagattacgc gcagaaaaaa aggatctcaa gaagatcctt   4080
tgatcttttc tacgggtct gacgctcagt ggaacgaaaa ctcacgttaa gggattttgg   4140
tcatgagatt atcaaaaagg atcttcacct agatcctttt aaattaaaaa tgaagtttta   4200
aatcaatcta agtatatat gagtaaactt ggtctgacag ttaccaatgc ttaatcagtg   4260
aggcacctat ctcagcgatc tgtctatttc gttcatccat agttgcctga ctccccgtcg   4320
```

-continued

```
tgtagataac tacgatacgg gagggcttac catctggccc cagtgctgca atgataccgc    4380
gagacccacg ctcaccggct ccagatttat cagcaataaa ccagccagcc ggaagggccg    4440
agcgcagaag tggtcctgca actttatccg cctccatcca gtctattaat tgttgccggg    4500
aagctagagt aagtagttcg ccagttaata gtttgcgcaa cgttgttgcc attgctacag    4560
gcatcgtggt gtcacgctcg tcgtttggta tggcttcatt cagctccggt tcccaacgat    4620
caaggcgagt tacatgatcc cccatgttgt gcaaaaaagc ggttagctcc ttcggtcctc    4680
cgatcgttgt cagaagtaag ttggccgcag tgttatcact catggttatg gcagcactgc    4740
ataattctct tactgtcatg ccatccgtaa gatgcttttc tgtgactggt gagtactcaa    4800
ccaagtcatt ctgagaatag tgtatgcggc gaccgagttg ctcttgcccg gcgtcaatac    4860
gggataatac cgcgccacat agcagaactt taaaagtgct catcattgga aaacgttctt    4920
cggggcgaaa actctcaagg atcttaccgc tgttgagatc cagttcgatg taacccactc    4980
gtgcacccaa ctgatcttca gcatctttta ctttcaccag cgtttctggg tgagcaaaaa    5040
caggaaggca aaatgccgca aaaagggaa taagggcgac acggaaatgt tgaatactca    5100
tactcttcct ttttcaatat tattgaagca tttatcaggg ttattgtctc atgagcggat    5160
acatatttga atgtatttag aaaaataaac aatagggt tccgcgcaca tttccccgaa    5220
aagtgccacc tgacgtcgac ggatcgggag atctcccgat cccctatggt gcactctcag    5280
tacaatctgc tctgatgccg catagttaag ccagtatctg ctccctgctt gtgtgttgga    5340
ggtcgctgag tagtgcgcga gcaaaattta agctacaaca aggcaaggct tgaccgacaa    5400
ttgcatgaag aatctgctta gggttaggcg ttttgcgctg cttcgcgatg tacgggccag    5460
atatacgcgt tgacattgat tattgactag ttattaatag taatcaatta cggggtcatt    5520
agttcatagc ccatatatgg agttccgcgt tacataactt acggtaaatg gcccgcctgg    5580
ctgaccgccc aacgaccccc gcccattgac gtcaataatg acgtatgttc ccatagtaac    5640
gccaataggg actttccatt gacgtcaatg ggtggagtat ttacggtaaa ctgcccactt    5700
ggcagtacat caagtgtatc atatgccaag tacgccccct attgacgtca atgacggtaa    5760
atggcccgcc tggcattatg cccagtacat gaccttatgg gactttccta cttggcagta    5820
catctacgta ttagtcatcg ctattaccat ggtgatgcgg ttttggcagt acatcaatgg    5880
gcgtggatag cggtttgact cacggggatt tccaagtctc cacccattg acgtcaatgg    5940 gagtttgttt tggcaccaaa atcaacggga ctttccaaaa tgtcgtaaca actccgcccc    6000
attgacgcaa atgggcggta ggcgtgtacg gtgggaggtc tatataagca gagctctctg    6060
gctaactaga gaacccactg cttactggct tatcgacc                            6098
```

<210> SEQ ID NO 997
<211> LENGTH: 24
<212> TYPE: DNA
<213> ORGANISM: Artificial
<220> FEATURE:
<223> OTHER INFORMATION: primer Rad1EX2-R12

<400> SEQUENCE: 997

```
ctttcacagt cctgtacatc ttgt                                             24
```

<210> SEQ ID NO 998
<211> LENGTH: 4661
<212> TYPE: DNA
<213> ORGANISM: Artificial
<220> FEATURE:

<223> OTHER INFORMATION: ATF7IP mRNA from coding sequence NM_018179.3
<300> PUBLICATION INFORMATION:
<308> DATABASE ACCESSION NUMBER: GenBank NM_018179.3

<400> SEQUENCE: 998

| | | | | | |
|---|---|---|---|---|---|
| uuuuugaauc | ugcggaggcg | gcggcggugg | cagcggcggc | gcggcgacug | aagcgcgcga | 60 |
| aaagcugagg | cggcaacguc | ggggacggcu | gcgcgggacg | gcucuguagg | aaggaacuug | 120 |
| guucccccuc | ccucagcuuc | cgccccaaaa | gauucagaau | ggacaguuua | gaagaaccuc | 180 |
| agaaaaagu | cuuuaaggcu | cgaaaaacga | ugagagugag | ugaucgucag | caacuugaag | 240 |
| caguguacaa | ggucaaagaa | gaacuguuga | aaacugaugu | caagcuguua | aauggcaacc | 300 |
| augaaaaugg | agauuuggac | ccaaccucac | cuuuggaaaa | cauggauuac | auuaaagaca | 360 |
| aggaagaggu | gaauggcauu | gaagagauuu | guuuugaucc | ugaaggaagu | aaagcagaau | 420 |
| ggaaggaaac | acccuguauc | cuaaguguua | auguaaaaaa | caagcaggau | gaugauuuaa | 480 |
| auugugaacc | uuugucuccc | cauaauauaa | cuccagaacc | agucucuaaa | cugccugcug | 540 |
| aaccaguuuc | ugguugaucca | gccccugguug | aucuggaugc | cggagauccaa | gccuccggag | 600 |
| uacuggccuc | ugguugauucc | accucugguug | aucccaccuc | uagcgagccc | uccucuagug | 660 |
| augcugccuc | ugguugaugca | accucugguug | augcccuuc | ugguugaugug | ucccugguug | 720 |
| augccaccuc | ugguugaugcc | acugcugaugc | aucucuccuc | ugguugauccc | accucuagug | 780 |
| aucccauccc | aggugaaccg | gucccuguug | aacccauuuc | ugguugauugu | gccgcugaug | 840 |
| auauagccuc | uaguugaaaua | acuucugguug | aucggcuuc | uggagcacca | gcuuccacug | 900 |
| auccagcccuc | ugaugaucug | gcccucggug | aucuauccuc | uagugaacug | gcccucgaug | 960 |
| aucuggccac | uggugaacug | gcccucgaug | agcugacuuc | ugaaucaacc | uuugaucgua | 1020 |
| ccuuugaacc | aaagucugua | ccaguuugug | aaccaguucc | ugaaauugac | aauauagaac | 1080 |
| caaguagcaa | uaagaaugau | gauuuucuug | aaaaaaaugg | agcugaugaa | aaauuagagc | 1140 |
| aaauucagag | uaaagacuca | uuggaugaga | aaaauaaagc | ugauaauaau | auugaugcua | 1200 |
| augaagaaac | ucuagaaaca | gaugauacaa | cuauuguuc | agaucgaccu | ccugaaaaug | 1260 |
| aaaagaaggu | agaggaagau | auuaucacag | agcuugcucu | uggagaagau | gcuauaucua | 1320 |
| gcaguaugga | aauugaccaa | ggugaaaaga | augaagauga | aacuucugca | gaucuuguag | 1380 |
| aaacgauuaa | ugaaaauguu | auugaagaua | caaaaguga | gaauaucuua | gaaaauacag | 1440 |
| acucuaugga | gacagaugaa | aucauuccua | uuuuggaaaa | gcuugcaccu | ucugaggaug | 1500 |
| aacuuacuug | cuuuucuaaa | acaucucucc | uuccaaucga | ugagacaaau | ccagauuugg | 1560 |
| aagagaaaau | ggaaaguucu | uugguucac | caucuaaaca | agaaaguagu | gagaguuugc | 1620 |
| caaaagaagc | cuuucugguc | cucucugaug | aagaggauau | uucggguugaa | aaagaugagu | 1680 |
| cugaaguuau | aucgcaaaau | gaaacgugcu | cuccagcaga | aguagaaagu | aaugaaaagg | 1740 |
| acaacaaacc | ugaggaagaa | gagcaaguaa | uacaugaaga | ugaugaaaga | ccuucugaga | 1800 |
| aaaaugaauu | uucuagacga | aaacguucua | aaucagaaga | cauggacaau | guacagucua | 1860 |
| aacgucgucg | auauauggaa | gaagaauaug | aggcagaauu | ucaaguaaag | auuacagcca | 1920 |
| aaggagacau | uaaccagaaa | cuucaaaagg | uuauacagug | guugcuggaa | gaaaaauugu | 1980 |
| gugcgcugca | gugugcugua | uuugauaaga | cuuuggcaga | auugaaaaca | cgagugggaaa | 2040 |
| agauugaaug | uaacaagagg | cauaaaacag | uucucacuga | acuacaggcc | aagauagcca | 2100 |
| gguuaaccaa | acgcuuugaa | gcagccaaag | aagaucuuaa | gaaagacau | gaacauccac | 2160 |
| ccaacccacc | aguaucacca | ggaaaaacug | uaaaugaugu | caacagcaau | aauaacaugu | 2220 |

-continued

```
cuuacagaaa ugcaggcaca gugagacaga ugcuggaguc caaaagaaau guaagcgaga    2280
gugcaccacc auccuuucaa acuccuguga auacaguauc uucaaccaau cuugucacuc    2340
cuccagcagu ugucaguagu caaccuaaau ugcagacucc agugacuucg gguuccuca     2400 cagcaacguc aguucuuccu gcacccaaua cagcuacugu aguugcuacu acucaggugc    2460
cuaguggaaa uccccagccu acaaucucuu uacagccuuu gccagugauu uugcauguac    2520
cuguugcagu auccucccag ccucagcuuc uacagagcca uccagggacu ugguugacua    2580
aucaaccauc uggcaauguu gaauucauuu cugugcaaag cccaccuaca gugagugguc    2640
uuaccaaaaa uccaguaucc uugccauccu ugccaaaucc cacuaaacca aacaacguuc    2700
cuucugugcc caguccuagu auucaaagga acccuacugc cagugcugca ccauugggaa    2760
caacacuugc ugugcaggcu guccaacag cacacucuau uguacaagcc acaaggacuu     2820
cuuuacccac aguggccca ucaggacucu auaguccauc aacuaaucga gguccuauac     2880
agaugaaaau uccaauuucu gcauuuagua cuucgucugc ugcagaacag aacagcaaua    2940
ccaccccaag aauugaaaac cagacaaaca aaacaauaga ugcuucuguc aguaagaaag    3000
cagcugauag cacaucacag uguggaaaag ccacuggcag ugauucaagu ggugucauug    3060
aucucacaau ggaugaugaa gagaguggag cuucacaaga ccccaaaaaa cuaaaucaca    3120
cuccuguauc aaccaugagu ucuucucagc cugugucacg accauugcaa cccauacaac    3180
cagcaccgcc ucuucaacca ucuggggugc caacaagugg accaucucag accaccauac    3240
acuuacuacc uacagcucca acuaccguga auguaacaca ucguccagua acucagguga    3300
ccacaagacu cccuguacca agagcuccug caaaccacca ggugguuuau acaacucuuc    3360
cugcaccacc agcucaggcu cccuugcgag gaacuguuau gcaggcuccu gcuuucggc     3420 aggucaaucc ccaaaauagu guuacaguuc gagugccuca acaaccaca uauguuguaa     3480 acaauggacu aacccuggga ucaacaggac cucagcucac agugcaucac cgaccaccac    3540
aagugcauac ugagccccca cgccccgugc acccagcacc cuuaccagaa gcuccacaac    3600
cacagcgucu gccccagaa gcugccagca caucucugcc ucagaagcca cacuugaagu     3660
uagcacgcgu ucagagucaa aauggcauag uacugucaug gagugccug gagguggauc     3720 gaagcugugc cacuguugau agcuaccauc ucuaugcuua ccaugaggaa cccagugcca    3780
cugugcccuc acaauggaaa aagauugggg aagucaaggc acuucccuug ccauggcau    3840 guacucucac ccaguuugua ucgguagca aauacuacuu ugcaguacga gccaaggaua     3900
uuuauggacg uuugggccu uucugugauc cucagucaac agaugugauc ucuucuaccc    3960
agagcaguua aaccuuggag ccuuauauu uccucuuuu aaauuuccca ccuuugguc       4020 uuguuuuaa ucuugugcau gauaccccau guaaauucca ccuugugcaa gauucuugg     4080 acagaugugu guauacacua cauuuguuua uaaccagaag caaauaaac ucagcccaca     4140 aagcuagaau cuuuuccugg acaguuuagg cuuggggguu uggaaaugua aauguguacc    4200
uugcuuuagu uuugaggcug gggaauaugu gugguguuu augugugugu uuccuuaugu     4260 agguguauu gcauuggagu ucccauuuu cauucucaaa uuuaccucuu aaaguacgaa      4320
guaaguagau caaaggauuu gagaugugua acuggcauga uucugcuuuu gaaggaucua    4380
uaguaucauu uuaguuaagu gggucaaaca gaaucaaaac aaacccaaa gaaauaaaua     4440 aaaacaaaa uggcuaaaua guuuaaaaua ggguaauucg aacacaggaa aggaucuauu     4500
uguuguuucu uuugucuggu cuccugaguu guuaauuagg ugaaaaaga ucugcaaugg    4560
```

-continued

| | |
|---|---|
| ccccucccu uuccuaaucu ggcuuuuaca uuuauuuugu gccuuaaaga uuaacuacaa | 4620 |
| agauaaacau ggccaaaaau aaauaaauaa auauggccau a | 4661 |

<210> SEQ ID NO 999
<211> LENGTH: 8761
<212> TYPE: RNA
<213> ORGANISM: Human
<220> FEATURE:
<223> OTHER INFORMATION: EP300 mRNA NM_001429.3
<300> PUBLICATION INFORMATION:
<308> DATABASE ACCESSION NUMBER: GenBank NM_001429.3

<400> SEQUENCE: 999

| | |
|---|---|
| gccgaggagg aagagguuga uggcggcggc ggagcuccga gagaccucgg cugggcaggg | 60 |
| gccggccgug gcgggccggg gacugcgccu cuagagccgc gaguucucgg gaauucgccg | 120 |
| cagcggacgc gcucggcgaa uuugugcucu gugcccucc uccgggcuug ggcccaggcc | 180 |
| cggcccucg cacuugcccu uaccuuuucu aucgaguccg cauccucuc cagccacugc | 240 |
| gacccggcga agagaaaaag gaacuucccc caccccucg ggugccgucg gagccccca | 300 |
| gcccacccu ggguggcggcg cggggacccc gggccgaaga agagauuucc ugaggauucu | 360 |
| gguuuuccuc gcuuguaucu ccgaaagaau uaaaaauggc cgagaugug guggaaccgg | 420 |
| ggccgccuuc agccaagcgg ccuaaacucu caucccggc ccucucgcg uccgccagcg | 480 |
| auggcacaga uuuggcucu cuauuugacu uggagcacga cuuaccagau gaauuaauca | 540 |
| acucuacaga auugggacua accaauggug gugauauuaa ucagcuucag acaagucuug | 600 |
| gcaugguaca agaugcagcu ucuaaacaua aacagcuguc agaauugcug cgaucuggua | 660 |
| guucccuaa ccucaauaug ggaguuggug gcccagguca agucauggcc agccaggccc | 720 |
| aacagagcag uccuggauua gguuugauaa auagcauggu caaagcccca augacacagg | 780 |
| caggcuugac uucucccaac augggagugg gcacuagugg accaaaucag gguccuacgc | 840 |
| agucaacagg uaugaugaac aguccaguaa aucagccugc caugggaaug aacacaggga | 900 |
| ugaaugcggg caugaauccu ggaaugguugg cugcaggcaa uggacaaggg auaaugccua | 960 |
| aucaagucau gaacgguuca auuggagcag gccgagggcg acagaauaug caguaccccaa | 1020 |
| acccaggcau gggaagugcu ggcaacuuac ugacugagcc ucuucagcag ggcucucccc | 1080 |
| agauggggag acaaacagga uugagaggcc cccagccucu uaagauggga augaugaaca | 1140 |
| accccaaucc uuaugguuca ccauauacuc agaauccugg acagcagauu ggagccagug | 1200 |
| gccuuggucu ccagauucag acaaaaacug uacuaucaaa uaacuuaucu ccauuugcua | 1260 |
| uggacaaaaa ggcaguuccu ggugaggaa ugcccaacau ggucaacag ccagccccgc | 1320 |
| agguccagca gccaggccug gugacuccag uugcccaagg gauggguucu ggagcacaua | 1380 |
| cagcugaucc agagaagcgc aagcucaucc agcagcagcu uguucuccuu uugcaugcuc | 1440 |
| acaagugcca gcgccgggaa caggccaaug gggaagugag gcagugcaac cuucccccacu | 1500 |
| gucgcacaau gaagaaugnc cuaaaccaca ugacacacug ccagcaggc aagucuugcc | 1560 |
| aaguggcaca cugugcaucu ucucgacaaa ucauuucaca cuggaagaau uguacaagac | 1620 |
| augauuugcc ugugugucuc ccccucaaaa augcugguga uagagaaau caacagccaa | 1680 |
| uuuugacugg agcacccguu ggacuggaa uccuagcuc ucuaggggug ggucaacagu | 1740 |
| cugcccccaa ccuaagcacu guuaucaga uugaucccag cuccauagaa agagccuaug | 1800 |
| cagcucuugg acuacccuau caaguaaauc agaugccgac acaaccccag gugcaagcaa | 1860 |
| agaaccagca gaaucagcag ccugggcagu cuccccaagg caugcggccc augagcaaca | 1920 |

```
ugagugcuag uccuauggga guaaauggag guguaggagu ucaaacgccg agucuucuuu   1980
cugacucaau guugcauuca gccauaaauu cucaaaaccc aaugaugagu gaaaaugcca   2040
gugugcccuc ccuggguccu augccaacag cagcucaacc auccacuacu ggaauucgga   2100
aacaguggca cgaagauauu acucaggauc uucgaaauca ucuuguucac aaacucgucc   2160
aagccauauu uccuacgccg gauccugcug cuuuaaaaga cagacggaug gaaaaccuag   2220
uugcauaugc ucggaaaguu gaaggggaca guaugaauc ugcaaacaau cgagcggaau   2280
acuaccaccu ucuagcugag aaaaucuaua agauccagaa agaacuagaa gaaaaacgaa   2340
ggaccagacu acagaagcag aacaugcuac caaaugcugc aggcaugguu ccaguuucca   2400
ugaauccagg gccuaacaug ggacagccgc aaccaggaau gacuucuaau ggcccucuac   2460
cugacccaag uaugauccgu ggcagugugc caaaccagau gaugccucga auaacuccac   2520
aaucugguuu gaaucaauuu ggccagauga gcauggccca gccccuauu guaccccggc   2580 aaacccucuc ucuucagcac cauggacagu uggcucaacc uggagcucuc aacccgccua   2640
ugggcuaugg gccucguaug caacagccuu ccaaccaggg ccaguuccuu ccucagacuc   2700
aguucccauc acagggaaug aauguaacaa auaucccuuu ggcuccgucc agcggucaag   2760 cuccagugu caagcacaa augucuaguu cuuccugccc ggugaacucu ccuauaaugc   2820
cuccaggguc ucaggggagc cacauucacu gucccagcu uccuaaacca gcucuucauc   2880
agaauucacc cucgccugua ccuagucgua cccccacccc ucaccauacu cccccaagca   2940
uaggggcuca gcagccacca gcaacaacaa uuccagcccc uguccuaca ccuccugcca   3000 ugccaccugg gccacagucc caggcucuac auccccucc aaggcagaca ccuacaccac   3060
caacaacaca acuuccccaa caagugcagc cuucacuucc ugcugcaccu ucugcugacc   3120
agccccagca gcagccucgc ucacagcaga gcacagcagc gucuguuccu accccaacag   3180
caccgcugcu uccuccgcag ccugcaacuc cacuuuccca gccagcugua agcauugaag   3240
gacagguauc aaauccucca ucuacuagua gcacagaagu gaauucucag gccauugcug   3300
agaagcagcc uucccaggaa gugaagaugg aggccaaaau ggaaguggau caaccagaac   3360
cagcagauac ucagccggag gauauuucag agucuaaagu ggaagacugu aaaauggaau   3420
cuaccgaaac agaagagaga agcacugagu uaaaaacuga aauaaaagag gaggaagacc   3480
agccaaguac uucagcuacc caguucaucuc cggcuccagg acagucaaag aaaaagauuu   3540
ucaaaccaga gaacuacga caggcacuga ugccaacuuu ggaggcacuu uaccgucagg   3600
auccagaauc ccuucccuuu cgucaaccug uggacccuca gcuuuaagga aucccugauu   3660
acuuugauau ugugaagagc cccauggauc uuucuaccau uaagaggaag uuagacacug   3720
gacaguauca ggagcccugg caguaugcg augauauuug gcuuauguuc aauaaugccu   3780
gguuauauaa ccggaaaaca ucacggguau acaaauacug cuccaagcuc ucugaggucu   3840
uugaacaaga aauugaccca gugaugcaaa gccuuggaau a cuguguggc agaaaguugg   3900 aguucucucc acagacacug guugcuacg gcaaacaguu gugcacaaua ccucgugaug   3960
ccacuuauua caguuaccag aacaggauauc auuucugua gaaguguuuc aaugagaucc   4020
aaggggagag cguucuuug ggggaugacc cuucccagcc ucaaacuaca auaaauaaag   4080
aacaauuuuc caagagaaaa aaugacacac uggauccuga acuguuuguu gaauguacag   4140
agugcggaag aaagaugcau cagaucugu ccuucaccca ugaucaucuu ggccugcug   4200 gauucgucug ugauggcugu uuaaagaaaa gugcacgaac uaggaaagaa aauaaguuuu   4260
```

| | |
|---|---|
| cugcuaaaag guugccaucu accagacuug gcaccuuucu agagaaucgu gugaaugacu | 4320 |
| uucugaggcg acagaaucac ccugagucag gagaggucac uguuagagua guucaugcuu | 4380 |
| cugacaaaac cguggaagua aaaccaggca ugaaagcaag guuuguggac aguggagaga | 4440 |
| uggcagaauc cuuuccauac cgaaccaaag cccucuuugc cuuugaagaa auugauggug | 4500 |
| uugaccugug cuucuuuggc augcauguuc aagaguaugg cucugacugc ccuccaccca | 4560 |
| accagaggag aguauacaua ucuuaccucg auaguguuca uuucuuccgu ccuaaaugcu | 4620 |
| ugaggacugc agucuaucau gaaauccuaa uuggauauuu agaauauguc aagaaauuag | 4680 |
| guuacacaac agggcauauu ugggcauguc caccaaguga gggagaugau uauaucuucc | 4740 |
| auugccaucc uccugaccag aagauaccca agcccaagcg acugcaggaa ugguacaaaa | 4800 |
| aaaugcuuga caaggcugua ucagagcgua uugccauga cuacaaggau auuuuuaaac | 4860 |
| aagcuacuga agauagauua acaagugcaa aggaauugcc uuauuucgag ggugauuucu | 4920 |
| ggcccaaugu ucuggaagaa agcauuaagg aacuggaaca ggaggaagaa gagagaaaac | 4980 |
| gagaggaaaa caccagcaau gaaagcacag augugaccaa gggagacagc aaaaaugcua | 5040 |
| aaaagaagaa uaauaagaaa accagcaaaa auaagagcag ccugaguagg ggcaacaaga | 5100 |
| agaaacccgg gaugcccaau guaucuaacg accucucaca gaaacuauau gccaccaugg | 5160 |
| agaagcauaa agaggucuuc uuugugaucc gccucauugc uggcccugcu gccaacuccc | 5220 |
| ugccucccau uguugauccu gauccucuca uccccgcga ucugauggau ggucgggaug | 5280 |
| cguuucucac gcuggcaagg gacaagcacc uggaguucuc uucacuccga agagccagu | 5340 |
| ggucaccau gugcaugcug guggagcugc acacgcagag ccaggaccgc uuugucuaca | 5400 |
| ccugcaauga augcaagcac cauguggaga cacgcuggca cuguacuguc gugaggauu | 5460 |
| augacuugug uauccaccgc uauaacacua aaaaccauga ccacaaaaug gagaaacuag | 5520 |
| gccuuggcuu agaugaugag agcaacaacc agcaggcugc agccacccag agcccaggcg | 5580 |
| auucucgccg ccuaguauc cagcgcugca uccagucucu ggccaugcu ugccagugu | 5640 |
| ggaaugccaa uugcucacug ccauccugcc agaagaugaa gcgguugug cagcauacca | 5700 |
| agggguugcaa acggaaaaacc aauggcgggu gccccaucug caagcagcuc auugcccucu | 5760 |
| gcugcuacca ugccaagcac ugccaggaga acaaaugccc ggugccguuc ugccuaaaca | 5820 |
| ucaagcagaa gcccggcag caacagcugc agcaccgacu acagcaggcc caaaugcuuc | 5880 |
| gcaggaggau ggccagcaug cagcggacug guguggugg gcagcaacag ggccucccuu | 5940 |
| cccccacucc ugccacucca acgacaccaa cuggccaaca gccaaccacc cgcagacgc | 6000 |
| cccagcccac uucucagccu cagccuaccc cucccaauag caugccaccc uacuugccca | 6060 |
| ggacucaagc ugcuggcccu guccccagg guaaggcagc aggccaggug accccuccaa | 6120 |
| ccccuccuca gacugcucag ccaccccuuc cagggccccc accugcagca guggaaaugg | 6180 |
| caaugcagau ucagagagca gcggagacgc agcgccagau ggcccacgug caaauuuuuc | 6240 |
| aaaggccaau ccaacaccag augccccga ugacucccau ggccccaug gguaugaacc | 6300 |
| caccucccau gaccagaggu cccagugggc auuggagcc agggauggga ccgacaggga | 6360 |
| ugcagcaaca gccacccugg agccaaggag gauugccuca gccccagcaa cuacagucug | 6420 |
| ggaugccaag gccagccaug augucagugg cccagcaugg ucaaccuuug aacauggcuc | 6480 |
| cacaaccagg auugggccag guaggauca gcccacucaa accaggcacu gugucucaac | 6540 |
| aagccuuaca aaaccuuuug cggacucuca ggucucccag cucuccccug cagcagcaac | 6600 |
| aggugcuuag uauccuucac gccaacccccc agcuguuggc ugcauucauc aagcagcggg | 6660 |

```
cugccaagua ugccaacucu aauccacaac ccaucccugg gcagccuggc augccccagg    6720
ggcagccagg gcuacagcca ccuaccaugc caggucagca gggggoccac uccaauccag    6780 ccaugcagaa caugaaucca augcaggcgg gcguucagag ggcuggccug ccccagcagc    6840
aaccacagca gcaacuccag ccacccaugg gagggaugag ccccaggcu cagcagauga     6900 acaugaacca caacaccaug ccuucacaau ccgagacau cuugagacga cagcaaauga    6960
ugcaacagca gcagcaacag ggagcagggc caggaauagg cccuggaaug gccaaccaua    7020
accaguccca gcaaccccaa ggaguuggcu acccaccaca gcagcagcag cggaugcagc    7080
aucacaugca acagaugcaa caaggaaaua ugggacagau aggccagcuu ccccaggccu    7140
ugggagcaga ggcaggugcc agucuacagg ccuaucagca gcgacuccuu cagcaacaga    7200
uggggucccc cguucagccc aaccccauga gccccagca gcauaugcuc ccaaaucagg    7260
cccagucccc acaccuacaa ggccagcaga ucccuaauuc ucucuccaau caagugcgcu    7320
cuccccagcc uguccuucu ccacggccac agcccagcc ccccacucc agucuucc       7380 caaggaugca gccucagccu ucuccacacc acguuucccc acagacaagu uccccacauc    7440
cuggacuggu agcugcccag gccaacccca uggaacaagg gcauuugcc agcccggacc    7500 agaauucaau gcuuucucag cuugcuagca auccaggcau ggcaaaccuc cauggugcaa    7560
gcgccacgga ccugggacuc agcaccgaua acucagacuu gaauucaaac cucucacaga    7620
guacacuaga cauacacuag agacaccuug uaguauuuug ggagcaaaaa aauuauuuuc    7680
ucuuaacaag acuuuuugua cugaaaacaa uuuuuuugaa ucuuucguag ccuaaaagac    7740
aauuuuccuu ggaacacaua agaacugugc aguagccguu ugugguuuaa agcaaacaug    7800
caagaugaac cugagggaug auagaauaca agaauauau uuuguuaug gcugguuacc      7860 accagccuuu cuuccccuuu gugugugugg uucaagugug cacgggagg aggcugaggc     7920 cugugaagcc aaacaauaug cuccugccuu gcaccuccaa uagguuuau uauuuuuuu      7980 aaauuaauga acauauguaa uauuaauagu uauuauuuac uggugcagau gguugacauu    8040
uuucccuauu uuccucacuu uauggaagag uuaaaacauu ucuaaaccag aggacaaaag    8100
ggguuaaugu uacuuuaaaa uuacauucua uauauauaua aauauauauu               8160
aaaauaccag uuuuuuuucu cugggugcaa agauguucau ucuuuaaaaa aauguuuaaa    8220
aaaaaaaaaa aacugccuuu cuucccucca gucaacuuu gugcuccag aaaauuuucu      8280 auucuguaag ucugagcgua aaacuucaag uauuaaaaua auuugacau guagagagaa     8340 aaugacuuu uucaaaaaua uacaggggca gcugccaaau ugauguauua uauauugugg     8400
uuucuguuuc uugaaagaau uuuuuucguu auuuuuacau cuaacaaagu aaaaaaauua    8460 aaagaggu aagaaacgau uccgguggga ugauuuaac augcaaaaug ucccugggg         8520 uuucuucuuu gcuugcuuuc uuccuccuua cccuaccccc cacucacaca cacacacaca    8580
cacacacaca cacacacaca cacacacuuu cuauaaaacu ugaaaauagc aaaaacccuc    8640
aacuguugua aaucaugcaa uuaaaguuga uuacuuauaa auaugaacuu ggaucacug     8700 uauagacugu uaaauuugau uucuuauuac cuauuguuaa auaaacugug ugagacagac    8760
a                                                                    8761
```